(12) United States Patent
Lee et al.

(10) Patent No.: US 12,150,663 B2
(45) Date of Patent: Nov. 26, 2024

(54) END TOOL OF SURGICAL INSTRUMENT, AND ELECTROCAUTERIZATION SURGICAL INSTRUMENT COMPRISING SAME

(71) Applicant: LIVSMED INC., Seongnam-si (KR)

(72) Inventors: Jung Joo Lee, Seongnam-si (KR); Heejin Kim, Seongnam-si (KR); Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/413,760

(22) Filed: Jan. 16, 2024

(65) Prior Publication Data
US 2024/0148397 A1 May 9, 2024

Related U.S. Application Data

(63) Continuation of application No. PCT/KR2022/010390, filed on Jul. 15, 2022.

(30) Foreign Application Priority Data

Jul. 16, 2021 (KR) .......................... 10-2021-0093831
Dec. 6, 2021 (KR) .......................... 10-2021-0173270

(51) Int. Cl.
| | | |
|---|---|---|
| *A61B 17/285* | (2006.01) | |
| *A61B 17/28* | (2006.01) | |
| *A61B 17/29* | (2006.01) | |
| *A61B 18/14* | (2006.01) | |

(52) U.S. Cl.
CPC ........ *A61B 17/285* (2013.01); *A61B 17/2812* (2013.01); *A61B 17/29* (2013.01); *A61B 18/1442* (2013.01)

(58) Field of Classification Search
CPC ... A61B 17/285; A61B 17/2812; A61B 17/29; A61B 18/1442
See application file for complete search history.

(56) References Cited

U.S. PATENT DOCUMENTS

| | | | |
|---|---|---|---|
| 6,554,844 B2 * | 4/2003 | Lee ..................... | A61B 5/0084 606/1 |
| 7,101,363 B2 * | 9/2006 | Nishizawa ............. | A61B 34/71 606/1 |
| 8,821,480 B2 * | 9/2014 | Burbank ................ | A61B 34/30 606/1 |
| 10,743,948 B2 * | 8/2020 | Remm ................... | A61B 34/30 |
| 10,758,298 B2 * | 9/2020 | Felder ................... | A61B 46/10 |
| 11,534,232 B2 * | 12/2022 | Reid ..................... | A61B 34/35 |
| 2011/0106145 A1 | 5/2011 | Jeong | |
| 2012/0215220 A1 | 8/2012 | Manzo et al. | |
| 2020/0038127 A1 | 2/2020 | Chaplin et al. | |

(Continued)

FOREIGN PATENT DOCUMENTS

| | | |
|---|---|---|
| EP | 3266392 A2 | 1/2018 |
| JP | 2006-061364 A | 3/2006 |

(Continued)

*Primary Examiner* — Julian W Woo
(74) *Attorney, Agent, or Firm* — Bridgeway IP Law Group, PLLC; Sang Ho Lee; Hyun Woo Shin

(57) ABSTRACT

Provided is a surgical instrument for electrocautery, and in particular, a surgical instrument for electrocautery installed on a robot arm or manually operable in order to be used in laparoscopic surgery or other various surgeries.

20 Claims, 124 Drawing Sheets

(56) References Cited

U.S. PATENT DOCUMENTS

| | | |
|---|---|---|
| 2020/0281644 A1 | 9/2020 | Felder et al. |
| 2021/0045825 A1 | 2/2021 | Lee et al. |

FOREIGN PATENT DOCUMENTS

| | | |
|---|---|---|
| JP | 2019-530530 A | 10/2019 |
| KR | 10-2010-0001823 A | 1/2010 |
| KR | 10-2012-0003091 A | 1/2012 |
| KR | 10-2016-0101538 A | 8/2016 |
| KR | 10-2019-0109449 A | 9/2019 |
| KR | 10-2019-0112195 A | 10/2019 |
| KR | 10-2118721 B1 | 6/2020 |
| KR | 10-2122508 B1 | 6/2020 |
| KR | 10-2153408 B1 | 9/2020 |
| KR | 10-2308205 B1 | 10/2021 |
| WO | 2020/055705 A1 | 3/2020 |
| WO | 2020/076447 A1 | 4/2020 |
| WO | 2020/089790 A1 | 5/2020 |
| WO | 2020/198372 A1 | 10/2020 |

* cited by examiner (a)

(b)

(a)

(b)

END TOOL OF SURGICAL INSTRUMENT, AND ELECTROCAUTERIZATION SURGICAL INSTRUMENT COMPRISING SAME

CROSS-REFERENCE TO RELATED APPLICATION

This application is a continuation application of international application No. PCT/KR2022/010390, filed on Jul. 15, 2022, which claims priority to Korean Patent Application Nos. 10-2021-0093831, filed on Jul. 16, 2021, and 10-2021-0173270 filed on Dec. 6, 2021, the entire disclosures of which are incorporated herein in their entirety by reference.

TECHNICAL FIELD

One or more embodiments of the present disclosure relate to an end tool of a surgical instrument and a surgical instrument for electrocautery including the same, and in particular, to an end tool of a surgical instrument and a surgical instrument for electrocautery including the end tool that is capable of rotating in two or more directions and intuitively matching a movement of a manipulation portion, wherein the surgical instrument may be installed on a robot arm or manually operable in order to be used in laparoscopic surgery or other various surgeries.

BACKGROUND ART

Surgical operations in many cases require cutting and joining of body tissues including organs, muscular tissues, connective tissues, and blood vessels. Over the centuries, sharp blades and sutures have been used for cutting and joining. However, bleeding occurs when cutting body tissues, in particular, relatively highly vascularized tissue during surgical operation. Therefore, doctors require surgical instruments and methods to slow or reduce bleeding during surgical operations.

Recently, it has become possible to use an electric surgical instrument that uses electrical energy to perform certain surgical tasks. For example, regarding surgical instruments such as graspers, scissors, tweezers, blades, needles, and hooks, electric surgical instruments including one or more electrodes formed to receive electric energy have been developed. Electrical energy supplied through the electrodes may be used to coagulate, bond, or cut the patient's body tissues. In particular, when electrical energy is used, amputation and hemostasis may be performed at the same time.

Electric surgical instruments are typically classified into two types: monopolar and bipolar. In a monopolar electric surgical instrument, electrical energy of a specific polarity is supplied to one or more electrodes of the instrument. And electricity of different polarity is electrically connected to the patient. In a bipolar electric surgical instrument, one or more electrodes are electrically connected to a first polarity electrical energy source, and one or more electrodes are electrically connected to a second polarity electrical energy source opposite to the first polarity.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

DESCRIPTION OF EMBODIMENTS

Technical Problem

The present disclosure is directed to providing a surgical instrument for electrocautery including an end tool that is capable of rotating in two or more directions, and moving to intuitively match a movement of a manipulation portion, in a manually operable surgical instrument for electrocautery that is installed on a robot arm or manually operable for use in laparoscopic surgery or other various surgeries.

Solution to Problem

One aspect of the present disclosure provides an end tool of a surgical instrument, the end tool including a first jaw and a second jaw that are rotatable independently from each other, a first jaw pulley connected to the first jaw and formed to be rotatable about a first rotation shaft, a second jaw pulley connected to the second jaw, formed to be rotatable about the first rotation shaft, and formed to be spaced a predetermined distance from the first jaw pulley, a blade assembly that includes a blade moving between a proximal end and a distal end of the first jaw, and of which at least a part is formed between the first jaw pulley and the second jaw pulley, and a blade wire of which at least a part is in contact with the blade assembly to transfer a driving force required to move the blade to the blade.

The blade assembly may include a guide tube that accommodates at least a part of the blade wire therein and is formed to be bendable to a certain degree.

When blade wire may pass through the inside of the guide tube and may be connected to the blade.

When the guide tube is curved to a certain degree, the blade wire inside the guide tube may also be curved together with the guide tube.

The blade wire may be formed to be movable along the guide tube in the guide tube.

The end tool may further include a first link having one end coupled to the first jaw and the other end coupled to the first jaw pulley to connect the first jaw and the first jaw pulley, and a second link having one end coupled to the second jaw and the other end coupled to the second jaw pulley to connect the second jaw and the second jaw pulley.

The first link may be fixedly coupled to each of the first jaw and the first jaw pulley, and when the first jaw pulley rotates about the first rotation shaft, the first link and the first jaw may rotate about the first rotation shaft together with the first jaw pulley in an integrated manner.

The guide tube may be formed to extend toward the blade through the first link.

One end of the second link may be connected to the second jaw pulley so that the second link is formed to be rotatable relative to the second jaw pulley, and the other end of the second link may be connected to the second jaw so that the second jaw is formed to be movable relative to the second link.

When the second jaw pulley rotates, the rotation of the second jaw pulley may be transferred to the second jaw by the second link connected to the second jaw pulley.

The end tool may further include an actuation rotation shaft inserted through the first link and the second jaw, wherein the second jaw may be formed to be rotatable about the actuation rotation shaft with respect to the first link.

A rotational motion of the second jaw pulley about the first rotation shaft may be converted into a rotational motion of the second jaw about the actuation rotation shaft by the second link.

When the second jaw pulley rotates, the second link connected to the second jaw pulley may apply a force to the second jaw so that the second jaw rotates about the actuation rotation shaft.

The first rotation shaft and the actuation rotation shaft may be formed substantially parallel to each other.

The first rotation shaft and the actuation rotation shaft may be formed substantially perpendicular to each other.

The end tool may further include an end tool hub including a first jaw pulley coupling portion, a second jaw pulley coupling portion, and a guide portion, wherein the first jaw pulley coupling portion and the second jaw pulley coupling portion are formed to face each other and the guide portion connects the first jaw pulley coupling portion and the second jaw pulley coupling portion, wherein the first jaw pulley may be disposed adjacent to the first jaw pulley coupling portion of the end tool hub, the second jaw pulley may be disposed adjacent to the second jaw pulley coupling portion of the end tool hub, and at least a part of the blade assembly may be formed between the first jaw pulley and the second jaw pulley.

The guide tube may be formed to extend toward the first jaw or the second jaw through the end tool hub.

When the first jaw pulley and the second jaw pulley rotate in the same direction about the first rotation shaft, a yaw motion in which the first jaw and the second jaw rotate in the same direction may be performed.

When the second jaw pulley relatively rotates about the first rotation shaft with respect to the first jaw pulley, an actuation motion in which the second jaw relatively rotates with respect to the first jaw may be performed.

The end tool may include a pair of end tool first jaw pitch main pulleys that are formed on one side of the first jaw pulley and formed to be rotatable about a third rotation shaft forming a certain angle with the first rotation shaft, and a pair of end tool second jaw pitch main pulleys formed on one side of the second jaw pulley and formed to be rotatable about the third rotation shaft.

The end tool may be formed to be yaw-rotatable about the first rotation shaft and simultaneously pitch-rotatable about the third rotation shaft.

The end tool may further include a first jaw wire of which at least a part is wound on the first jaw pulley and the pair of end tool first jaw pitch main pulleys, and a second jaw wire of which at least a part is wound on the second jaw pulley and the pair of end tool second jaw pitch main pulleys.

The blade may move between the proximal end and the distal end of the end tool by the blade wire.

Another aspect of the present disclosure provides an end tool of a surgical instrument, the end tool including a first jaw and a second jaw that are rotatable independently from each other, a first jaw pulley connected to the first jaw and formed to be rotatable about a first rotation shaft, a second jaw pulley connected to the second jaw and formed to be rotatable about a shaft that is substantially the same as or parallel to the first rotation shaft, an end tool hub which has one end through which the first rotation shaft is inserted and the other end through which a third rotation shaft different from the first rotation shaft is inserted and in which at least a part of the first jaw pulley and the second jaw pulley is accommodated, a blade at least a part of which is accommodated in the first jaw or the second jaw and which is formed to be movable between a proximal end and a distal end of the first jaw or the second jaw, a guide tube formed to extend toward the blade through the end tool hub, and a blade wire which has one end connected to the blade to transmit a driving force required to move the blade to the blade and at least a part of which is disposed in the guide tube.

The end tool hub may include a body portion, a first jaw pulley coupling portion and a second jaw pulley coupling portion that are formed to extend in one direction from the body portion and formed to face each other, and a first pitch pulley portion and a second pitch pulley portion that are formed to extend in a direction opposite to the one direction from the body portion and formed to face each other.

The first jaw pulley may be disposed adjacent to the first jaw pulley coupling portion of the end tool hub, the second jaw pulley may be disposed adjacent to the second jaw pulley coupling portion of the end tool hub, and at least a part of the guide tube may be disposed between the first jaw pulley and the second jaw pulley.

A yaw slit through which the guide tube passes may be formed between the first jaw pulley coupling portion and the second jaw pulley coupling portion.

A yaw round portion having a predetermined curvature may be formed at one side of the yaw slit and guides a bending path of the guide tube in a yaw direction.

The first rotation shaft may include a first sub-shaft formed on a side of the first jaw pulley coupling portion and a second sub-shaft formed on a side of the second jaw pulley coupling portion, and the yaw slit may be formed between the first sub-shaft and the second sub-shaft of the first rotation shaft.

A pitch slit through which the guide tube passes may be formed between the first pitch pulley portion and the second pitch pulley portion.

A pitch round portion having a predetermined curvature may be formed at one side of the pitch slit and guides a bending path of the guide tube in a pitch direction.

The third rotation shaft may include a first sub-shaft formed at a side of the first pitch pulley portion and a second sub-shaft formed at a side of the second pitch pulley portion, and the pitch slit may be formed between the first sub-shaft and the second sub-shaft of the third rotation shaft.

A yaw slit through which the guide tube passes may be formed between the first jaw pulley coupling portion and the second jaw pulley coupling portion, and a pitch slit through which the guide tube may pass may be formed between the first pitch pulley portion and the second pitch pulley portion, wherein the yaw slit and the pitch slit may be formed to be connected to each other.

The end tool may further include a first jaw wire of which at least a part is wound on the first jaw pulley, and a second jaw wire of which at least a part is wound on the second jaw pulley.

The end tool may further include a first jaw auxiliary pulley and a second jaw auxiliary pulley disposed between the first and second jaw pulleys and the body portion of the end tool hub.

The first jaw wire may be located on a common internal tangent of the first jaw pulley and the first jaw auxiliary pulley, and a rotation angle of the first jaw pulley may be increased by the first jaw auxiliary pulley.

A first wire guide portion and a second wire guide portion, which have cross sections formed to be curved with a predetermined curvature, may be formed in a region of the body portion adjacent to the first jaw pulley and the second jaw pulley.

The first jaw wire may be located on a common internal tangent of the first jaw pulley and the first wire guide portion, and a rotation angle of the first jaw pulley may be increased by the first wire guide portion.

A first electrode may be formed on a surface of the first jaw, the surface facing the second jaw, and a second electrode may be formed on a surface of the second jaw, the surface facing the first jaw.

Electrocautery for a tissue may be performed while an electric current flows in the first electrode and the second electrode.

When the electrocautery is finished, the blade wire may move and accordingly the blade may be moved from a proximal end toward a distal end of the first jaw, thereby cutting the tissue.

At least a part of the guide tube may be disposed between the first jaw pulley and the second jaw pulley.

The guide tube may accommodate at least a part of the blade wire therein and is formed to be bendable to a certain degree.

Another aspect of the present disclosure provides an end tool of a surgical instrument, the end tool including a first jaw and a second jaw that are rotatable independently from each other, a first jaw pulley coupled to the first jaw and formed to be rotatable about a first rotation shaft, a first link having one end coupled to the first jaw and the other end coupled to the first jaw pulley to connect the first jaw and the first jaw pulley, a first jaw wire of which at least a part is wound on the first jaw pulley, a second jaw pulley coupled to the second jaw and formed to be rotatable about the first rotation shaft, a second link having one end coupled to the second jaw and the other end coupled to the second jaw pulley to connect the second jaw and the second jaw pulley, a second jaw wire of which at least a part is wound on the second jaw pulley, a pair of end tool first jaw pitch main pulleys that are formed on one side of the first jaw pulley and formed to be rotatable about a third rotation shaft forming a certain angle with the first rotation shaft, a pair of end tool second jaw pitch main pulleys that are formed on one side of the second jaw pulley and formed to be rotatable about an axis that is substantially the same as or parallel to the third rotation shaft, an end tool hub which has one end through which the first rotation shaft is inserted and the other end through which a third rotation shaft is inserted and in which at least a part of the first jaw pulley and the second jaw pulley is accommodated, a guide tube that is disposed to pass through the end tool hub and is formed to be bendable to a certain degree, a blade wire of which at least a part is inserted through the guide tube, and a blade that is connected to the blade wire, is at least partially accommodated in the first jaw or the second jaw, and moves between a proximal end and a distal end of the first jaw or the second jaw according to the movement of the blade wire.

The first link may be fixedly coupled to each of the first jaw and the first jaw pulley, and when the first jaw pulley rotates about the first rotation shaft, the first link and the first jaw may rotate about the first rotation shaft together with the first jaw pulley in an integrated manner.

The first jaw pulley and the first link may be integrally formed.

One end of the second link may be connected to the second jaw pulley so that the second link is formed to be rotatable relative to the second jaw pulley, and the other end of the second link may be connected to the second jaw so that the second jaw is formed to be movable relative to the second link.

The end tool may further include an actuation rotation shaft serving as a central axis of rotation of the second jaw with respect to the first jaw or the first link.

A rotational motion of the second jaw pulley about the first rotation shaft may be converted into a rotational motion of the second jaw about the actuation rotation shaft by the second link.

When the second jaw pulley relatively rotates with respect to the first jaw pulley, the second link connected to the second jaw pulley may apply a force to the second jaw so that the second jaw rotates about the actuation rotation shaft.

The first rotation shaft may be an axis of rotation of each of the first jaw pulley and the second jaw pulley, and the actuation rotation shaft may be an axis of rotation of the second jaw with respect to the first jaw.

The first rotation shaft and the actuation rotation shaft may be formed to be spaced a predetermined distance from each other by the first link and the second link.

One end of the second link may be axially coupled to the second jaw pulley, and the other end of the second link may be axially coupled to the second jaw.

A guide pin may be formed at one end of the second link, and a slit may be formed in each of the first link and the second jaw, wherein the guide pin may be inserted into the slit of the first link and the slit of the second jaw.

When the second jaw pulley rotates, the guide pin of the second link connected to the second jaw pulley may perform a linear movement along the slit of the first link.

The guide pin may apply a force to the second jaw while moving along the slit of the first link, so that the second jaw rotates about the actuation rotation shaft.

The second jaw wire may include a second jaw wire (R) and a second jaw wire (L), a first coupling portion to which the second jaw wire (R) may be coupled is formed on one surface of the second jaw pulley, and a second coupling portion to which the second jaw wire (L) is coupled may be formed on the other surface of the second jaw pulley.

In one side and the other side of a plane passing through the first rotation shaft and perpendicular to the third rotation shaft, the first coupling portion to which the second jaw wire (R) is coupled may be formed on the other side, which is a side opposite to the one side to which the second jaw wire (R) is input, so that a rotation angle of the second jaw pulley may be increased by increasing a length of the second jaw wire (R) wound on the second jaw pulley, and the second coupling portion to which the second jaw wire (L) is coupled may be formed on the one side, which is a side opposite to the other side to which the second jaw wire (L) is input, so that the rotation angle of the second jaw pulley may be increased by increasing a length of the second jaw wire (L) wound on the second jaw pulley.

The first rotation shaft may include a first sub-shaft and a second sub-shaft, and the guide tube may pass between the first sub-shaft and the second sub-shaft of the first rotation shaft.

The third rotation shaft may include a first sub-shaft and a second sub-shaft, and the guide tube passes between the first sub-shaft and the second sub-shaft of the third rotation shaft.

A yaw motion of the end tool may be performed by rotating the first jaw pulley and the second jaw pulley in the same direction about the first rotation shaft.

An actuation motion of the end tool may be performed by rotating relatively the second jaw pulley about the first rotation shaft with respect to the first jaw pulley.

Another aspect of the present disclosure provides a surgical instrument for electrocautery, the surgical instrument including an end tool having a first jaw and a second jaw each formed to be rotatable, wherein the rotation is made in two or more directions, a manipulation portion configured to control rotation of the end tool in the two or more directions, a power transmission portion having a first jaw wire connected to the manipulation portion to transfer the rotation of the manipulation portion to the first jaw and a second jaw wire connected to the manipulation portion to transfer the rotation of the manipulation portion to the second jaw, and a connecting portion formed to extend in a first direction (X-axis), and having one end coupled to the end tool and the other end coupled to the manipulation portion to connect the manipulation portion and the end tool, wherein the end tool may include a first electrode coupled to the first jaw, a second electrode coupled to the second jaw and formed to face the first jaw, a first jaw pulley coupled to the first jaw and formed to be rotatable about a first rotation shaft, a second jaw pulley coupled to the second jaw and formed to be rotatable about a shaft that is substantially same as or parallel to the first rotation shaft, a blade assembly including a blade moving between a proximal end and a distal end of the end tool and disposed adjacent to the first jaw pulley or the second jaw pulley, and a blade wire of which at least a part is in contact with the blade assembly to transfer a driving force required to move the blade to the blade.

At least a part of the manipulation portion may extend toward the end tool.

When the manipulation portion is rotated in the two or more directions, the end tool may be rotated in directions substantially the same as manipulation directions of the manipulation portion.

A direction in which the end tool is formed at the one end of the connecting portion and a direction in which the manipulation portion is formed at the other end of the connecting portion may be identical directions with respect to an extending axis (X-axis) of the connecting portion.

The manipulation portion may be formed to extend in a direction away from a user who grips the surgical instrument for electrocautery.

An end portion of the manipulation portion may be formed toward the end tool so that an end portion of a finger of a user gripping the manipulation portion faces the end tool.

The connecting portion may include a curved portion that is formed to be curved once or more while connecting the end tool to the manipulation portion.

The curved portion may have a cross section formed as an approximately semi-circular shape, and a direction in which the manipulation portion is formed at an end portion of the curved portion and a direction in which the end tool is formed at a point where the connecting portion and the end tool are connected may be formed to be substantially identical.

At least a part of the manipulation portion may be formed to be accommodated in the curved portion during at least one movement of the manipulation portion.

The surgical instrument may further include an end tool jaw auxiliary pulley formed on one side of the first and second jaw pulleys and formed to be rotatable about a second rotation shaft.

Two strands of the first jaw wire wound on the first jaw pulley may be arranged, by the end tool jaw auxiliary pulley, on one side with respect to an extending axis (X-axis) of the connecting portion, and two strands of the second jaw wire wound on the second jaw pulley may be arranged, by the end tool jaw auxiliary pulley, on the other side with respect to the extending axis (X-axis) of the connecting portion.

Any one side of the first jaw wire wound on the first jaw pulley may be formed to pass between the first jaw pulley and the end tool jaw auxiliary pulley, and any one side of the second jaw wire wound on the second jaw pulley may be formed to pass between the second jaw pulley and the end tool jaw auxiliary pulley.

The first jaw wire may be located on an internal tangent of the first jaw pulley and the end tool jaw auxiliary pulley, and the second jaw wire may be located on an internal tangent of the second jaw pulley and the end tool jaw auxiliary pulley.

The blade assembly may include a guide tube that accommodates at least a part of the blade wire therein and is formed to be bendable to a certain degree.

The blade wire may pass through the inside of the guide tube and is connected to the blade.

When the guide tube is curved to a certain degree, the blade wire inside the guide tube may also be curved together with the guide tube.

The blade wire may be formed to be movable along the guide tube in the guide tube.

The surgical instrument may further include a first link having one end coupled to the first jaw and the other end coupled to the first jaw pulley to connect the first jaw and the first jaw pulley, and a second link having one end coupled to the second jaw and the other end coupled to the second jaw pulley to connect the second jaw and the second jaw pulley.

The first link may be fixedly coupled to each of the first jaw and the first jaw pulley, and when the first jaw pulley rotates about the first rotation shaft, the first link and the first jaw may rotate about the first rotation shaft together with the first jaw pulley in an integrated manner.

One end of the second link may be connected to the second jaw pulley so that the second link is formed to be rotatable relative to the second jaw pulley, and the other end of the second link may be connected to the second jaw so that the second jaw is formed to be movable relative to the second link.

The surgical instrument may further include an end tool hub including a first jaw pulley coupling portion, a second jaw pulley coupling portion, and a guide portion, wherein the first jaw pulley coupling portion and the second jaw pulley coupling portion are formed to face each other and the guide portion connects the first jaw pulley coupling portion and the second jaw pulley coupling portion, wherein the first jaw pulley may be disposed adjacent to the first jaw pulley coupling portion of the end tool hub, the second jaw pulley may be disposed adjacent to the second jaw pulley coupling portion of the end tool hub, and at least a part of the blade assembly may be formed between the first jaw pulley and the second jaw pulley.

The guide tube may be formed to extend toward the first jaw or the second jaw through the end tool hub.

Electrocautery for a tissue may be performed while an electric current flows in the first electrode and the second electrode.

When the electrocautery is finished, the blade wire may move and accordingly the blade may move between the proximal end and the distal end of the first jaw, thereby cutting the tissue.

The surgical instrument may include a pair of end tool first jaw pitch main pulleys that are formed on one side of the first jaw pulley and formed to be rotatable about a third rotation shaft forming a certain angle with the first rotation shaft, and a pair of end tool second jaw pitch main pulleys that are formed on one side of the second jaw pulley and formed to be rotatable about a shaft that is substantially the same as or parallel to the third rotation shaft.

The end tool may be formed to be yaw-rotatable about the first rotation shaft and simultaneously pitch-rotatable about the third rotation shaft.

Another aspect of the present disclosure provides a method for surgery by using a surgical instrument for electrocautery, the method including arranging a tissue between a first jaw and a second jaw of an end tool of a surgical instrument for electrocautery, closing the second jaw with respect to the first jaw by rotating a second jaw pulley, to which the second jaw is connected, about the first rotation shaft with respect to a first jaw pulley to which the first jaw is connected, performing electrocautery of the tissue between the first jaw and the second jaw when an electric current flows in a first electrode connected to the first jaw and a second electrode connected to the second jaw, and cutting the tissue by moving a blade of a blade assembly from a proximal end toward a distal end of the first jaw by a blade wire, the blade assembly being at least partially disposed between the first jaw pulley and the second jaw pulley.

The blade assembly may further include a guide tube that accommodates at least a part of the blade wire therein and is formed to be bendable to a certain degree, and the cutting of the tissue may include moving the blade wire in the guide tube from the proximal end toward the distal end of the first jaw, and moving the blade coupled to the blade wire from the proximal end toward the distal end of the first jaw.

The blade wire may pass through the inside of the guide tube and is connected to the blade.

When the guide tube is curved to a certain degree, the blade wire inside the guide tube may also be curved together with the guide tube.

In the cutting of the tissue, the blade wire may move along the guide tube in the guide tube.

The surgical instrument may further include a first link having one end coupled to the first jaw and the other end coupled to the first jaw pulley to connect the first jaw and the first jaw pulley, and a second link having one end coupled to the second jaw and the other end coupled to the second jaw pulley to connect the second jaw and the second jaw pulley.

The first jaw pulley and the second jaw pulley may be formed to be spaced a predetermined distance from each other, and the blade assembly may be formed between the first jaw pulley and the second jaw pulley.

The end tool may include a pair of end tool first jaw pitch main pulleys that are formed on one side of the first jaw pulley and formed to be rotatable about a third rotation shaft forming a certain angle with the first rotation shaft, and a pair of end tool second jaw pitch main pulleys that are formed on one side of the second jaw pulley and formed to be rotatable about a shaft that is substantially the same as or parallel to the third rotation shaft.

The end tool may be formed to be yaw-rotatable about the first rotation shaft and simultaneously pitch-rotatable about the third rotation shaft.

Other aspects, features, advantages other than those described above will become apparent from the following drawings, claims, and detailed description of the disclosure.

Advantageous Effects of Disclosure

According to the present disclosure, a manipulation direction of a manipulation portion by an operator and an operating direction of an end tool are intuitively identical to each other, so that the operator's convenience can be improved, and the accuracy, reliability and speed of surgery can be improved.

BRIEF DESCRIPTION OF DRAWINGS (a) of FIG. 1 is a conceptual diagram of a pitch motion of a conventional surgical instrument, and (b) of FIG. 1 is a conceptual diagram of a yaw motion.

(c) of FIG. 1 is a conceptual diagram of a pitch motion of another conventional surgical instrument, and (d) of FIG. 1 is a conceptual diagram of a yaw motion.

(e) of FIG. 1 is a conceptual diagram of a pitch motion of a surgical instrument according to the present disclosure, and (f) of FIG. 1 is a conceptual diagram of a yaw motion.

FIG. 2 is a perspective view illustrating a surgical instrument for electrocautery according to a first embodiment of the present disclosure.

FIGS. 3, 4, 5, and 6 are perspective views illustrating an end tool of the surgical instrument for electrocautery of FIG. 2.

Figure 2:
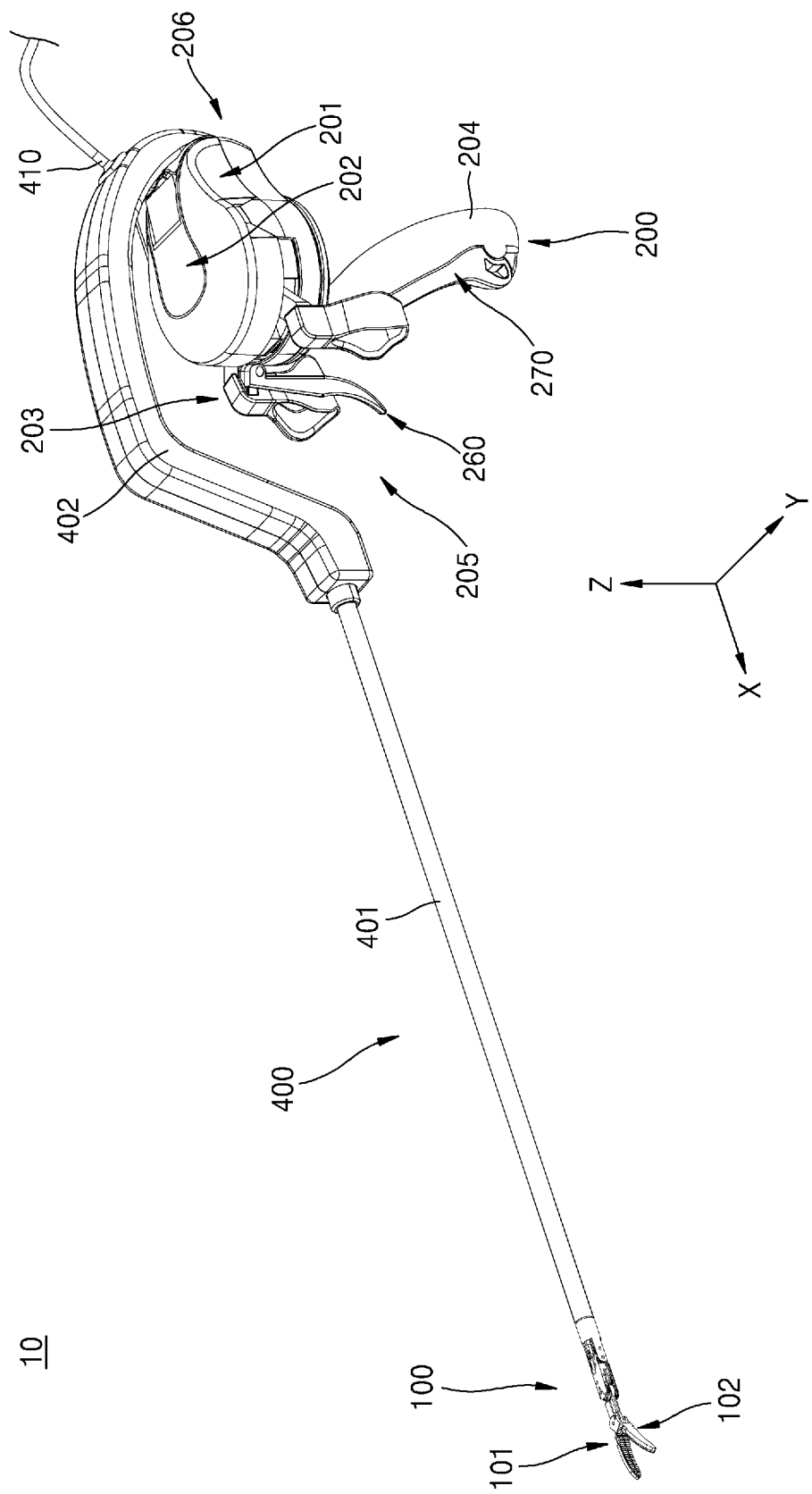
Figure 17:
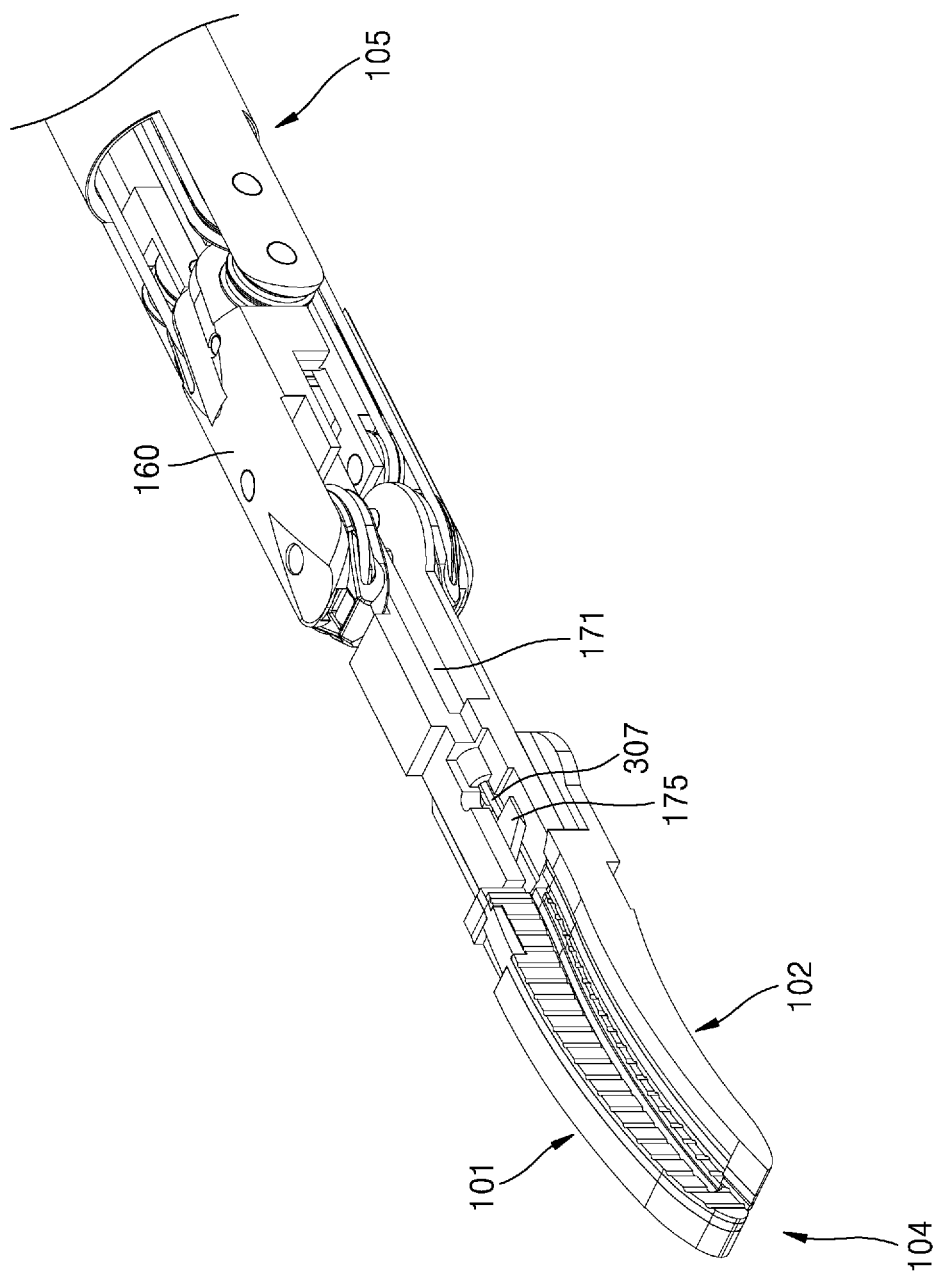
Figure 18:
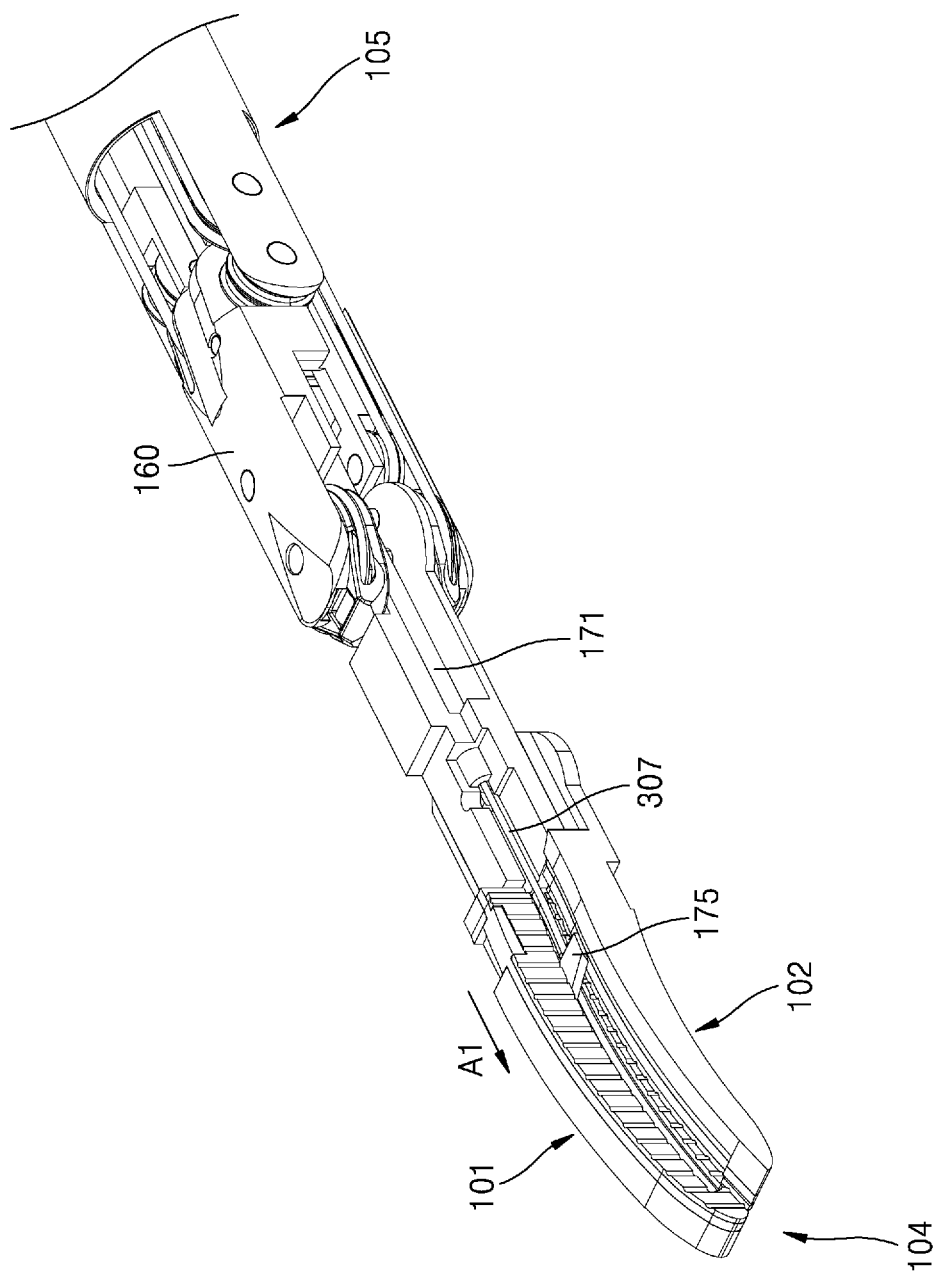
Figure 19:
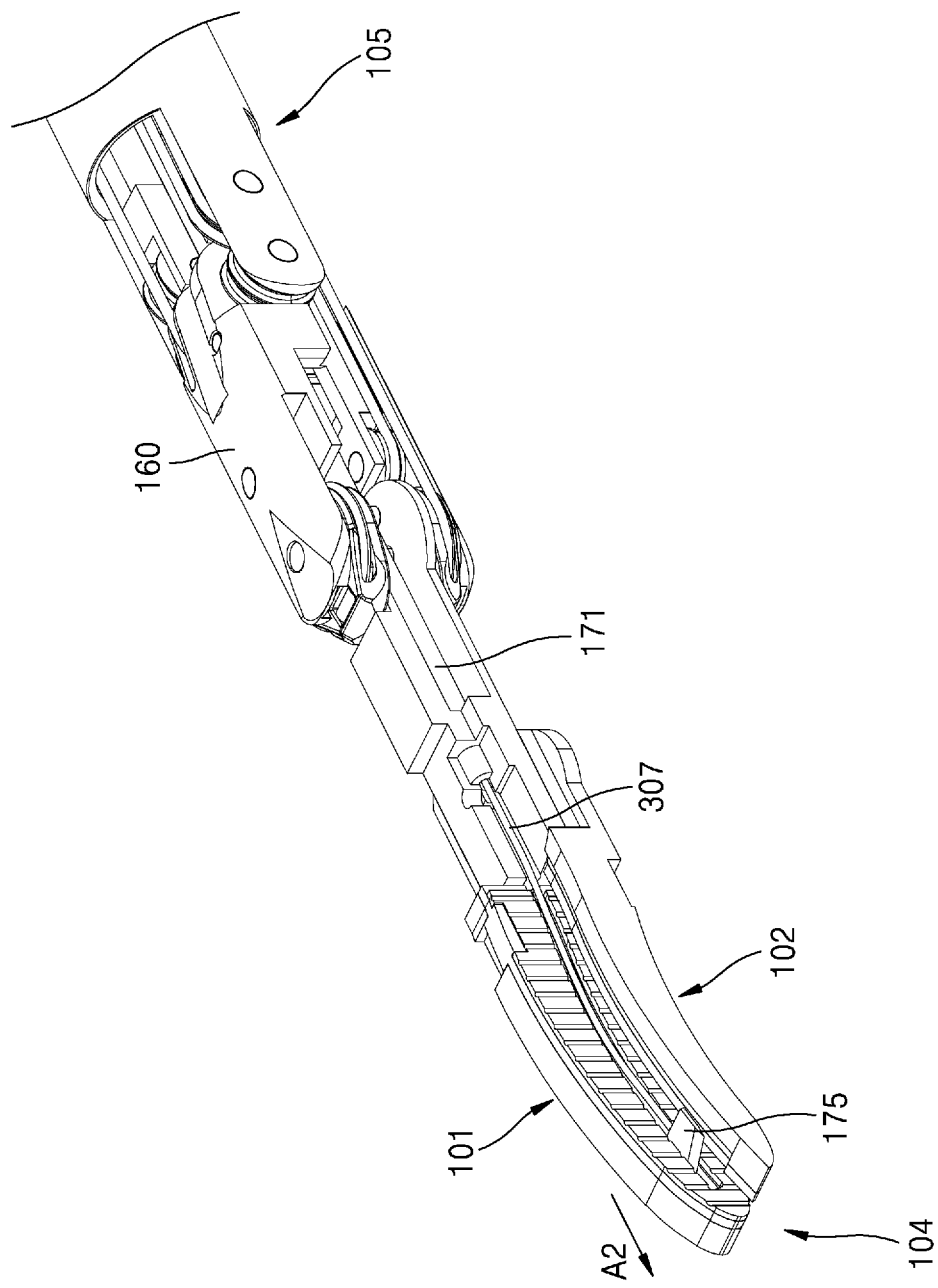

FIGS. 17, 18, and 19 are perspective views illustrating a cutting motion of the end tool of the surgical instrument for electrocautery of FIG. 2.

Figure 20:
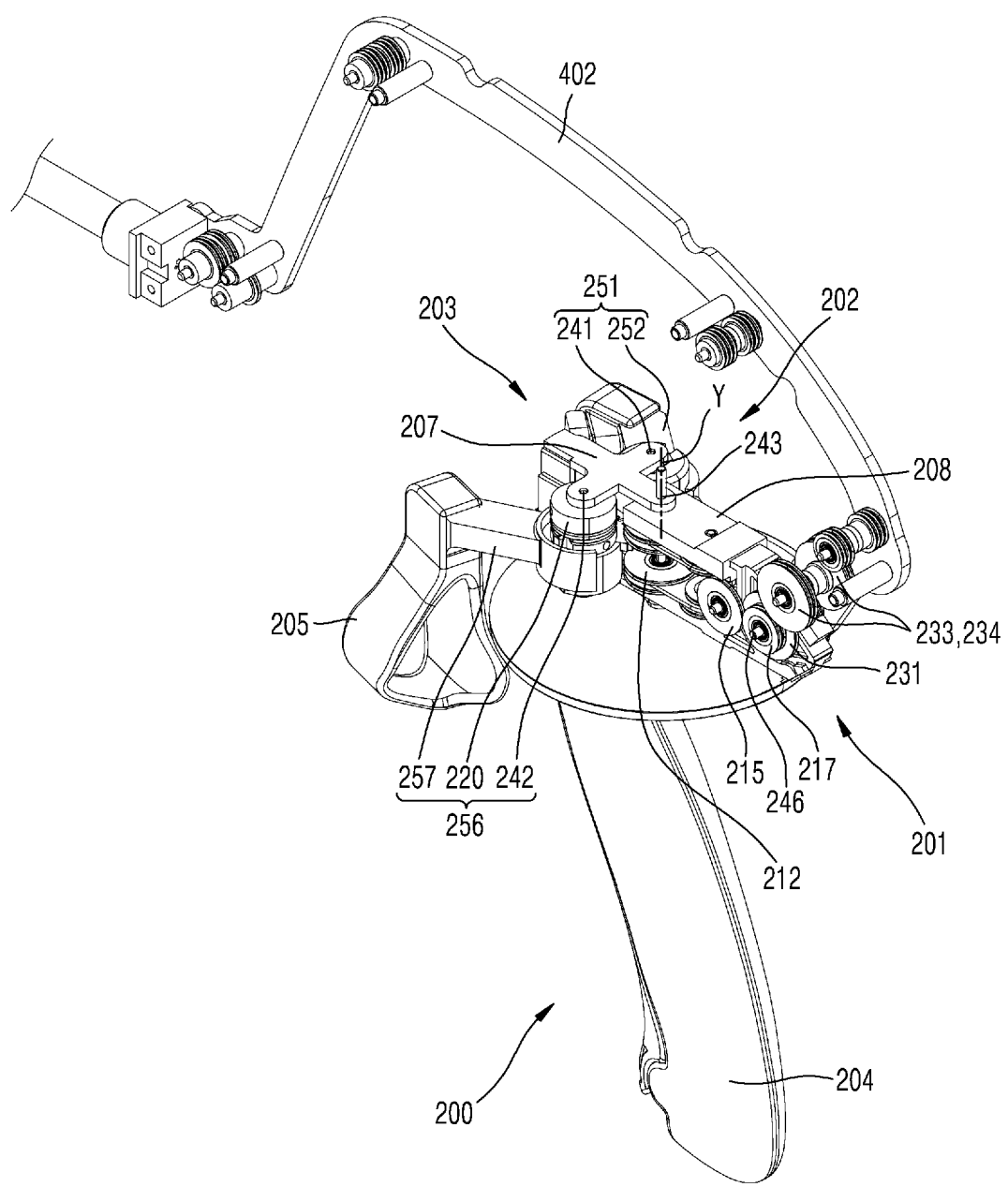
Figure 21:
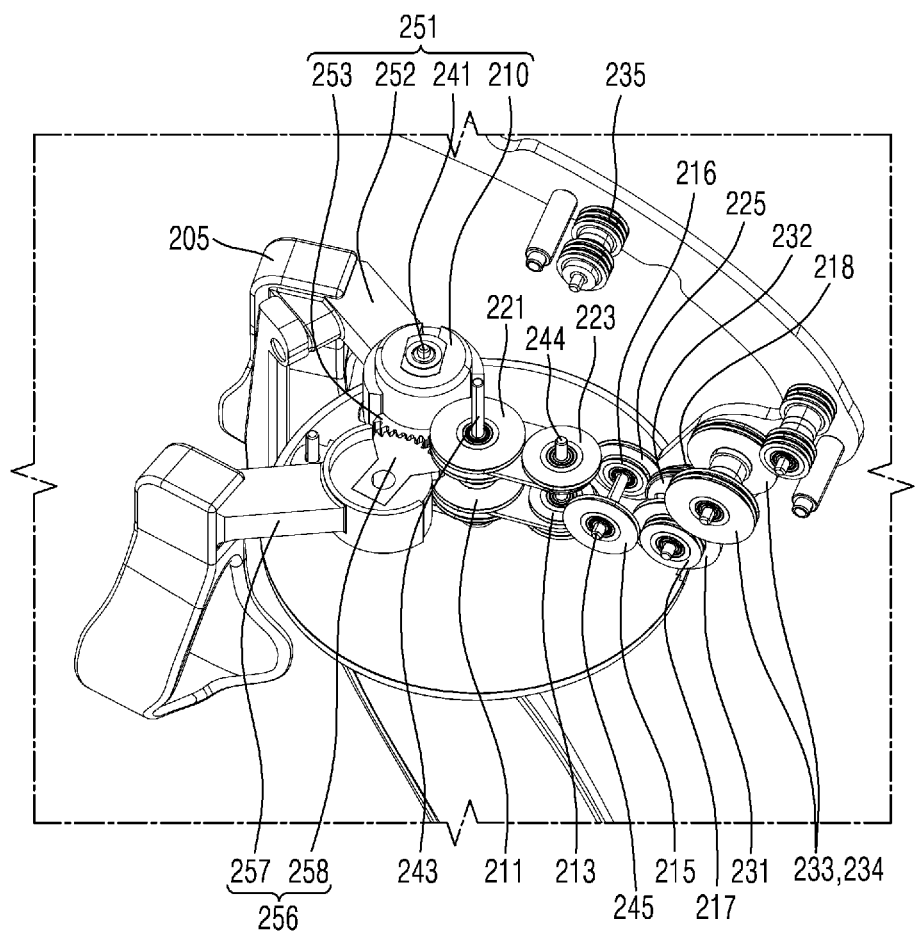

FIGS. 20 and 21 are perspective views illustrating a manipulation portion of the surgical instrument for electrocautery of FIG. 2.

Figure 22:
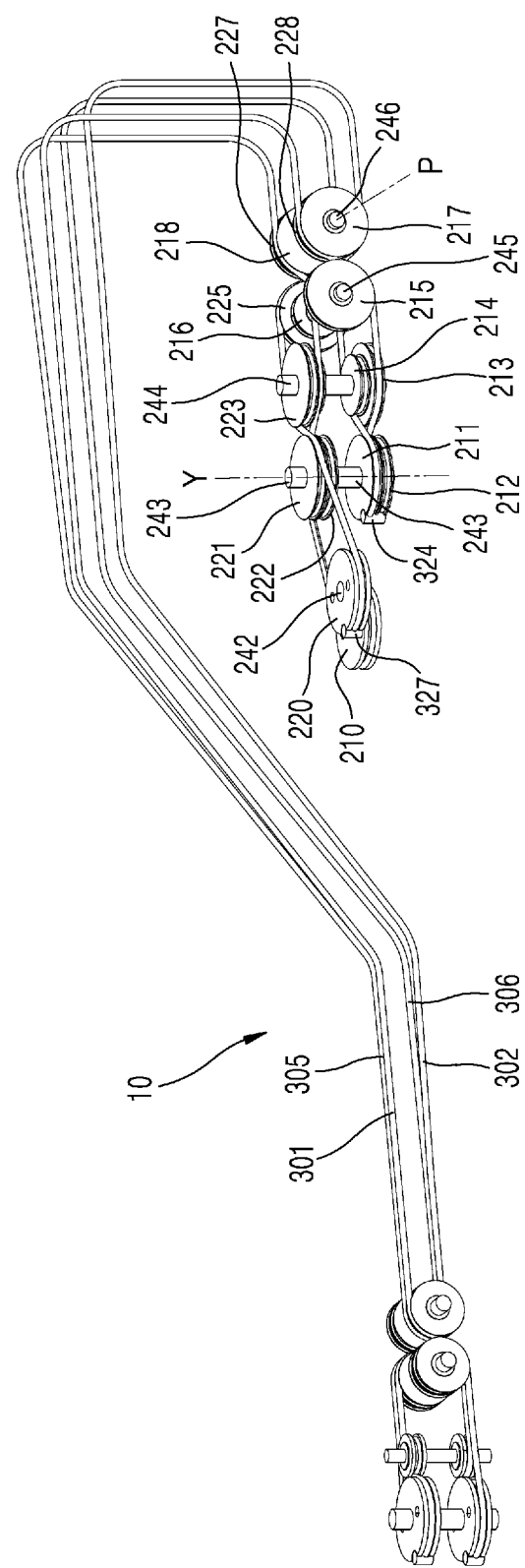

FIG. 22 is a view schematically illustrating only a configuration of pulleys and wires constituting joints of the surgical instrument for electrocautery of FIG. 2.

Figure 23:
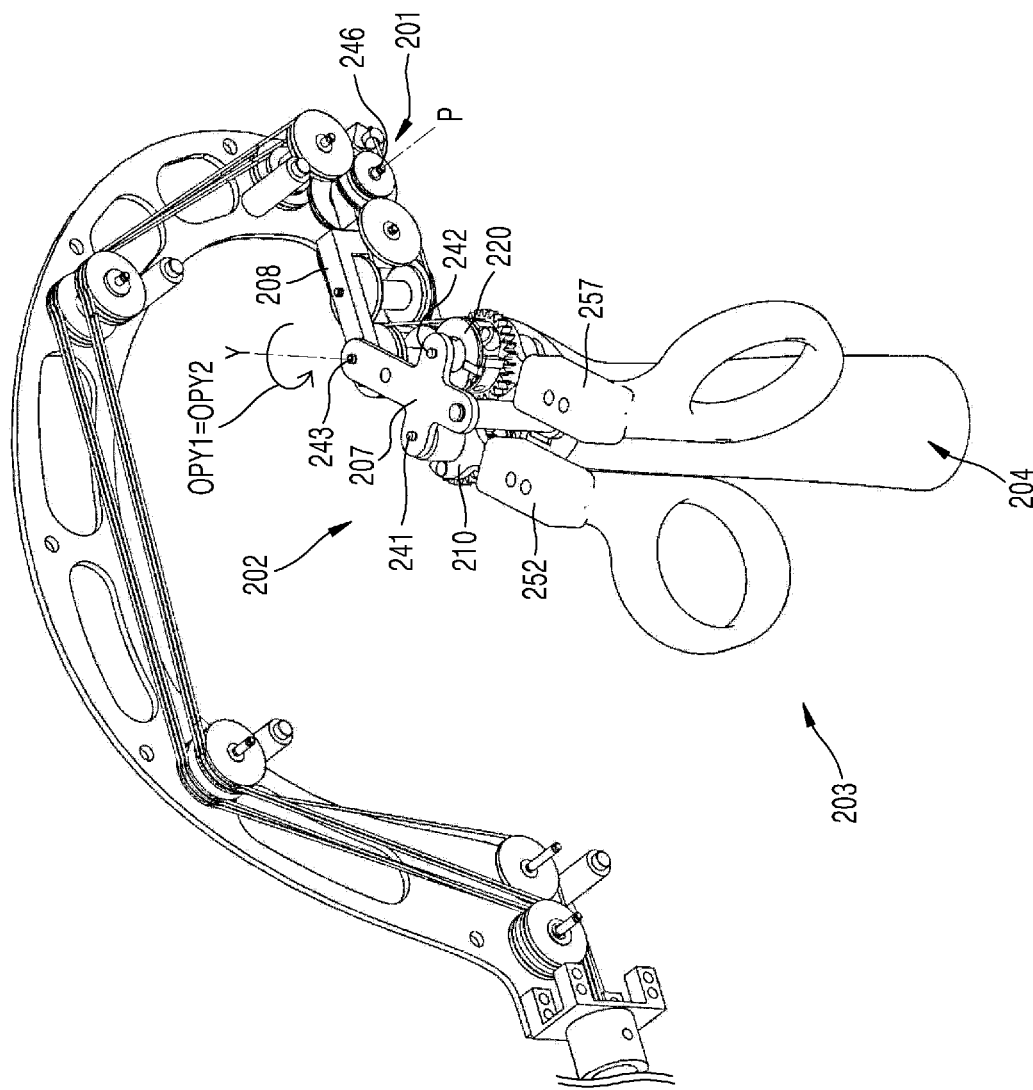
Figure 23:
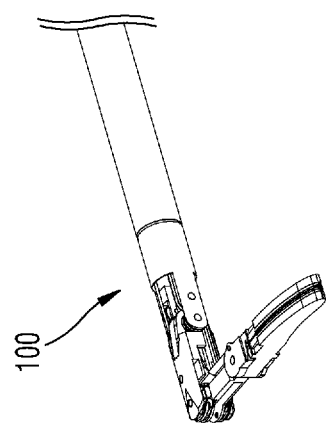

FIG. 23 is a perspective view illustrating a yaw motion of the surgical instrument for electrocautery of FIG. 2.

Figure 24:
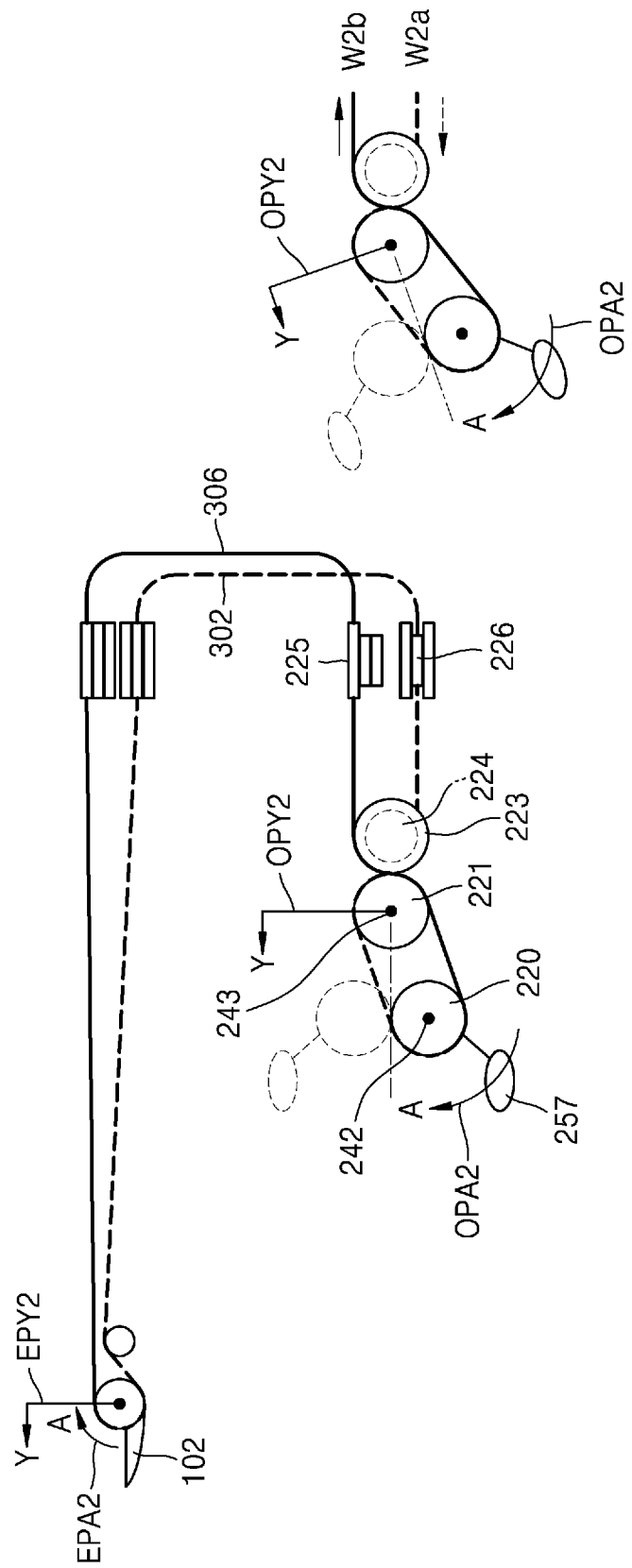
Figure 25:
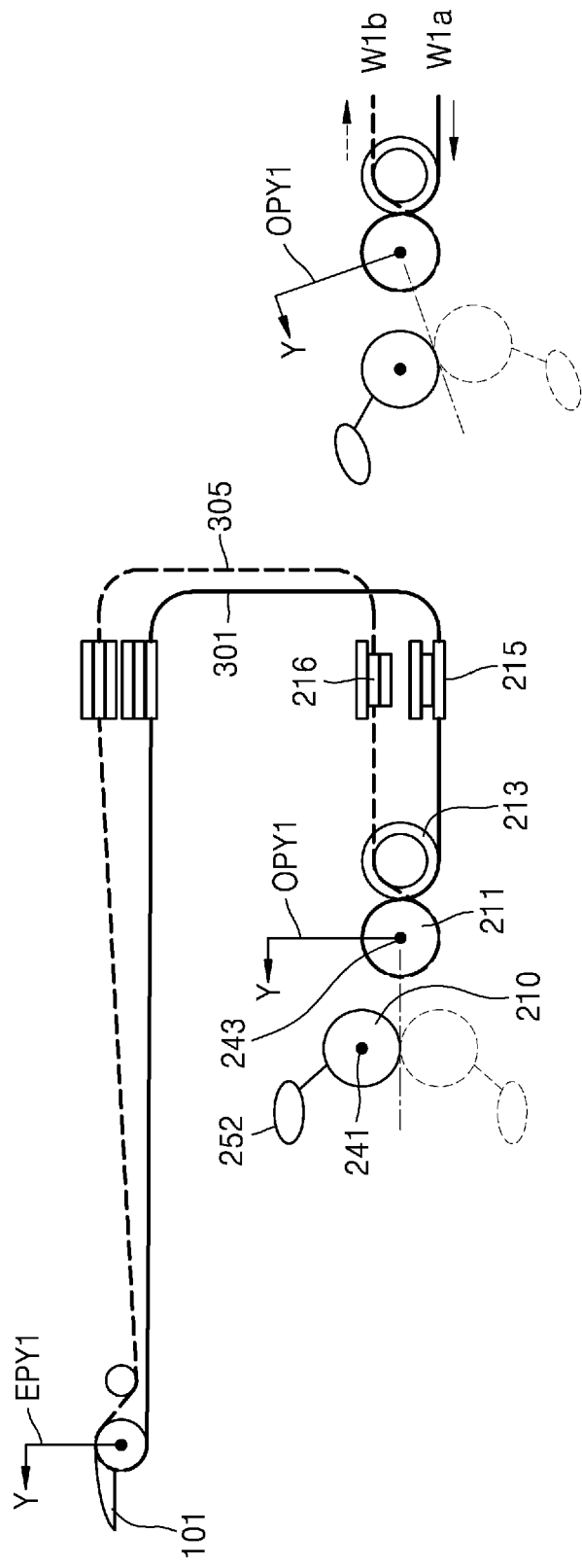

FIGS. 24 and 25 are views illustrating a configuration of pulleys and wires relating to an actuation motion and a yaw motion of the surgical instrument for electrocautery shown in FIG. 2 in detail with respect to each of a first jaw and a second jaw.

Figure 26:
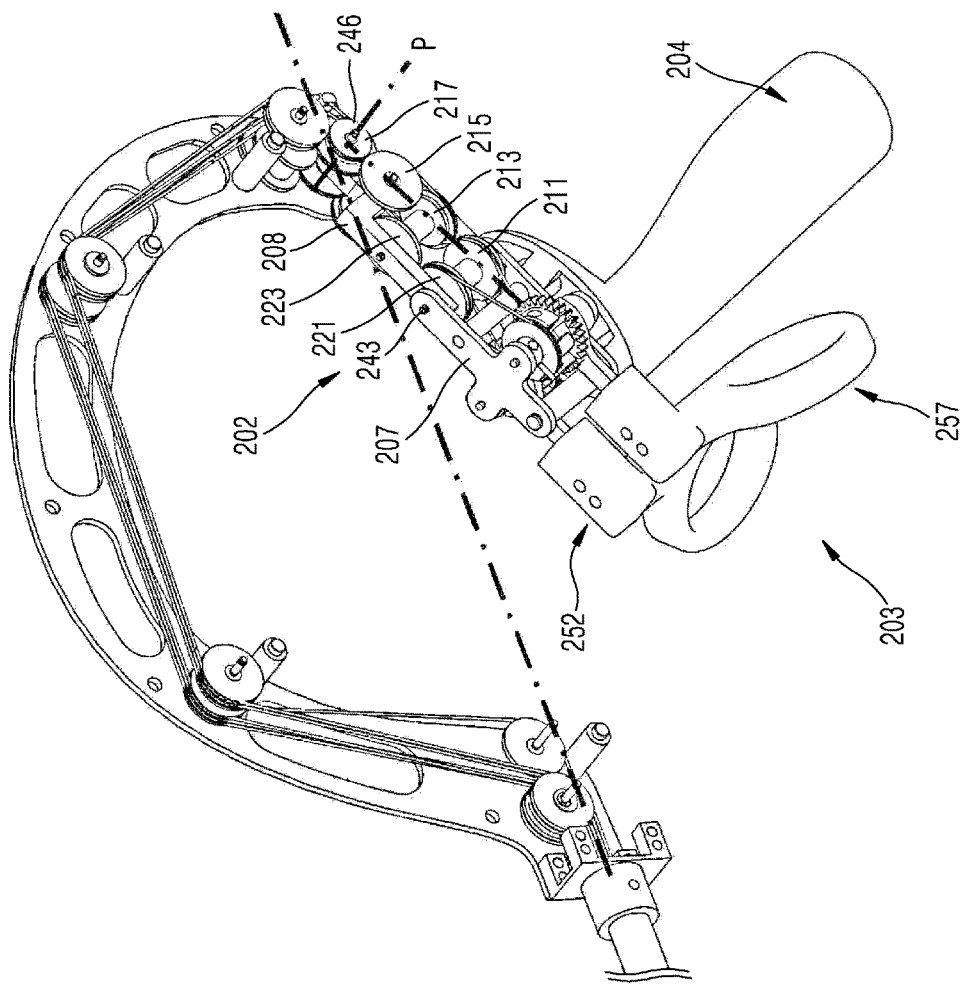
Figure 26:
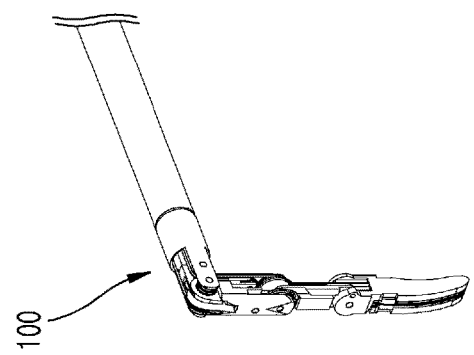

FIG. 26 is a perspective view illustrating a pitch motion of the surgical instrument for electrocautery of FIG. 2.

Figure 27:
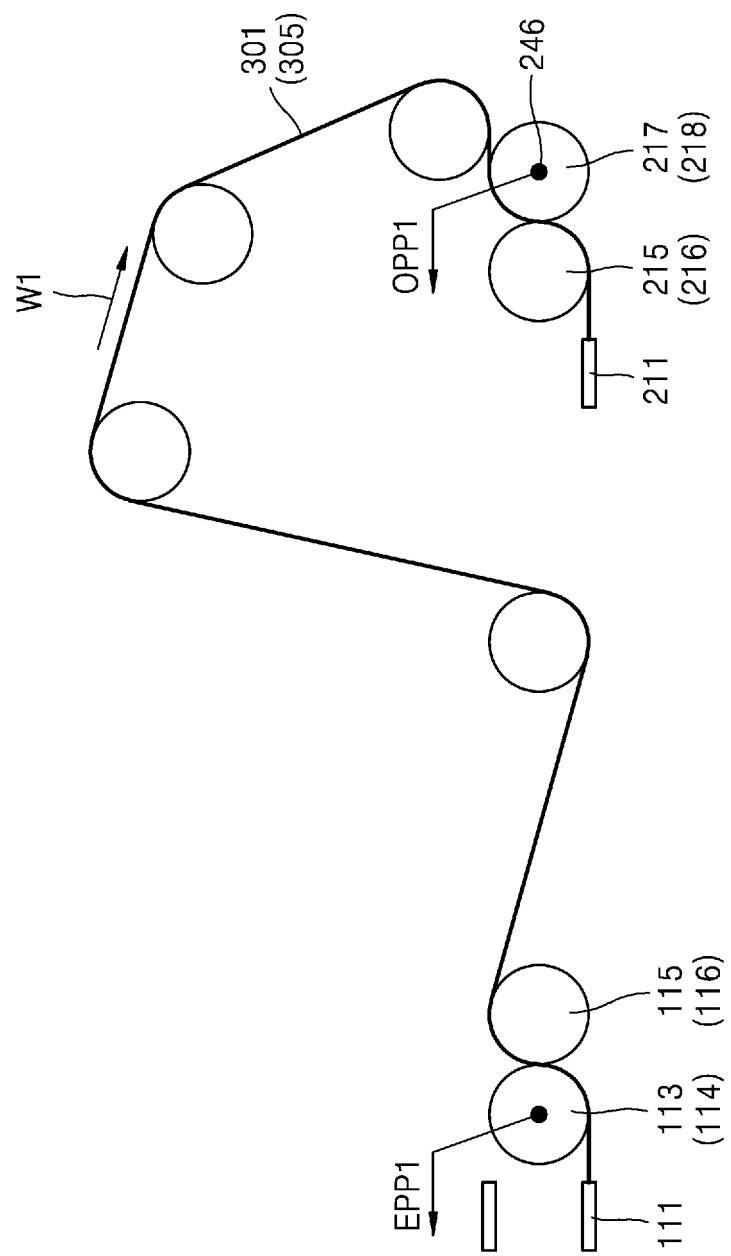
Figure 28:
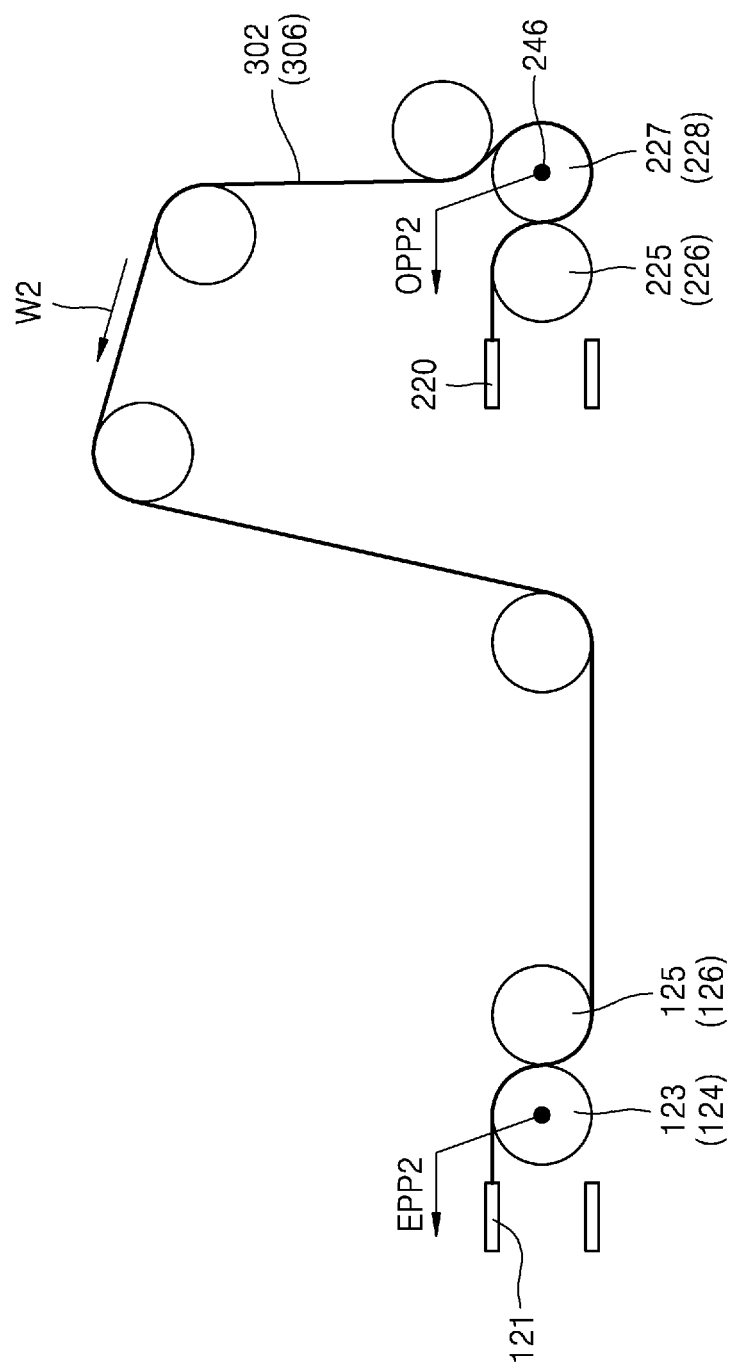

FIGS. 27 and 28 are views illustrating a configuration of pulleys and wires relating to a pitch motion of the surgical instrument for electrocautery shown in FIG. 2, in detail with respect to each of the first jaw and the second jaw.

Figure 29:
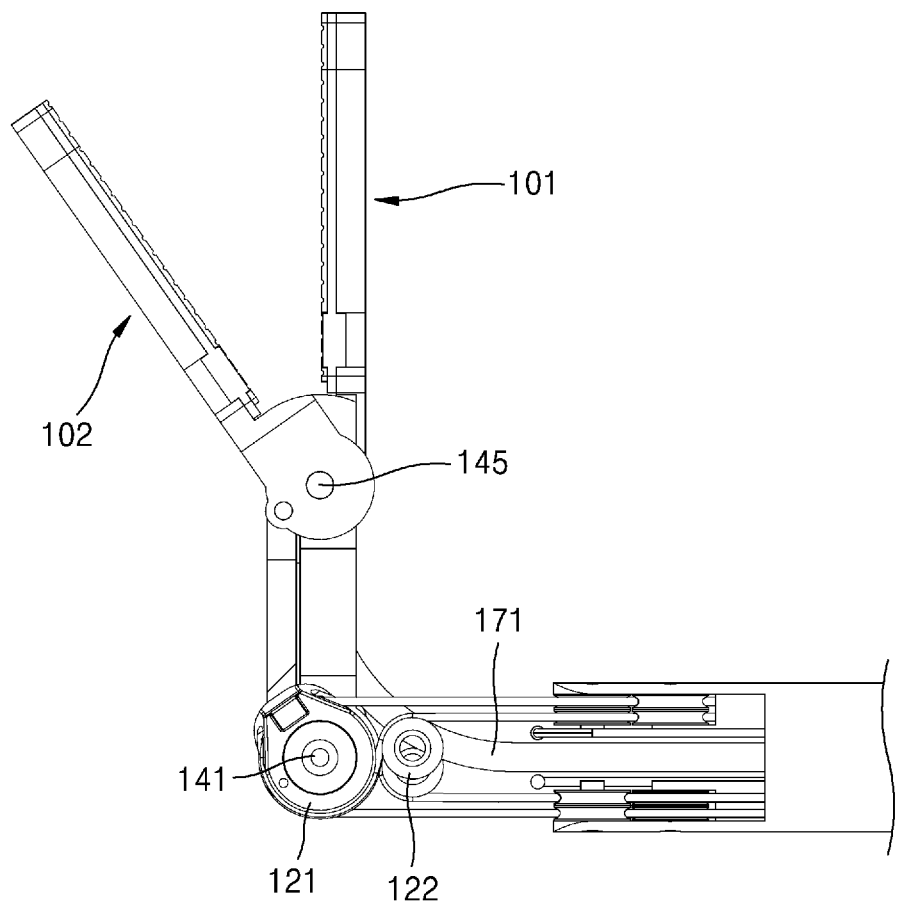
Figure 30:
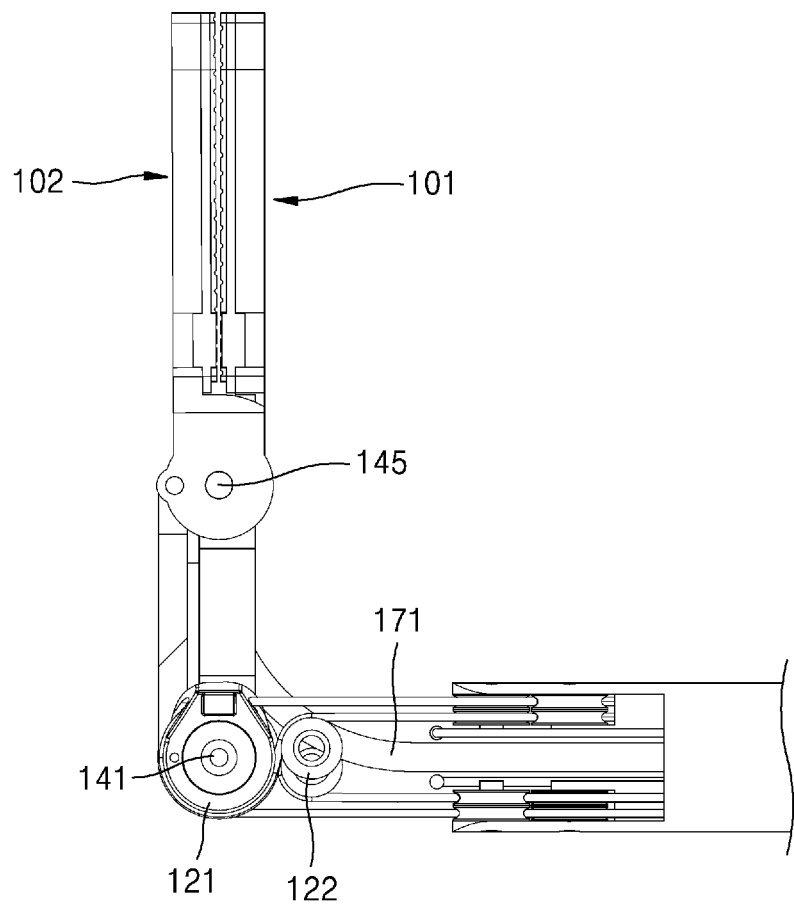

FIGS. 29 and 30 are views illustrating a process of performing an opening and closing motion while the end tool of the surgical instrument for electrocautery of FIG. 2 is yaw-rotated by −90°.

Figure 31:
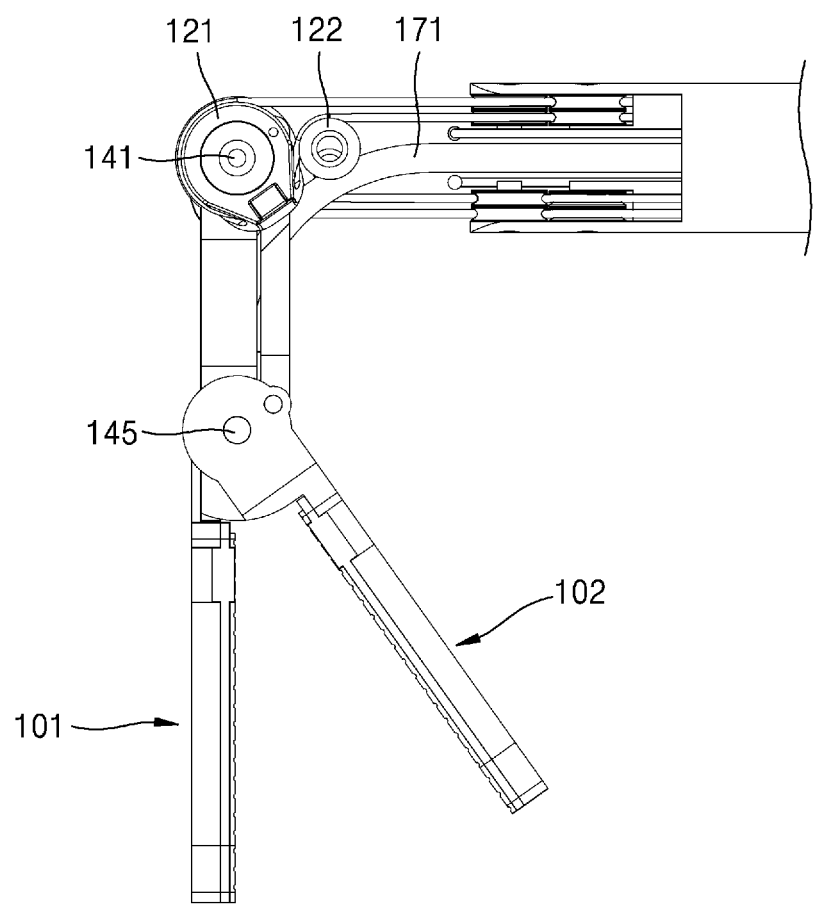
Figure 32:
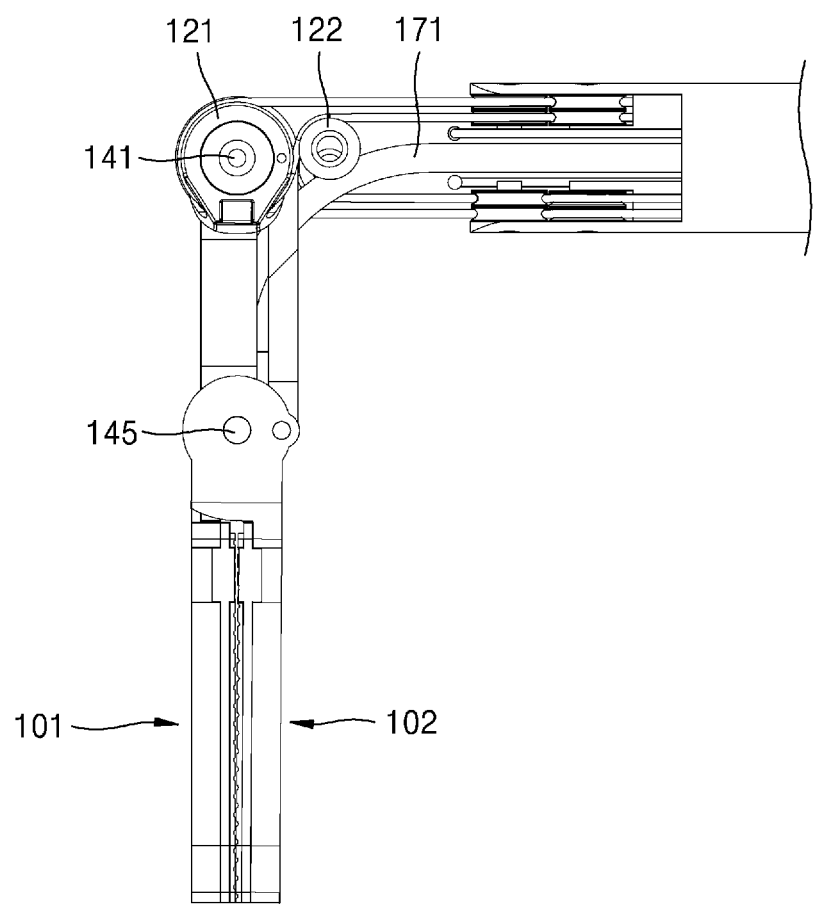

FIGS. 31 and 32 are views illustrating a process of performing an opening and closing motion while the end tool of the surgical instrument for electrocautery of FIG. 2 is yaw-rotated by +90°.

Figure 33:
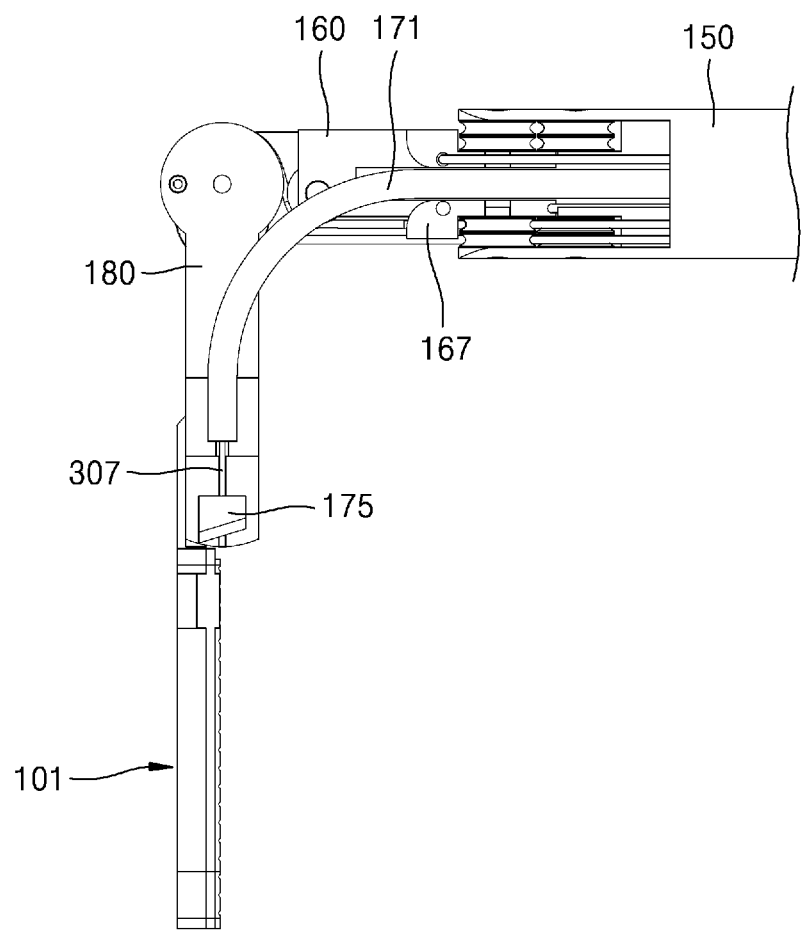
Figure 34:
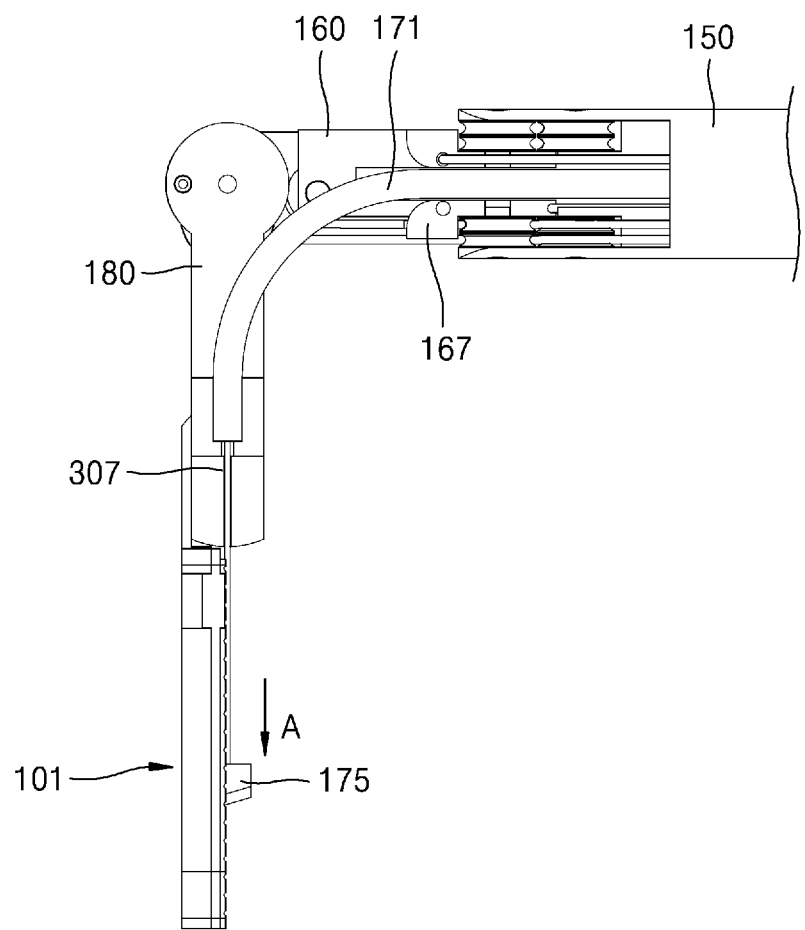

FIGS. 33 and 34 are views illustrating a process of performing a cutting motion while the end tool of the surgical instrument for electrocautery of FIG. 2 is yaw-rotated by +90°.

Figure 35:
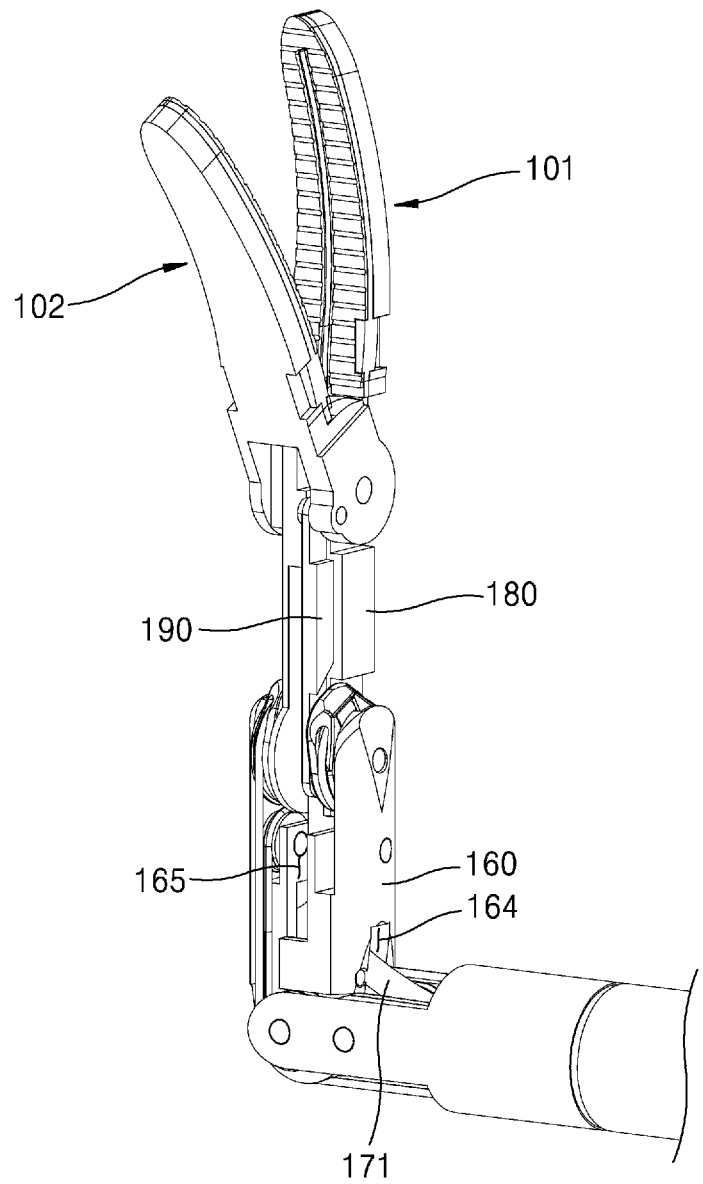

FIG. 35 is a view illustrating a state in which the end tool of the surgical instrument for electrocautery of FIG. 2 is pitch-rotated by −90°.

Figure 36:
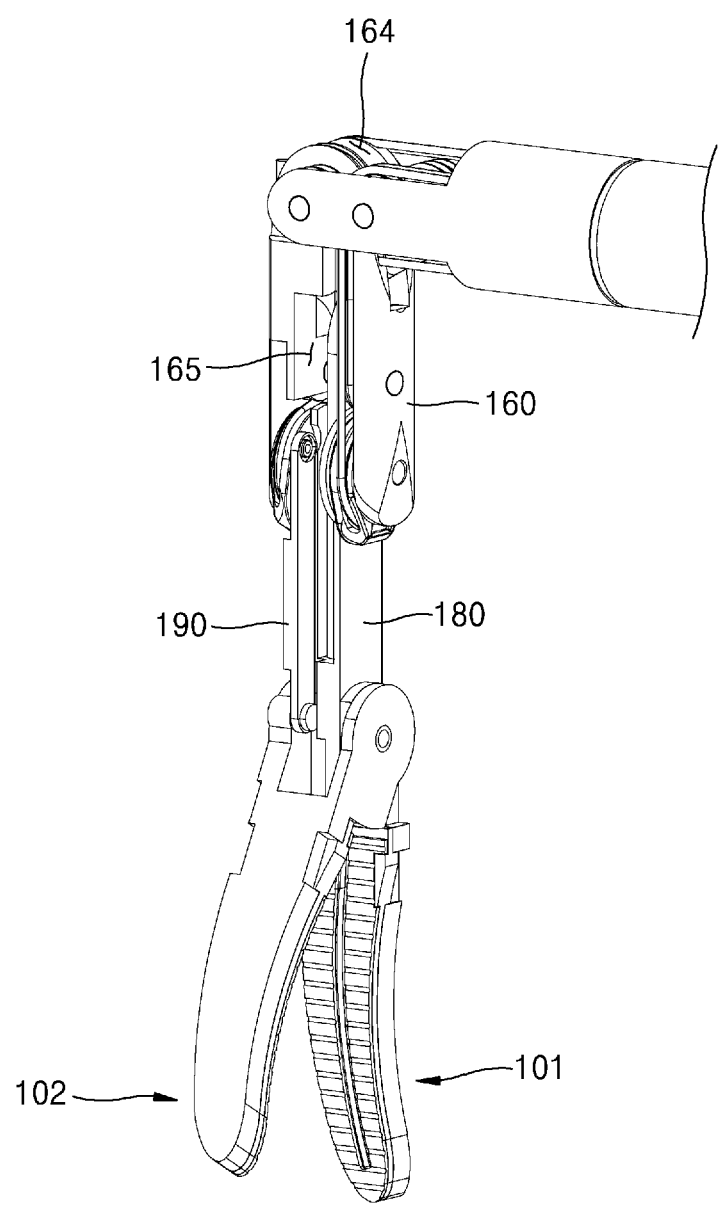

FIG. 36 is a view illustrating a state in which the end tool of the surgical instrument for electrocautery of FIG. 2 is pitch-rotated by +90°.

Figure 37:
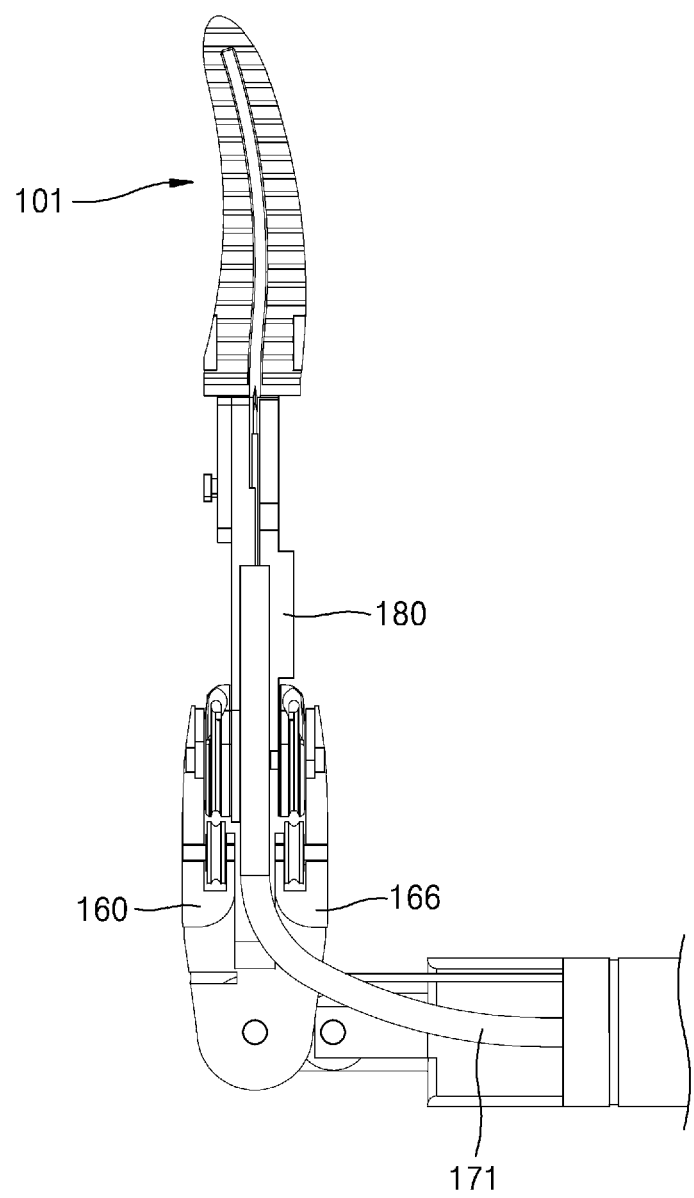

FIG. 37 is a cut-away perspective view of the end tool of the surgical instrument for electrocautery of FIG. 35.

Figure 38:
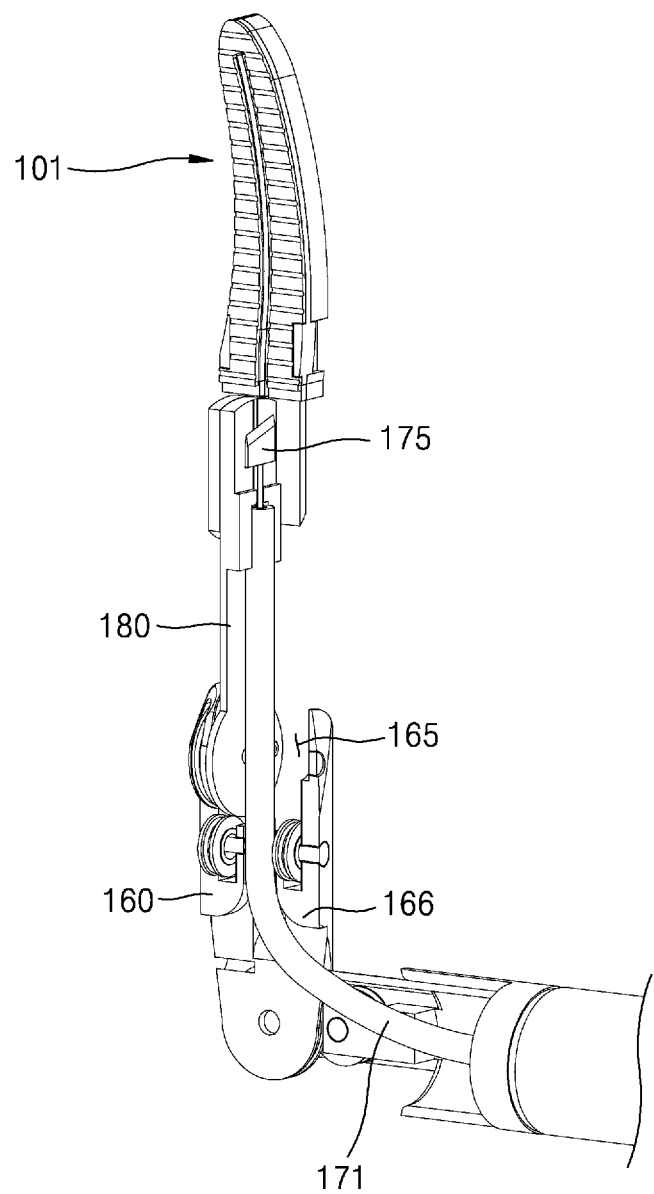
Figure 39:
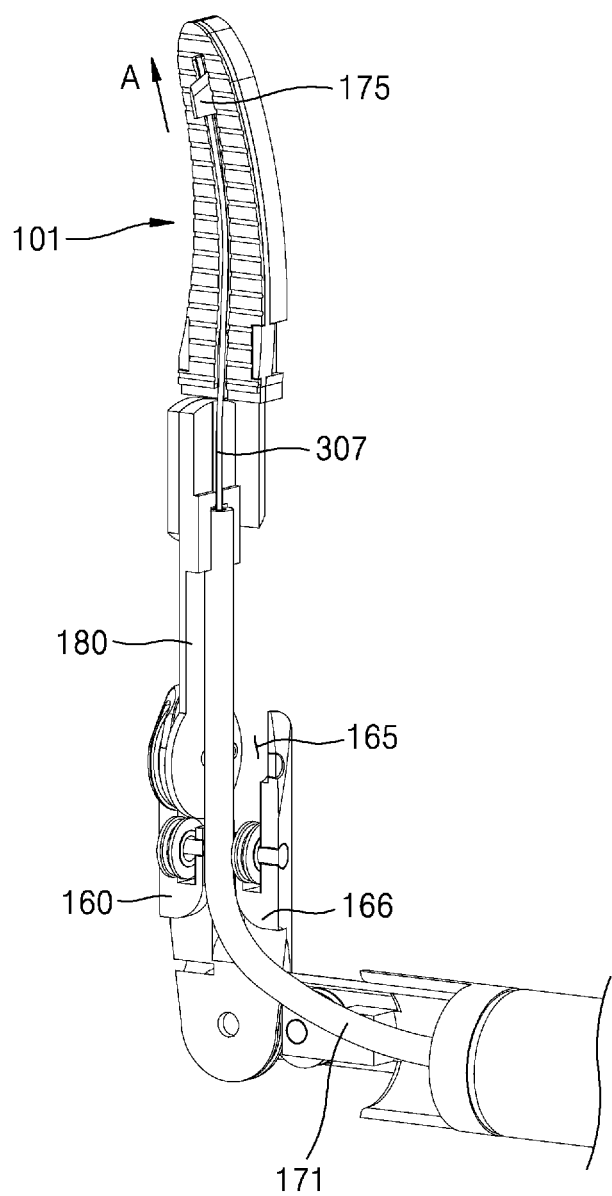

FIGS. 38 and 39 are views illustrating a process of performing a cutting motion while the end tool of the surgical instrument for electrocautery of FIG. 2 is pitch-rotated by −90°.

Figure 40:
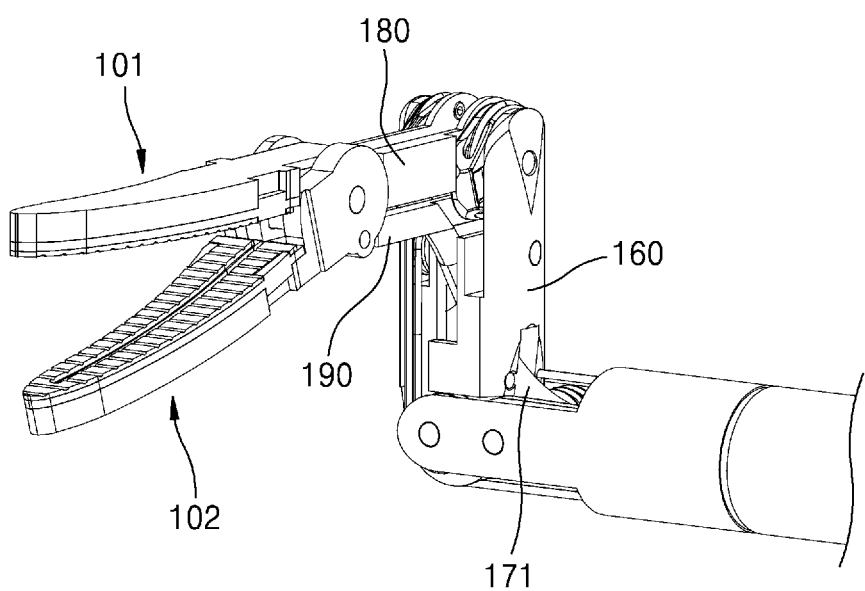

FIG. 40 is a plan view illustrating a state in which the end tool of the surgical instrument for electrocautery of FIG. 2 is pitch-rotated and yaw-rotated.

Figure 41:
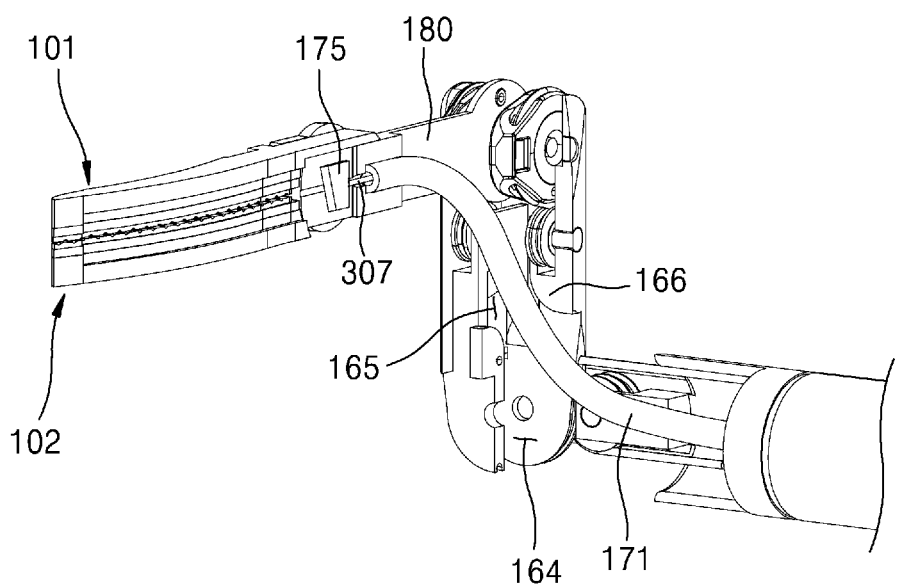
Figure 42:
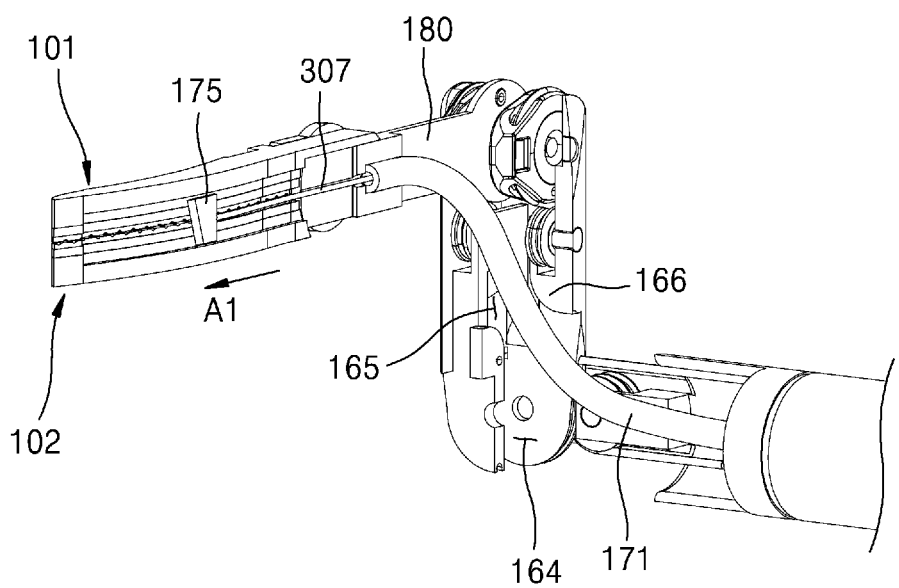
Figure 43:
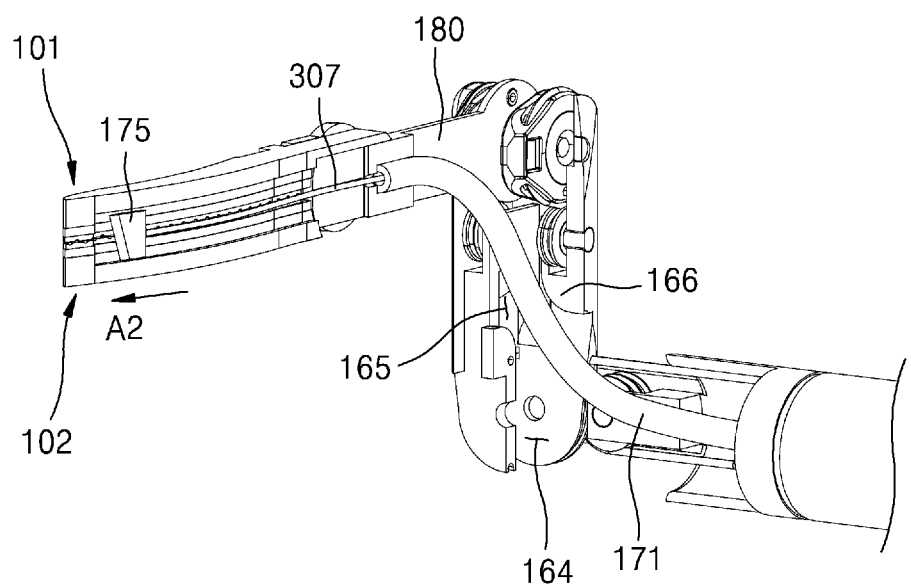

FIGS. 41, 42, and 43 are views illustrating a state of performing a cutting motion while the end tool of the surgical instrument for electrocautery of FIG. 2 is pitch-rotated by −90° and simultaneously yaw-rotated by +90°.

FIGS. 44, 45, 46, and 47 are views illustrating an end tool of a surgical instrument for electrocautery according to a first modified example of the first embodiment of the present disclosure.

Figure 44:
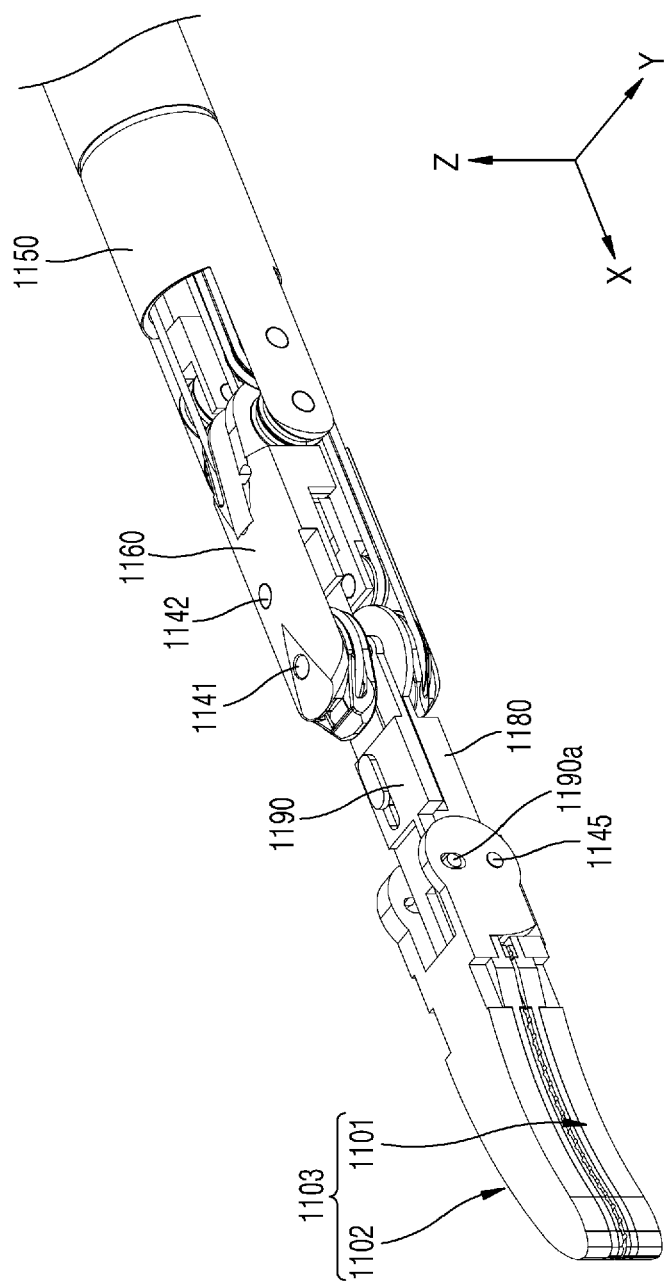
Figure 48:
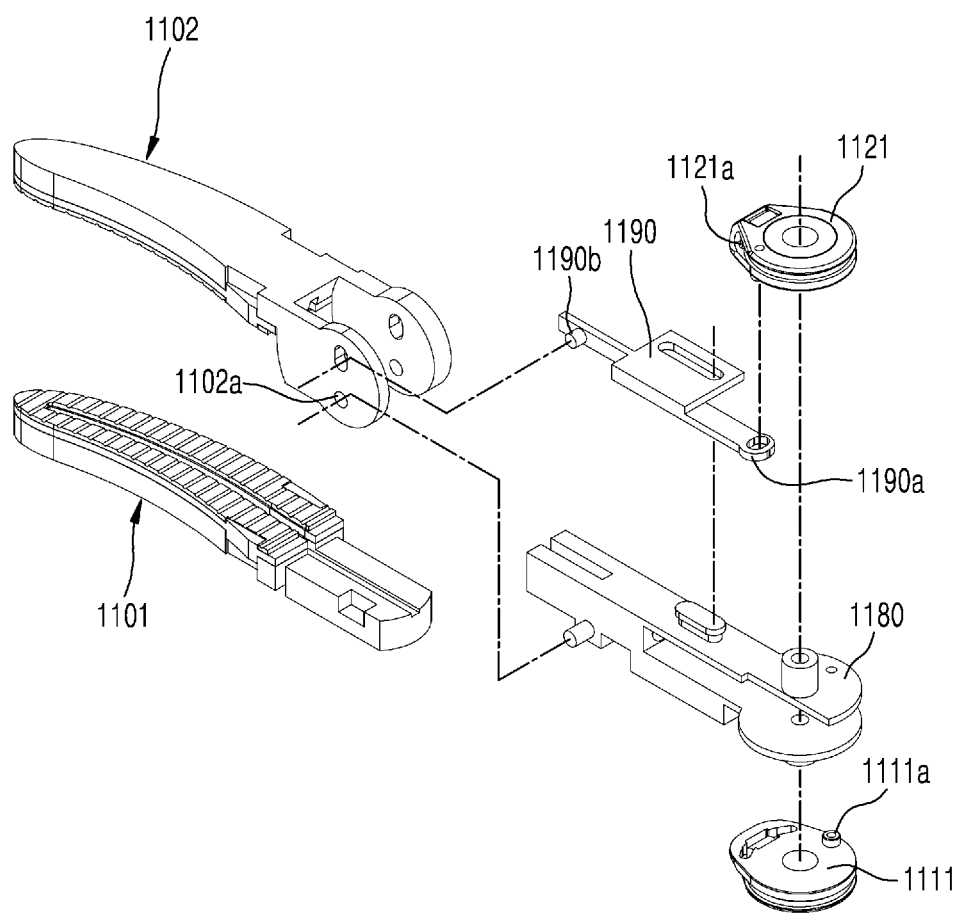

FIG. 48 is an exploded perspective view illustrating jaws-links-jaw pulleys of the end tool of the surgical instrument for electrocautery of FIG. 44.

Figure 49:
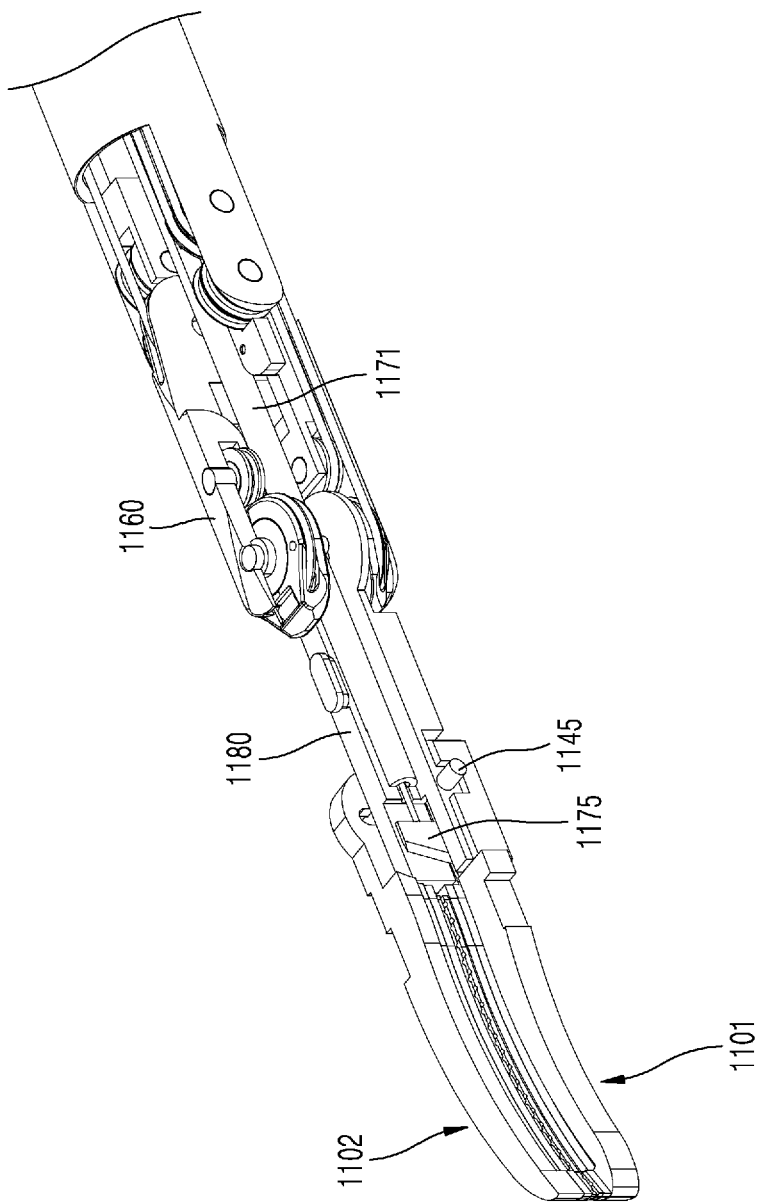
Figure 50:
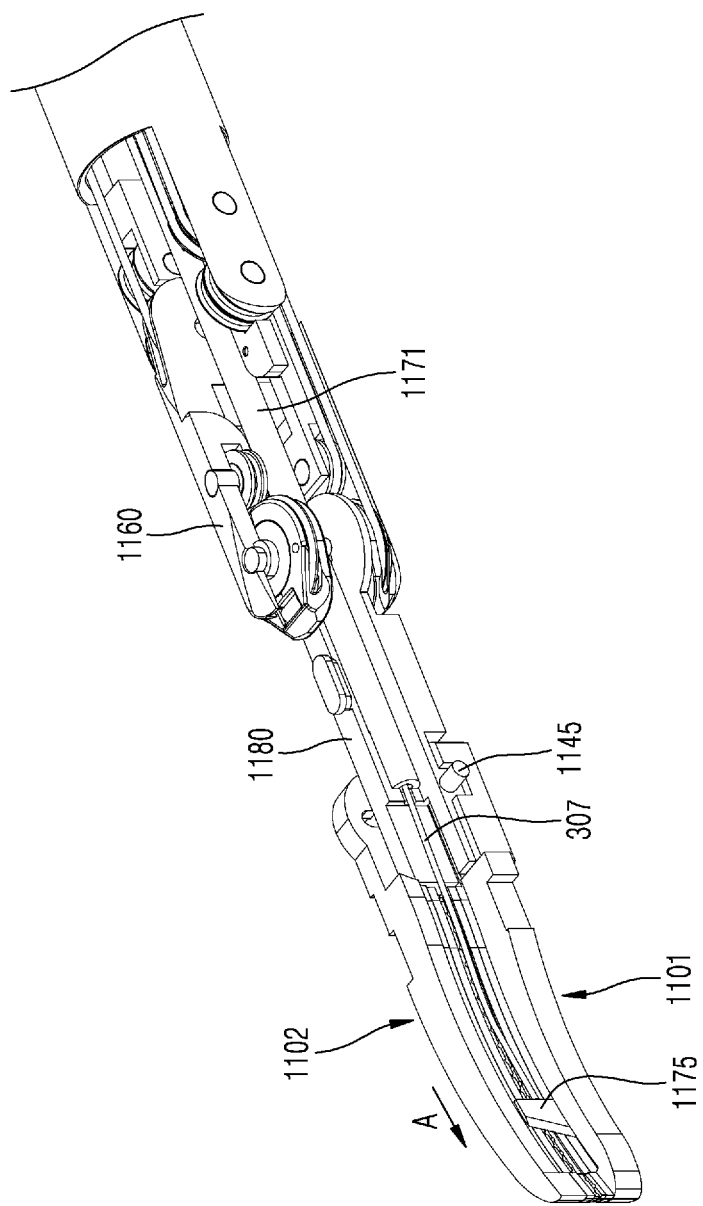

FIGS. 49 and 50 are views illustrating a process in which the end tool of the surgical instrument for electrocautery of FIG. 44 performs a cutting motion.

Figure 51:
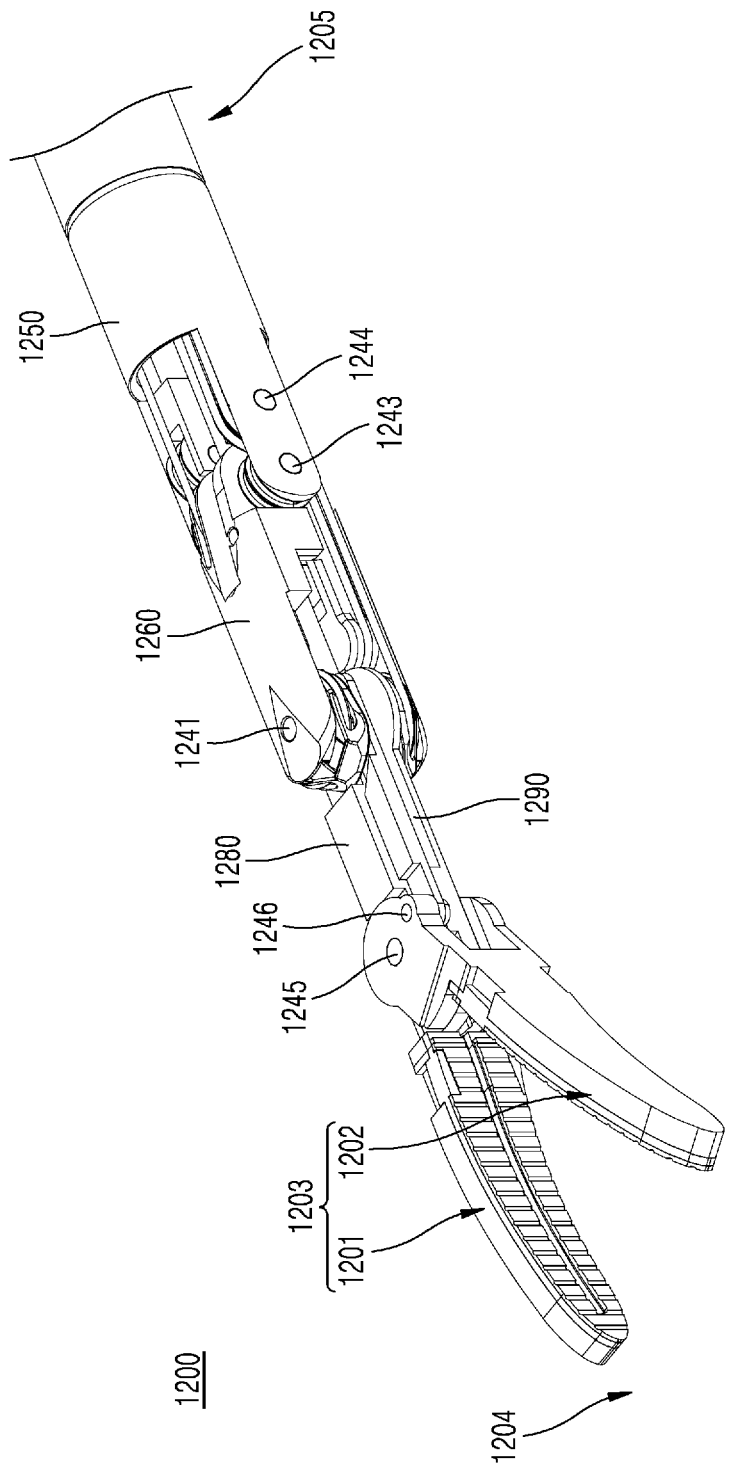
Figure 52:
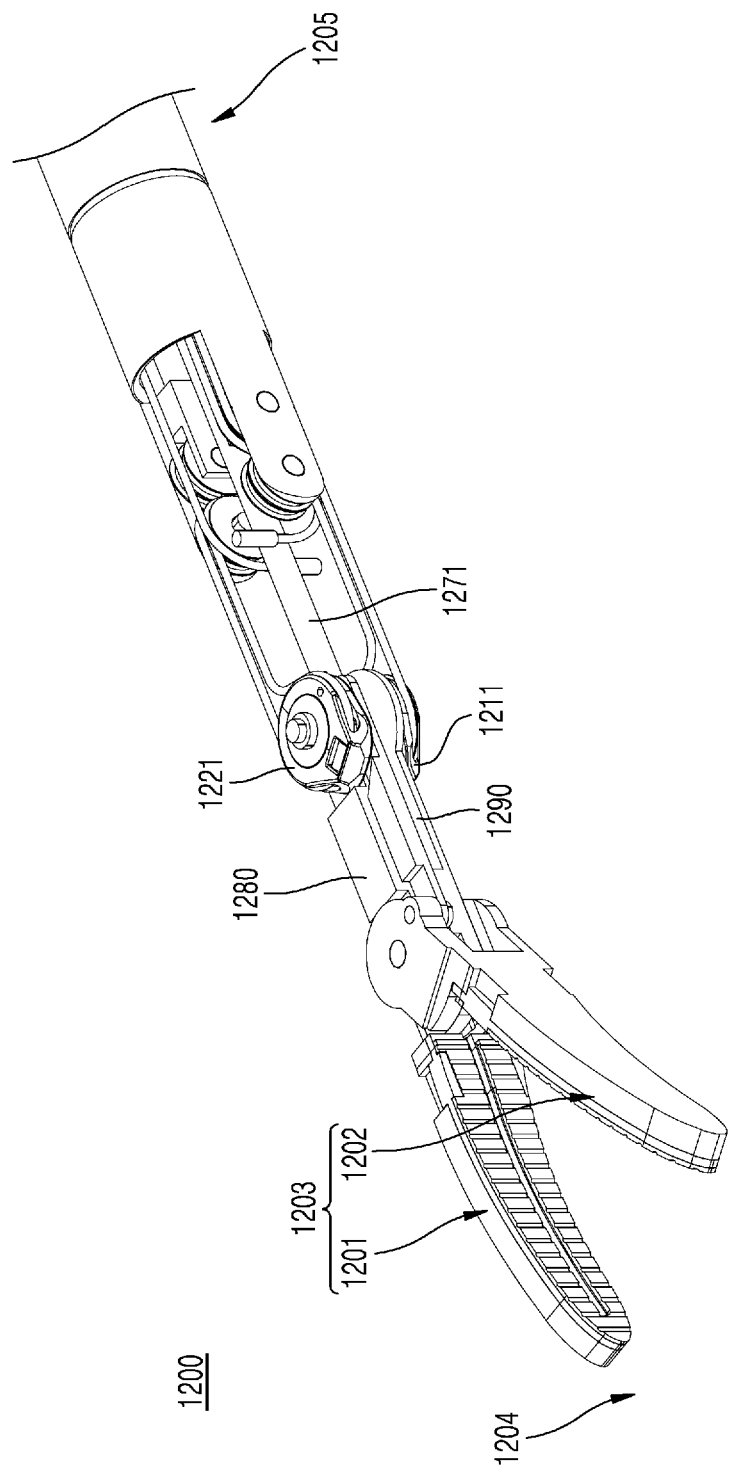

FIGS. 51 and 52 are views illustrating an end tool of a surgical instrument for electrocautery according to a second modified example of the first embodiment of the present disclosure.

Figure 53:
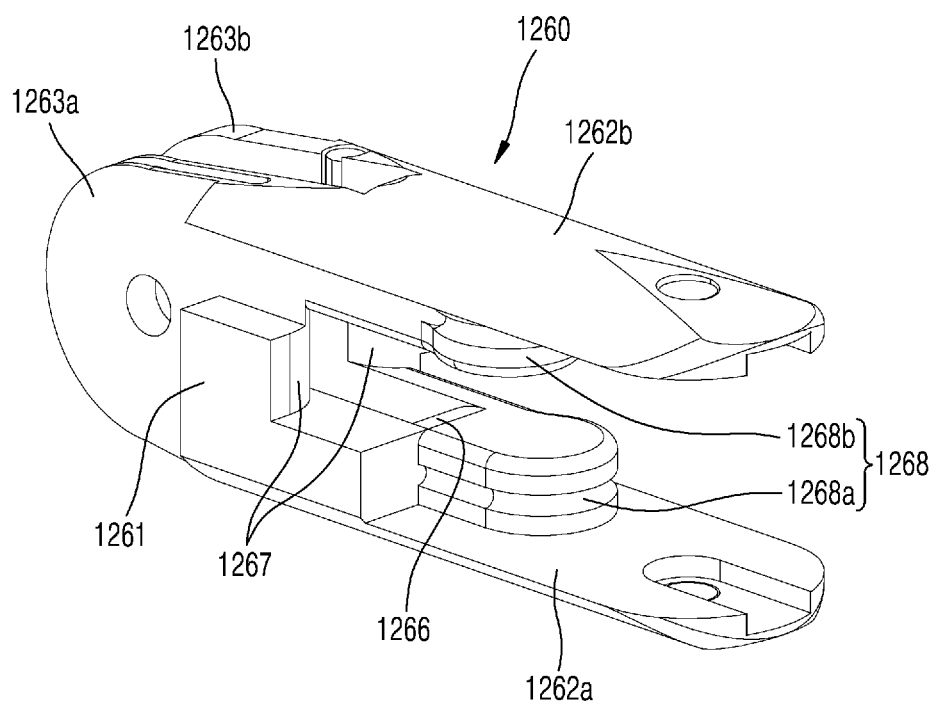

FIG. 53 is a perspective view illustrating an end tool hub of the end tool of the surgical instrument for electrocautery of FIG. 51.

Figure 54:
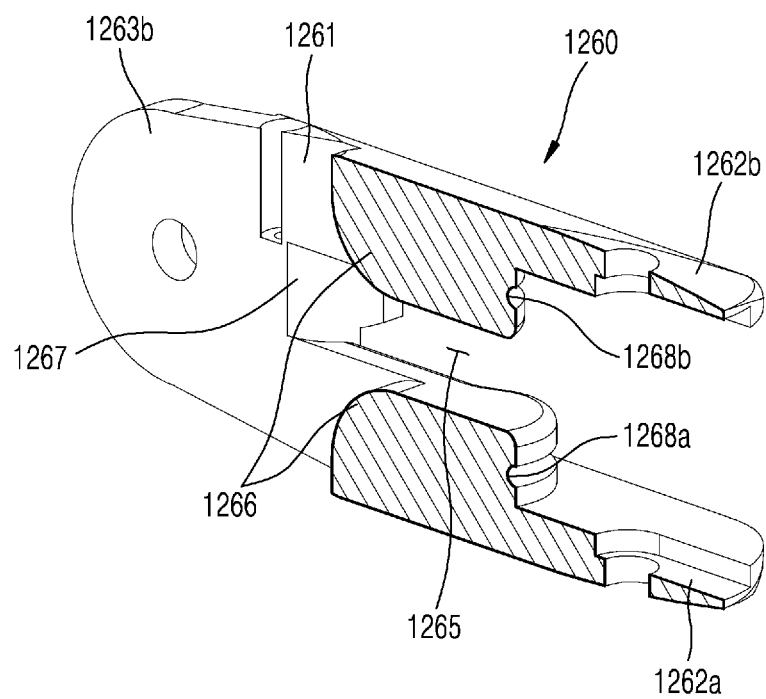
Figure 55:
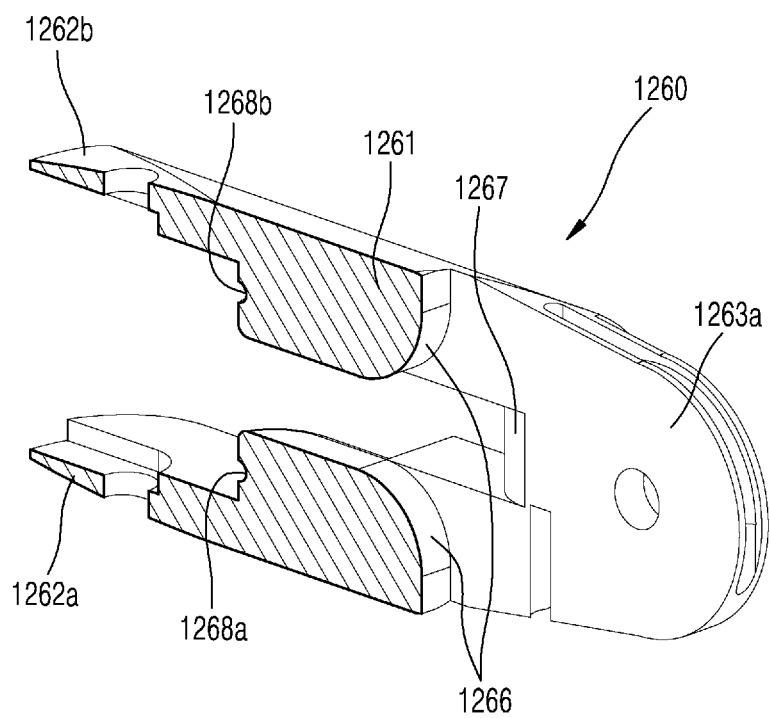

FIGS. 54 and 55 are cut-away perspective views of the end tool hub of FIG. 53.

Figure 56:
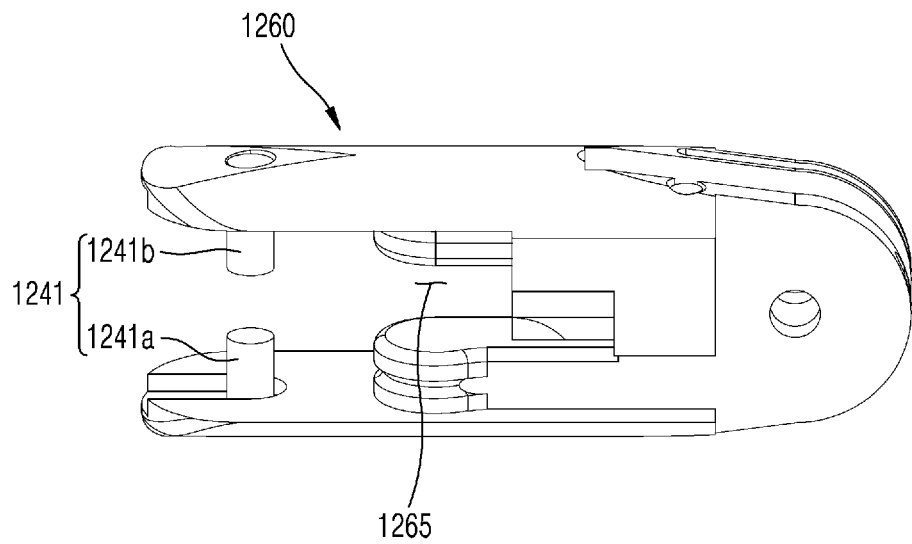
Figure 57:
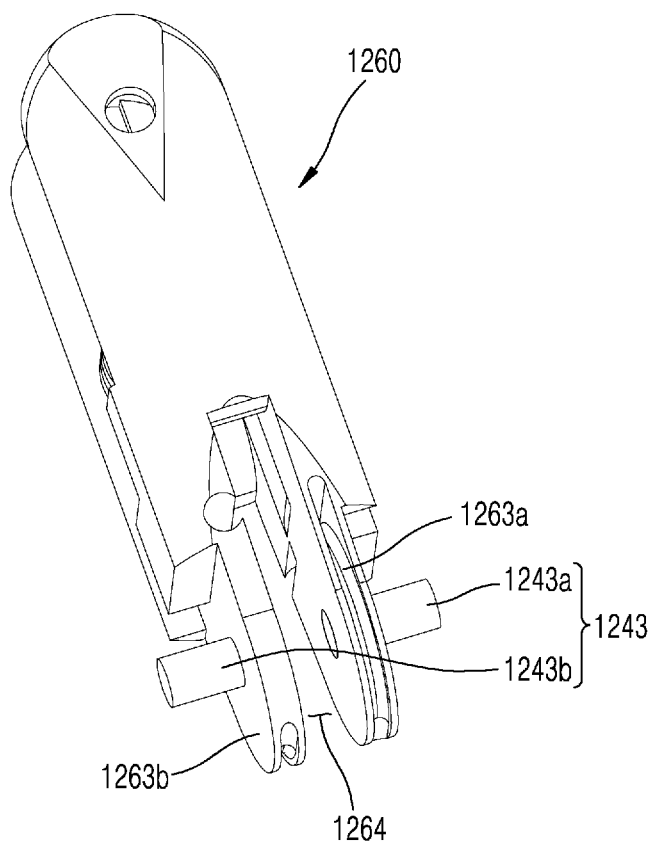

FIGS. 56 and 57 are perspective views of the end tool hub of FIG. 53.

Figure 58:
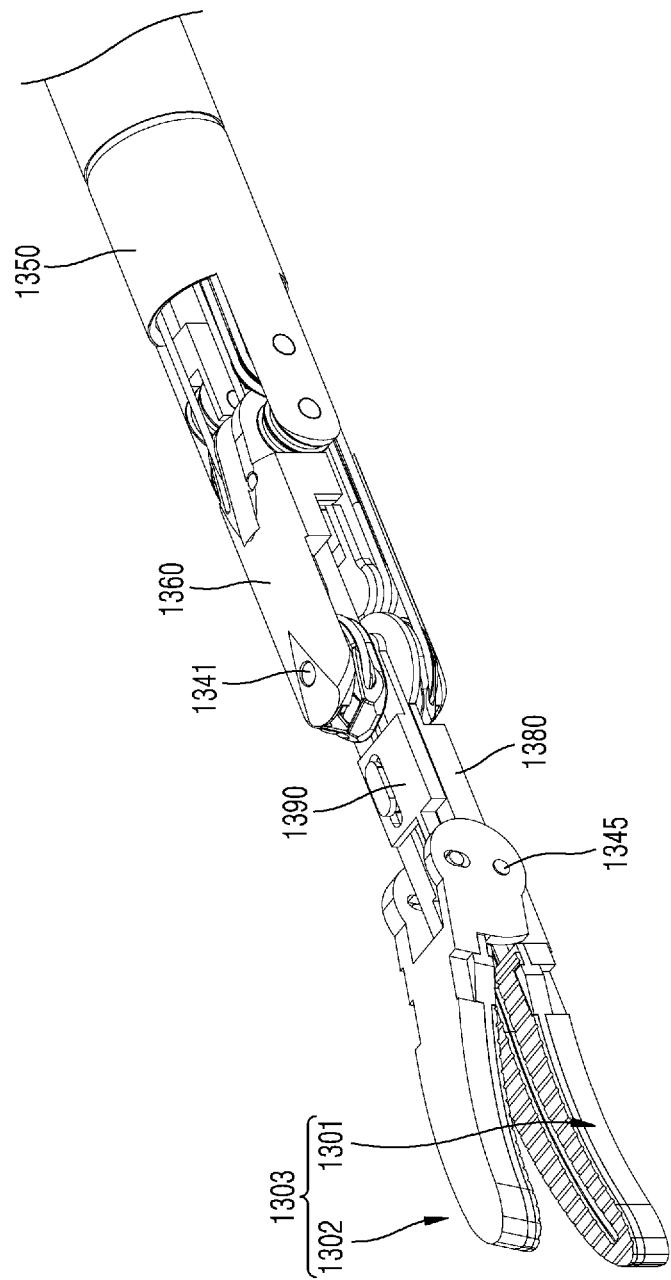
Figure 59:
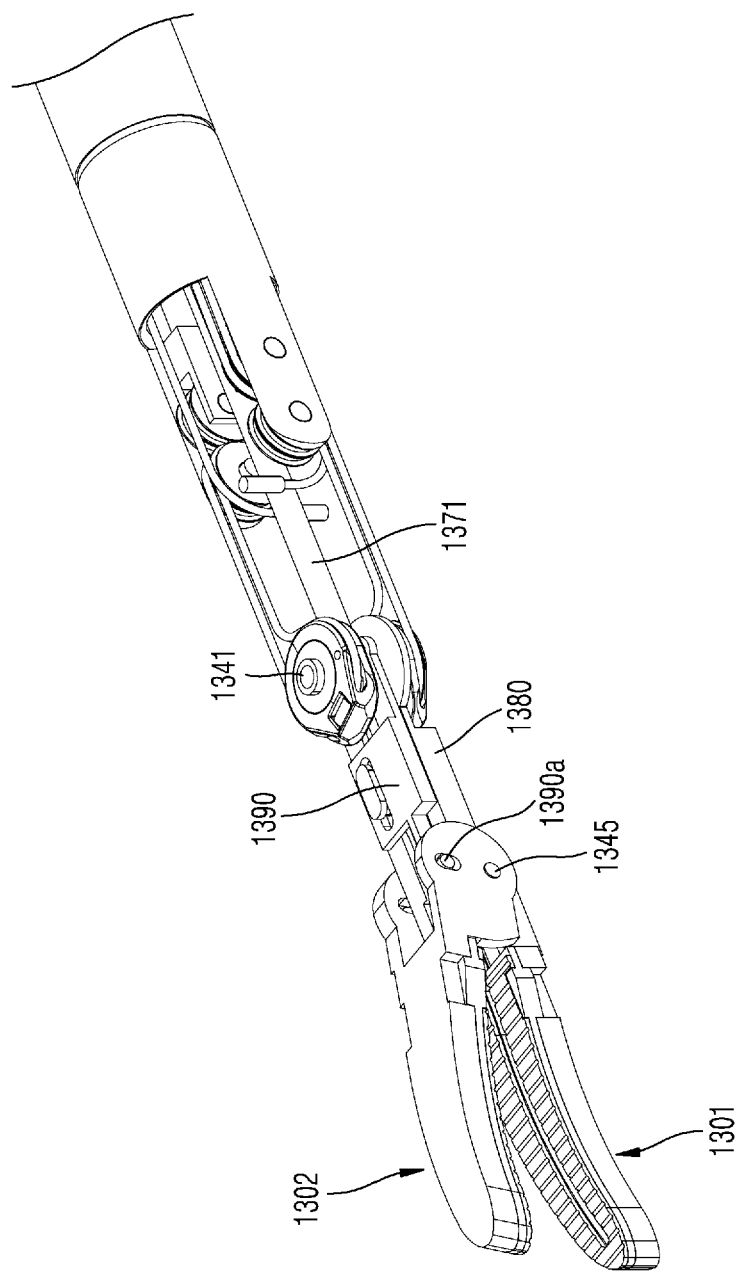

FIGS. 58 and 59 are views illustrating an end tool of a surgical instrument for electrocautery according to a third modified example of the first embodiment of the present disclosure.

Figure 60:
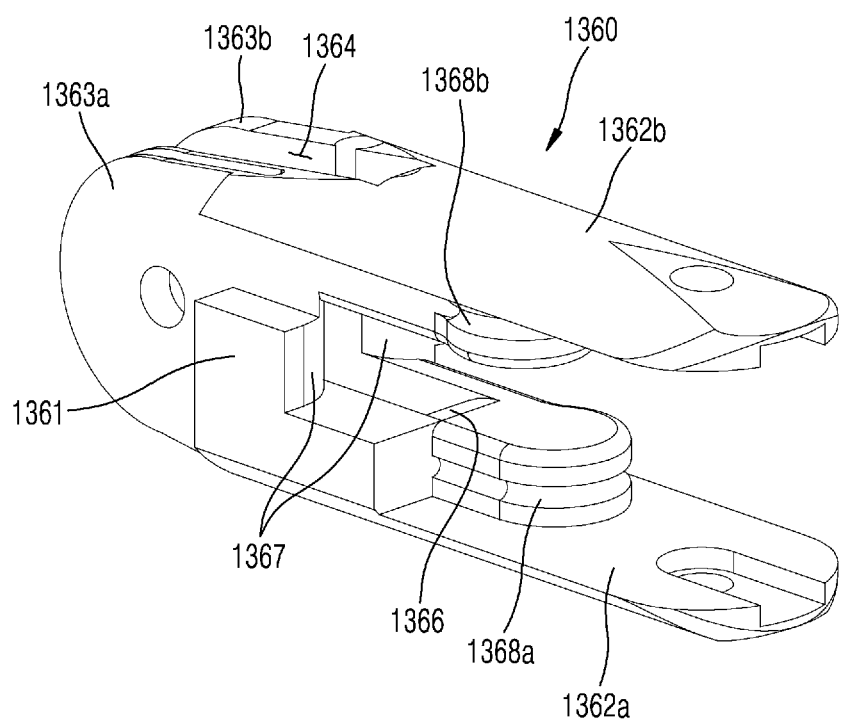

FIG. 60 is a perspective view illustrating an end tool hub of the end tool of the surgical instrument for electrocautery of FIG. 58.

Figure 61:
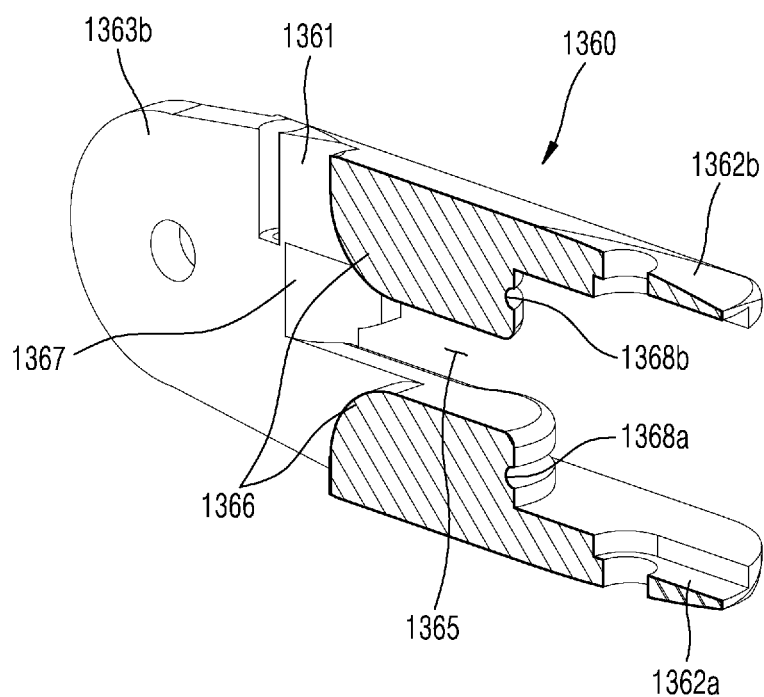

FIG. 61 is a cut-away perspective view of the end tool hub of FIG. 60.

Figure 62:
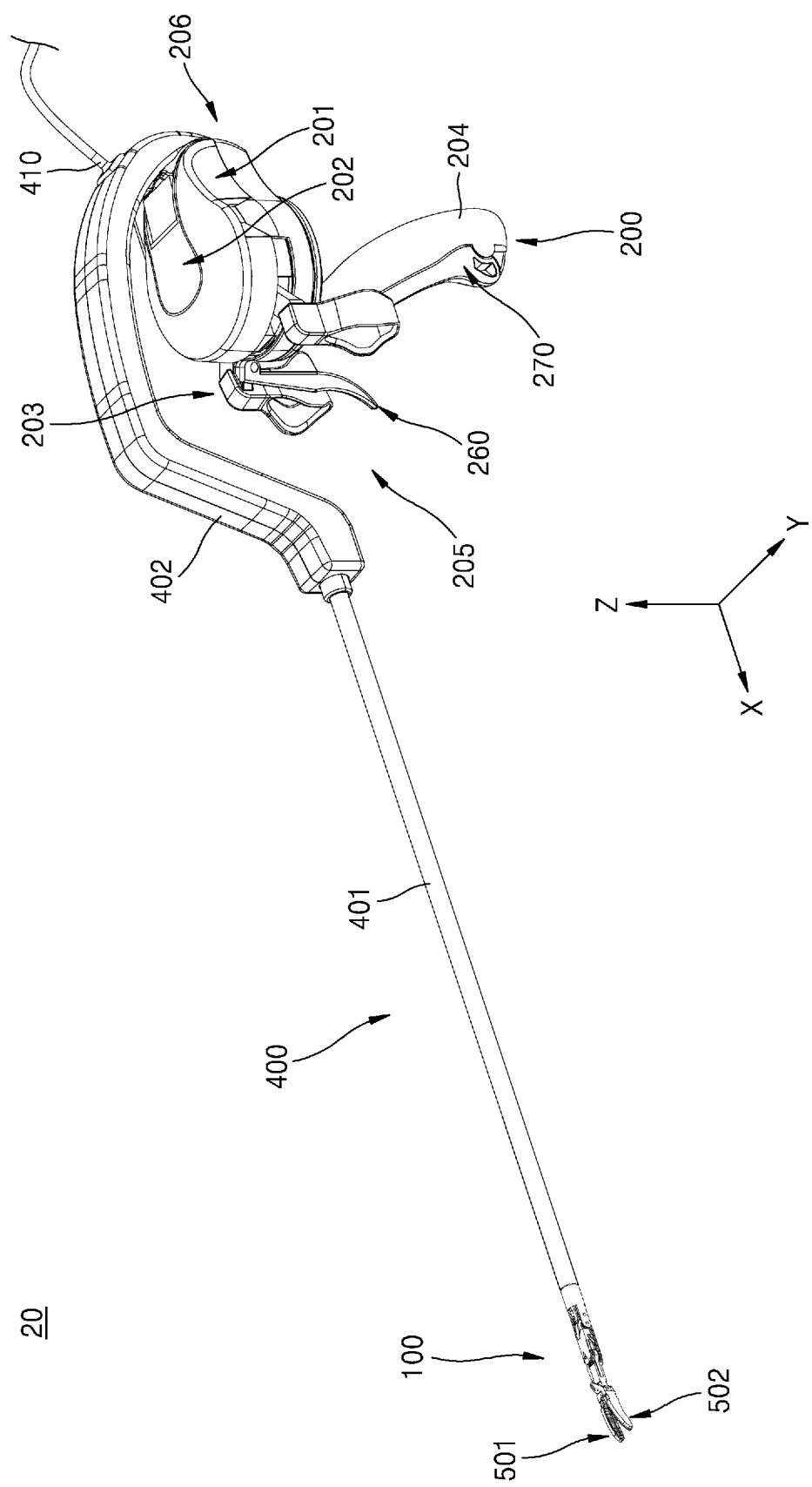
Figure 63:
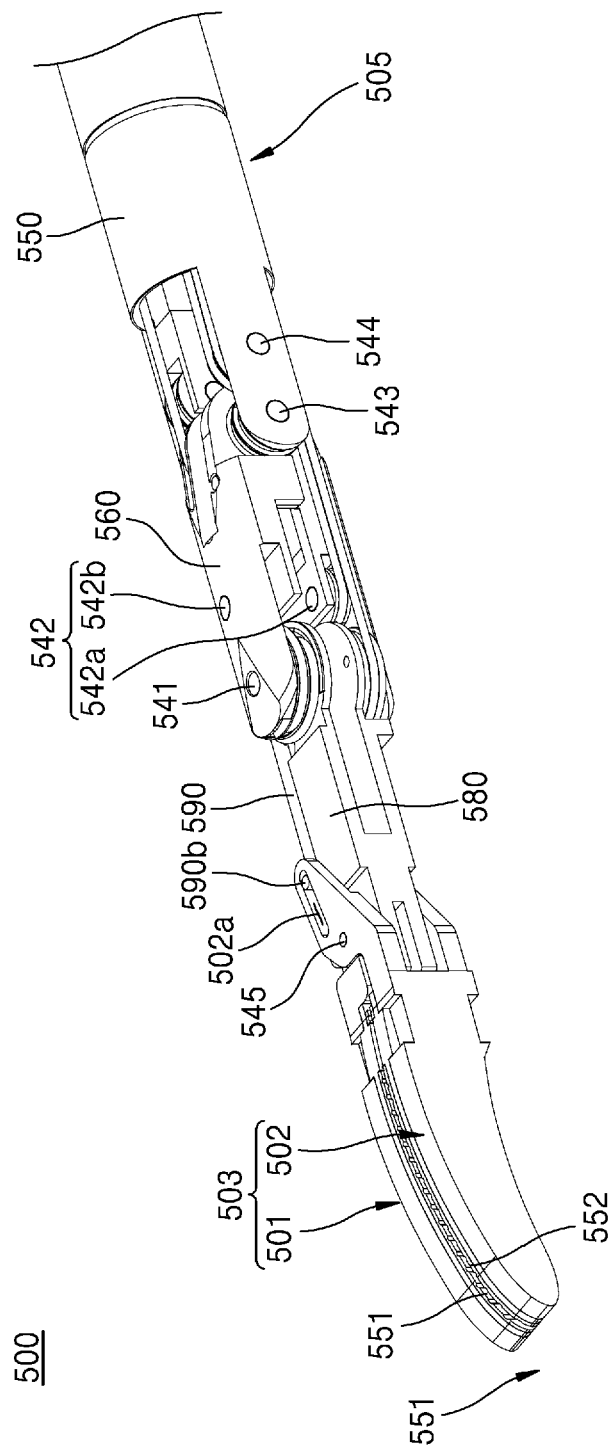
Figure 64:
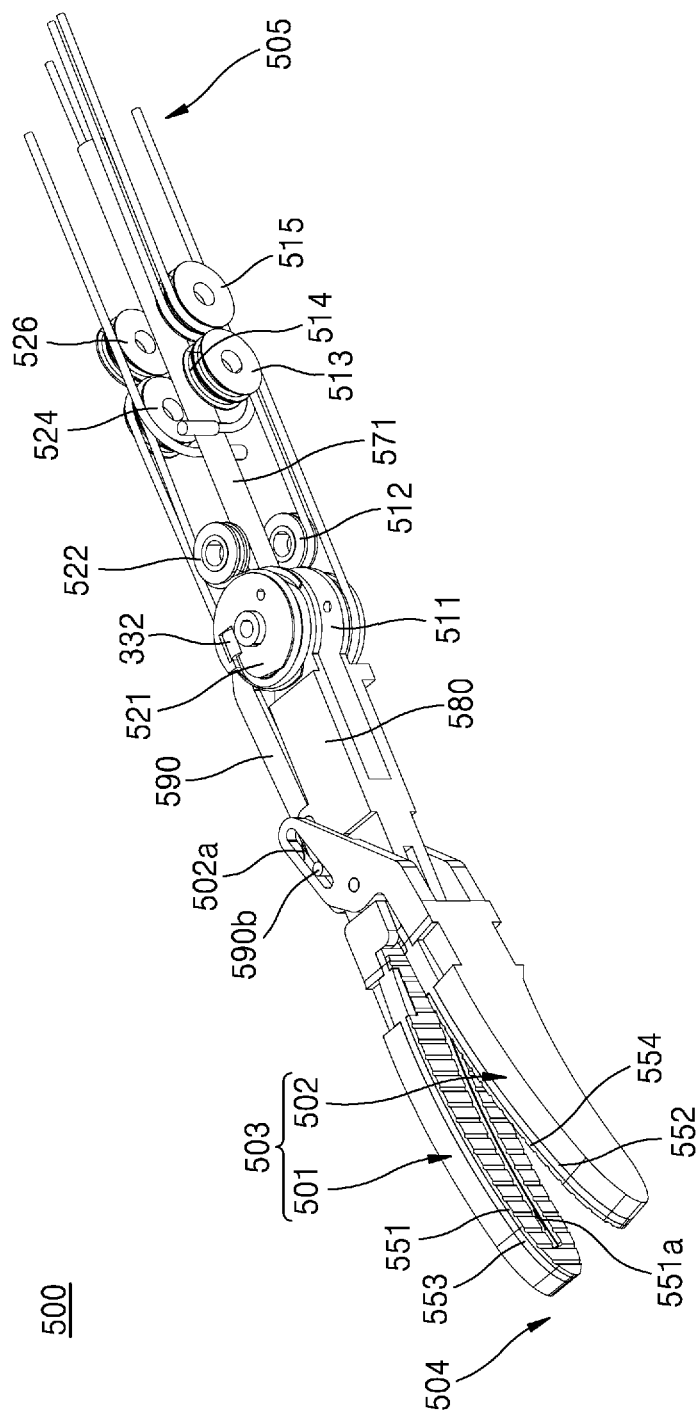
Figure 65:
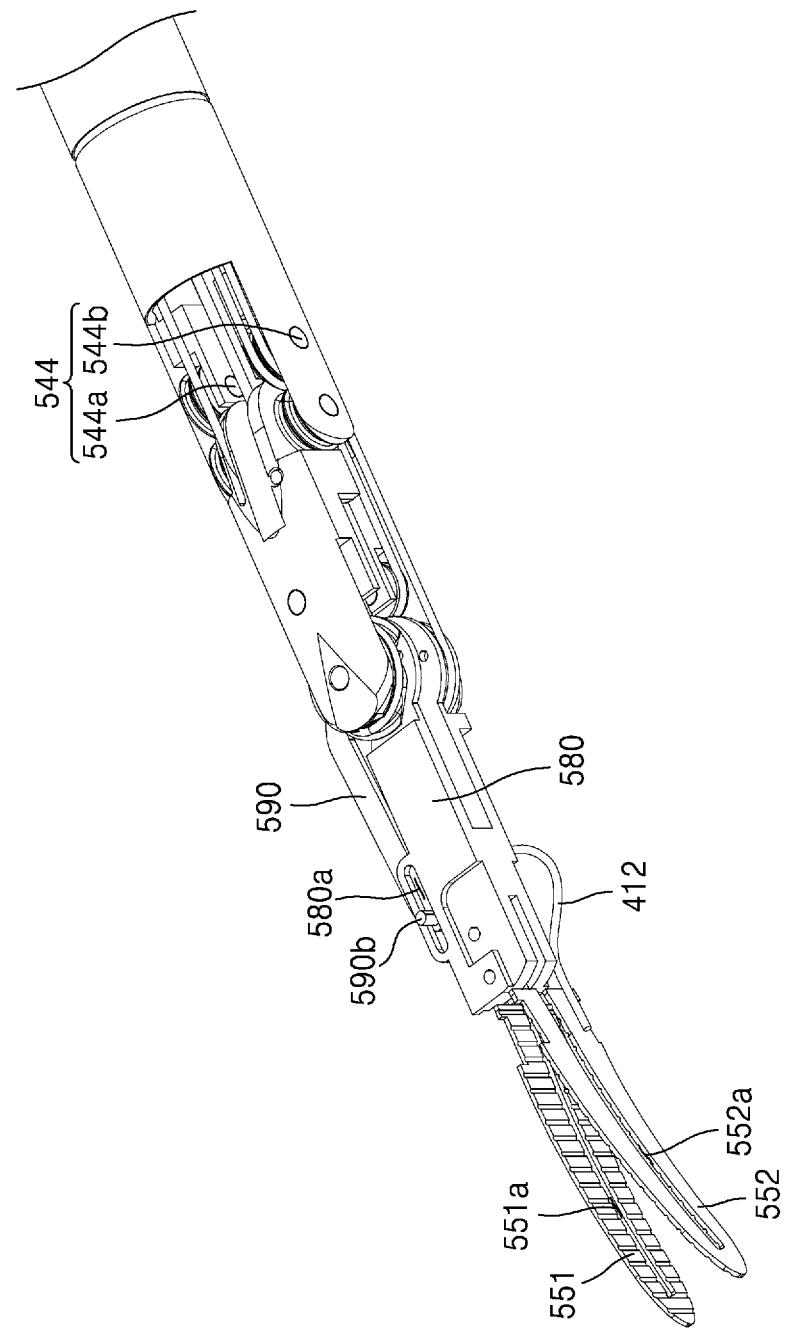
Figure 66:
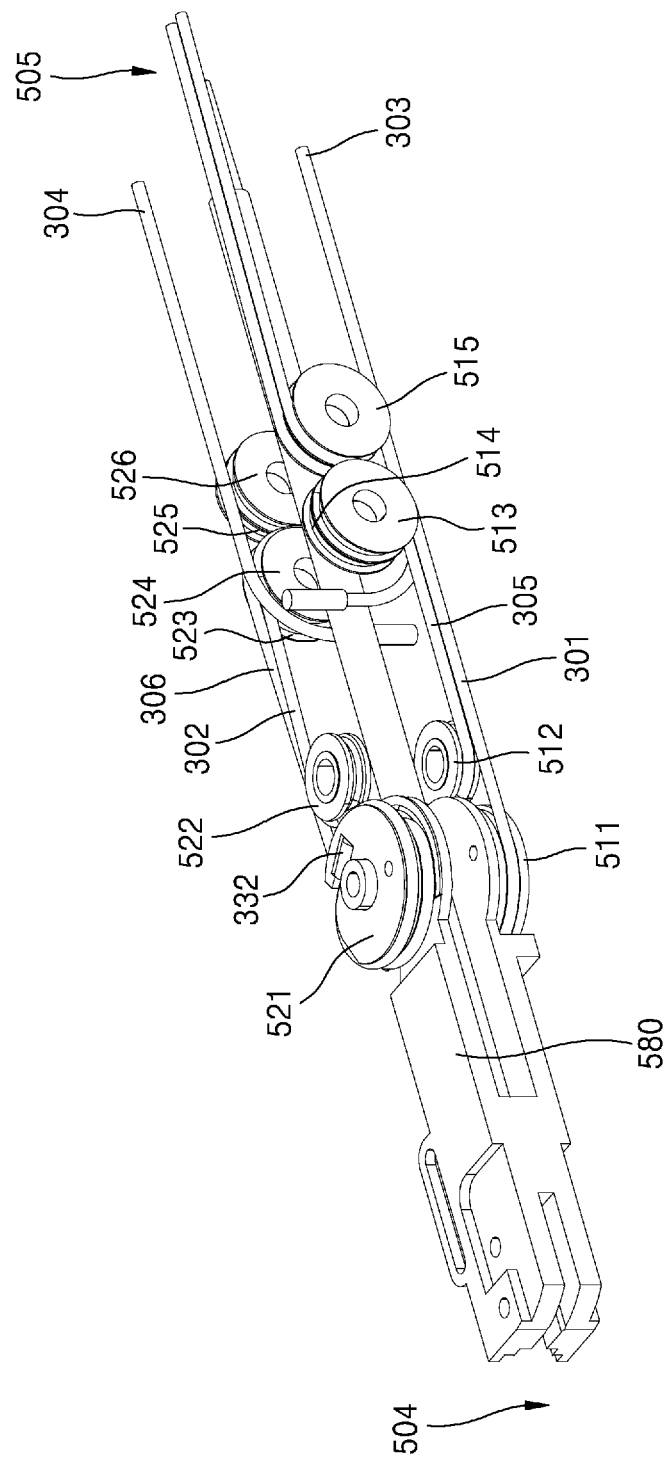
Figure 67:
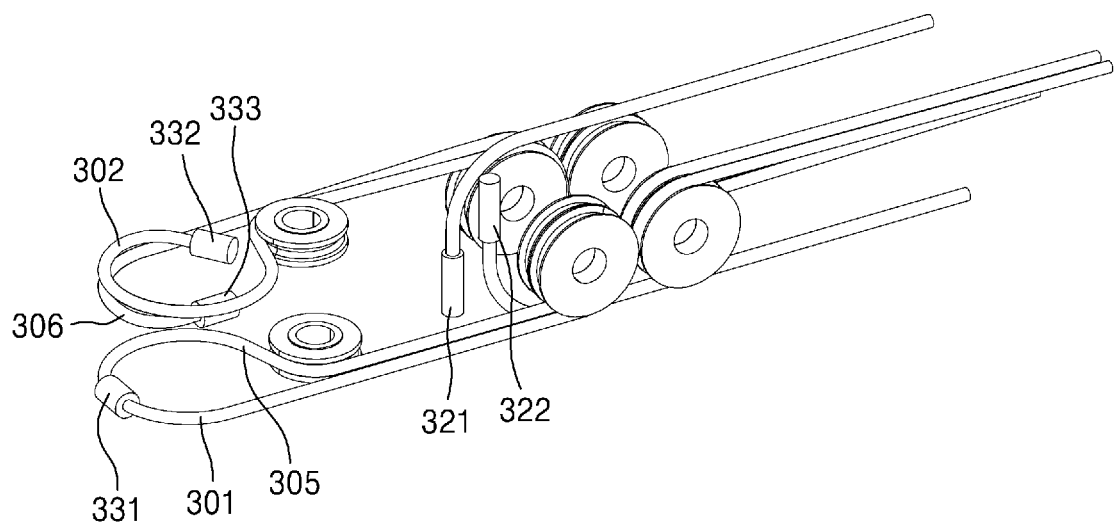
Figure 68:
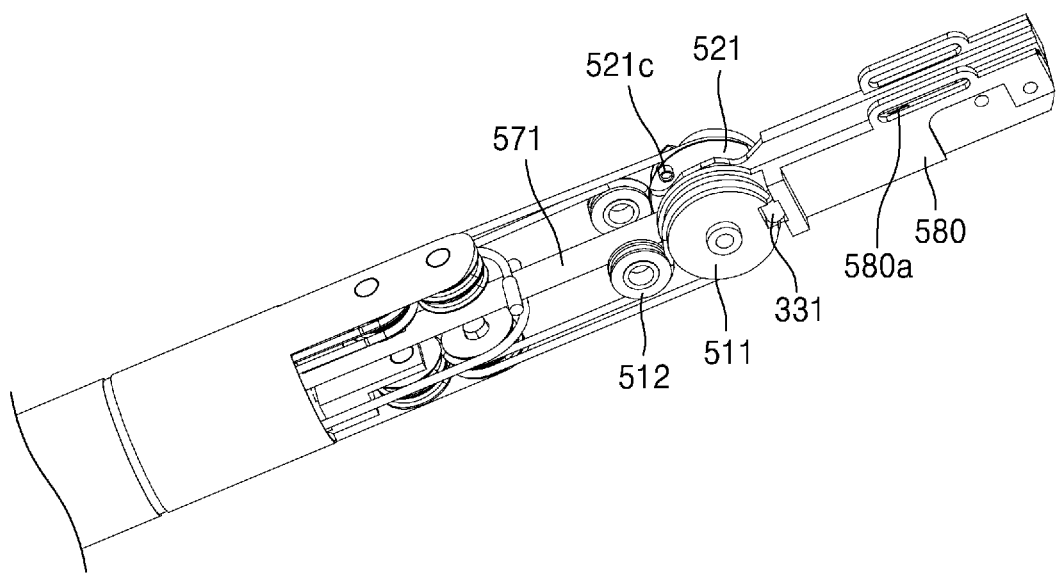

FIG. 62 is a perspective view illustrating a surgical instrument for electrocautery according to a second embodiment of the present disclosure.

FIGS. 63, 64, 65, 66, 67, and 68 are perspective views illustrating the end tool of the surgical instrument for electrocautery of FIG. 62.

Figure 69:
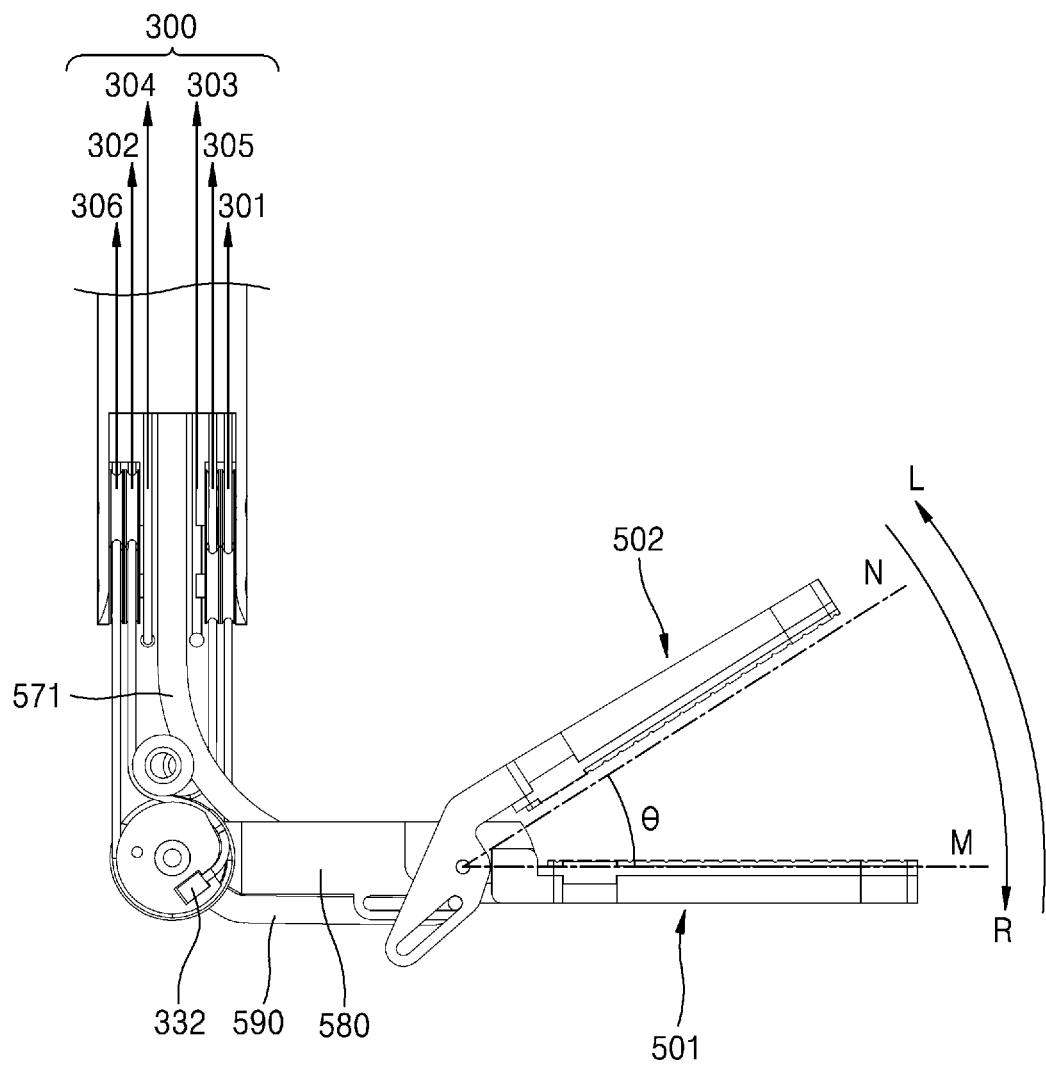
Figure 70:
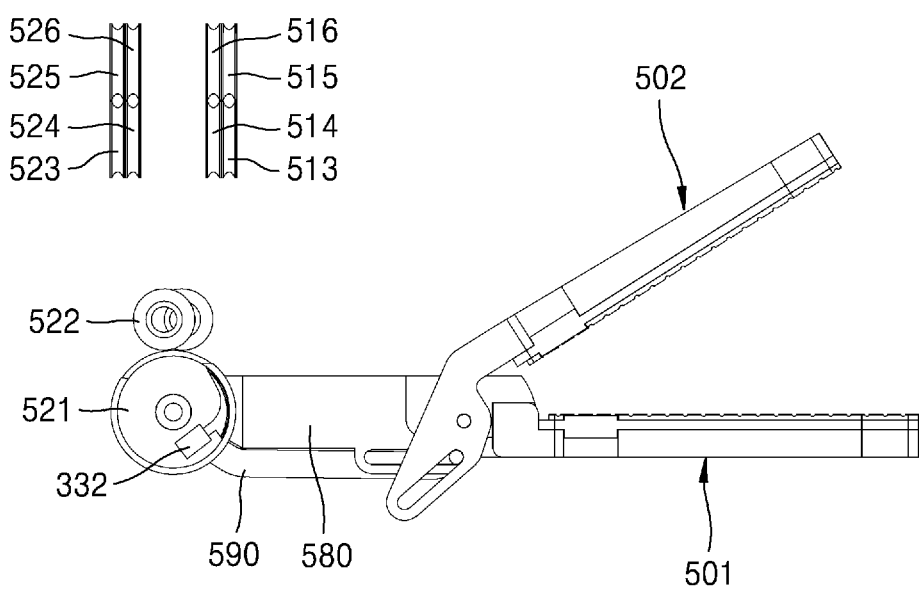

FIGS. 69 and 70 are plan views illustrating the end tool of the surgical instrument for electrocautery of FIG. 62.

Figure 71:
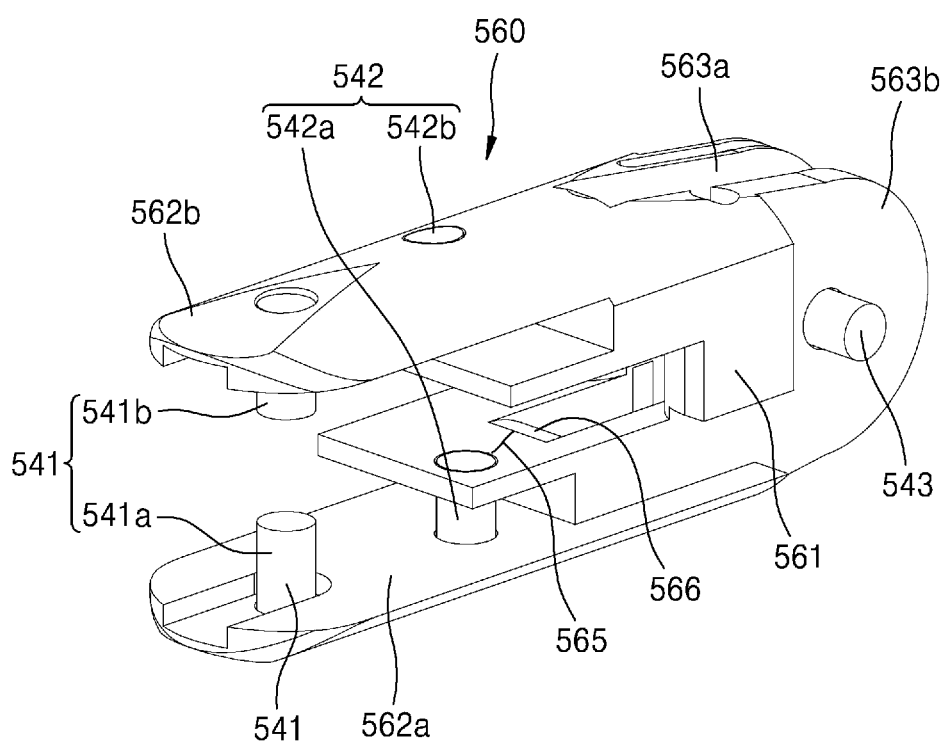
Figure 72:
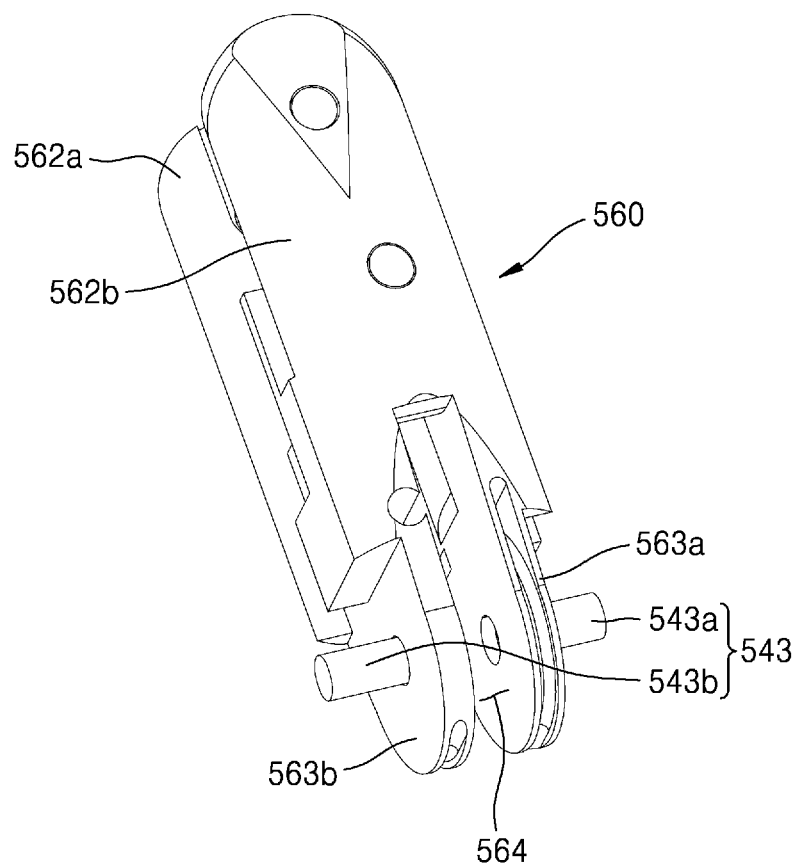

FIGS. 71 and 72 are perspective views illustrating an end tool hub of the end tool of the surgical instrument for electrocautery of FIG. 62.

Figure 73:
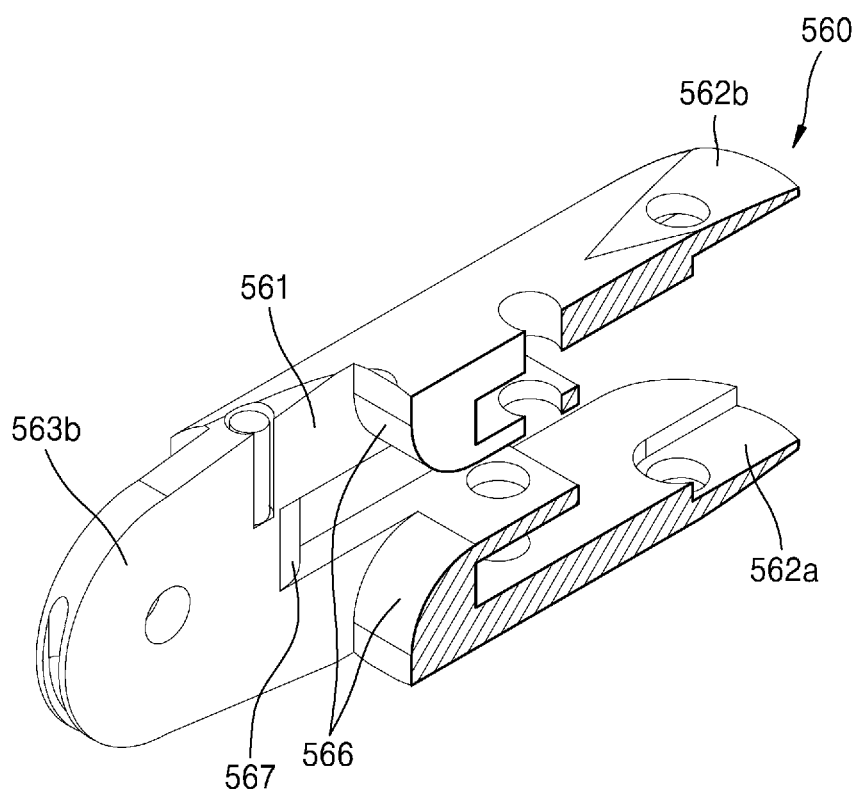

FIG. 73 is a cut-away perspective view of the end tool hub of FIG. 71.

Figure 74:
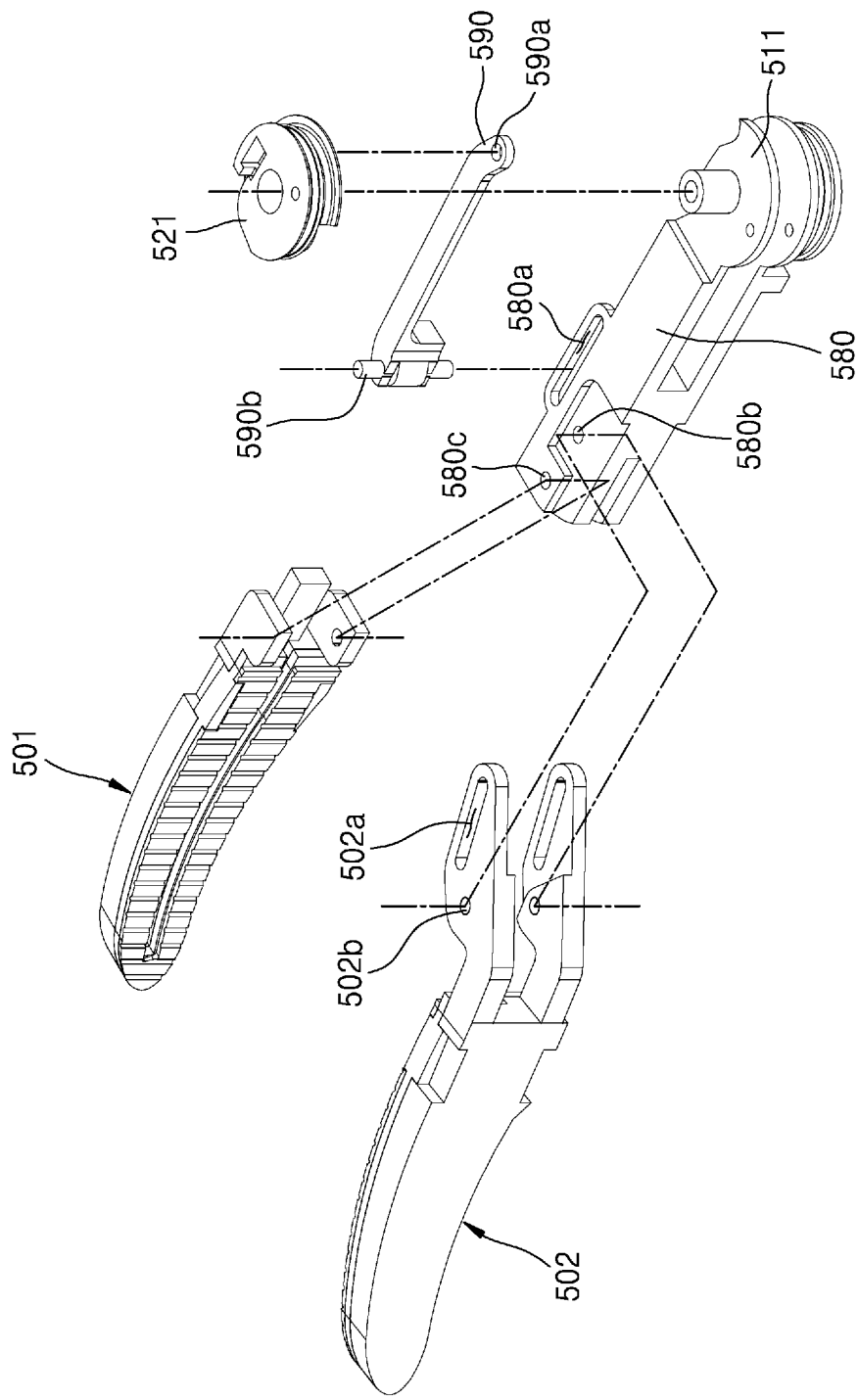
Figure 75:
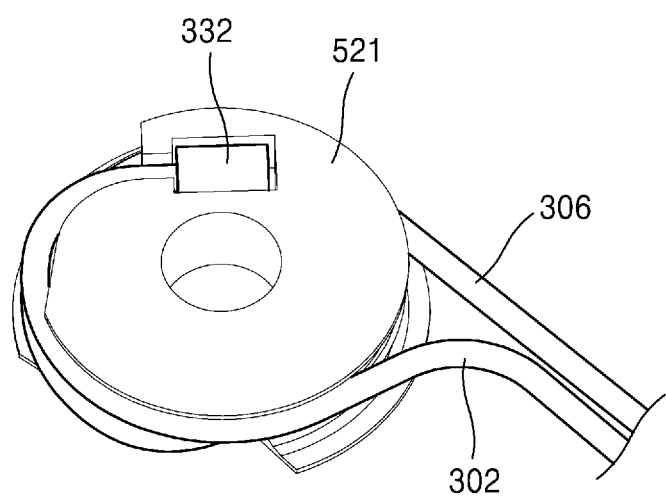
Figure 76:
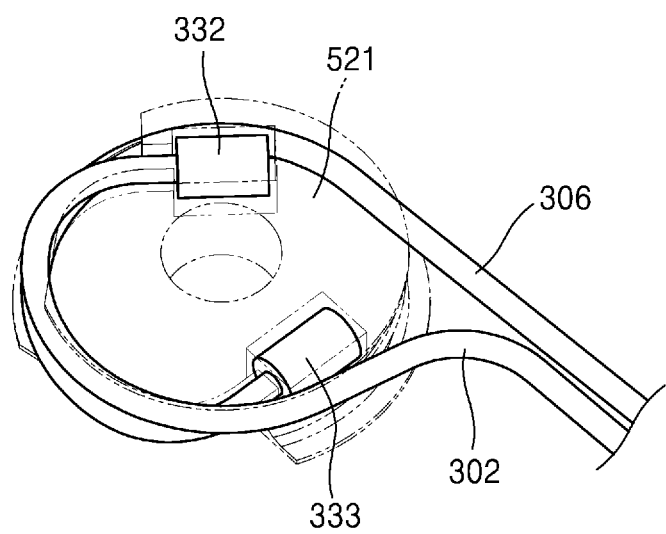
Figure 77:
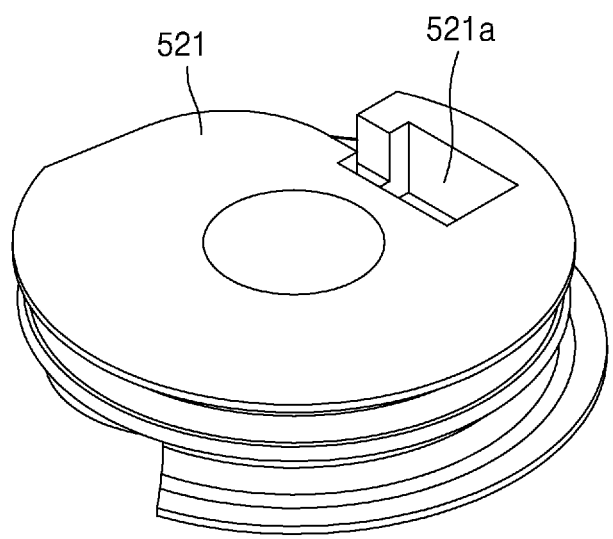
Figure 78:
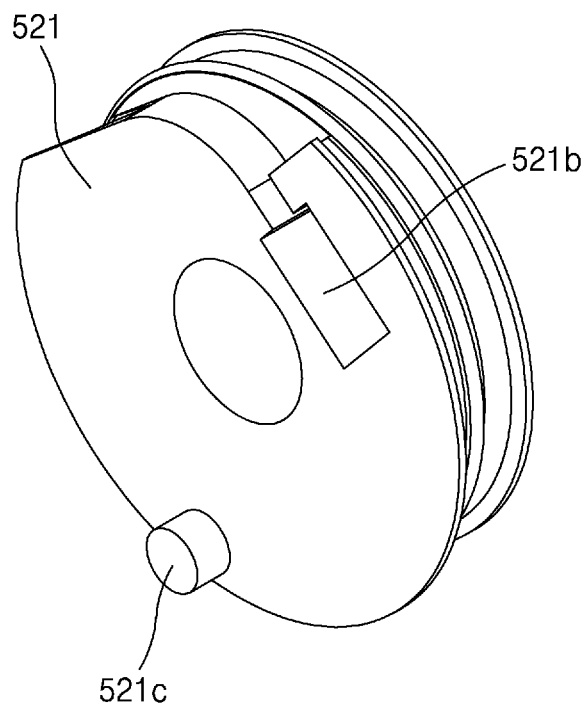

FIG. 74 is an exploded perspective view illustrating jaws-links-jaw pulleys of the end tool of the surgical instrument for electrocautery of FIG. 62.

FIGS. 75, 76, 77, and 78 are perspective views illustrating a second jaw pulley of the end tool of the surgical instrument for electrocautery of FIG. 62.

Figure 79:
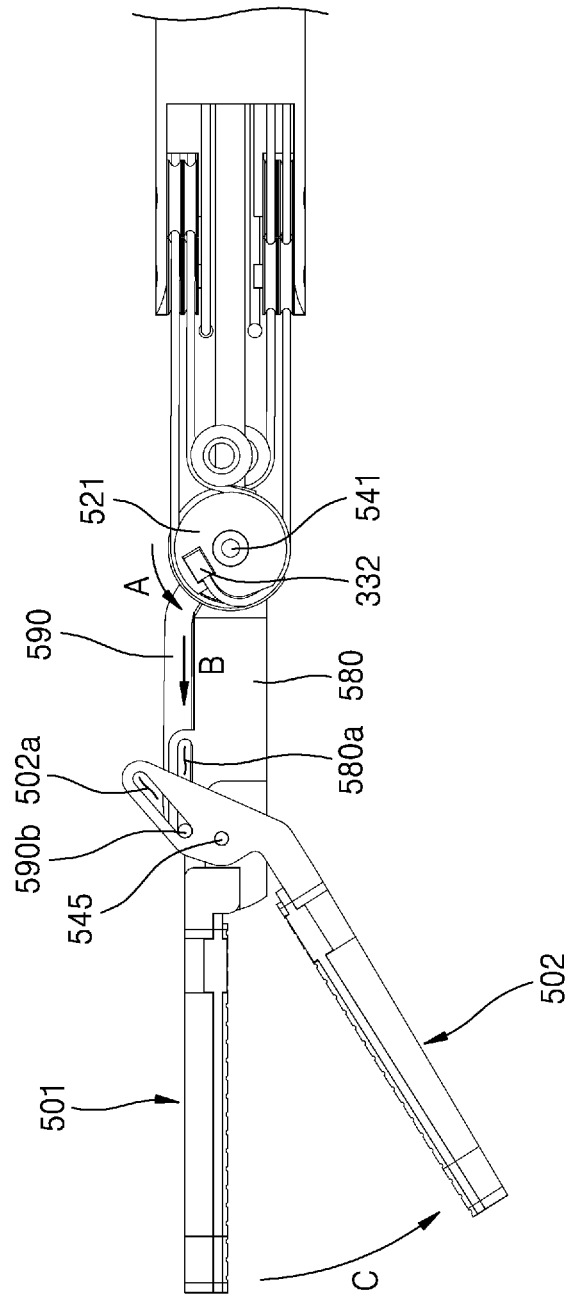
Figure 80:
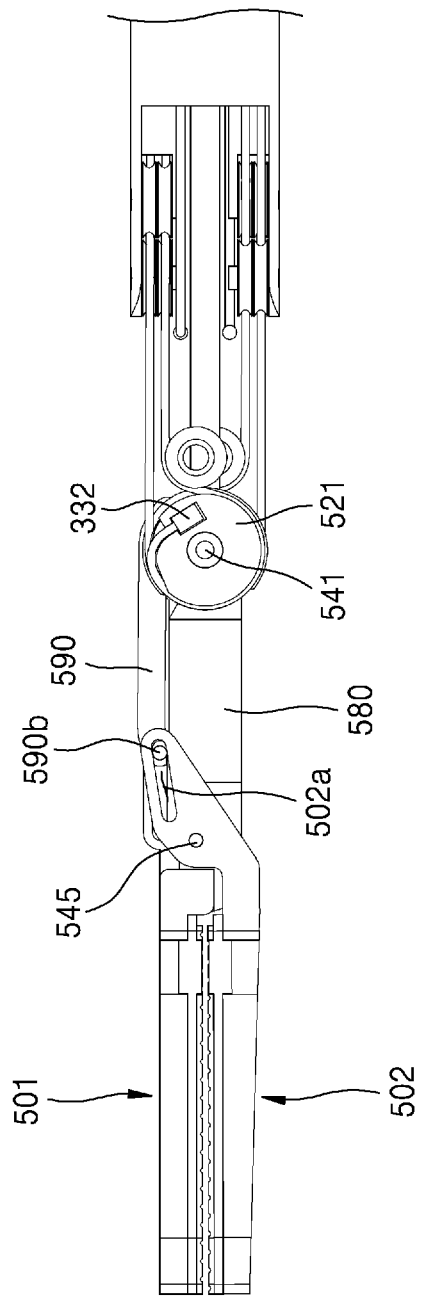

FIGS. 79 and 80 are plan views illustrating an opening and closing motion of the end tool of the surgical instrument for electrocautery of FIG. 62.

Figure 81:
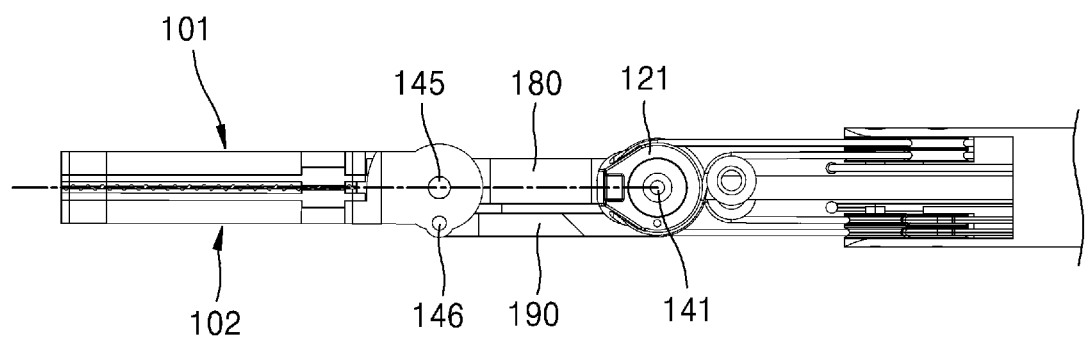
Figure 81:
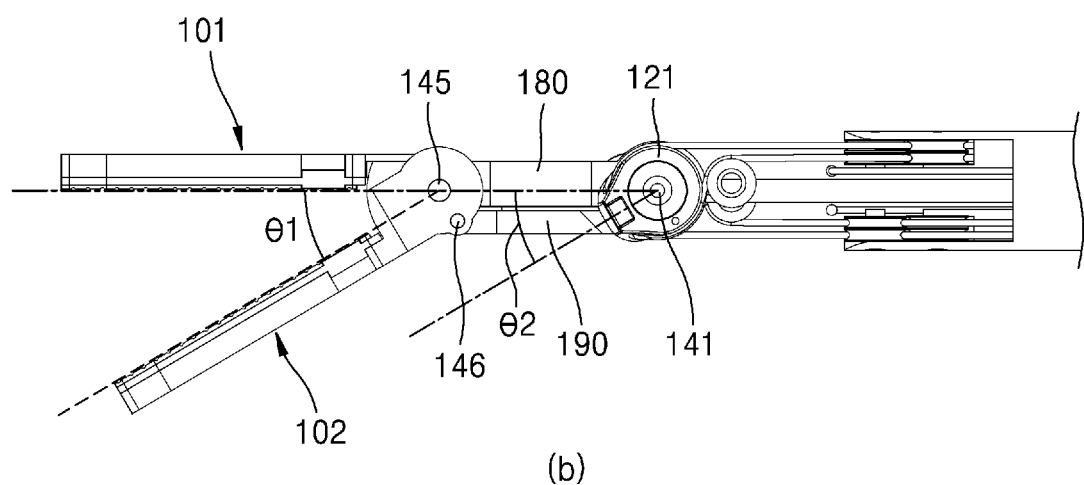
Figure 82:
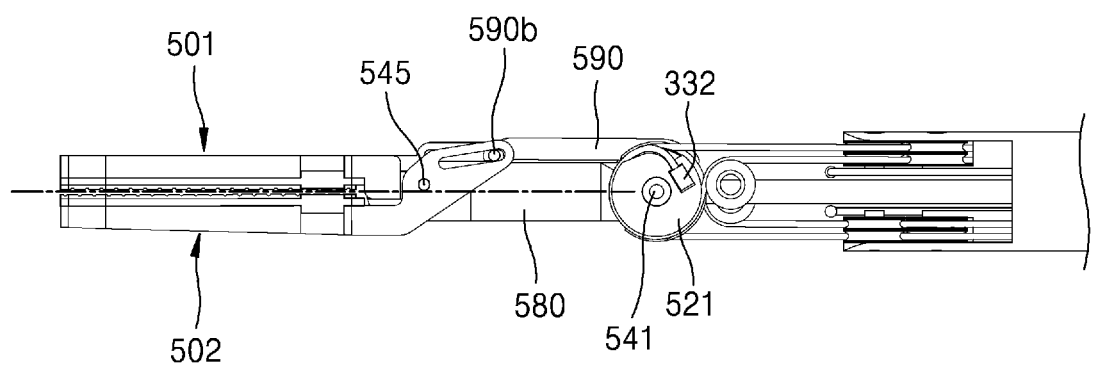
Figure 82:
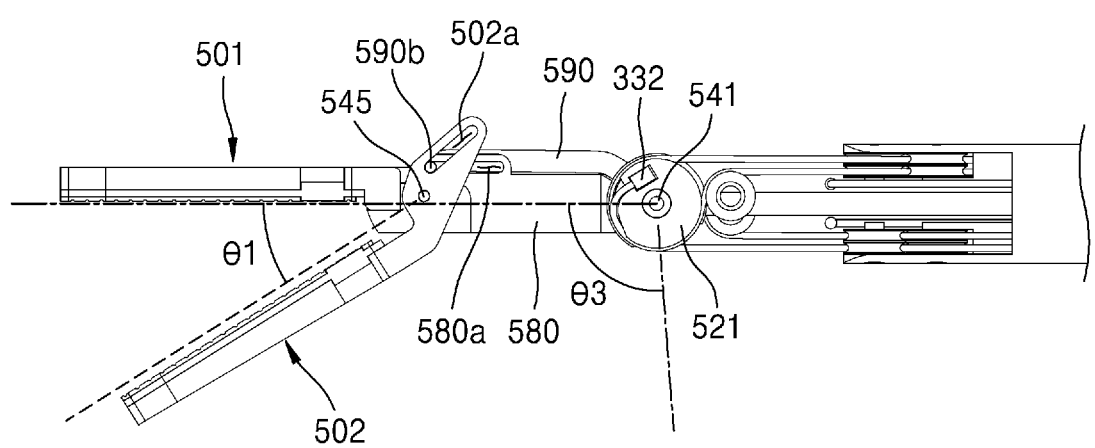

FIG. 81 is a view illustrating a jaw opening/closing process of the first embodiment of the present disclosure shown in FIG. 2 or the like, and FIG. 82 is a view illustrating a jaw opening/closing process of the second embodiment of the present disclosure.

Figure 83:
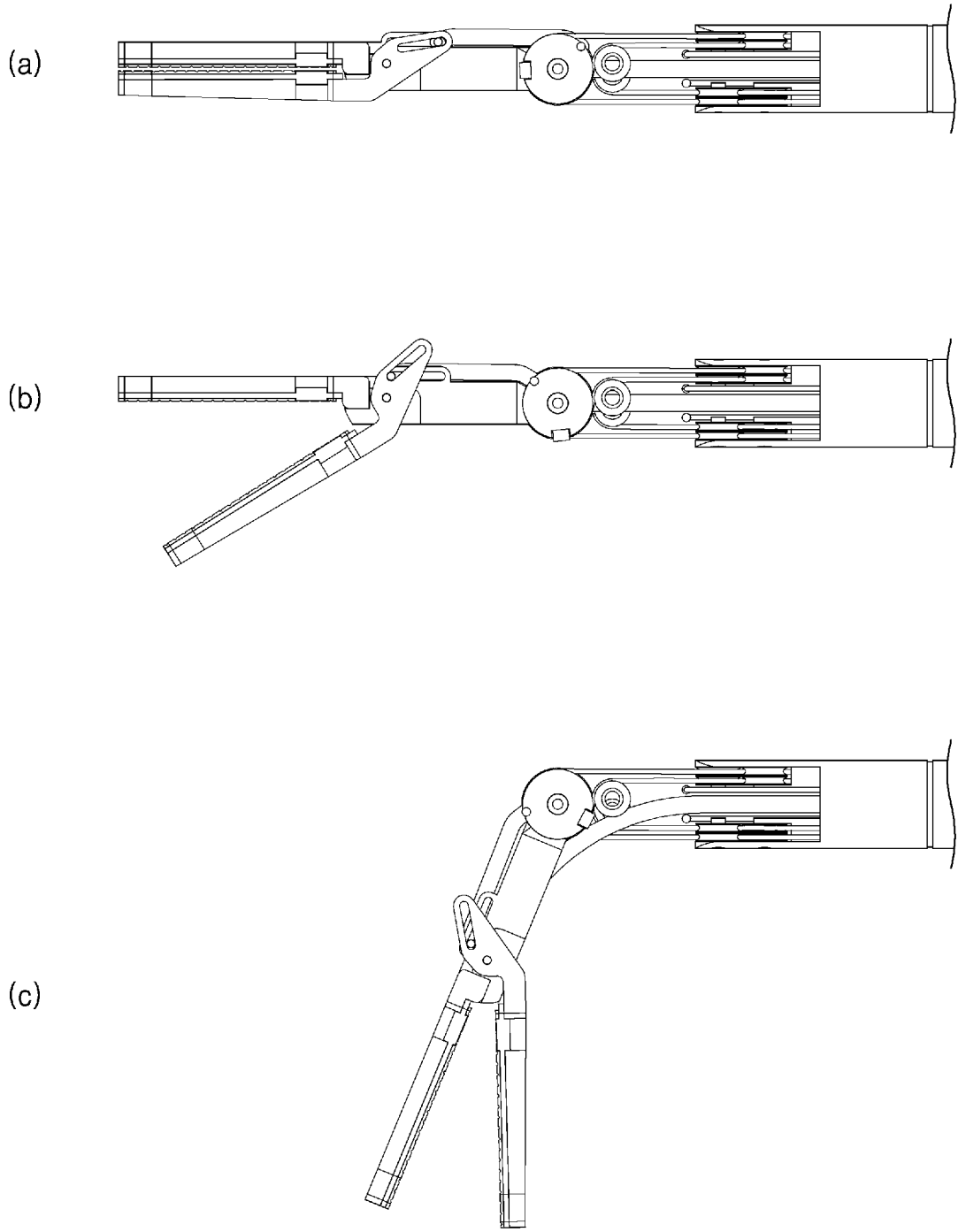
Figure 84:
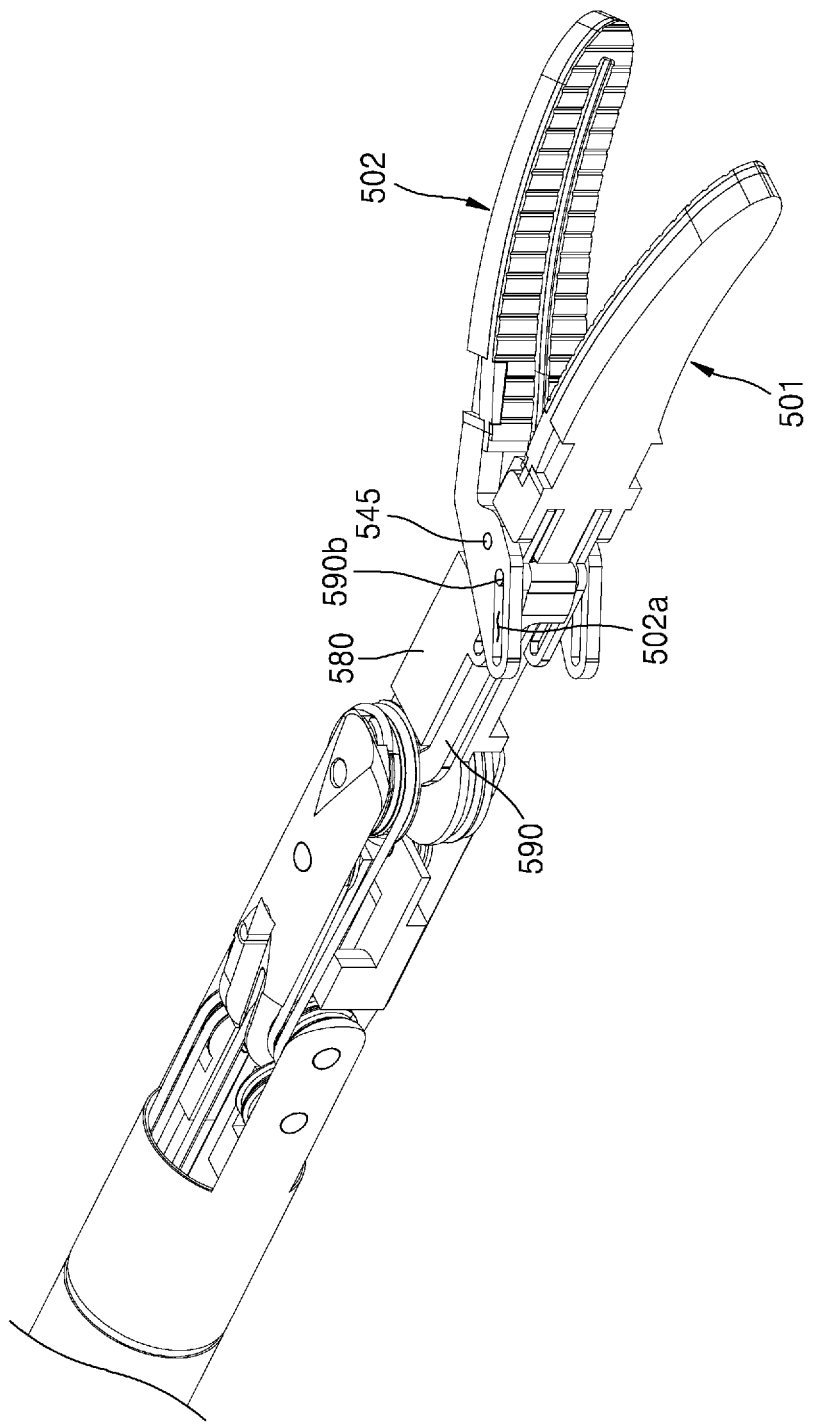
Figure 85:
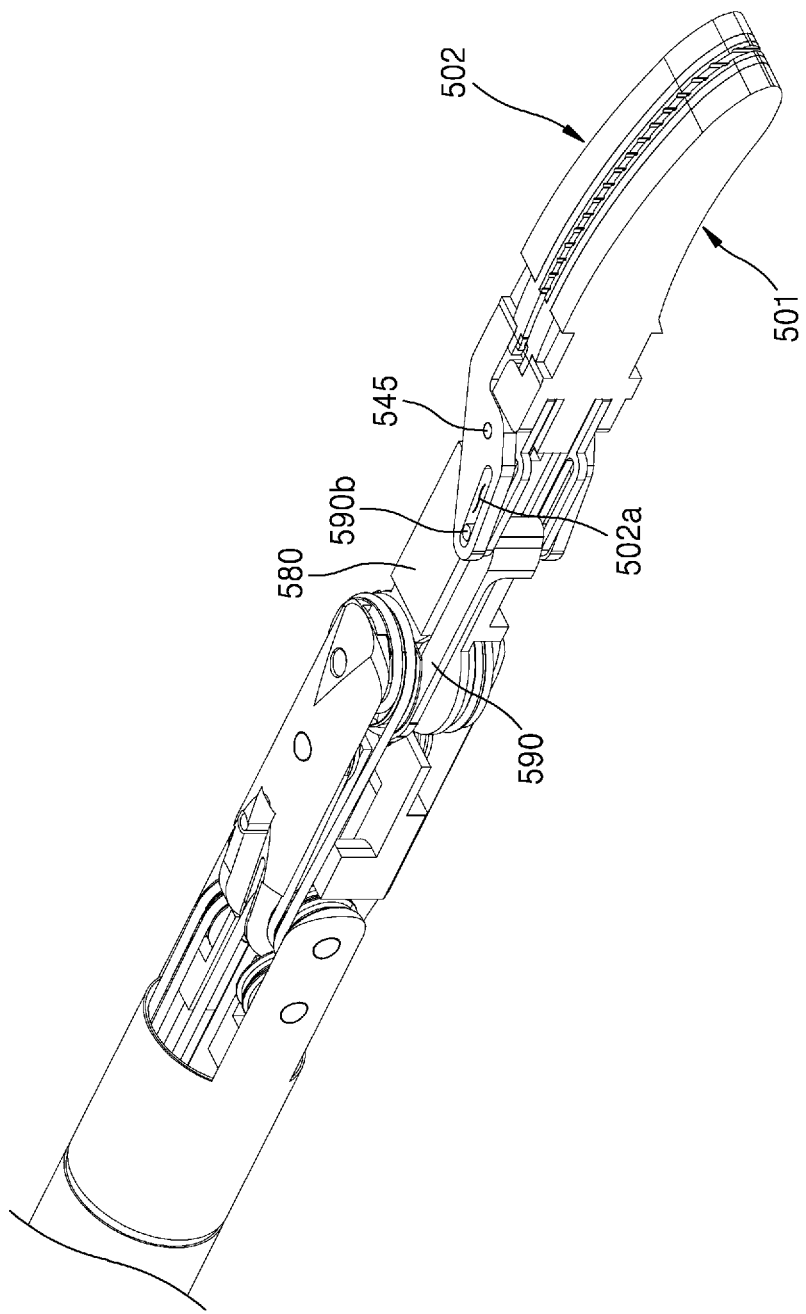
Figure 86:
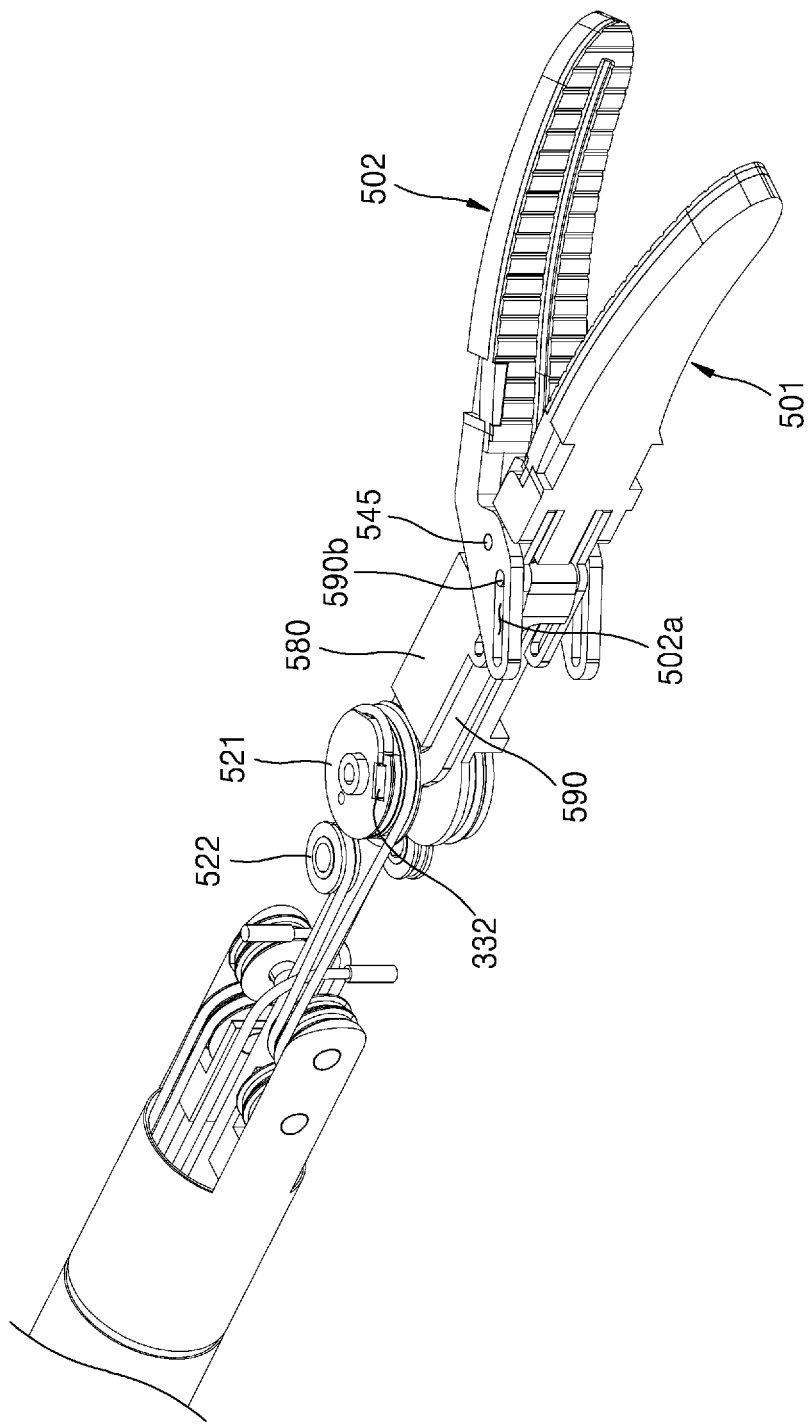
Figure 87:
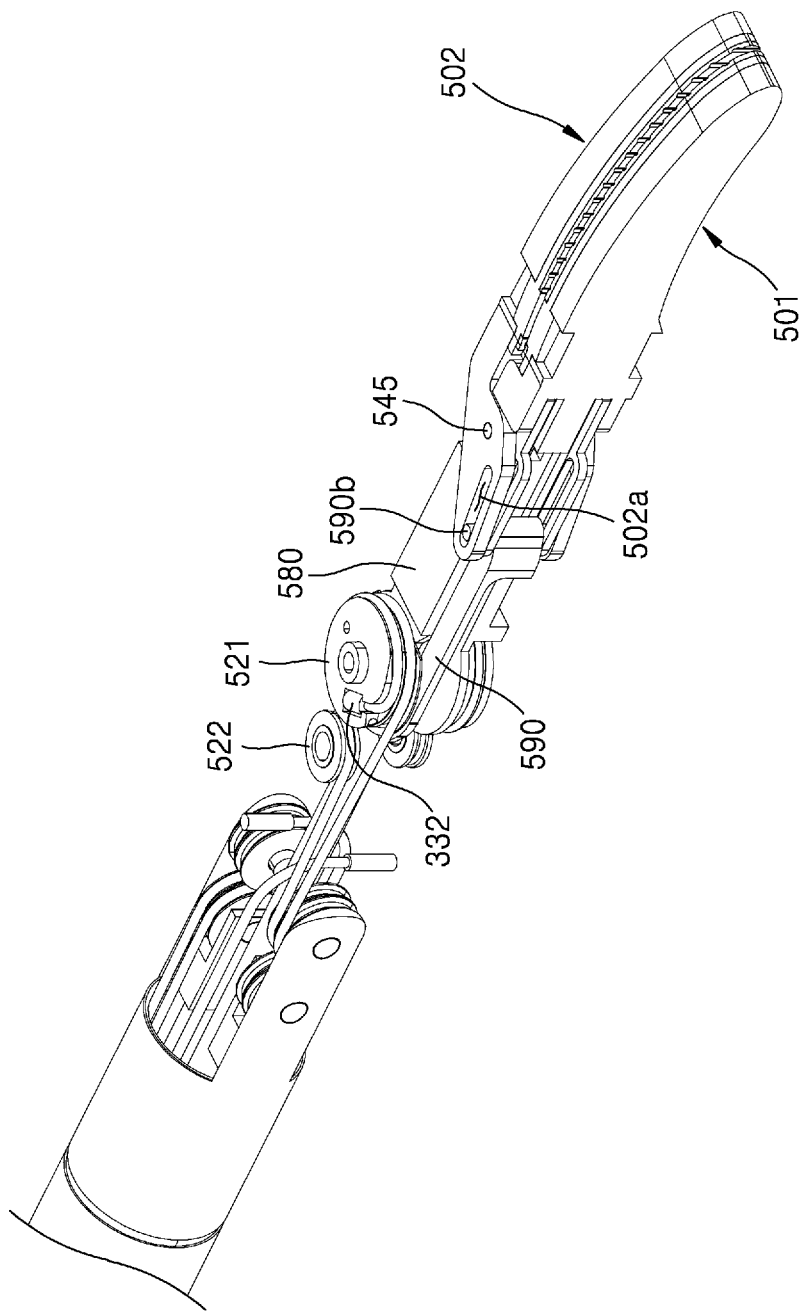

FIG. 83 is a view illustrating a case in which a pin/slot-type structure of the second embodiment of the present disclosure is configured in a normal pulley rather than a multi-layered pulley.

FIGS. 84, 85, 86, and 87 are perspective views illustrating an opening and closing motion of the end tool of the surgical instrument for electrocautery of FIG. 62

Figure 88:
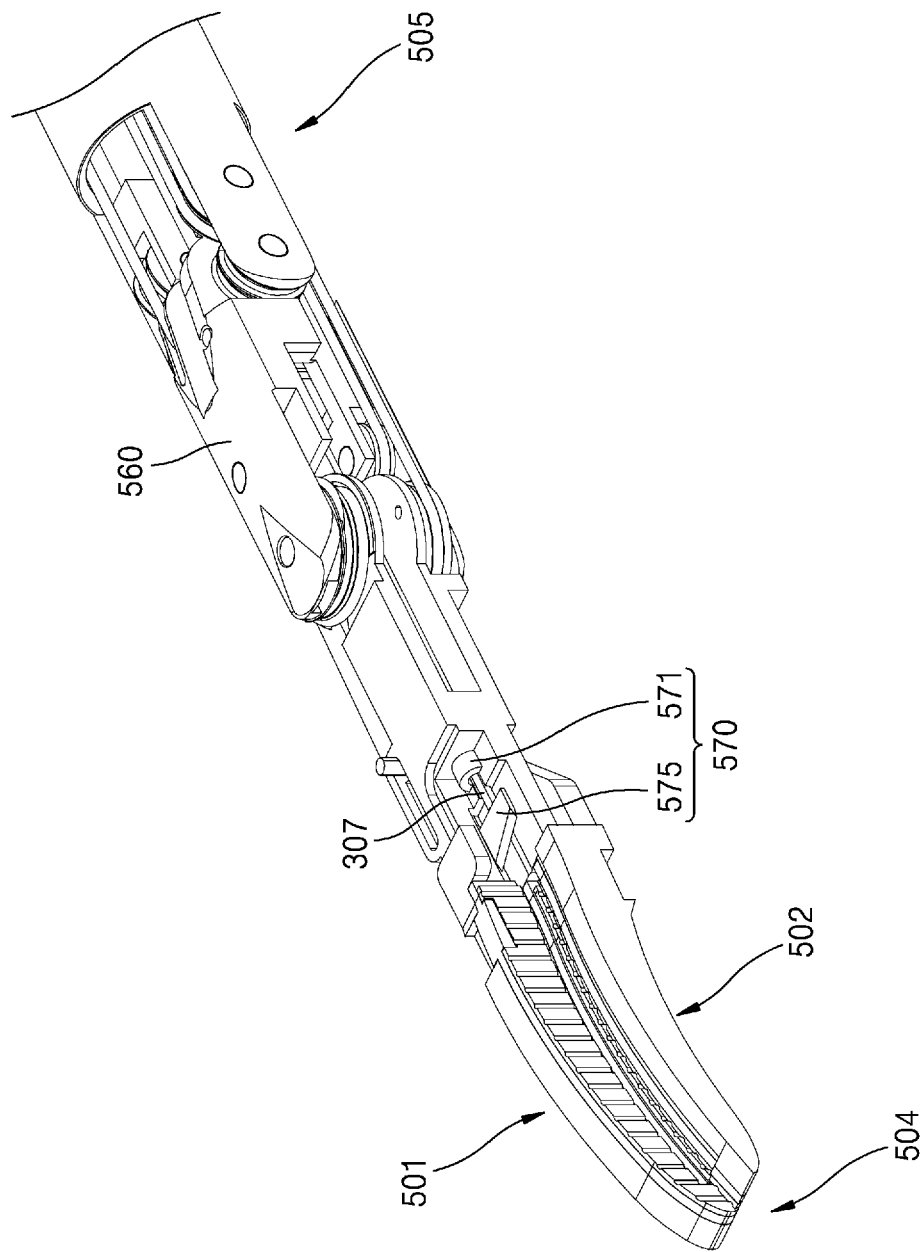
Figure 89:
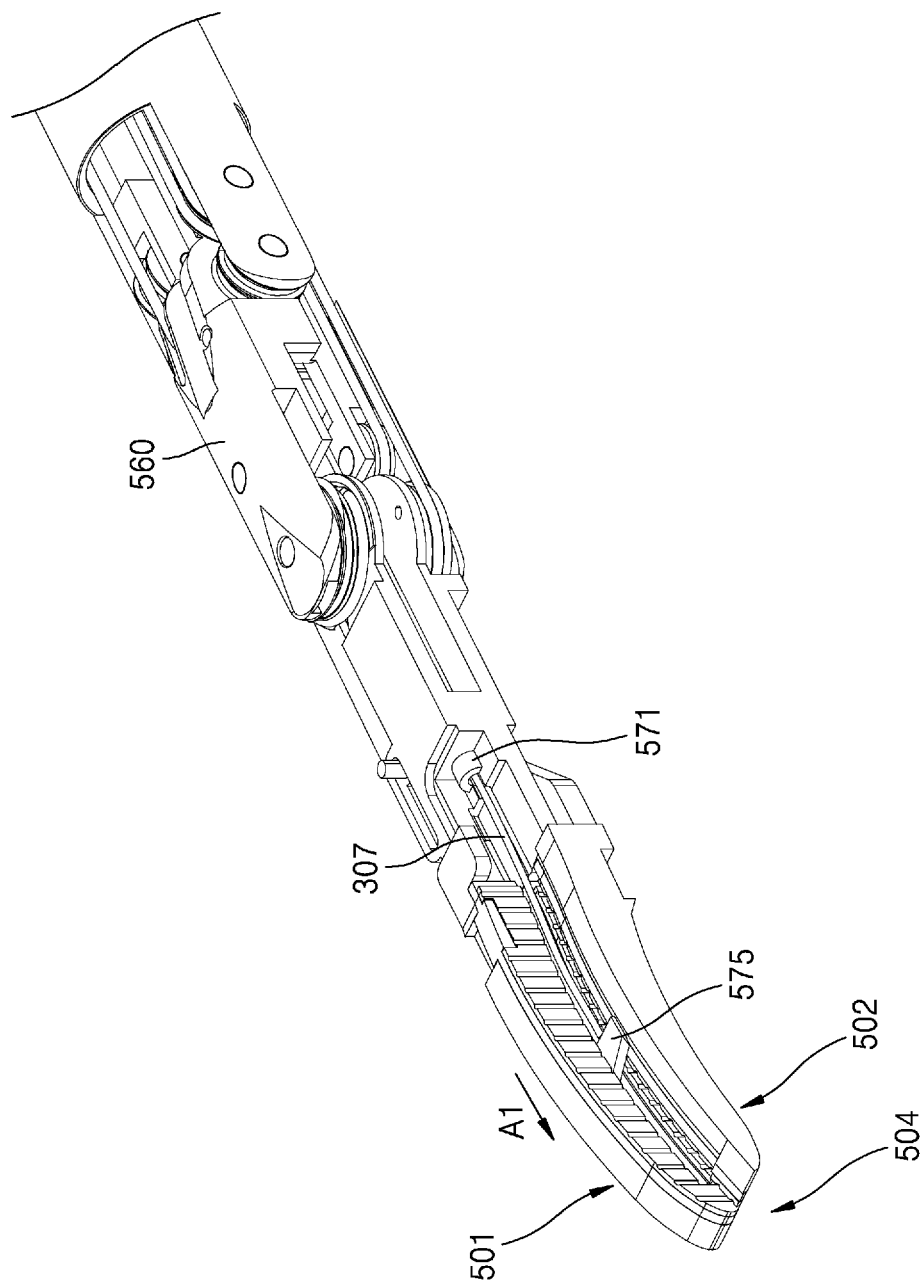
Figure 90:
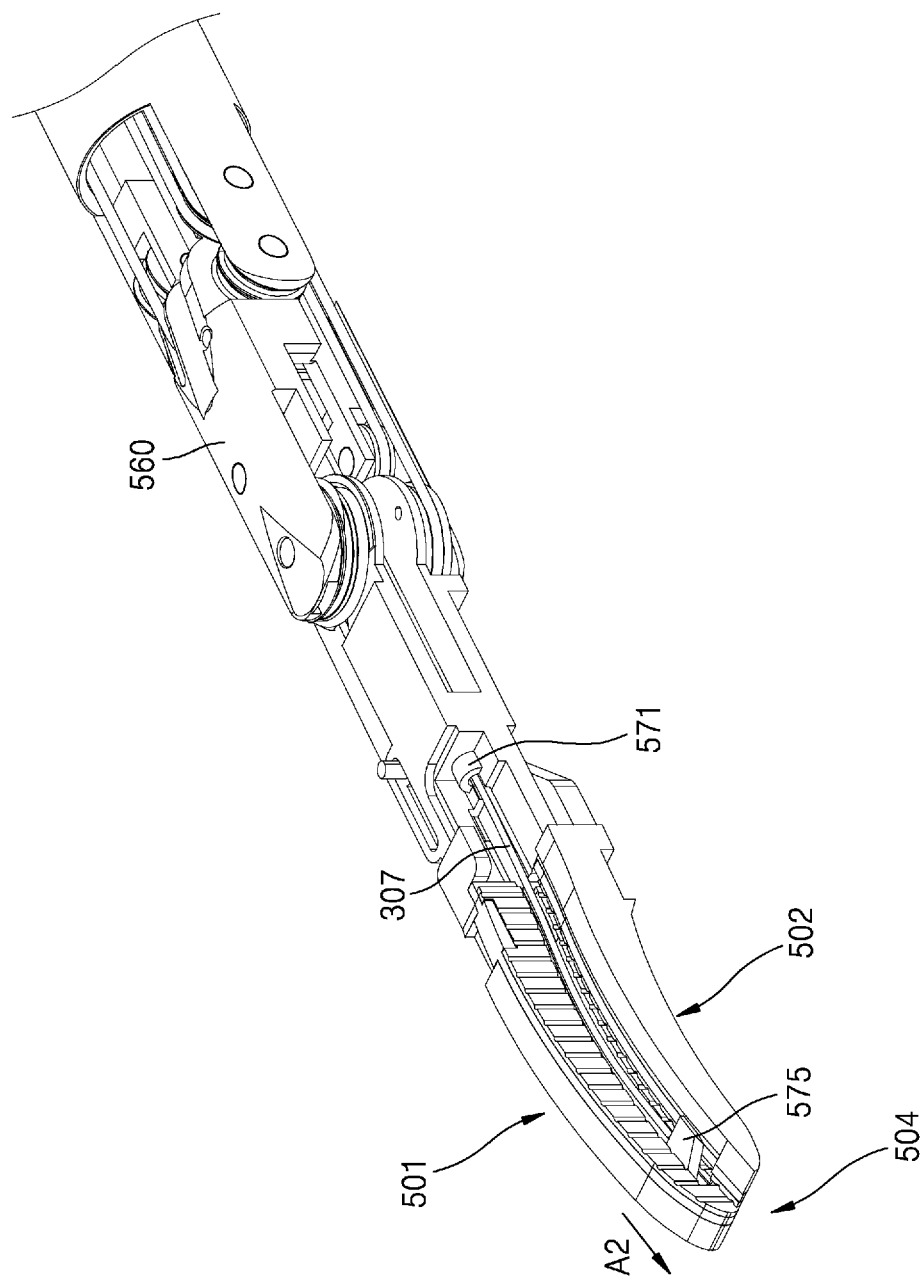

FIGS. 88, 89, and 90 are perspective views illustrating a cutting motion of the end tool of the surgical instrument for electrocautery of FIG. 62.

Figure 91:
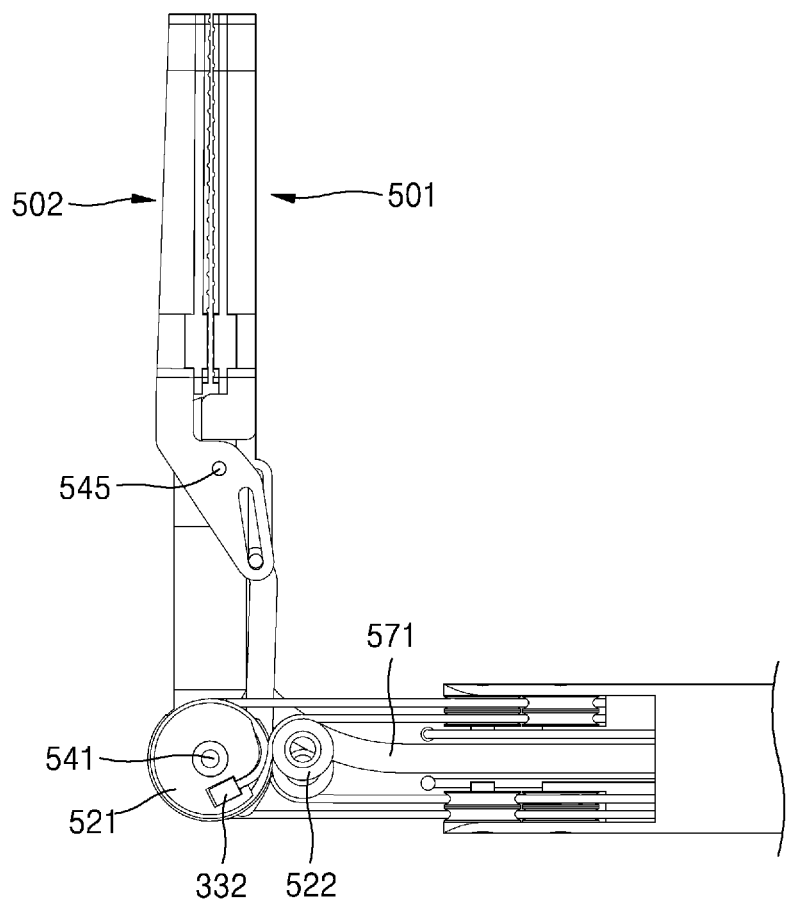
Figure 92:
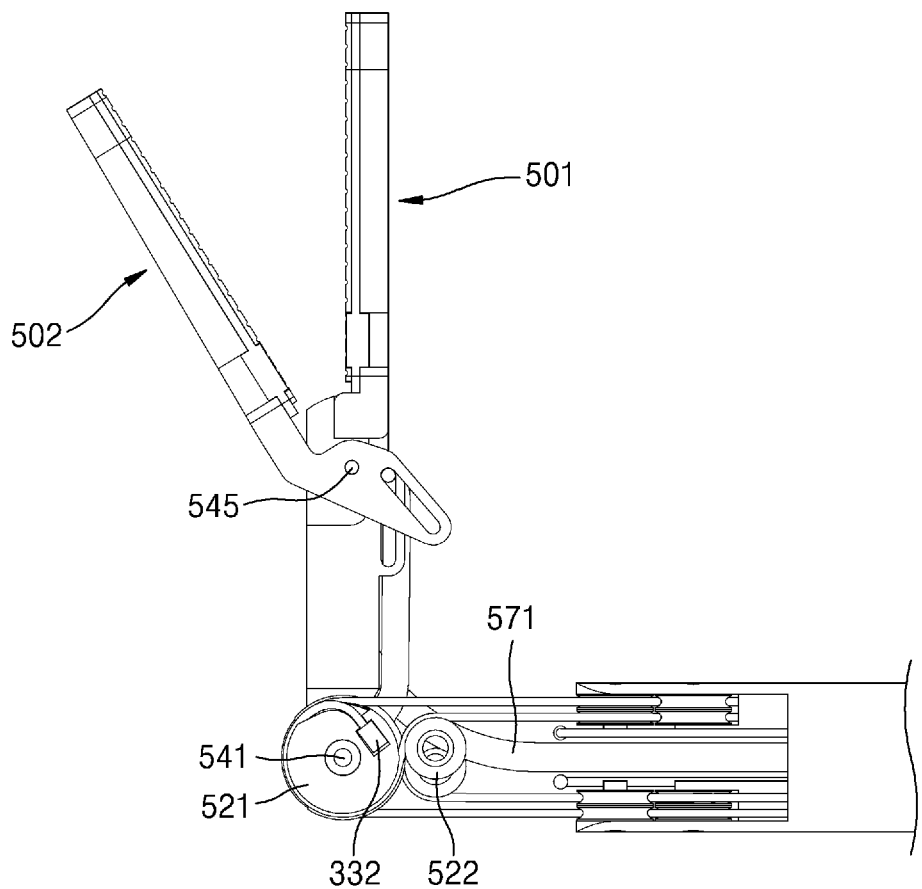

FIGS. 91 and 92 are views illustrating a process of performing an opening and closing motion while the end tool of the surgical instrument for electrocautery of FIG. 62 is yaw-rotated by −90°.

Figure 93:
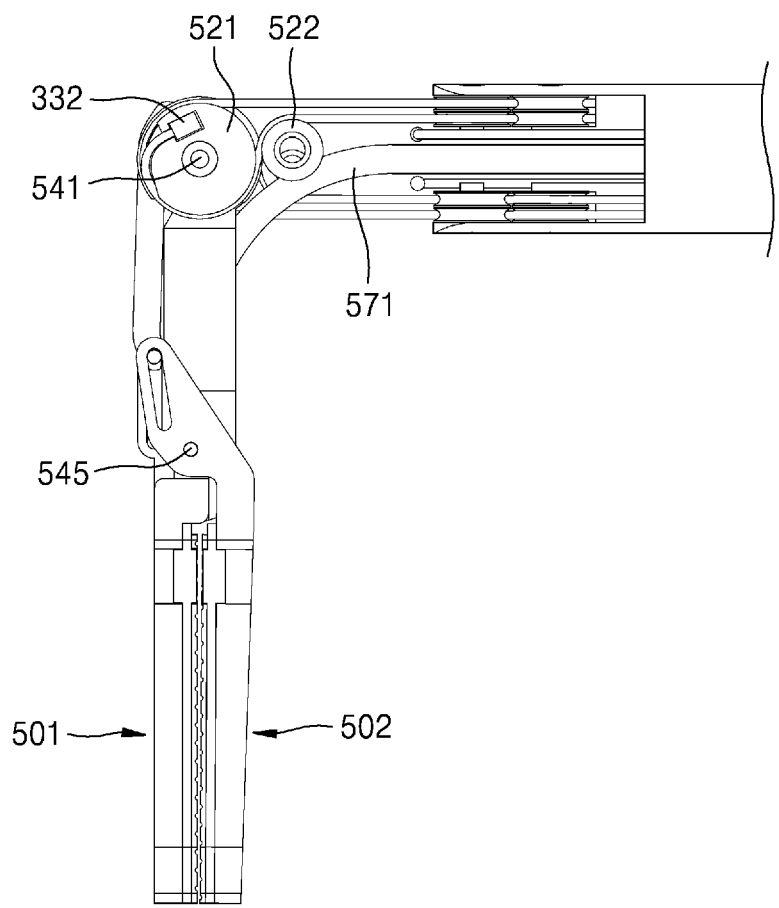
Figure 94:
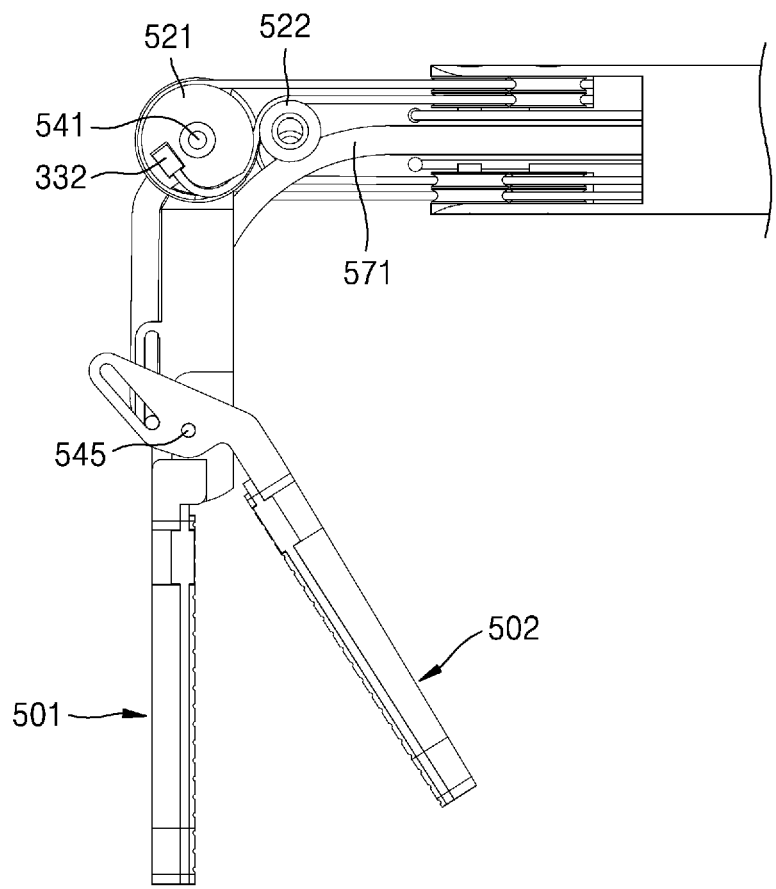

FIGS. 93 and 94 are views illustrating a process of performing an opening and closing motion while the end tool of the surgical instrument for electrocautery of FIG. 62 is yaw-rotated by +90°.

Figure 95:
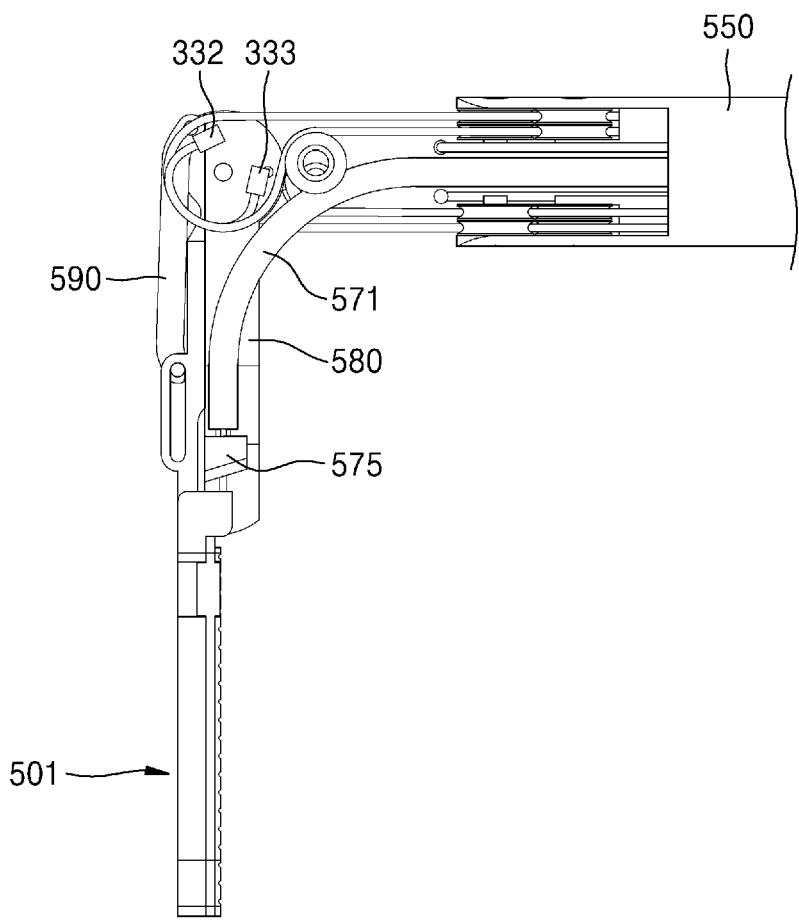
Figure 96:
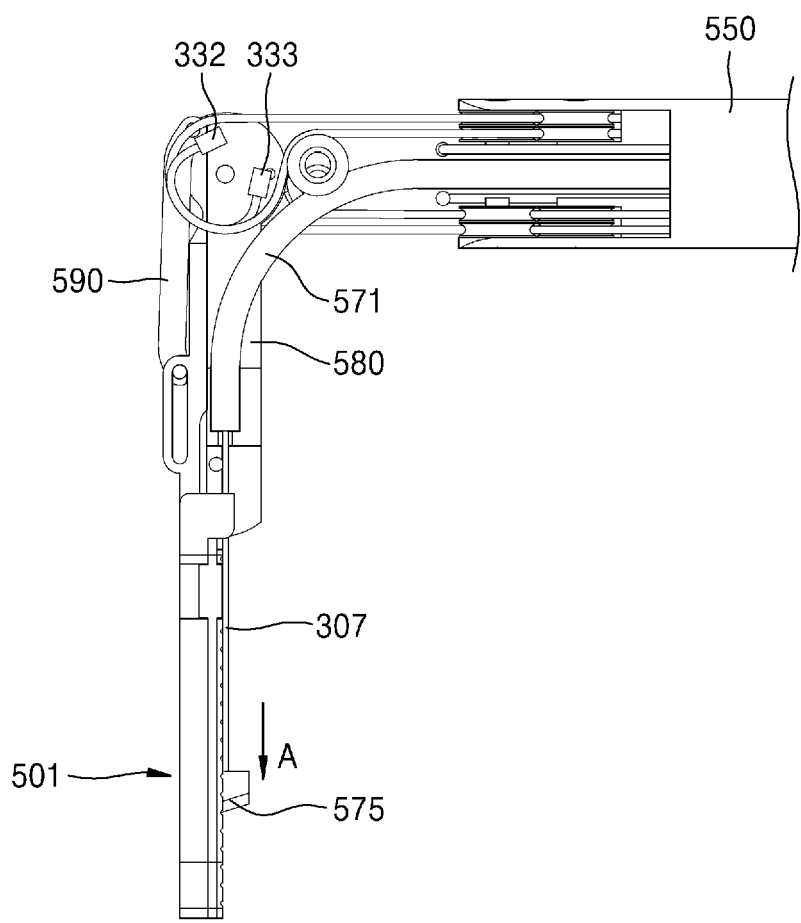

FIGS. 95 and 96 are views illustrating a process of performing a cutting motion while the end tool of the surgical instrument for electrocautery of FIG. 62 is yaw-rotated by +90°.

Figure 97:
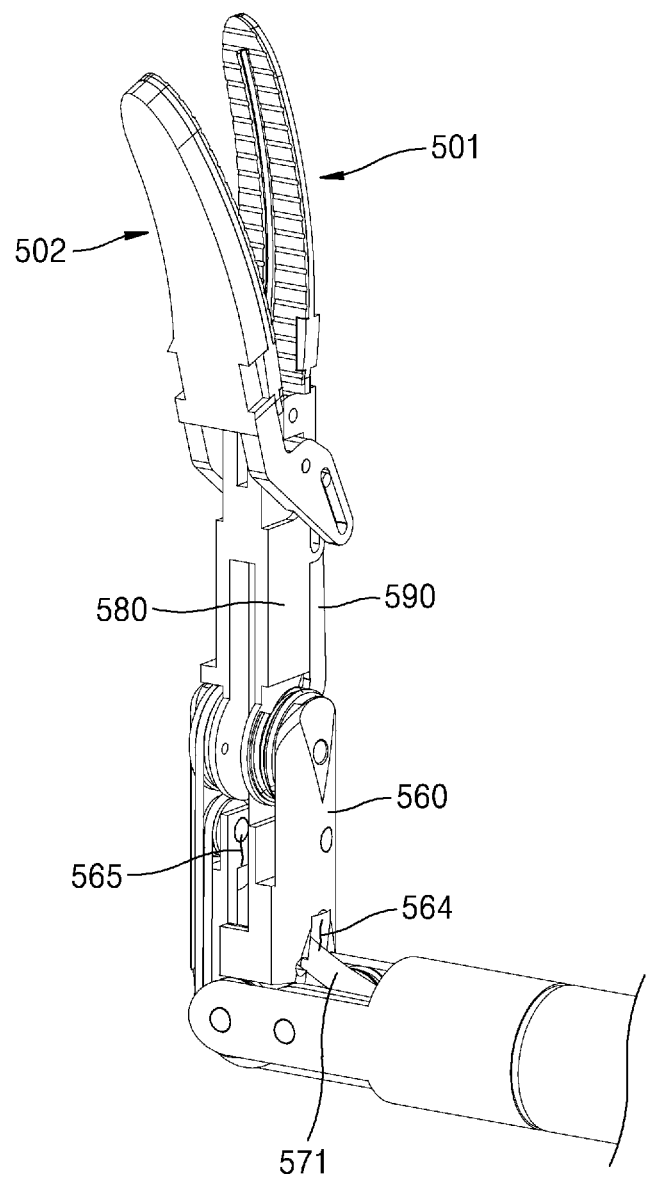

FIG. 97 is a view illustrating a state in which the end tool of the surgical instrument for electrocautery of FIG. 62 is pitch-rotated by −90°.

Figure 98:
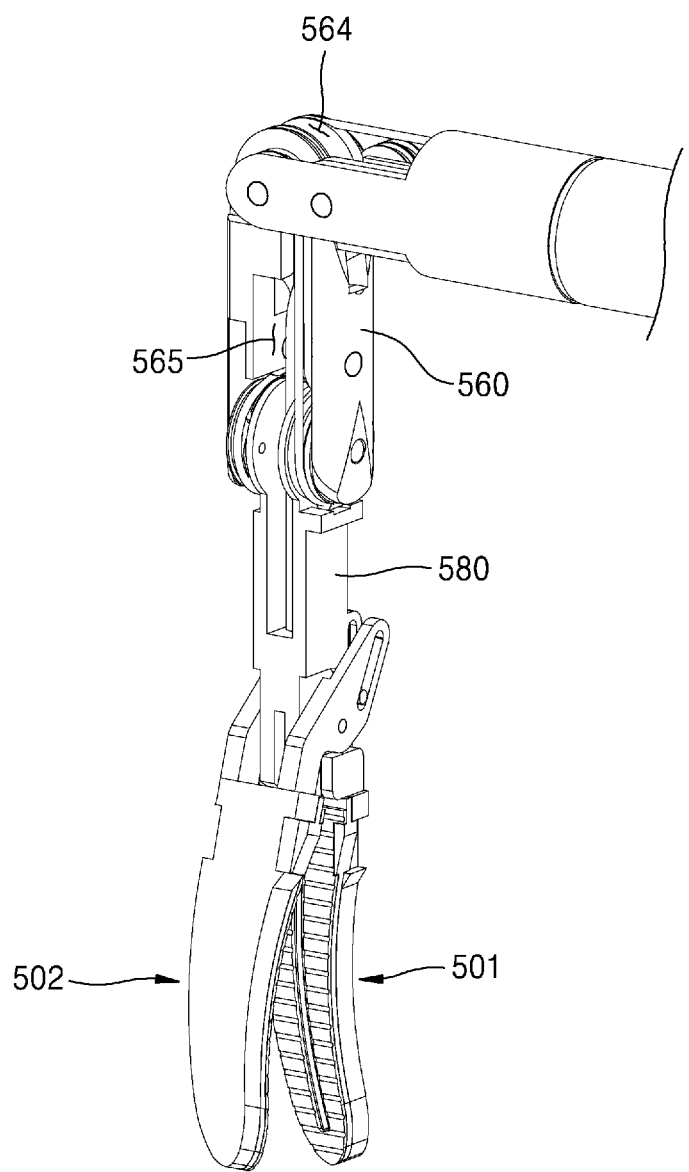

FIG. 98 is a view illustrating a state in which the end tool of the surgical instrument for electrocautery of FIG. 62 is pitch-rotated by +90°.

Figure 99:
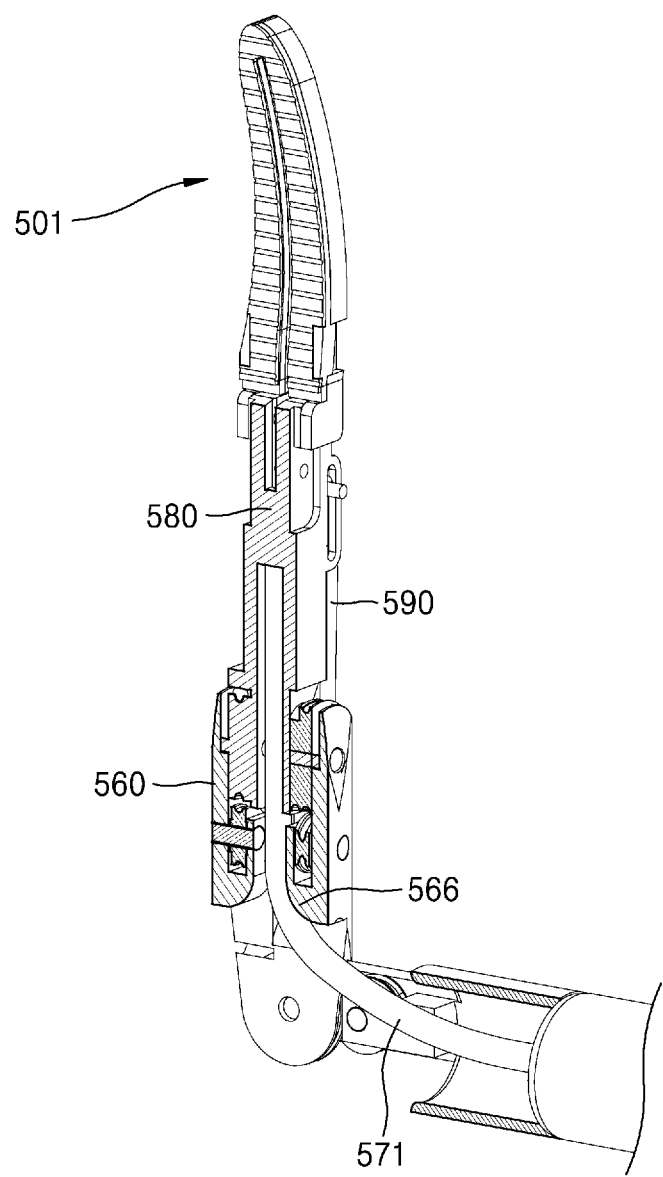

FIG. 99 is a cut-away perspective view of the end tool of the surgical instrument for electrocautery of FIG. 97.

Figure 100:
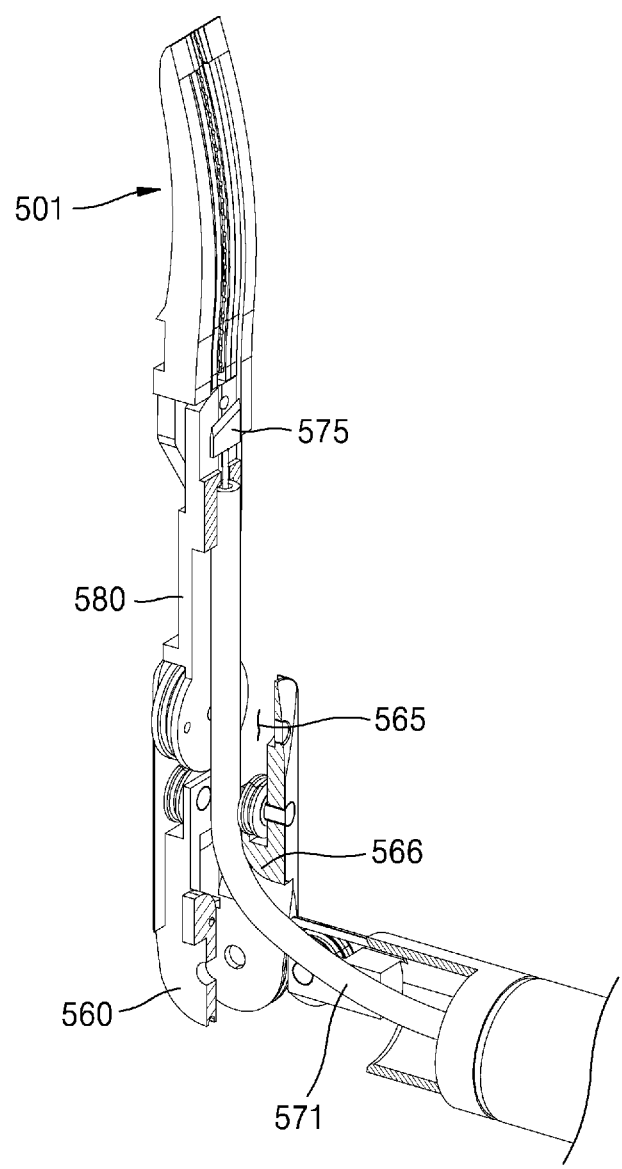
Figure 101:
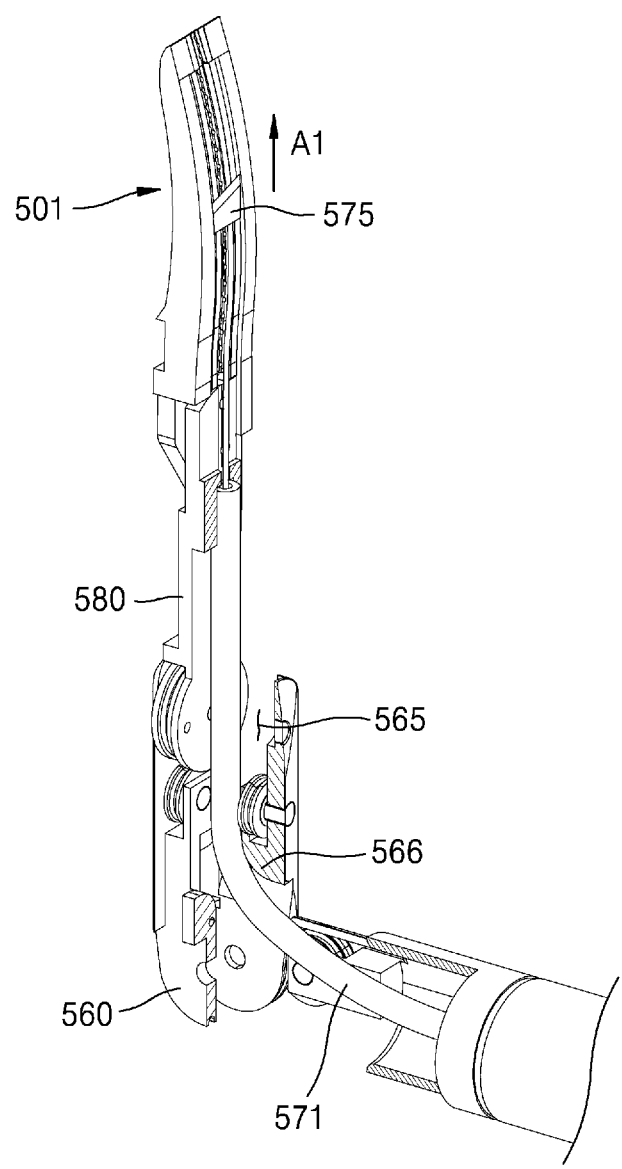
Figure 102:
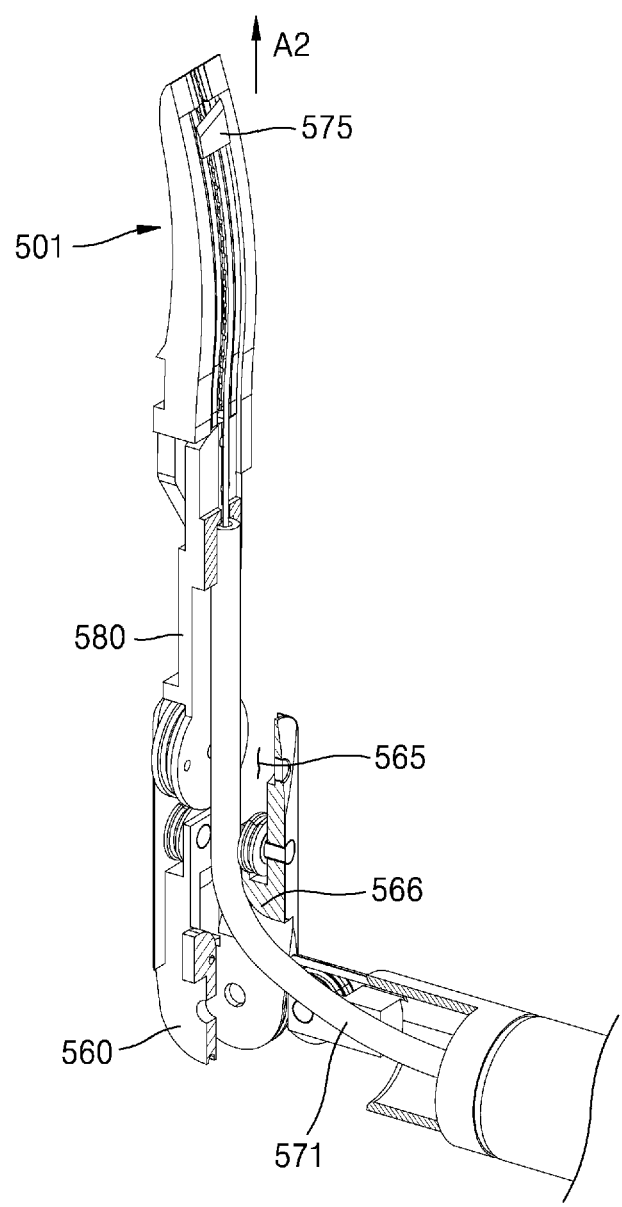

FIGS. 100, 101, and 102 are views illustrating a process of performing a cutting motion while the end tool of the surgical instrument for electrocautery of FIG. 62 is pitch-rotated by −90°.

Figure 103:
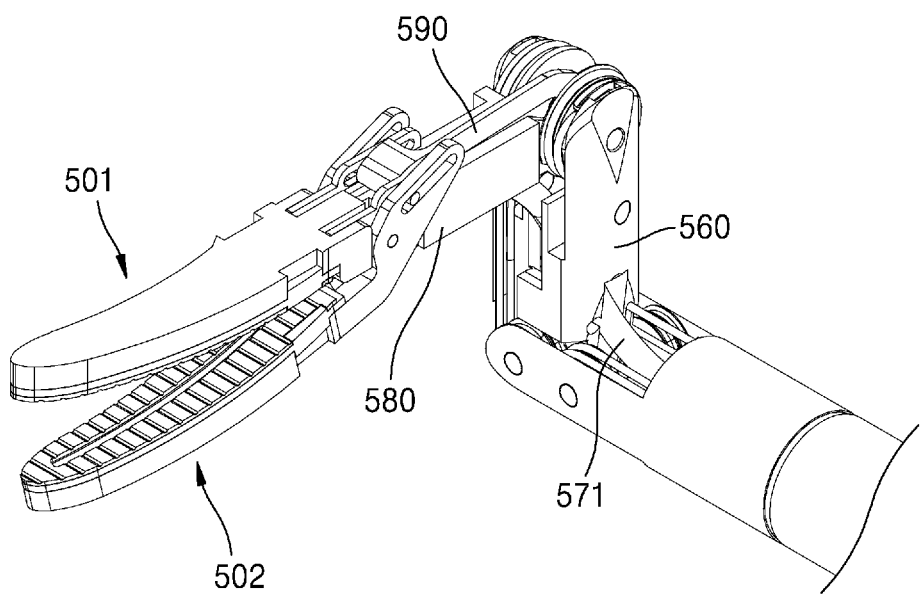

FIG. 103 is a plan view illustrating a state in which the end tool of the surgical instrument for electrocautery of FIG. 62 is pitch-rotated and yaw-rotated.

Figure 104:
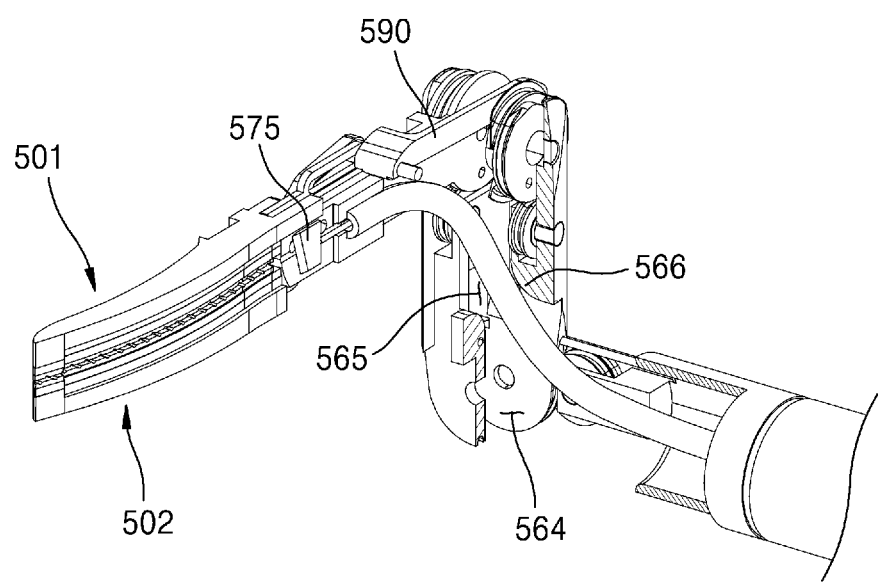
Figure 105:
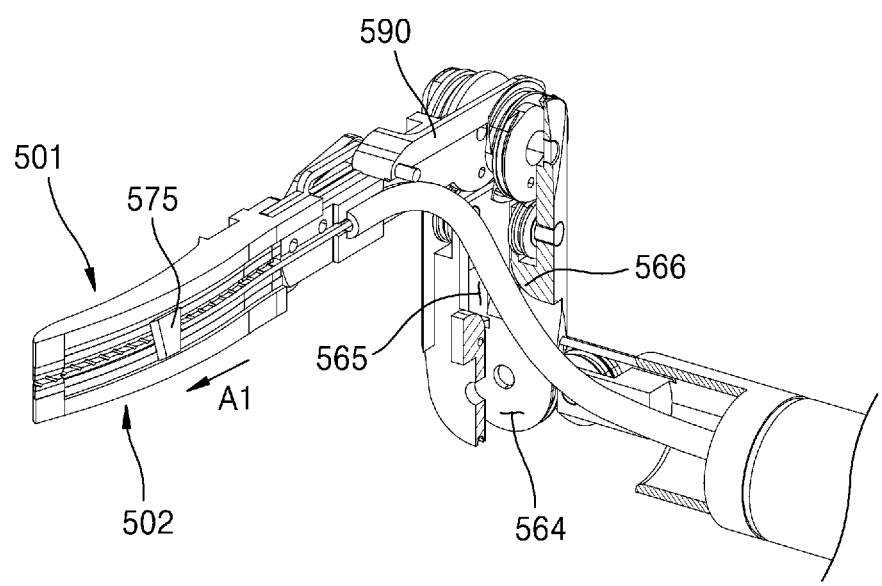
Figure 106:
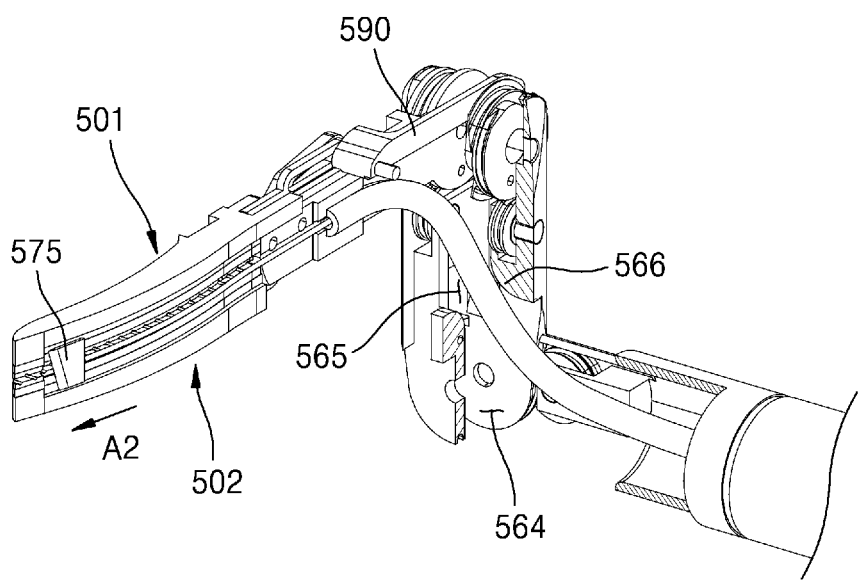

FIGS. 104, 105, and 106 are views illustrating a state of performing a cutting motion while the end tool of the surgical instrument for electrocautery of FIG. 62 is pitch-rotated by −90° and simultaneously yaw-rotated by +90°.

Figure 107:
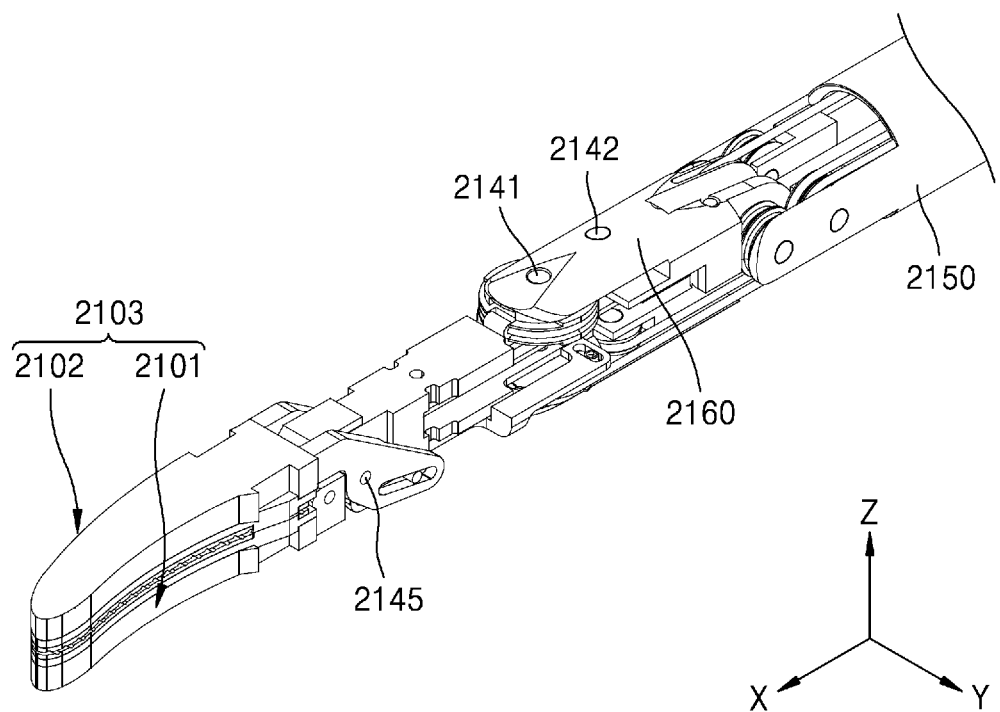
Figure 108:
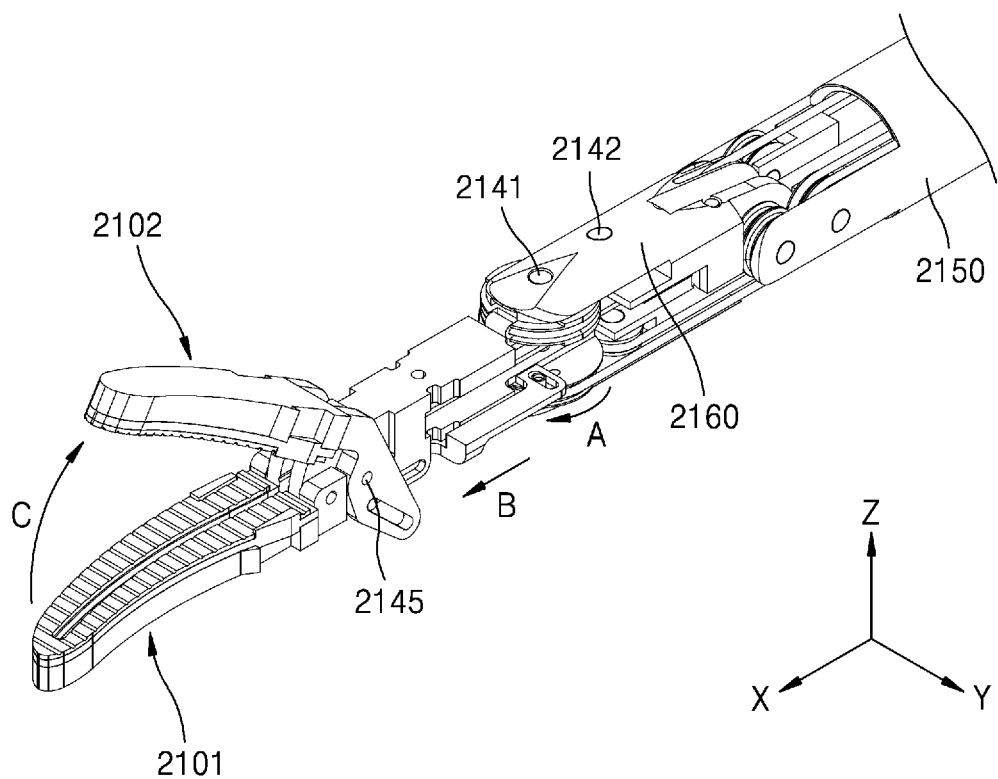
Figure 109:
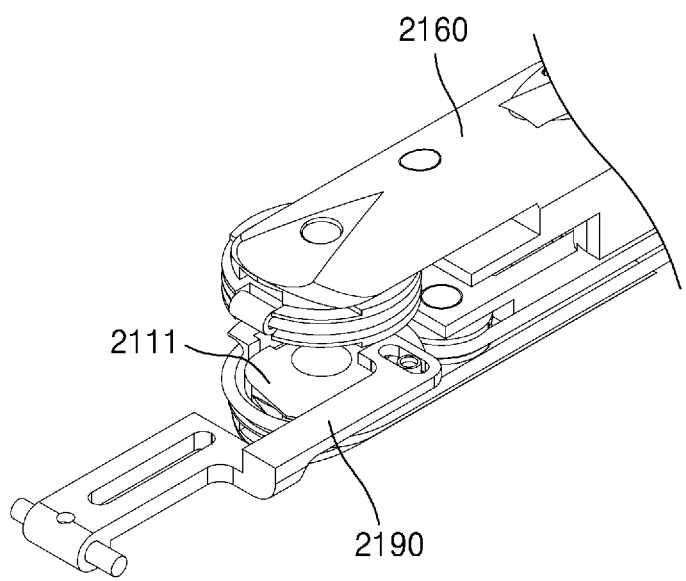
Figure 110:
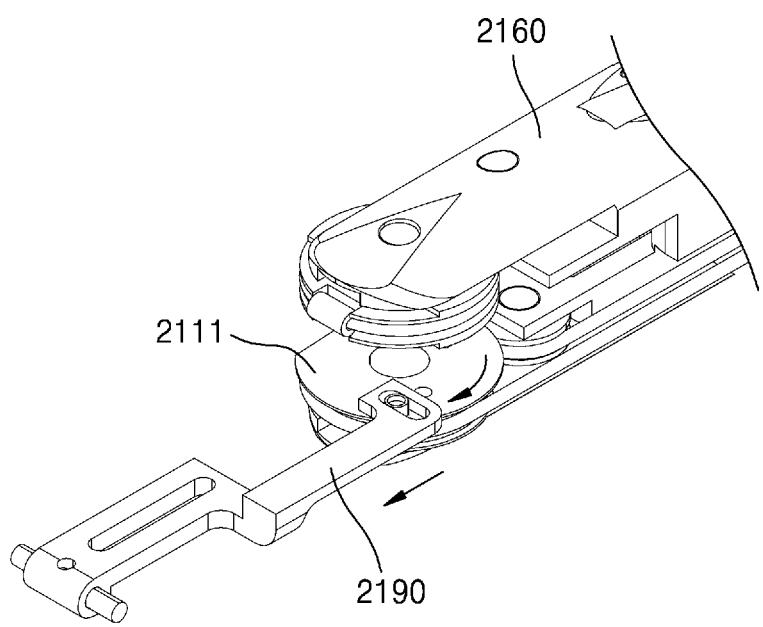
Figure 111:
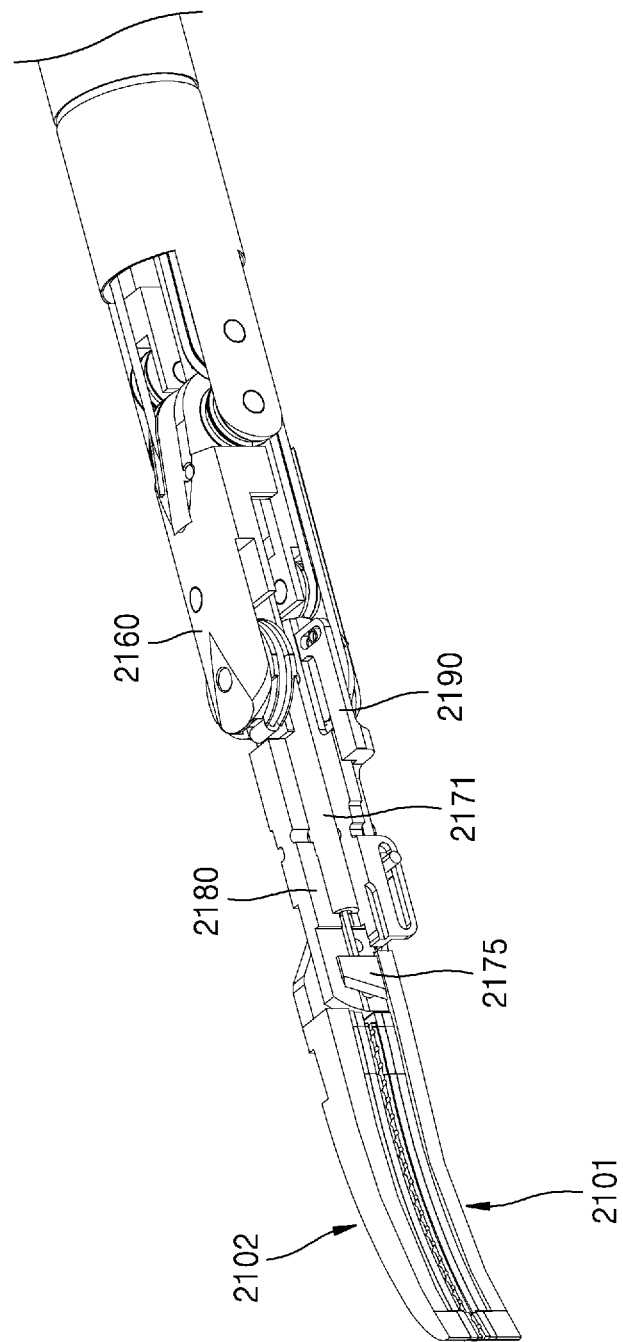
Figure 112:
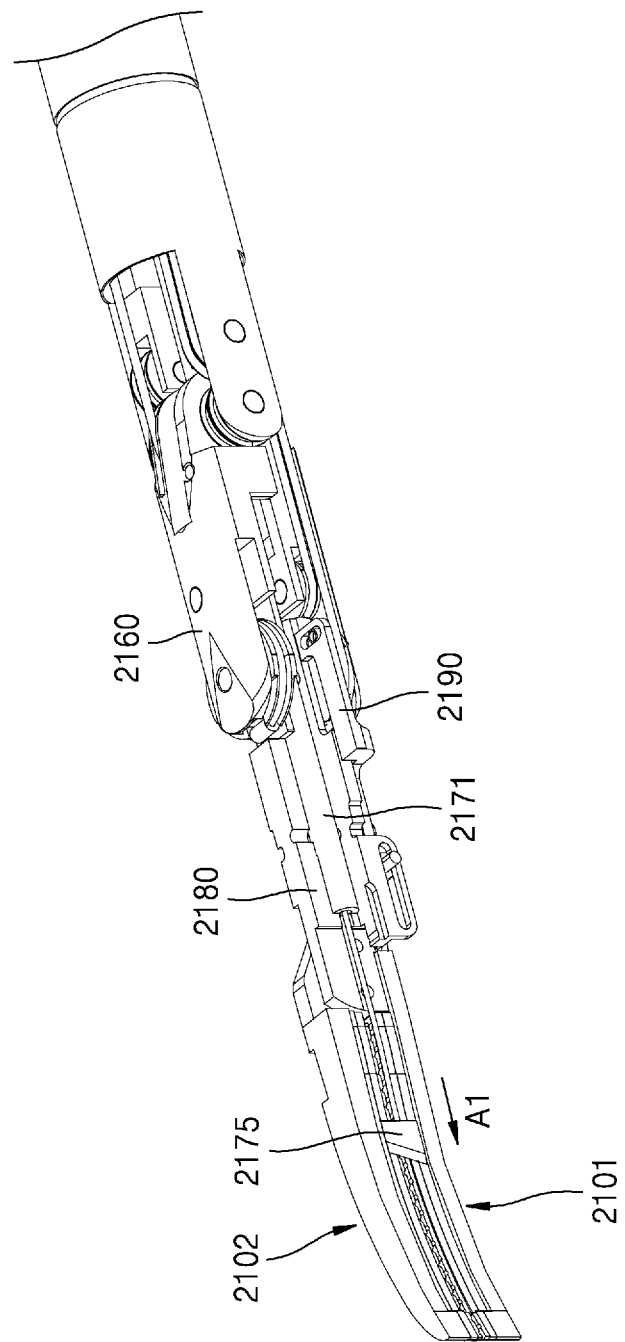
Figure 113:
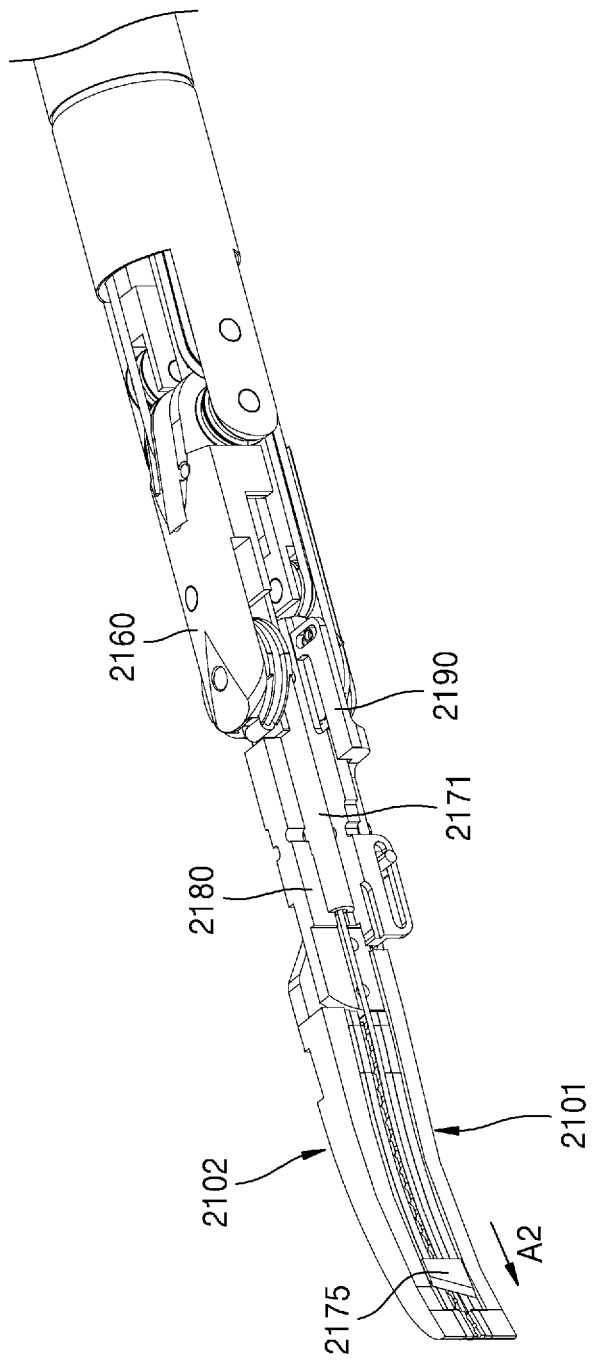

FIGS. 107, 108, 109, and 110 are views illustrating an end tool of a surgical instrument for electrocautery according to a first modified example of the second embodiment of the present disclosure FIGS. 111, 112, and 113 are views illustrating a process in which the end tool of the surgical instrument for electrocautery of FIG. 107 performs a cutting motion.

Figure 114:
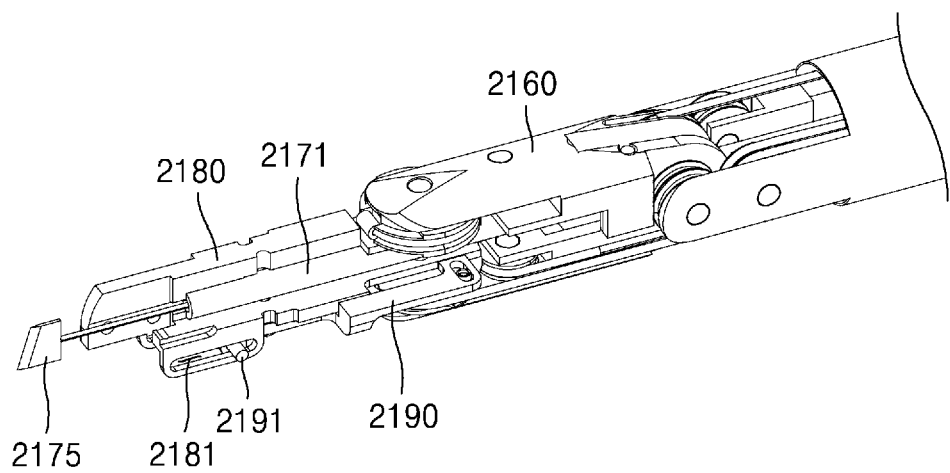

FIG. 114 is a view illustrating the end tool of the surgical instrument for electrocautery of FIG. 107.

Figure 115:
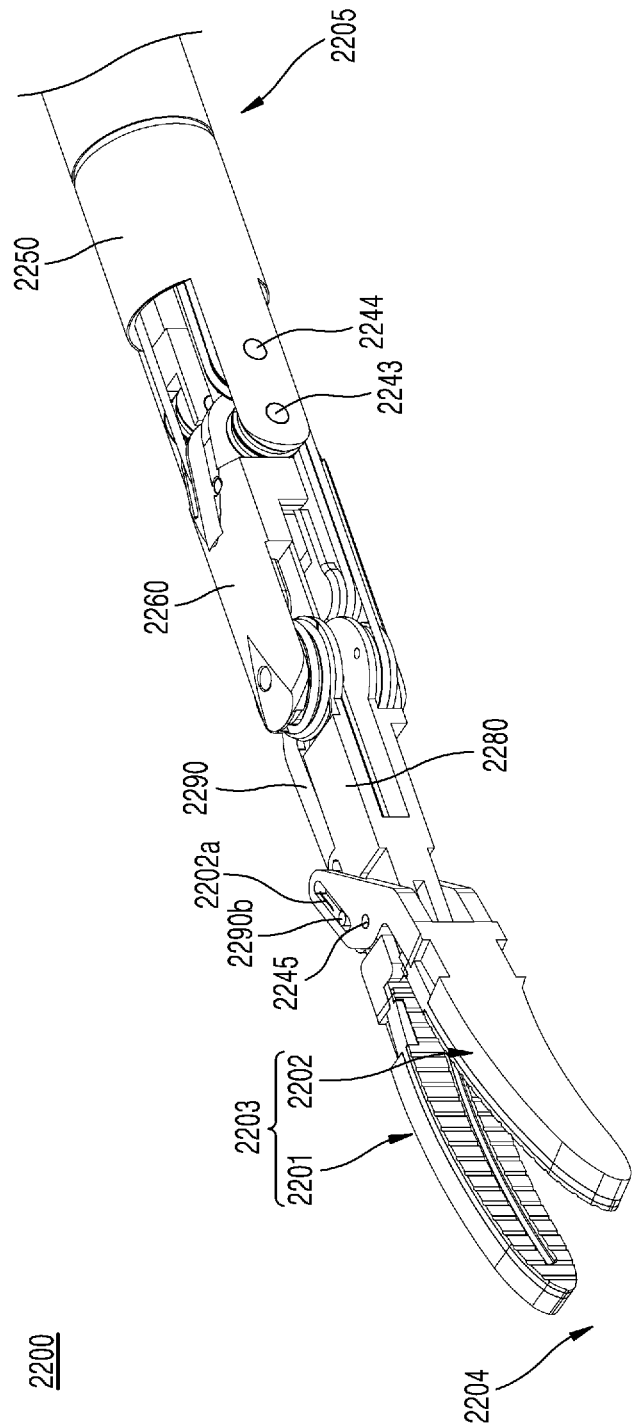
Figure 116:
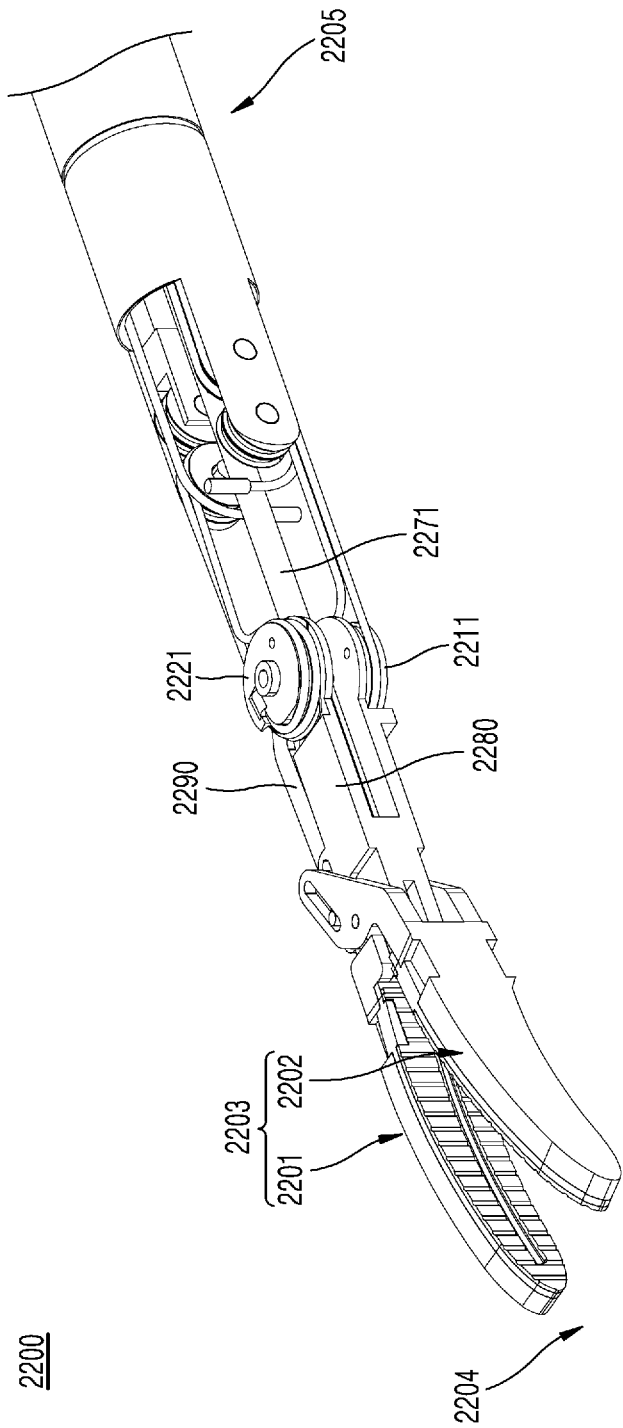

FIGS. 115 and 116 are views illustrating an end tool of a surgical instrument for electrocautery according to a second modified example of the second embodiment of the present disclosure.

Figure 117:
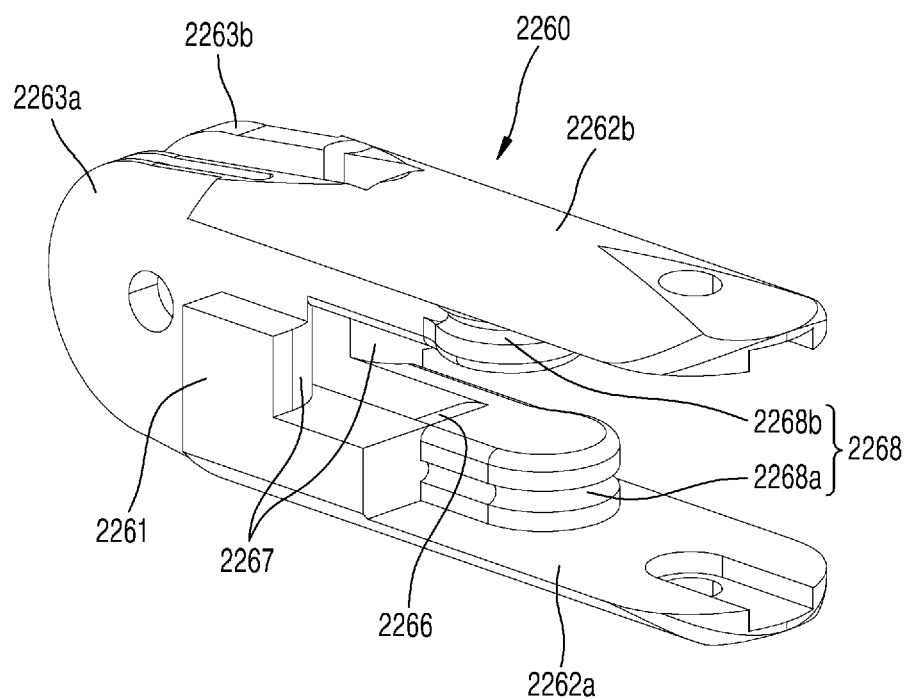

FIG. 117 is a perspective view illustrating an end tool hub of the end tool of the surgical instrument for electrocautery of FIG. 115.

Figure 118:
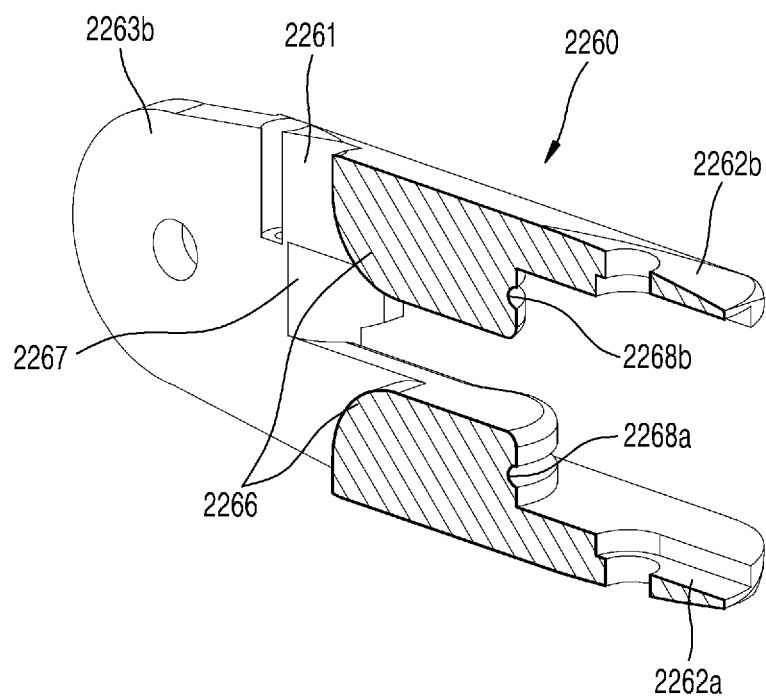
Figure 119:
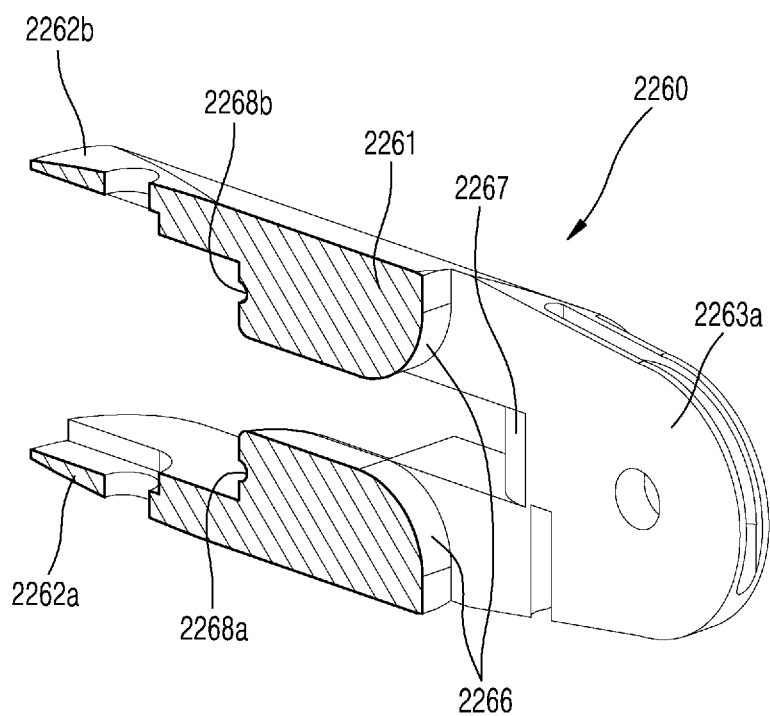

FIGS. 118 and 119 are cut-away perspective views of the end tool hub of FIG. 117.

Figure 120:
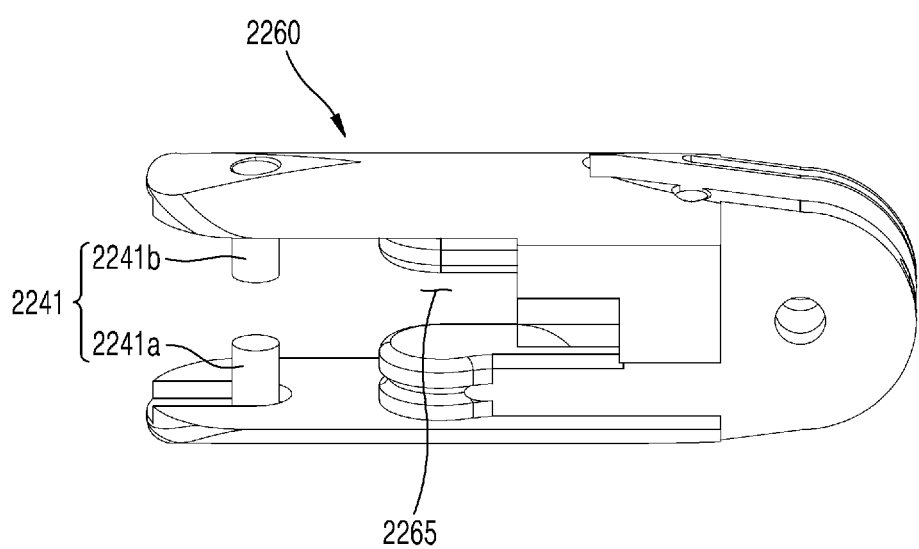
Figure 121:
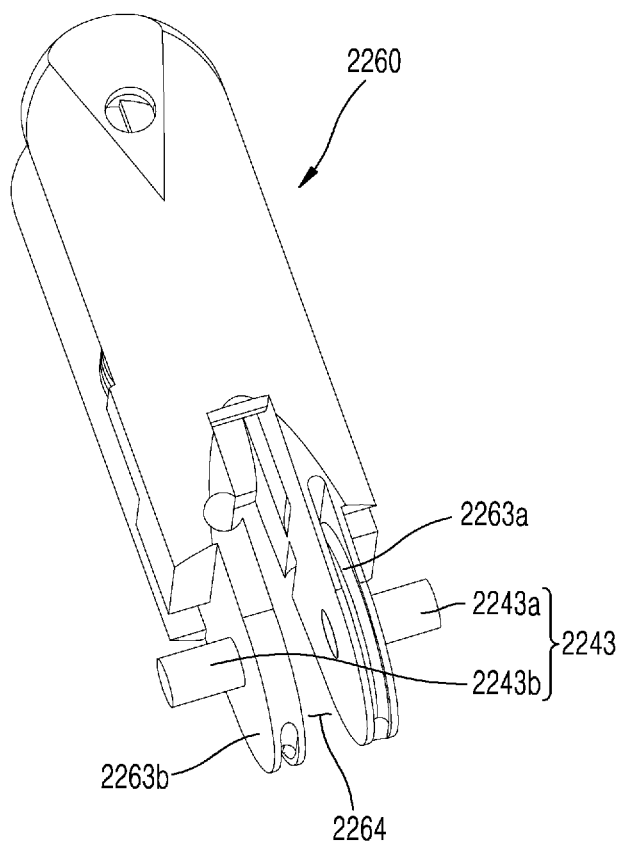

FIGS. 120 and 121 are perspective views of the end tool hub of FIG. 117.

Figure 122:
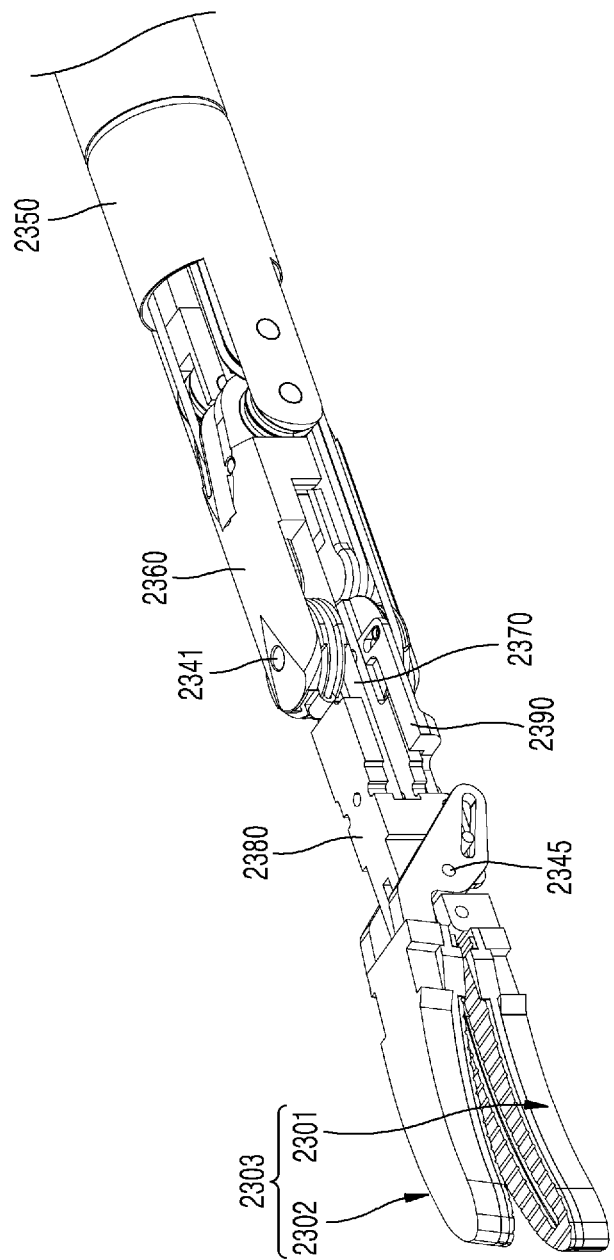
Figure 123:
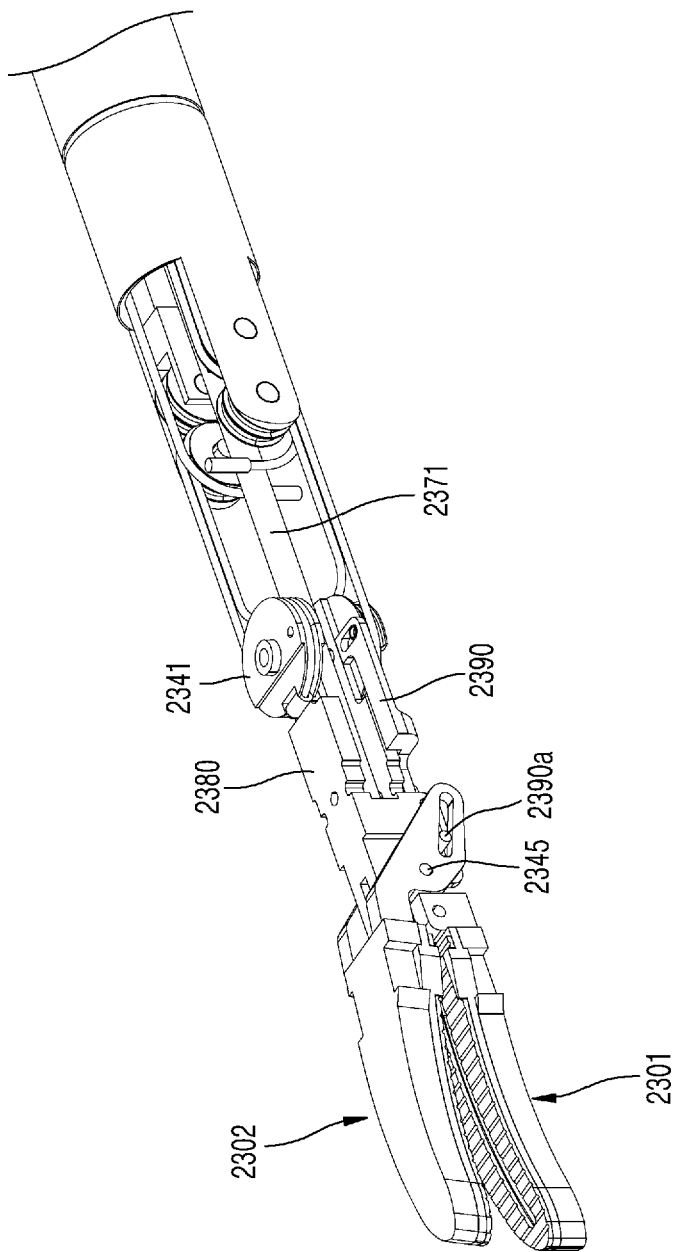

FIGS. 122 and 123 are views illustrating an end tool of a surgical instrument for electrocautery according to a third modified example of the second embodiment of the present disclosure.

Figure 124:
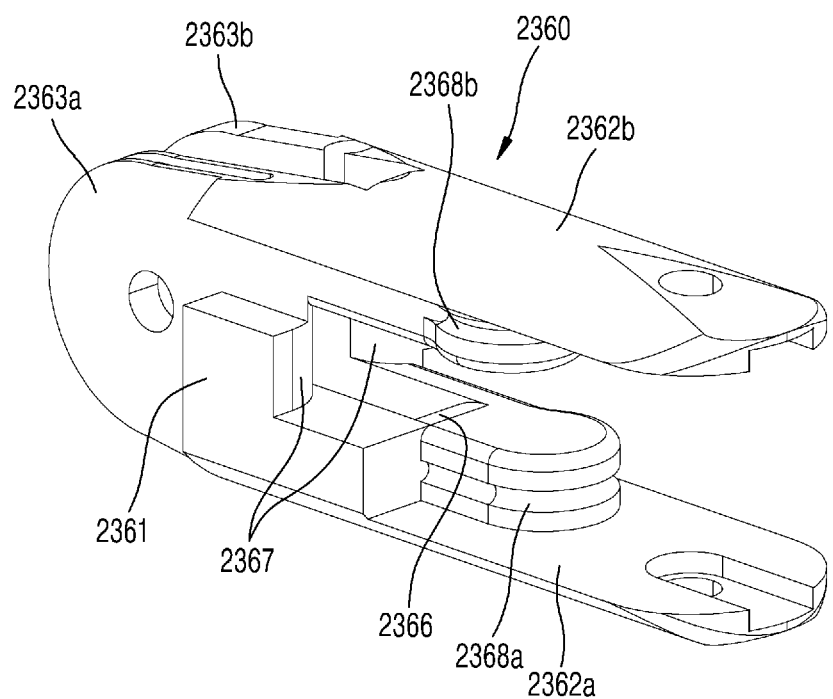

FIG. 124 is a perspective view illustrating an end tool hub of the end tool of the surgical instrument for electrocautery of FIG. 122.

MODE OF DISCLOSURE

As the present disclosure allows for various changes and numerous embodiments, example embodiments will be illustrated in the drawings and described in detail. However, this is not intended to limit the present disclosure to particular modes of practice, and it is to be appreciated that all modifications, equivalents, and/or alternatives that do not depart from the spirit and technical scope are encompassed in the disclosure. In the description of embodiments, certain detailed explanations of the related art are omitted when they are deemed as unnecessarily obscuring the essence of the present disclosure.

While such terms as "first," "second," etc., may be used to describe various components, such components must not be limited by the above terms. The above terms are used only to distinguish one component from another.

The terms used in the present application are merely used to describe example embodiments, and are not intended to limit the present disclosure. As used herein, the singular forms "a," "an" and "the" are intended to include the plural forms as well, unless the context clearly indicates otherwise. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, embodiments of the present disclosure are described in detail with reference to the attached drawings. Like or corresponding reference numerals in the drawings denote like elements, and any redundant descriptions thereon will be omitted.

In addition, in describing various embodiments of the present disclosure, each embodiment does not have to be interpreted or practiced independently, and It should be understood that the technical concepts described in each embodiment may be interpreted or implemented in combination with other embodiments described individually.

In the surgical instrument for electrocautery according to the present disclosure, with respect to one or more motions from a pitch motion, a yaw motion, and an actuation motion, when a manipulation portion is rotated in one direction, an end tool may rotate in a direction intuitively the same as the manipulation direction of the manipulation portion.

Figure 1:
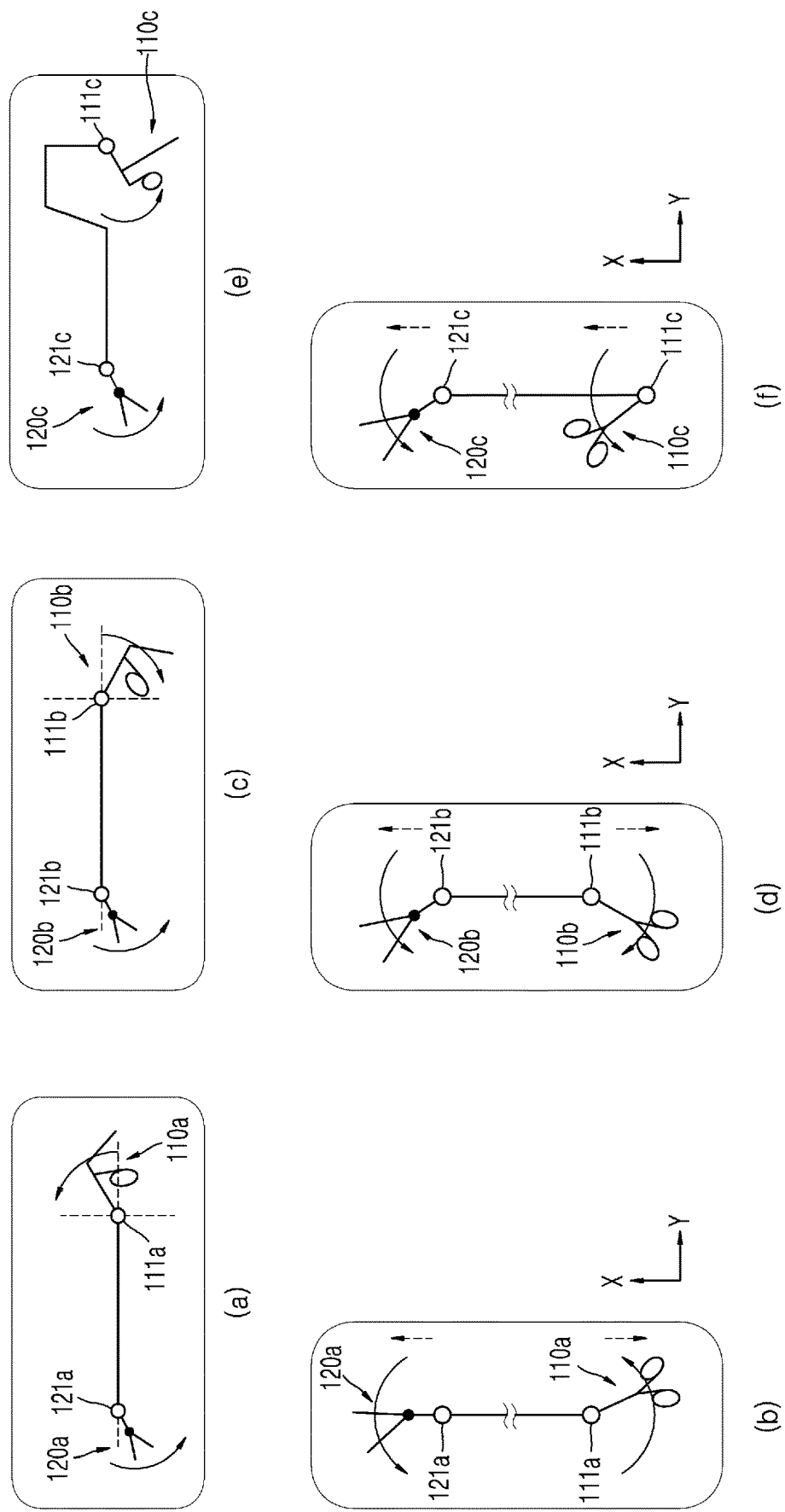

(a) of FIG. 1 is a conceptual diagram of pitch motion of a conventional surgical instrument, and (b) of FIG. 1 is a conceptual diagram of yaw motion.

With reference to (a) of FIG. 1, in performing a pitch motion of a conventional surgical instrument, with an end tool 120a formed in front of a rotation center 121a of the end tool 120a and a manipulation portion 110a formed behind a rotation center 111a of the manipulation portion 110a, when the manipulation portion 110a is rotated in the clockwise direction, the end tool 120a may also be rotated in the clockwise direction, and when the manipulation portion 110a is rotated in the counterclockwise direction, the end tool 120a may also be rotated in the counterclockwise direction. With reference to (b) of FIG. 1, in performing a yaw motion of a conventional surgical instrument, with the end tool 120a formed in front of the rotation center 121a of the end tool 120a and the manipulation portion 110a formed behind the rotation center 111a of the manipulation portion 110a, when the manipulation portion 110a is rotated in the clockwise direction, the end tool 120a may also be rotated in the clockwise direction, and when the manipulation portion 110a is rotated in the counterclockwise direction, the end tool 120a may also be rotated in the counterclockwise direction. In this case, from the viewpoint of left and right sides of a user, when the user moves the manipulation portion 110a to the left, the end tool 120a may move to the right, and when the user moves the manipulation portion 110a to the right, the end tool 120a may move to the left. As a result, as the user manipulation direction is opposite to the end tool operation direction, the user may make a mistake, and have difficulty in manipulating the instrument.

(c) of FIG. 1 is a conceptual diagram of pitch motion of another conventional surgical instrument, and (d) of FIG. 1 is a conceptual diagram of yaw motion.

With reference to (c) of FIG. 1, some of the conventional surgical instruments may be formed in a mirror-symmetrical manner, and in performing a pitch motion, in a state where an end tool 120b is formed in front of a rotation center 121b of the end tool 120b, and a manipulation portion 110b is formed behind a rotation center 111b of the manipulation portion 110b, when the manipulation portion 110b is rotated in the clockwise direction, the end tool 120b may rotate in the counterclockwise direction, and when the manipulation portion 110b is rotated in the counterclockwise direction, the end tool 120b may rotate in the clockwise direction. In this case, from the viewpoint of rotation direction of the manipulation portion 110b and the end tool 120b, a rotation direction in which a user rotates the manipulation portion 110b may be opposite to a resulting rotation direction of the end tool 120b. Not only this may result in causing confusion about the manipulation direction to a user, but also movements of joints are not intuitive, which may lead to a mistake. In addition, with reference to (d) FIG. 1, in performing a yaw motion, in a state where the end tool 120b is formed in front of the rotation center 121b of the end tool 120b, and the manipulation portion 110b is formed behind the rotation center 111b of the manipulation portion 110b, when the manipulation portion 110b is rotated in the clockwise direction, the end tool 120b may rotate in the counterclockwise direction, and when the manipulation portion 110b is rotated in the counterclockwise direction, the end tool 120b may rotate in the clockwise direction. In this case, from the viewpoint of rotation direction of the manipulation portion 110b and the end tool 120b, a rotation direction in which a user rotates the manipulation portion 110b may be opposite to a resulting rotation direction of the end tool 120*b*. Not only this may result in causing confusion about the manipulation direction to a user, but also movements of joints are not intuitive, which may lead to a mistake. As such, in the pitch or yaw manipulation by a user of the conventional surgical instruments, there may be a discrepancy between the user manipulation direction and the operation direction of the end tool in terms of rotation direction or left and right direction. This is due to a configuration difference between the end tool and the manipulation portion in the joint configuration of the conventional surgical instruments. That is, the end tool may be formed in front of the rotation center of the end tool, whereas the manipulation portion may be formed behind the rotation center of the manipulation portion. To overcome such issue, in the surgical instrument according to an embodiment of the present disclosure shown in (e) and (f) of FIG. 1, an end tool 120*c* may be formed in front of a rotation center 121*c* of the end tool 120*c*, and a manipulation portion 110*c* may also be formed in front of a rotation center 111*c* of the manipulation portion 110*c* so that motions of the manipulation portion 110*c* and the end tool 120*c* are intuitively matched. In other words, unlike the existing examples of a configuration in which a manipulation portion approaches a user with respect to its joint (i.e., away from an end tool) as shown in (a), (b), (c), (d) of FIG. 1, in the surgical instrument according to an embodiment shown in (e) and (f) of FIG. 1, at least a part of the manipulation portion may become closer to the end tool than the joint of the manipulation portion in more than one moments during a manipulation process.

In other words, in the case of the conventional surgical instruments shown in (a), (b), (c), and (d) of FIG. 1, as the end tool may be formed in front of its rotation center whereas the manipulation portion may be formed behind its rotation center, the end tool of which front portion moves when its rear portion is fixed may move through a motion of the manipulation portion of which rear portion moves when its front portion is fixed, which is an intuitively unmatching structure. For this reason, a discrepancy in an aspect of left and right direction or an aspect of rotation direction in manipulation of a manipulation portion and motion of an end tool may occur, causing confusion to a user, and the manipulation of the manipulation portion may not be intuitively and quickly performed, which may lead to a mistake. On the contrary, in a surgical instrument according to an embodiment, as both of an end tool and a manipulation portion move based on rotation centers formed behind the end tool and the manipulation portion, respectively, structurally speaking, the motions thereof may intuitively match. In other words, as a moving portion of the end tool moves based on its rotation center formed therebehind, and similarly, a moving portion of the manipulation portion also moves based on its rotation center formed therebehind, structurally, the motions thereof may match intuitively. According to the foregoing, the user may intuitively and quickly control the direction of the end tool, and the possibility of causing a mistake may be significantly reduced. Hereinafter, a detailed mechanism enabling such function will be described.

First Embodiment of a Surgical Instrument for Electrocautery

Figure 9:
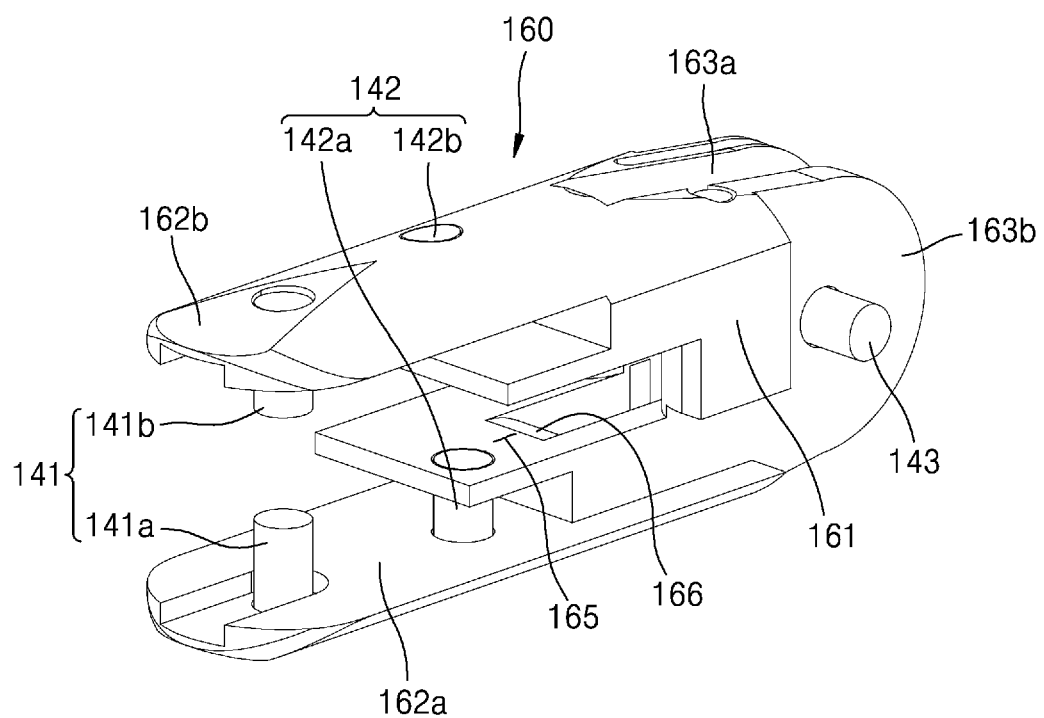
FIGS. 9 and 10 are perspective views illustrating an end tool hub of the end tool of the surgical instrument for electrocautery of FIG. 2.
Figure 10:
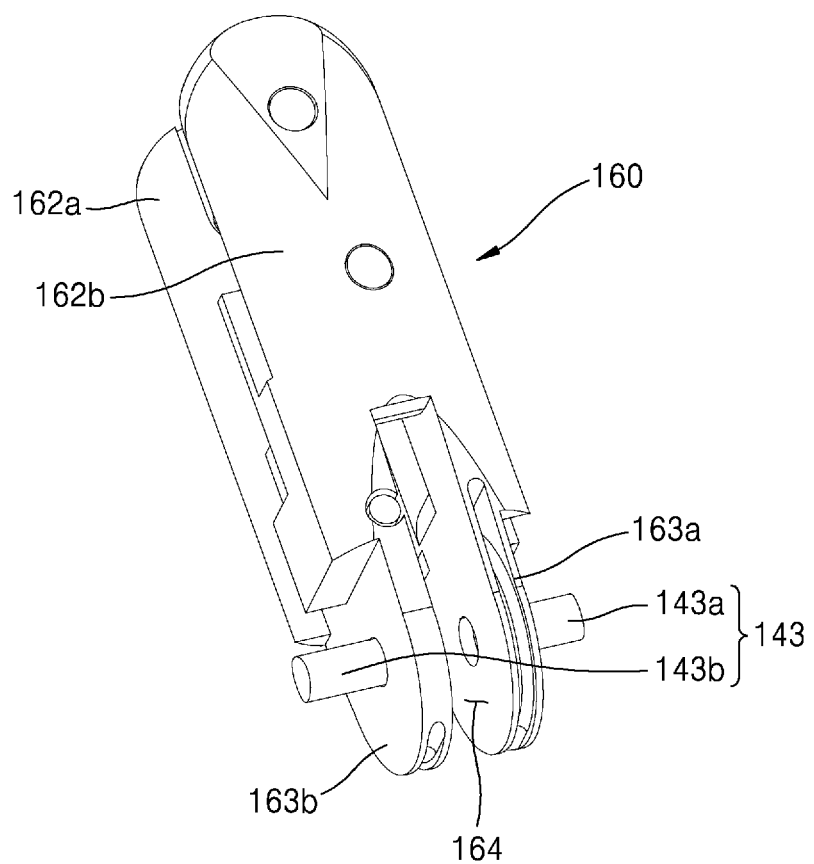
Figure 11:
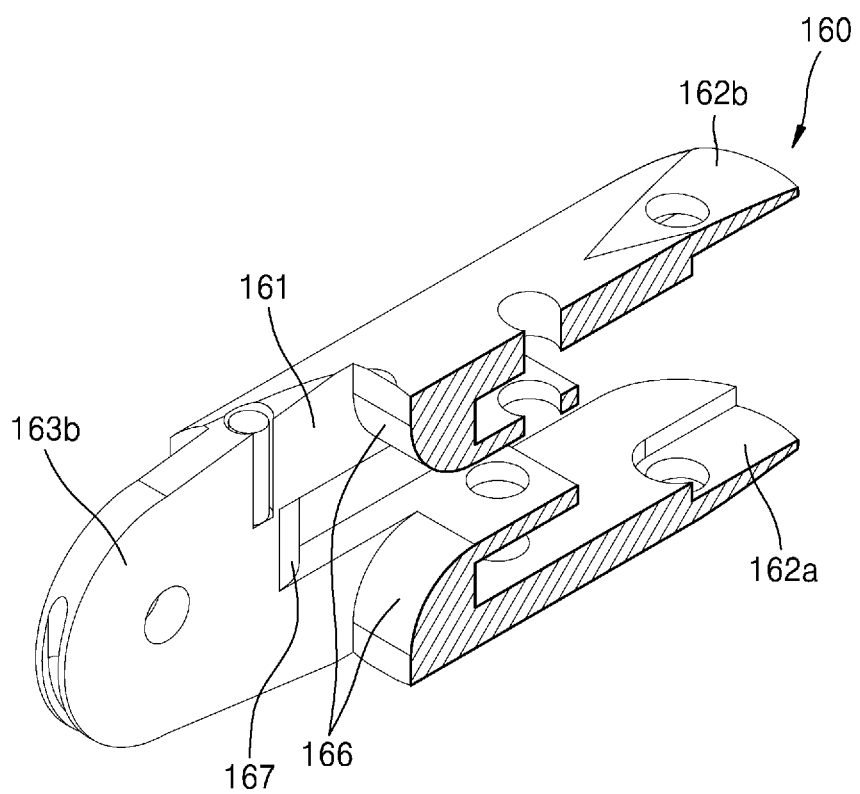
FIG. 11 is a cut-away perspective view of the end tool hub of FIG. 9.
Figure 12:
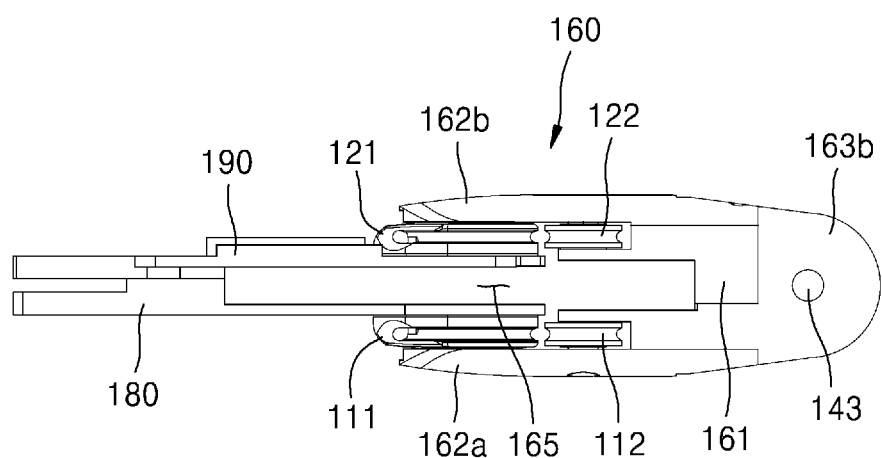
FIG. 12 is a side view illustrating links and the end tool hub of the end tool of the surgical instrument for electrocautery of FIG. 2.
Figure 13:
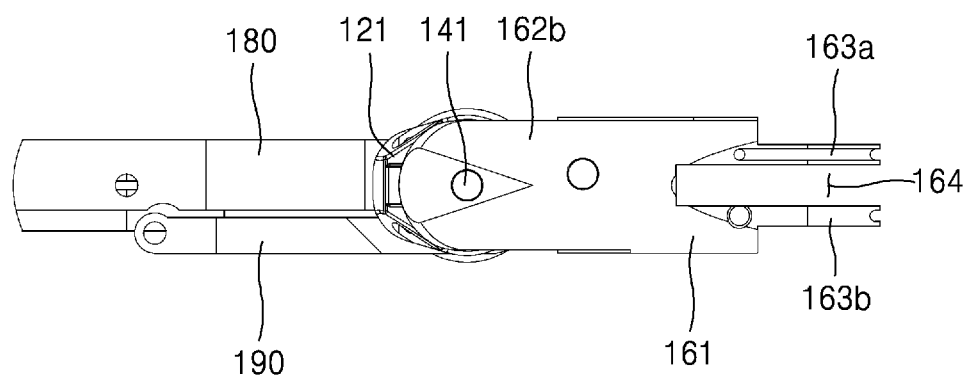
FIG. 13 is a plan view illustrating the links and the end tool hub of the end tool of the surgical instrument for electrocautery of FIG. 2.
Figure 14:
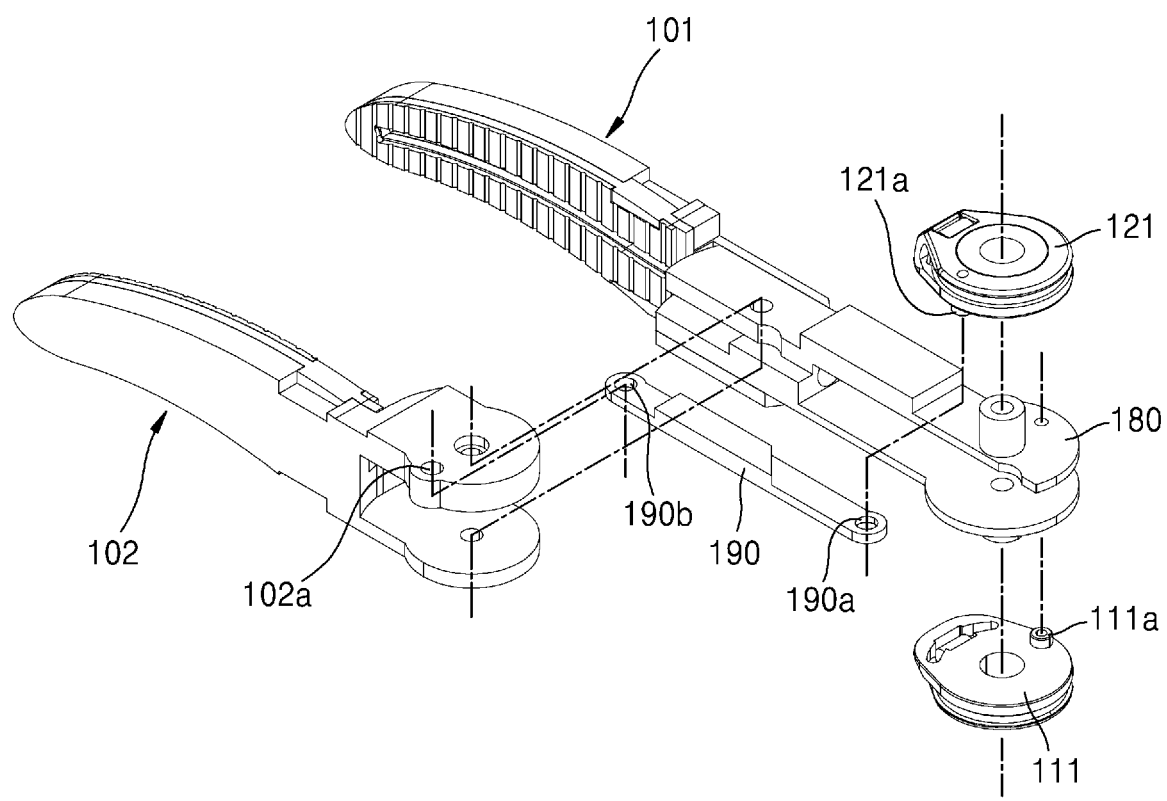
FIG. 14 is an exploded perspective view illustrating jaws-links-jaw pulleys of the end tool of the surgical instrument for electrocautery of FIG. 2.

FIG. 2 is a perspective view showing a surgical instrument for electrocautery according to a first embodiment of the present invention, and FIGS. 3, 4, 5 and 6 are perspective views showing end tool of the surgical instrument for electrocautery of FIG. 2. FIGS. 9 and 10 are perspective views illustrating an end tool hub of the end tool of the surgical instrument for electrocautery of FIG. 2. FIG. 11 is a cut-away perspective view of the end tool hub of FIG. 9. FIG. 12 is a side view illustrating links and the end tool hub of the end tool of the surgical instrument for electrocautery of FIG. 2. FIG. 13 is a plan view illustrating the links and the end tool hub of the end tool of the surgical instrument for electrocautery of FIG. 2. FIG. 14 is an exploded perspective view illustrating jaws-links-jaw pulleys of the end tool of the surgical instrument for electrocautery of FIG. 2.

First, with reference to FIG. 2, the electric cauterization surgical instrument 10 according to the first embodiment may include an end tool 100, a manipulation portion 200, a power transmission portion 300, and a connection portion 400.

Here, the connection portion 400 may be formed in the shape of a hollow shaft, and one or more wires and electric wires may be accommodated therein. As the manipulation portion 200 is coupled to one end of the connection portion 400, and the end tool 100 is coupled to the other end, the connection portion 400 may connect the manipulation portion 200 to the end tool 100. The connection portion 400 of the electric cauterization surgical instrument 10 according to the first embodiment may include a straight portion 401 and a curved portion 402. The straight portion 401 may be formed at a part of the connection portion 400 to which the end tool 100 is coupled, and the curved portion 402 may be formed at another part of the connection portion 400 to which the manipulation portion 200 is coupled. As such, as the end of the connection portion 400 coupled to the manipulation portion 200 is curved, a pitch manipulation portion 201, a yaw manipulation portion 202, and an actuation manipulation portion 203 may be arranged on an extension line of the end tool 100 or adjacent to the extension line of the end tool 100. In other words, at least a part of the pitch manipulation portion 201 and the yaw manipulation portion 202 may be accommodated in a concave portion formed by the curved portion 402. According to the shape of the curved portion 402 described above, the shape and motion of the manipulation portion 200 and the end tool 100 may match each other more intuitively.

Meanwhile, a plane on which the curved portion 402 is formed may be a pitch plane which is substantially the same as the XZ plane of FIG. 2. As such, as the curved portion 402 is formed on the plane substantially identical to the XZ plane, interference between the manipulation portions may be reduced. For intuitive operation of the end tool 100 and the manipulation portion 200, the plane may be configured otherwise in addition to the foregoing (i.e., the XZ plane).

Meanwhile, a connector 410 may be formed at the curved portion 402. The connector 410 may be connected to an external power supply (not illustrated), and the connector 410 may be connected to a jaw 103 through electric wires 411 and 412 to transfer electrical energy supplied from the external power supply (not illustrated) to the jaw 103. The connector 410 may be of a bipolar type having two electrodes, or the connector 410 may be of a monopolar type having one electrode.

The manipulation portion 200 may be formed at one end of the connection portion 400 and may include an interface which can be directly manipulated by a doctor, e.g., an interface in the shape of a pincer, a stick, a lever, etc. When the doctor manipulates the interface, the end tool 100, which is connected to the interface and inserted into the body of a patient, may be operated and perform a surgery. Here, although FIG. 2 illustrates that the manipulation portion 200 is formed in the shape of a handle which may be rotated while fingers are inserted, the present disclosure is not limited thereto, and various types of manipulation portions connected to the end tool 100 and manipulating the end tool 100 may be applicable.

The end tool 100 may be formed at the other end of the connection portion 400 and may be inserted into a body of a patient to perform operations required for a surgery. As an example of the end tool 100, a pair of jaws 103 for performing a grip motion may be used as illustrated in FIG. 2. However, the technical concepts of the present disclosure are not limited thereto, and various other surgical instruments may be used as the end tool 100. For example, a one-armed cautery may be used as the end tool 100. As the end tool 100 is connected to the manipulation portion 200 by the power transmission portion 300, the end tool 100 may receive driving power of the manipulation portion 200 through the power transmission portion 300 and perform motions required for a surgery, such as a grip motion, a cutting motion, a suturing motion, etc.

Here, the end tool 100 of the electric cauterization surgical instrument 10 according to the first embodiment may be formed to be rotatable in at least one direction, and for example, the end tool 100 may be formed to perform a yaw movement and an actuation movement around the Z-axis of FIG. 2 simultaneously with performing a pitch movement around the Y-axis of FIG. 2.

Each of the pitch, yaw, and actuation motions used in the present disclosure are defined as follows.

First, the pitch motion may refer to a motion that the end tool 100 rotates up and down with respect to a direction in which the connection portion 400 extends (i.e., the X-axis direction of FIG. 2), that is, a movement of rotating around the Y-axis of FIG. 2. In other words, the pitch motion may refer to a movement that the end tool 100 extending from the connection portion 400 in the direction in which the connection portion 400 extends (i.e., the X-axis direction in FIG. 2) rotates up and down around the Y-axis with respect to the connection portion 400.

Next, the yaw motion may refer to a motion that the end tool 100 rotates left and right with respect to the direction in which the connection portion 400 extends (i.e., the X-axis direction of FIG. 2), that is, a motion of rotating around the Z-axis of FIG. 2. In other words, the yaw motion may refer to a movement that the end tool 100 extending from the connection portion 400 in the direction in which the connection portion 400 extends (i.e., the X-axis direction in FIG. 2) rotates left and right around the Z-axis with respect to the connection portion 400. That is, the yaw motion means a movement that the two jaws 103 formed at the end tool 100 rotate around the Z-axis in the same direction.

The actuation motion may refer to a motion that the end tool 100 rotates around the same rotation shaft as in the yaw motion or a rotation shaft that is parallel to that in the yaw motion, or and two jaws 103 rotate in opposite directions by which the jaws 103 are closed together or opened up. That is, the actuation motion may refer to a movement that the two jaws 103 formed at the end tool 100 rotate in opposite directions around the Z-axis. In an embodiment, the actuation motion may refer to a motion in which, while one of the jaws is stopped, the other jaw rotates with respect to the jaw that is stopped. That is, the actuation motion may refer to a motion in which one jaw rotates with respect to the other jaw.

The power transmission portion 300 may transfer the driving power of the manipulation portion 200 to the end tool 100 by connecting the manipulation portion 200 to the end tool 100, and may include a plurality of wires, pulleys, links, joints, gears, etc.

The end tool 100, the manipulation portion 200, the power transmission portion 300, etc. of the electric cauterization surgical instrument 10 of FIG. 2 will be described in detail later.

(Intuitive Driving)

Hereinafter, the intuitive driving of the electric cauterization surgical instrument 10 of the present disclosure is described.

First, a user may hold with his or her palm and rotate a first handle 204 around the Y-axis (i.e., a rotation shaft 246 of FIG. 25) to perform the pitch motion, and may rotate the first handle 204 around the Z-axis (i.e., a rotation shaft 243 of FIG. 25) to perform the yaw motion. In addition, the user may insert his or her thumb and index finger into a first actuation extension portion 252 and/or a second actuation extension portion 257 formed in the shape of a handle at one end of the actuation manipulation portion 203 and manipulate the actuation manipulation portion 203 to perform the actuation motion.

In the electric cauterization surgical instrument 10 according to the first embodiment of the present disclosure, when the manipulation portion 200 rotates in one direction with respect to the connection portion 400, the end tool 100 may rotate in a direction intuitively the same as a manipulation direction of the manipulation portion 200. In other words, when the first handle 204 of the manipulation portion 200 rotates in one direction, the end tool 100 may also rotate in a direction intuitively the same as the aforementioned direction to perform a pitch motion or a yaw motion. Here, the intuitively same direction may indicate that the moving direction of a finger of a user holding the manipulation portion 200 is substantially the same as the moving direction of an end portion of the end tool 100. The same direction may not be a perfectly matching direction on three-dimensional (3D) coordinates. For example, the sameness of the direction may be understood as a certain degree of sameness, with which, when the finger of the user moves to the left, the end portion of the end tool 100 may also move to the left, and when the finger of the user moves downwards, the end portion of the end tool 100 may also move downwards.

To this end, in the electric cauterization surgical instrument 10 according to the first embodiment, the manipulation portion 200 and the end tool 100 may be formed in the same direction with respect to a plane perpendicular to the extension axis (the X-axis) of the connection portion 400. That is, when seen based on the YZ plane of FIG. 2, the manipulation portion 200 may be formed to extend in the +X-axis direction, and at the same time, the end tool 100 may also be formed to extend in the +X-axis direction. In other words, the formation direction of the end tool 100 at one end of the connection portion 400 and the formation direction of the manipulation portion 200 at the other end of the connection portion 400 may be described as the same direction based on the YZ plane. Alternatively, the manipulation portion 200 may be formed in a direction proceeding away from a body of a user holding the manipulation portion 200, i.e., a direction towards the end tool 100. That is, in the first handle 204, the first actuation manipulation portion 251, and the second actuation manipulation portion 256, etc., which are held and moved by a user for the actuation motion, the yaw motion, and the pitch motion, the moving portions thereof for the respective motions may extend in the +X axis direction in comparison with the rotation centers of each joint for the respective motions. Based on the foregoing, the moving portion of the end tool 100 may extend in the +X axis direction in comparison with the rotation center of each joint for the respective motions, and the manipulation portion 200 may also be configured in the same manner. Then, as described above with reference to FIG. 1, the user manipulation direction may match the operation direction of the end tool in terms of rotation direction and left and right direction, which leads to intuitively matching manipulation.

More specifically, in the case of a conventional surgical instrument, as a direction in which the user manipulates the manipulation portion and an actual operation direction of the end tool are different and not intuitively the same, an operator may have difficulty in intuitive operation, and may need to use much time to become familiar with directing the end tool in a desired direction. In one embodiment, in some cases, a malfunction may occur, which can cause a damage to a patient.

To overcome such issue, in the electric cauterization surgical instrument 10 according to the first embodiment, the manipulation direction of the manipulation portion 200 may be intuitively identical to the operation direction of the end tool 100, and to this end, a portion of the manipulation portion 200 which actually moves for the actuation motion, the yaw motion, and the pitch motion may extend in the +X-axis direction in comparison with a rotation center of a joint for the respective motions as in the end tool 100.

Hereinafter, the end tool 100, the manipulation portion 200, the power transmission portion 300, etc. of the electric cauterization surgical instrument 10 of FIG. 2 will be described in more detail.

(Power Transmission Portion)

Hereinafter, the power transmission portion 300 of the electric cauterization surgical instrument 10 of FIG. 2 will be described in more detail.

With reference to FIGS. 2 to 25, the power transmission portion 300 of the electric cauterization surgical instrument 10 according to an embodiment may include a wire 301, a wire 302, a wire 303, a wire 304, a wire 305, a wire 306, and a blade wire 307.

Here, the wire 301 and the wire 305 may form a pair and serve as a first jaw wire. The wire 302 and the wire 306 may form a pair to serve as a second jaw wire. Here, a component encompassing the wire 301 and the wire 305, which are the first jaw wire, and the wire 302 and the wire 306, which are the second jaw wire may be referred to as a jaw wire. The wire 303 and the wire 304 may form a pair to serve as a pitch wire.

In addition, the power transmission portion 300 of the electric cauterization surgical instrument 10 according to an embodiment may include a fastening member 321, a fastening member 322, a fastening member 323, a fastening member 324, a fastening member 326, and a fastening member 327, which are coupled to each end of the respective wires to combine the wires with the pulleys. Here, each fastening member may have various shapes as needed, such as a ball shape, a tube shape, etc.

Here, on the end tool 100's side, the fastening member 321/fastening member 322 may serve as a pitch wire-end tool fastening member, the fastening member 323 may serve as a first jaw wire-end tool fastening member, and the fastening member 326 may serve as a second jaw wire-end tool fastening member.

In addition, on the manipulation portion 200's side, the fastening member 324 may serve as a first jaw wire-manipulation portion fastening member, and the fastening member 327 may serve as a second jaw wire-manipulation portion fastening member. Furthermore, although it is not illustrated in the drawings, a pitch wire-manipulation portion fastening member and a blade wire-manipulation portion fastening member may be further arranged on the manipulation portion 200's side.

The combination relation among the wires, the fastening members, and each pulley is described in detail below.

First, the wire 301 and the wire 305, which are the first jaw wire, may be a single wire. The fastening member 323 which is the first jaw wire-end tool fastening member, may be fit into a middle point of the first jaw wire and when the fastening member 323 is fixed through crimping, two strands of the first jaw wire on either side of the fastening member 323 may be referred to as the wire 301 and the wire 305, respectively.

Alternatively, the wire 301 and the wire 305, which are the first jaw wire, may be formed as separate wires, and the wire 301 and the wire 305 may be connected to each other by the fastening member 323.

In one embodiment, as the fastening member 323 is coupled to a pulley 111, the wire 301 and the wire 305 may be fixedly coupled to the pulley 111. In this manner, the pulley 111 may rotate as the wire 301 and the wire 305 are pulled and unwound.

In the wire 301 and the wire 305, the first jaw wire-manipulation portion fastening member 324 may be coupled to an end opposite to the end to which the fastening member 323 is coupled.

As the first jaw wire-manipulation portion fastening member 324 is coupled to a pulley 211, the wire 301 and the wire 305 may be fixedly coupled to the pulley 211. As a result, when the pulley 211 is rotated by a motor or human force, the pulley 111 of the end tool 100 may rotate as the wire 301 and the wire 305 are pulled and unwound.

Similar to the above, each of the wire 302 and the wire 306, which are the second jaw wire, may be coupled to the second jaw wire-end tool fastening member 326 and the second jaw wire-manipulation portion fastening member 327, respectively. The fastening member 326 may be coupled to a pulley 121, and the second jaw wire-manipulation portion fastening member 327 may be coupled to a pulley 220. As a result, when the pulley 220 is rotated by a motor or human force, the pulley 121 of the end tool 100 may rotate as the wire 302 and the wire 306 are pulled and unwound.

Likewise, the wire 304, which is the pitch wire, may be coupled to the pitch wire-end tool fastening member 321 and the pitch wire-manipulation portion fastening member (not illustrated), respectively. In addition, the wire 303, which is a pitch wire, is combined with a fastening member 322, which is a pitch wire-end tool fastening member, and a pitch wire-manipulation portion fastening member (not illustrated).

Further, the fastening member 321 may be coupled to a first pitch pulley portion 163a of an end tool hub 160, the fastening member 322 may be coupled to a second pitch pulley portion 163b of the end tool hub 160, and the pitch wire-manipulation portion fastening member (not illustrated) may be coupled to a pulley 231. As a result, when the pulley 231 is rotated by a motor or human force, the end tool hub 160 of the end tool 100 may rotate as the wire 303 and the wire 304 are pulled and unwound.

Meanwhile, the end portion of the blade wire 307 may be coupled to a blade 175 to be described later, and the other end portion thereof may be coupled to the blade manipulation portion 260 of the manipulation portion 200. By the manipulation of the blade manipulation portion 260, a cutting motion may be performed while the blade wire 307 moves from a proximal end 105 of the end tool 100 to a distal end 104 thereof, or the blade wire 307 may return from the distal end 104 of the end tool 100 to the proximal end 105 thereof.

In this regard, at least a part of the blade wire 307 may be accommodated in a guide tube 171 to be described later. Therefore, when the guide tube 171 is curved according to the pitch motion or yaw motion of the end tool 100, the blade wire 307 accommodated therein may also be curved together with the guide tube 171. The guide tube 171 will be described in more detail later.

In an embodiment, the blade wire 307 may formed to move linearly along the longitudinal direction of the connection portion 400 within the connection portion 400. Since the end portion of the blade wire 307 is coupled to the blade 175, when the blade wire 307 linearly moves along the longitudinal direction of the connection portion 400, the blade 175 connected thereto also performs a linear motion. That is, when the blade wire 307 linearly moves along the longitudinal direction of the connection portion 400, the blade 175 connected thereto performs a cutting motion while moving toward the distal end 104 or the proximal end 105 of the end tool 100. This will be described in more detail later.

(End Tool)

Hereinafter, the end tool 100 of the electric cauterization surgical instrument 10 of FIG. 2 will be described in more detail.

FIG. 2 is a perspective view showing a surgical instrument for electrocautery according to a first embodiment of the present invention, and FIGS. 3, 4, 5 and 6 are perspective views showing end tool of the surgical instrument for electrocautery of FIG. 2. FIGS. 9 and 10 are perspective views illustrating an end tool hub of the end tool of the surgical instrument for electrocautery of FIG. 2. FIG. 11 is a cut-away perspective view of the end tool hub of FIG. 9. FIG. 12 is a side view illustrating links and the end tool hub of the end tool of the surgical instrument for electrocautery of FIG. 2. FIG. 13 is a plan view illustrating the links and the end tool hub of the end tool of the surgical instrument for electrocautery of FIG. 2. FIG. 14 is an exploded perspective view illustrating jaws-links-jaw pulleys of the end tool of the surgical instrument for electrocautery of FIG. 2.

Figure 3:
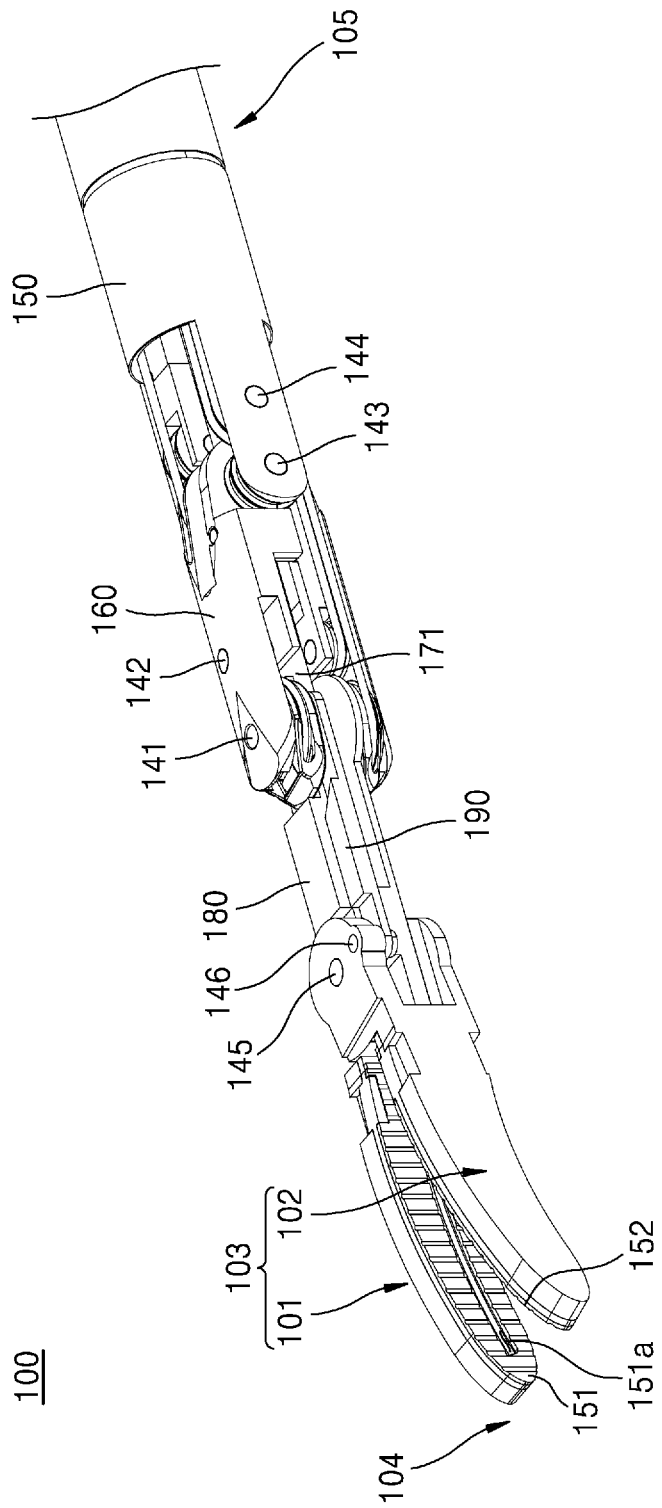
Figure 4:
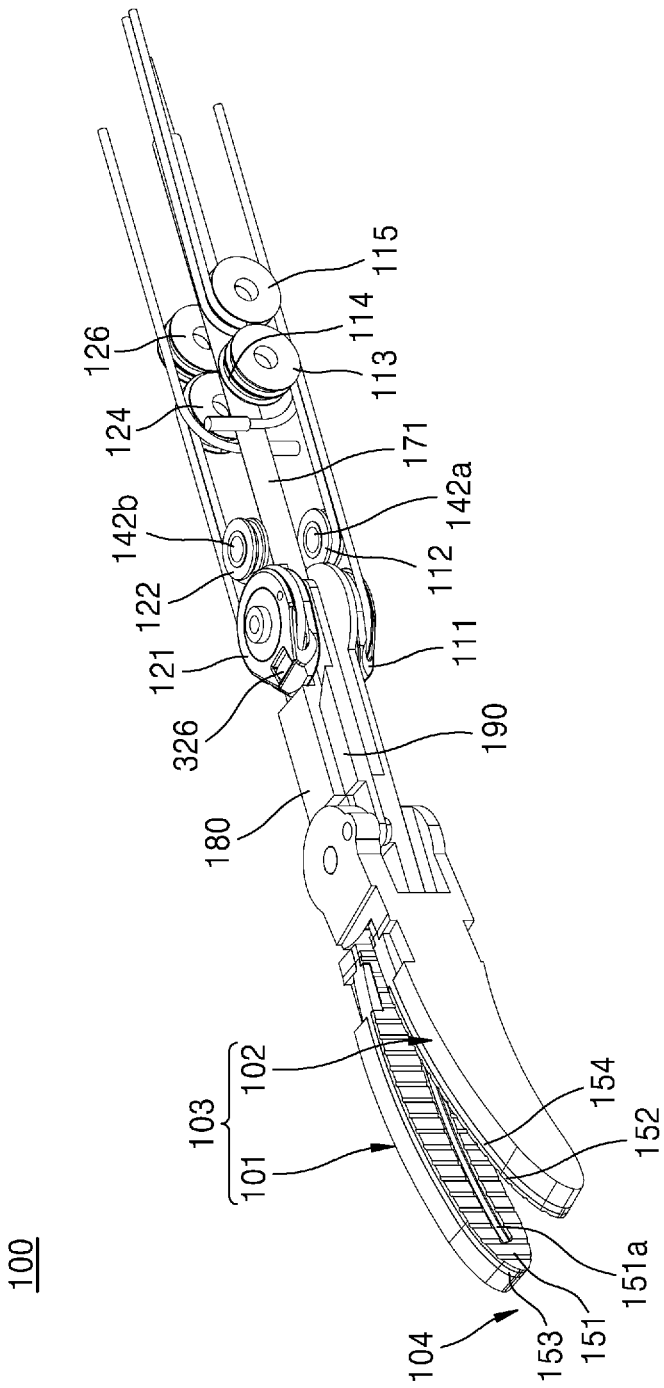
Figure 5:
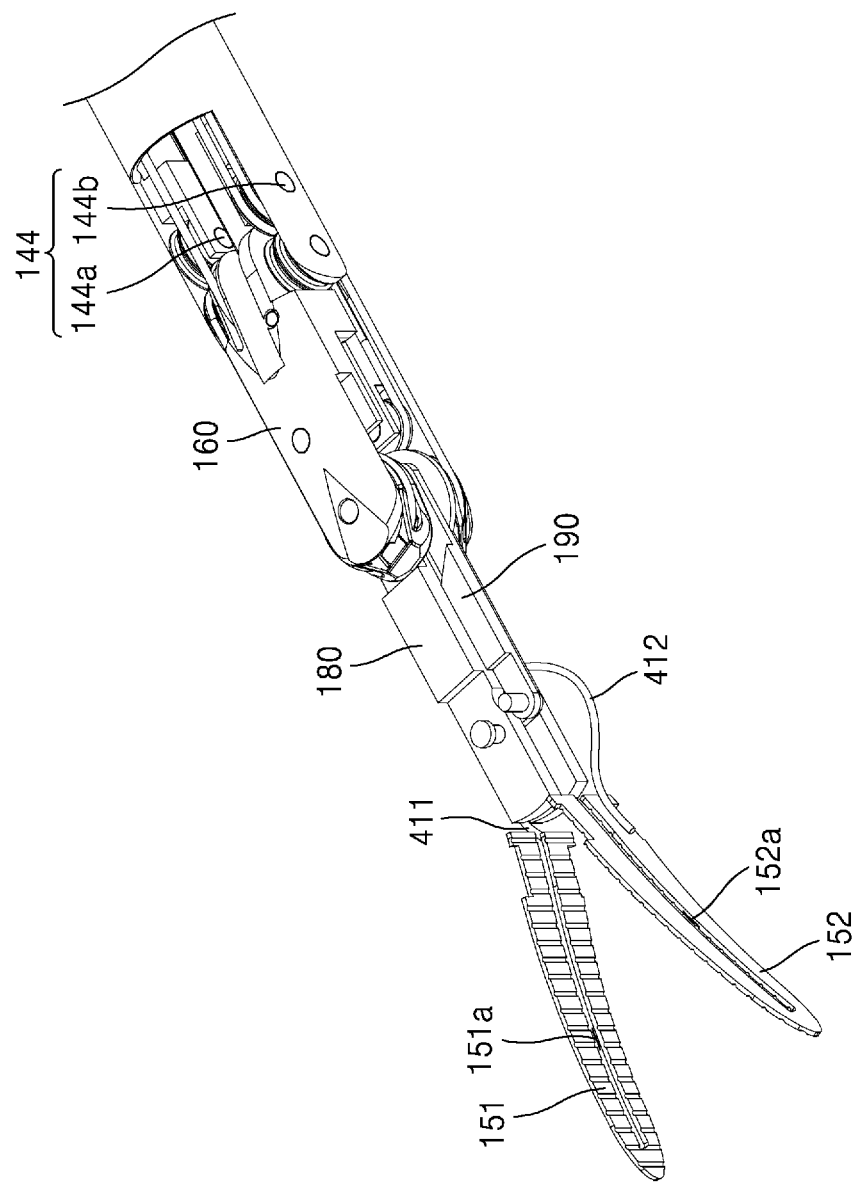
Figure 6:
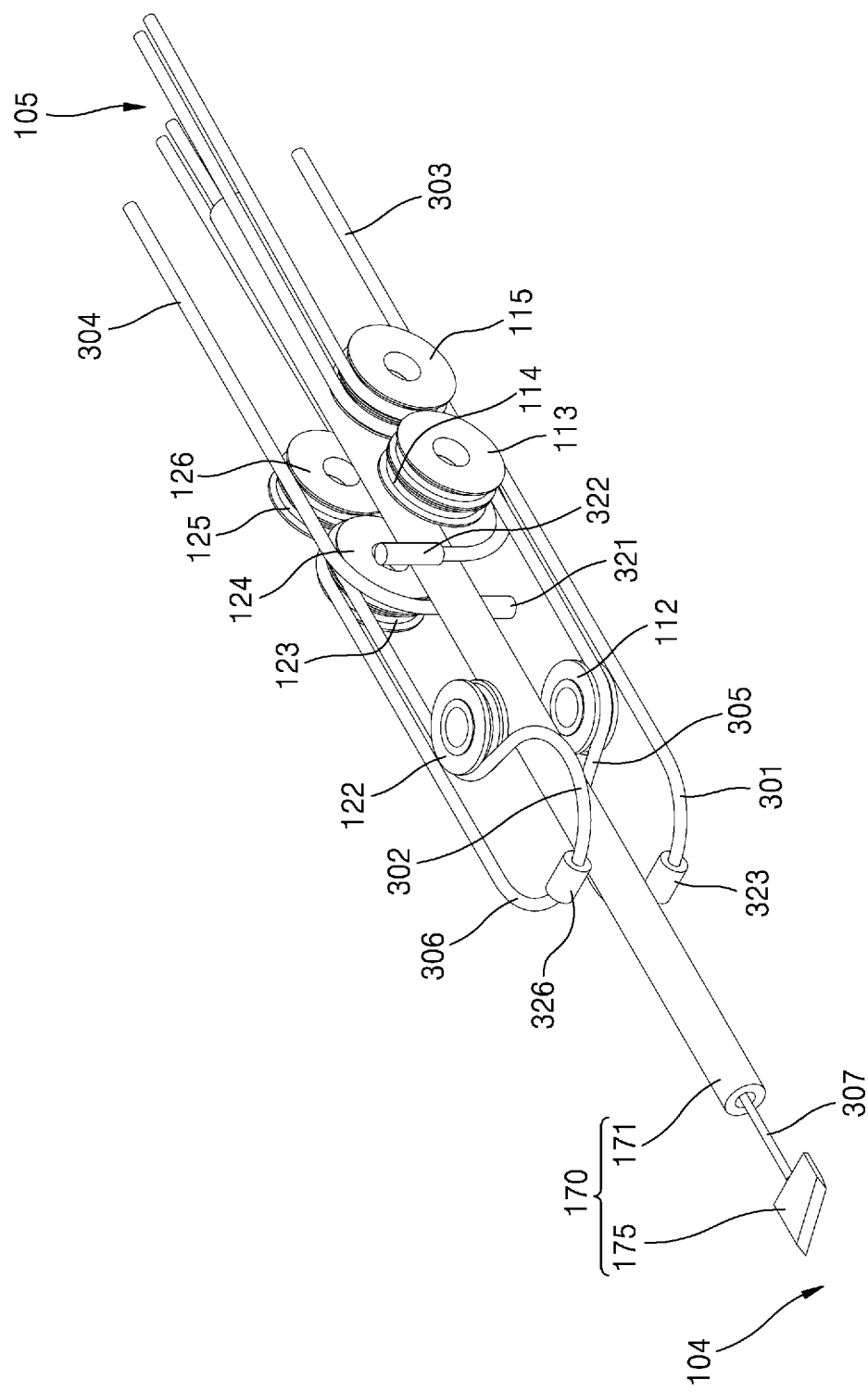
Figure 7:
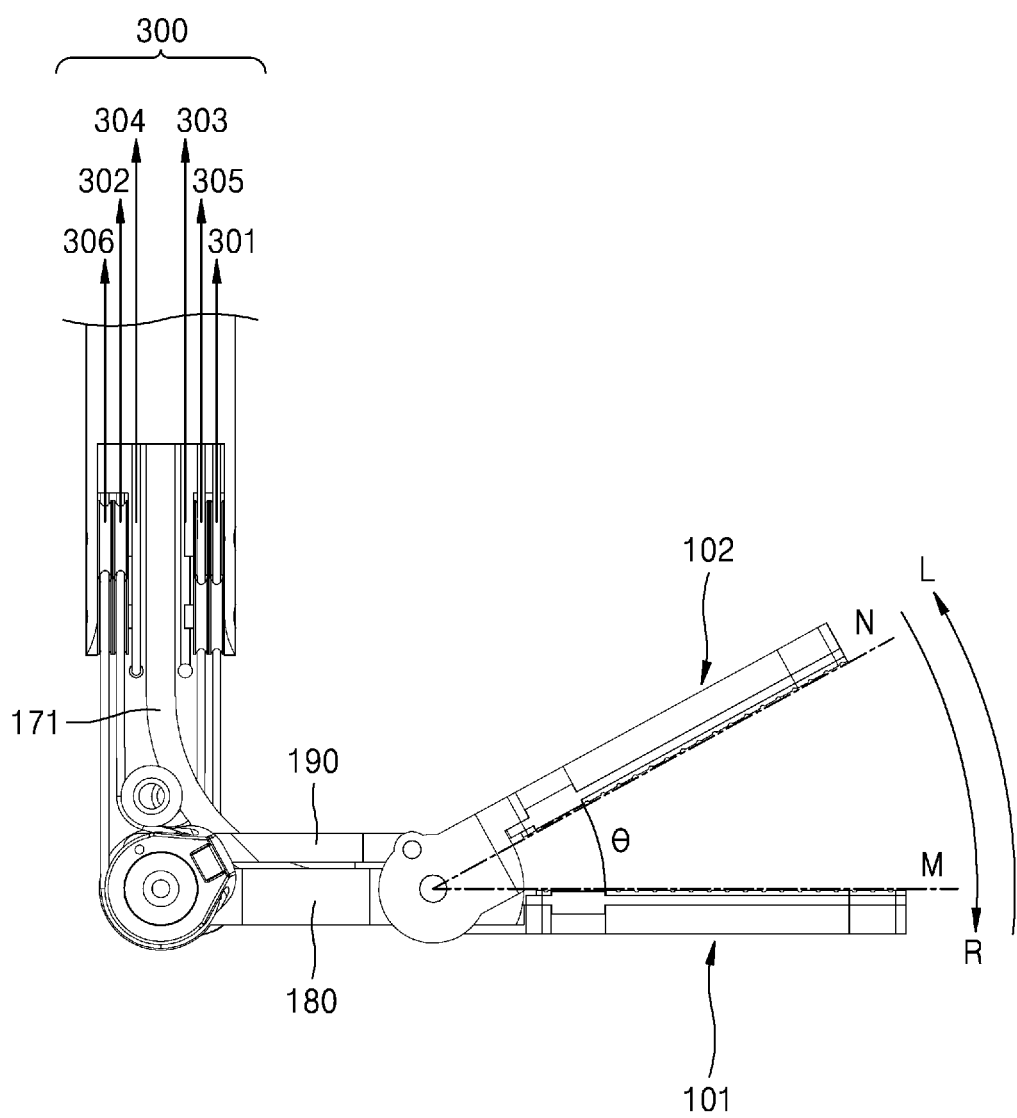
FIGS. 7 and 8 are plan views illustrating the end tool of the surgical instrument for electrocautery of FIG. 2.
Figure 8:
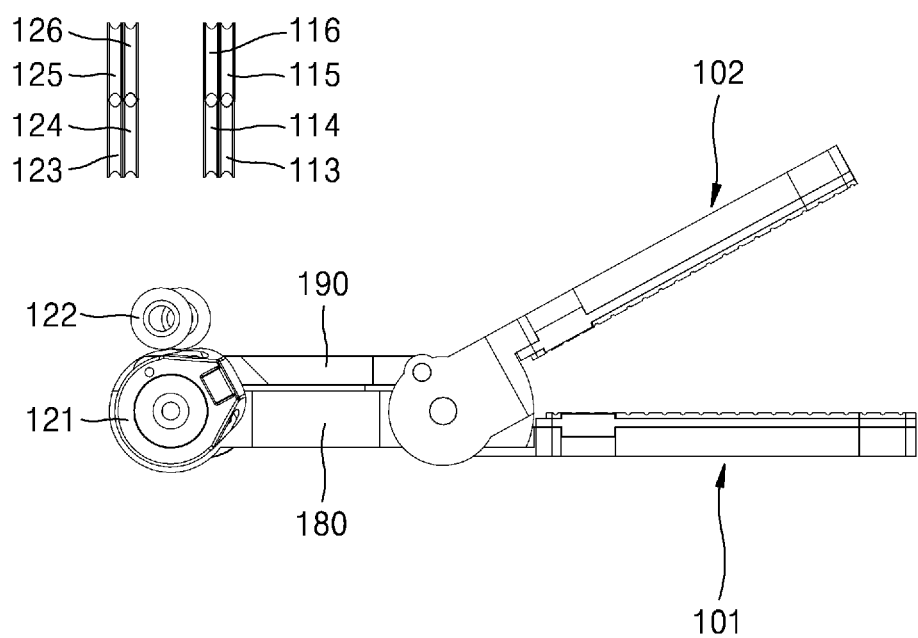

FIG. 3 shows a state in which the end tool hub 160 and the pitch hub 150 are coupled to the end tool 100, and FIG. 4 shows a state in which the end tool hub 160 is removed. FIG. 5 shows a state in which the first jaw 101 and the second jaw 102 are removed, and FIG. 6 shows a state in which the first jaw 101, the second jaw 102, the pulley 111, and the pulley 121 are removed. FIG. 7 mainly illustrates the wires, and FIG. 8 mainly illustrates the pulleys.

With reference to FIGS. 2 to 14, the end tool 100 of the first embodiment may include a pair of jaws for performing a grip motion, i.e., the first jaw 101 and the second jaw 102. A component encompassing each of the first jaw 101 and the second jaw 102 or both of the first jaw 101 and the second jaw 102 may be referred to as a jaw 103.

In addition, the end tool 100 may include a pulley 111, a pulley 112, a pulley 113, a pulley 114, a pulley 115, and a pulley 116, which are associated with the rotational motion of the first jaw 101. The end tool 100 may include a pulley 121, a pulley 122, a pulley 123, a pulley 124, a pulley 125, and a pulley 126, which are associated with the rotational motion of the second jaw 102.

Here, the drawings illustrate that the pulleys facing each other are arranged in parallel with each other; however, the technical concepts of the present disclosure are not limited thereto, and each pulley may be formed in various positions and sizes suitable for the configuration of the end tool 100.

In addition, the end tool 100 of the first embodiment may include the end tool hub 160 and a pitch hub 150.

A first rotation shaft 141 and a second rotation shaft 142 are inserted through the end tool hub 160, and the end tool hub 160 may also accommodate at least portions of the pulley 111 and the pulley 121 axially coupled to the rotation shaft 141 therein. In addition, the end tool hub 160 may accommodate at least a part of the pulley 112 and the pulley 122 axially coupled to the rotation shaft 142. The end tool hub 160 will be described in more detail later.

A third rotation shaft 143 and a fourth rotation shaft 144, which will be described later, are inserted through the pitch hub 150, and may be axially coupled with the first pitch pulley portion 163a and the second pitch pulley portion 163b of the end tool hub 160 by the third rotation shaft 143. Accordingly, the end tool hub 160 may be formed to be rotatable with respect to the pitch hub 150 around the third rotation shaft 143.

In addition, the pitch hub 150 may accommodate at least a part of the pulley 113, the pulley 114, the pulley 123, and the pulley 124, which are axially coupled to the third rotation shaft 143. Furthermore, the pitch hub 150 may accommodate at least a part of the pulley 115, the pulley 116, the pulley 125, and the pulley 126, which are axially coupled to the fourth rotation shaft 144.

One end portion of the pitch hub 150 may be connected to the end tool hub 160, and the other end portion of the pitch hub 150 may be connected to the connection portion 400.

In this regard, the end tool 100 according to the first embodiment of the present disclosure may include the first rotation shaft 141, the second rotation shaft 142, the third rotation shaft 143, and the fourth rotation shaft 144. As described above, the first rotation shaft 141 and the second rotation shaft 142 may be inserted through the end tool hub 160, and the third rotation shaft 143 and the fourth rotation shaft 144 may be inserted through the pitch hub 150.

The first rotation shaft 141, the second rotation shaft 142, the third rotation shaft 143, and the fourth rotation shaft 144 may be arranged sequentially from the distal end 104 to the proximal end 105 of the end tool 100. Accordingly, in the direction from the distal end 104, the first rotation shaft 141 may be referred to as a first pin, the second rotation shaft 142 may be referred to as a second pin, the third rotation shaft 143 may be referred to as a third pin, and the fourth rotation shaft 144 may be referred to as a fourth pin, sequentially.

Here, the first rotation shaft 141 may function as an end tool jaw pulley rotation shaft, the second rotation shaft 142 may function as an end tool jaw auxiliary pulley rotation shaft, the third rotation shaft 143 may function as an end tool pitch rotation shaft, and the fourth rotation shaft 144 may function as an end tool pitch auxiliary rotation shaft of the end tool 100.

Here, each of the rotation shafts may include two shafts which area first sub-shaft and a second sub-shaft. Alternatively, it may be said that each of the rotation shafts can be divided into two parts.

For example, the first rotation shaft 141 may include two shafts which are a first sub-shaft 141a and a second sub-shaft 141b. The second rotation shaft 142 may include two shafts of a first sub-shaft 142a and a second sub-shaft 142b. The third rotation shaft 143 may include two shafts of a first sub-shaft 143a and a second sub-shaft 143b. The fourth rotation shaft 144 may include two shafts of a first sub-shaft 144a and a second sub-shaft 144b.

This structure in which each rotation shaft is divided into two sub-shafts, is to allow the guide tube 171, which will be described later, to pass through the end tool hub 160 and the pitch hub 150. That is, the guide tube 171 may pass between the first sub-shaft and the second sub-shaft of each rotation shaft. This will be described in more detail later. In this regard, the first sub-shaft and the second sub-shaft may be disposed on the same axis or may be offset with respect to each other by a certain distance.

On the other hand, although the drawings show that each rotation shaft is divided into two sub-shafts, the technical concept of the present disclosure is not limited thereto. That is, each rotation shaft may be formed to be curved in the middle thereof, thereby forming an escape route for the guide tube 171.

One or more pulleys may be fit into each of the rotation shafts 141, 142, 143, and 144, which will be described in detail below.

Meanwhile, the end tool 100 may further include an actuation rotation shaft 145. In detail, the actuation rotation shaft 145 may be provided at a joint between the first jaw 101 and the second jaw 102, and in a state in which the first jaw 101 is fixed, the second jaw 102 may perform an actuation motion while rotating around the actuation rotation shaft 145. In this regard, the actuation rotation shaft 145 may be disposed at the distal end 104 further than the first rotation shaft 141.

Here, the end tool 100 of the first embodiment of the present disclosure is characterized in that the first rotation shaft 141, which is a yaw rotation shaft, and the actuation rotation shaft 145 are not the same axis but provided separately. That is, since the first rotation shaft 141, which is the rotation shaft of the pulley 111 and the pulley 112, which are the jaw pulley, and is the rotation shaft of the yaw motion, is spaced apart from the actuation rotation shaft 145, which is the rotation shaft of the second jaw 102 with respect to the first jaw 101 and the rotation shaft of the actuation motion, a space in which the guide tube 171 and the blade wire 307 accommodated therein can be gently bent, is guaranteed. The actuation rotation shaft 145 will be described in detail later.

The pulley 111 may function as an end tool first jaw pulley, and the pulley 121 may function as an end tool second jaw pulley. The pulley 111 may be referred to as a first jaw pulley, and the pulley 121 may be referred to as a second jaw pulley. The two components may be collectively referred to as an end tool jaw pulley or simply as a jaw pulley.

The pulley 111 and the pulley 121 which are the end tool jaw pulley may face each other and may be formed to be independently rotatable around the first rotation shaft 141 which is the end tool jaw pulley rotation shaft. Meanwhile, the pulley 111 and the pulley 121 may be spaced apart from each other at a certain distance, and a blade assembly accommodation portion may be arranged between the pulley 111 and the pulley 121. In one embodiment, at least a part of a blade assembly 170 to be described later may be arranged in the blade assembly accommodation portion. In other words, a blade assembly 170 including a guide tube 171 may be disposed between the pulley 111 and the pulley 121.

In this regard, the pulley 111 may be coupled to the first jaw 101 through a first link 180 to be described later, so that when the pulley 111 rotates around the first rotation shaft 141, the first jaw 101 rotates around the first rotation shaft 141 together therewith.

Meanwhile, the pulley 121 is connected to the second jaw 102 through a second link 190 to be described later, so that when the pulley 121 rotates around the first rotation shaft 141, the second jaw 102 connected thereto may rotate about the first rotation shaft 141 or the actuation rotation shaft 145.

In this regard, the pulley 111, the first link 180, the first jaw 101 are fixedly coupled to each other and move as one body. That is, when the pulley 111 rotates around the first rotation shaft 141, the first link 180 and the first jaw 101 may also rotate together with the pulley 111 around the first rotation shaft 141.

In this embodiment, the pulley 121, the second link 190, and the second jaw 102 are connected to each other but one component can move or rotate relatively with respect to another component. That is, the second link 190 is formed to be movable or rotatable with respect to the pulley 121, and the second jaw 102 is formed to be movable or rotatable with respect to the second link 190.

A yaw motion and an actuation motion of the end tool 100 may be performed according to the rotation of the pulley 111 and the pulley 121. That is, when the pulley 111 and the pulley 121 rotate in the same direction around the first rotation shaft 141, a yaw motion may be performed such that the first jaw 101 and the second jaw 102 rotate around the first rotation shaft 141. Meanwhile, when the pulley 121 alone rotates in a certain direction around the first rotation shaft 141, an actuation motion is performed such that the second jaw 102 rotates with respect to the first jaw 101 around the actuation rotation shaft 145.

The pulley 112 may function as an end tool first jaw auxiliary pulley, and the pulley 122 may function as an end tool second jaw auxiliary pulley. The two components may be collectively referred to as an end tool jaw auxiliary pulley or simply as an auxiliary pulley.

More specifically, the pulley 112 and the pulley 122 which are the end tool jaw auxiliary pulley may be additionally provided on one side of the pulley 111 and the pulley 121. In other words, the pulley 112 which is an auxiliary pulley may be arranged between the pulley 111 and the pulley 113/the pulley 114. In addition, the pulley 122 which is an auxiliary pulley may be arranged between the pulley 121 and the pulley 123/the pulley 124. The pulley 112 and the pulley 122 may be formed to be rotatable independently of each other around the second rotation shaft 142. Such auxiliary pulley will be described in more detail later.

The pulley 113 and the pulley 114 may function as an end tool first jaw pitch main pulley, and the pulley 123 and the pulley 124 may function as an end tool second jaw pitch main pulley. The two components may collectively be referred to as an end tool jaw pitch main pulley.

The pulley 115 and the pulley 116 may function as an end tool first jaw pitch subsidiary pulley, and the pulley 125 and the pulley 126 may function as an end tool second jaw pitch subsidiary pulley. The two components may collectively be referred to as an end tool jaw pitch subsidiary pulley.

Hereinafter, components associated with the rotation of the pulley 111 will be described.

The pulley 113 and the pulley 114 may function as the end tool first jaw pitch main pulley. That is, the pulley 113 and the pulley 114 may function as a main rotation pulley of the pitch motion of the first jaw 101. Here, the wire 301, which is the first jaw wire, may be wound around the pulley 113, and the wire 305, which is the first jaw wire, may be wound around the pulley 114.

The pulley 115 and the pulley 116 may function as the end tool first jaw pitch subsidiary pulley. That is, the pulley 115 and the pulley 116 may function as a subsidiary rotation pulley of the pitch motion of the first jaw 101. Here, the wire 301, which is the first jaw wire, may be wound around the pulley 115, and the wire 305, which is the first jaw wire, may be wound around the pulley 116.

On one side of the pulley 111 and the pulley 112, the pulley 113 and the pulley 114 may be arranged to face each other. The pulley 113 and the pulley 114 may be formed to be rotatable independently of each other around the third rotation shaft 143 which is the end tool pitch rotation shaft. In addition, on one side of each of the pulley 113 and the pulley 114, the pulley 115 and the pulley 116 may be arranged to face each other. The pulley 115 and the pulley 116 may be formed to be rotatable independently of each other around the fourth rotation shaft 144 which is the end tool pitch auxiliary rotation shaft. Although the drawings illustrate that the pulley 113, the pulley 115, the pulley 114, and the pulley 116 are formed to be rotatable around the Y-axis direction, the technical concepts of the present disclosure are not limited thereto, and the rotation shafts of each pulley may be formed in various directions suitable for their respective configurations.

The wire 301, which is the first jaw wire, may be wound sequentially so that at least a part thereof is in contact with the pulley 115, the pulley 113, and the pulley 111. In addition, the wire 305 connected to the wire 301 by the fastening member 323 may be sequentially wound so that at least a part thereof is in contact with the pulley 111, the pulley 112, the pulley 114, and the pulley 116.

In other words, the wire 301 and wire 305, which are the first jaw wire, may be sequentially wound so that at least a part thereof is in contact with the pulley 115, the pulley 113, the pulley 111, the pulley 112, the pulley 114, and the pulley 116, and the wire 301 and the wire 305 may be formed to move along the pulleys while rotating the pulleys.

Accordingly, when the wire 301 is pulled toward the arrow 301 of FIG. 7, the fastening member 323 coupled to the wire 301 and the pulley 111 coupled to the fastening member 323 may rotate in the direction of the arrow L of FIG. 7. On the contrary, when the wire 305 is pulled toward the arrow 305 of FIG. 7, the fastening member 323 coupled to the wire 305 and the pulley 111 coupled to the fastening member 323, may rotate in the direction of the arrow R of FIG. 7.

Next, components associated with the rotation of the pulley 121 will be described.

The pulley 123 and the pulley 124 may function as an end tool second jaw pitch main pulley. That is, the pulley 123 and the pulley 124 may function as a main rotation pulley of the pitch motion of the second jaw 102. Here, the wire 306, which is the second jaw wire, may be wound around the pulley 123, and the wire 302, which is the second jaw wire, may be wound around the pulley 124.

The pulley 125 and the pulley 126 may function as an end tool second jaw pitch subsidiary pulley. That is, the pulley 125 and the pulley 126 may function as a subsidiary rotation pulley of the pitch motion of the second jaw 102. Here, the wire 306, which is the second jaw wire, may be wound around the pulley 125, and the wire 302, which is the second jaw wire, may be wound around the pulley 126.

On one side of the pulley 121 and the pulley 122, the pulley 123 and the pulley 124 may be arranged to face each other. The pulley 123 and the pulley 124 may be formed to be rotatable independently of each other around the third rotation shaft 143 which is the end tool pitch rotation shaft. In addition, on one side of each of the pulley 123 and the pulley 124, the pulley 125 and the pulley 126 may be arranged to face each other. The pulley 125 and the pulley 126 may be formed to be rotatable independently of each other around the rotation shaft 144 which is the end tool pitch auxiliary rotation shaft. Although the drawings illustrate that the pulley 123, the pulley 125, the pulley 124, and the pulley 126 are formed to be rotatable around the Y-axis direction, the technical concepts of the present disclosure are not limited thereto, and the rotation shafts of each pulley may be formed in various directions suitable for their respective configurations.

The wire 306, which is the second jaw wire, may be wound sequentially so that at least a part thereof is in contact with the pulley 125, the pulley 123, and the pulley 121. In addition, the wire 302 connected to the wire 306 by the fastening member 326 may be sequentially wound so that at least a part thereof is in contact with the pulley 121, the pulley 122, the pulley 124, and the pulley 126.

In other words, the wire 306 and wire 302, which are the second jaw wire, may be sequentially wound so that at least a part thereof is in contact with the pulley 125, the pulley 123, the pulley 121, the pulley 122, the pulley 124, and the pulley 126, and the wire 306 and the wire 302 may be formed to move along the pulleys while rotating the pulleys.

Accordingly, when the wire 306 is pulled toward the arrow 306 of FIG. 7, the fastening member 326 coupled to the wire 306 and the pulley 121 coupled to the fastening member 326 may rotate in the direction of the arrow R of FIG. 7. On the contrary, when the wire 302 is pulled toward the arrow 302 of FIG. 7, the fastening member 326 coupled to the wire 302 and the pulley 121 coupled to the fastening member 326 may rotate in the direction of the arrow L of FIG. 7.

Hereinafter, the pulley 112 and the pulley 122 serving as an auxiliary pulley will be described in more detail.

As the pulley 112 and the pulley 122 are in contact with the wire 305 which is the first jaw wire and the wire 302 which is the second jaw wire to change an arrangement path of the wire 305 and the wire 302 to a certain extent, the pulley 112 and the pulley 122 may perform the function of expanding a rotation angle of each of the first jaw 101 and the second jaw 102.

That is, when no auxiliary pulley is arranged, each of first jaw and the second jaw may rotate up to the right angle; however, in an embodiment, by additionally arranging the pulley 112 and the pulley 122, which are auxiliary pulleys, the maximum rotation angle may be increased by θ as shown in FIG. 7. This enables the opening motion of the two jaws of the end tool 100 for the actuation motion when the two jaws are yaw-rotated by 90° in the L direction. This is because the second jaw 102 may rotate by the additional angle θ as shown in FIG. 7. Likewise, the actuation motion may be performed even when the two jaws are yaw-rotated in the L direction. In other words, through the pulley 112 and the pulley 122, a range of yaw rotation allowing the actuation motion may be expanded.

This will be described below in more detail.

When no auxiliary pulley is arranged, as the first jaw wire is fixedly coupled to the end tool first jaw pulley, and the second jaw wire is fixedly coupled to the end tool second jaw pulley, each of the end tool first jaw pulley and the end tool second jaw pulley may rotate only up to 90°. In this case, when the actuation motion is performed in a state where the first jaw and the second jaw are placed on the 90° line, the first jaw may be opened, but the second jaw may not be able to rotate over 90°. Accordingly, in the state where the first jaw and the second jaw perform the yaw motion over a certain angle, the actuation motion may not be performed smoothly.

To overcome the foregoing issue, in the electric cauterization surgical instrument 10 of the present disclosure, the pulley 112 and the pulley 122, which are auxiliary pulleys, may be further arranged on one side of the pulley 111 and the pulley 121. By arranging the pulley 112 and the pulley 122, the arrangement path of the wire 305 which is the first jaw wire and the wire 302 which is the second jaw wire may be changed to a certain extent, and a tangential direction of the wire 305 and the wire 302 may also be changed, which allows rotation of the fastening member 326 coupling the wire 302 to the pulley 121 up to the N line of FIG. 7. That is, the fastening member 326, which is a coupling portion between the wire 302 and the pulley 121, may be rotatable until it is positioned on a common internal tangent of the pulley 121 and the pulley 122. Likewise, the fastening member 323, which is a coupling portion of the wire 305 and the pulley 111, may be rotatable until it is positioned on a common internal tangent of the pulley 111 and the pulley 112, which allows expansion of the rotation range in the R direction.

In other words, by the pulley 112, the wire 301 and the wire 305, which are two strands of the first jaw wire wound around the pulley 111 may be arranged on one side with respect to a plane perpendicular to the Y-axis and passing through the X-axis. At the same time, by the pulley 122, the wire 302 and the wire 306, which are two strands of the second jaw wire wound around the pulley 121 may be arranged on another side with respect to the plane perpendicular to the Y-axis and passing through the X-axis.

In other words, the pulley 113 and the pulley 114 may be arranged on one side with respect to the plane perpendicular to the Y-axis and passing through the X-axis, and the pulley 123 and the pulley 124 may be arranged on another side with respect to the plane perpendicular to the Y-axis and passing through the X-axis.

In other words, the wire 305 may be arranged on an internal tangent of the pulley 111 and the pulley 112, and the rotation angle of the pulley 111 may be expanded by the pulley 112. In addition, the wire 302 may be arranged on an internal tangent of the pulley 121 and the pulley 122, and the rotation angle of the pulley 121 may be expanded by the pulley 122.

According to the present disclosure, as the rotational radius of the first jaw 101 and the second jaw 102 is widened, the range of yaw motion allowing a normal open-and-shut actuation motion may be expanded.

Hereinafter, the pitch motion of the present disclosure will be described in more detail.

When the wire 301 is pulled toward the arrow 301 of FIG. 7, and simultaneously the wire 305 is pulled toward the arrow 305 of FIG. 7 (i.e., both strands of the first jaw wire are pulled), as the wire 301 and the wire 305 are wound downward around the pulley 113 and the pulley 114 which are rotatable around the third rotation shaft 143 which is the end tool pitch rotation shaft, as illustrated in FIG. 6, the pulley 111 fixedly coupled to the wire 301 and the wire 305 and the end tool hub 160 coupled to the pulley 111 may rotate in the counterclockwise direction around the third rotation shaft 143, and as a result, the end tool 100 may rotate downwards performing the pitch motion. In this case, as the second jaw 102 and the wire 302 and the wire 306 fixedly coupled to the second jaw 102 are wound upwards around the pulley 123 and the pulley 124 which are rotatable around the third rotation shaft 143, the wire 302 and the wire 306 may be unwound in a direction opposite to the directions 302 and 306, respectively.

On the contrary, when the wire 302 is pulled towards the arrow 302 of FIG. 7, and simultaneously the wire 306 is pulled towards the arrow 306 of FIG. 7, as the wire 302 and the wire 306 are wound upwards around the pulley 123 and the pulley 124 which are rotatable around the third rotation shaft 143 which is the end tool pitch rotation shaft, as illustrated in FIG. 6, the pulley 121 fixedly coupled to the wire 302 and the wire 306 and the end tool hub 160 coupled to the pulley 121 may rotate around the third rotation shaft 143 in the clockwise direction, and as a result, the end tool 100 may rotate upwards, performing the pitch motion. In this case, as the first jaw 101 and the wire 301 and the wire 305 fixedly coupled to the first jaw 101 are wound downwards around the pulley 113 and the pulley 114 which are rotatable around the third rotation shaft 143, the wire 302 and the wire 306 may be unwound in a direction opposite to the directions 301 and 305, respectively.

Meanwhile, the end tool hub 160 of the end tool 100 of the electric cauterization surgical instrument 10 of the present disclosure further includes the first pitch pulley portion 163a and the second pitch pulley portion 163b which act as end tool pitch pulleys, and the manipulation portion 200 further includes a pulley 231 and a pulley 232 which are manipulation pitch pulleys, and the power transmission portion 300 may further include a wire 303 and a wire 304 which are pitch wires.

In detail, the end tool hub 160 including the first pitch pulley portion 163a and the second pitch pulley portion 163b may be formed to be rotatable around the third rotation shaft 143 which is an end tool pitch rotation shaft. In an embodiment, the wire 303 and the wire 304 may connect the first pitch pulley portion 163a and the second pitch pulley portion 163b of the end tool 100 with the pulley 231 and the pulley 232 of the manipulation portion 200.

Therefore, when the pulley 231 and the pulley 232 of the manipulation portion 200 rotate, the rotation of the pulley 231 and the pulley 232 is transmitted to the end tool hub 160 of the end tool 100 through the wire 303 and the wire 304, resulting in the rotation of the end tool hub 160 and the rotation of the end tool 100, thereby performing a pitch motion.

That is, to transmit the driving force of the pitch motion, the electric cauterization surgical instrument 10 according to the first embodiment of the present disclosure includes the first pitch pulley portion 163a and the second pitch pulley portion 163b of the end tool 100, the pulley 231 and the pulley 232 of the manipulation portion 200, and the wire 303 and the wire 304 of the power transmission portion 300. Accordingly, the pitch motion of the manipulation portion 200 is perfectly transmitted to the end tool 100, thereby improving motion reliability.

(Blade Wire and Guide Tube)

Hereinafter, the blade wire 307 and the guide tube 171 according to present disclosure will be described in more detail.

The guide tube 171 according to the present disclosure is formed to surround the blade wire 307 in a certain section, and in this regard, the blade wire 307 may move inside the guide tube 171. In other words, in a state where the blade wire 307 is inserted into the guide tube 171, the blade wire 307 may move with respect to the guide tube 171.

In this regard, the guide tube 171 may guide the path of the blade wire 307 by preventing the blade wire 307 from bending in an unintended direction when the blade wire 307 is pushed or pulled. Due to the guide tube 171, a cutting motion may be smoothly performed by the guide tube 171.

Meanwhile, the end portion of the guide tube 171 may be fixedly coupled to the end tool hub 160 or a first coupling portion (not illustrated) in the first link 180 to be described later. The other end portion of the guide tube 171 may be fixedly coupled to a second coupling portion (not illustrated) in the connection portion 400. In this way, since both end portions of the guide tube 171 are fixedly coupled to certain points (first coupling portion and second coupling portion), the entire length of the guide tube 171 may be maintained constant. Therefore, the length of the blade wire 307 inserted into the guide tube 171 may also be maintained constant.

Meanwhile, the guide tube 171 according to the present disclosure may include a flexible material so as to be bendable. Therefore, when the end tool 100 performs a yaw motion around the first rotation shaft 141 or a pitch motion around the third rotation shaft 143, the guide tube 171 may be curved while changing the shape thereof corresponding thereto. In an embodiment, when the guide tube 171 is bent, the blade wire 307 thereinside is also bent.

In this regard, although the length of the guide tube 171 is constant, the relative position and distance of the first coupling portion (not illustrated) and second coupling portion (not illustrated) may change as the end tool 100 performs a pitch rotation or a yaw rotation. Accordingly, there is a space needed for the guide tube 171 to bend smoothly as much as the change in distance. To this end, a pitch slit 164 and a yaw slit 165 may be provided to the end tool hub 160 to form a space in which the guide tube 171 to bend smoothly. The configuration of the end tool hub 160 will be described in detail later.

Meanwhile, as described above, the blade wire 307 is inserted through the guide tube 171, and the blade wire 307 may move with respect to the guide tube 171 inside the guide tube 171. That is, when the blade wire 307 is pulled while the guide tube 171 is fixed, the blade 175 connected to the blade wire 307 moves toward the proximal end 105, and when the blade wire 307 is pushed, the blade 175 connected to the blade wire 307 moves toward the distal end 104.

This will be described below in more detail.

In order to ensure the cutting motion using the blade 175, the blade 175 needs to be pushed or pulled by using the blade wire 307. In an embodiment, in order for the blade wire 307 to push and pull the blade 175, the guide tube 171 that guides the path of the blade wire 307 may be provided. In the case where the guide tube 171 does not guide the path of the blade wire 307, even when the blade wire 307 is pushed, the cutting may not be performed and the middle part of the blade wire 307 may be bent. Therefore, in order to reliably perform the cutting motion by using the blade 175, the blade wire 307 and the guide tube 171 must be included.

Meanwhile, in order to perform the cutting motion using the blade wire 307, the blade wire 307 needs to be pushed. Accordingly, to allow the blade wire 307 to receive a force, a wire that is somewhat stiff (i.e., hard to bend) may be used as the blade wire 307. However, a stiff (i.e., hard to bend) wire may have a small bendable range and when a certain level of force or more is applied, the wire may be permanently deformed.

From another point of view, in the case of a stiff (i.e., hard to bend) wire, there is a minimum radius of curvature (i.e., maximum curvature) within which the wire may be curved and straightened without permanent deformation. In other words, when the wire or guide tube is curved smaller than the specific radius of curvature (i.e., larger than the specific curvature), both the wire and the guide tube may be permanently deformed while being bent, making it impossible to perform cutting while moving back and forth. Therefore, there is a need to keep the blade wire 307 curved while having a gentle curvature.

Therefore, in order to prevent the blade wire 307 from being abruptly curved while passing through the pulleys, a space, in which the blade wire 307 is able to be gently bent, is required between the jaw 103 (i.e., the actuation rotation shaft 145) and the end tool hub 160 (i.e., the first rotation shaft 141 which is the yaw axis).

To this end, according to the present disclosure, due to the inclusion of the first link 180 and the second link 190, which are links connecting the pulley 111/the pulley 112, which are jaw pulleys, with the jaw 103, a space, in which the blade wire 307 and the guide tube 171 are able to be gently bent, is formed by spacing the jaw 103 (i.e., the actuation rotation shaft 145) from the end tool hub 160 (i.e., the first rotation shaft 141 which is the yaw axis) by a certain distance. At the same time, the rotation of the pulley 111/the pulley 112, which are jaw pulleys, is transmitted to the jaw 103 through the first link 180 and the second link 190.

In an embodiment, the blade wire 307 and the guide tube 171 are connected to the blade 175 through the end tool hub 160 and a space is needed in which the blade wire 307 and the guide tube 171 are able to be curved within the end tool hub 160. Accordingly, 1) the pitch slit 164 and the yaw slit 165 are formed within the end tool hub 160, wherein the pitch slit 164 and the yaw slit 165 correspond to a space in which the blade wire 307/the guide tube 171 pass therethrough and, at the same time, are bendable, 2) each rotation shaft is divided into two parts, and 3) the pitch round portion 166 and the yaw round portion 167 are additionally formed to guide the bending of the blade wire 307 and the guide tube 171.

From another point of view, the end portion of the guide tube 171 is fixed within the connection portion 400, and the other end portion thereof is curved in such a direction that, when moving while performing a pitch motion and a yaw motion, the guide tube 171 forms the gentlest curvature (hereinafter referred to as "maximum gentle curvature") according to the change in the distance of both end portion. As described above, only when the maximum gentle curvature of the natural state is made, the motion of the blade wire 307 is smooth and permanent deformation thereof does not occur.

Therefore, in order to ensure the maximum gentle curvature, the pitch slit 164 and the yaw slit 165 are formed on the path of the guide tube 171, and furthermore, the pitch round portion 166 and the yaw round portion 167 may be additionally formed in the end tool hub 160. As a result, the guide tube 171 may have such a shape that is the most similar to the maximum gentle curvature (although not having the maximum gentle curvature).

Hereinafter, the end tool hub 160 and the jaw-link-jaw pulley connection structure will be described in more detail.

(End Tool Hub)

Referring to FIGS. 9 to 14, the end tool hub 160 includes a body portion 161, a first jaw pulley coupling portion 162a, a second jaw pulley coupling portion 162b, the first pitch pulley portion 163a, the second pitch pulley portion 163b, the pitch slit 164, the yaw slit 165, the pitch round portion 166, and the yaw round portion 167.

The first jaw pulley coupling portion 162a and the second jaw pulley coupling portion 162b may be formed on the distal end side of the end tool hub 160. In this regard, the first jaw pulley coupling portion 162a and the second jaw pulley coupling portion 162b are formed to face each other, and the pulley 111 and the pulley 121 are accommodated therein. In this regard, the first jaw pulley coupling portion 162*a* and the second jaw pulley coupling portion 162*b* may be formed to be approximately parallel to a plane perpendicular to the first rotation shaft 141 that is a yaw rotation shaft.

The first jaw pulley coupling portion 162*a* and the second jaw pulley coupling portion 162*b* may be connected by the body portion 161. That is, the first jaw pulley coupling portion 162*a* and the second jaw pulley coupling portion 162*b*, which are parallel to each other, are coupled by the body portion 161 formed in a direction approximately perpendicular to the first jaw pulley coupling portion 162*a* and the second jaw pulley coupling portion 162*b*, so that the first jaw pulley coupling portion 162*a*, the second jaw pulley coupling portion 162*b*, and the body portion 161 form an approximately C-shape, and the pulley 111 and the pulley 121 are accommodated therein.

In other words, it may be said that the first jaw pulley coupling portion 162*a* and the second jaw pulley coupling portion 162*b* are formed to extend in the X-axis direction from the body portion 161.

In this regard, the pulley 111, which is a first jaw pulley, is disposed close to the first jaw pulley coupling portion 162*a* of the end tool hub 160, and the pulley 121, which is a second jaw pulley, is disposed close to the second jaw pulley coupling portion 162*b* of the end tool hub 160, and thus the yaw slit 165 may be formed between the first jaw pulley coupling portion 162*a* and the second jaw pulley coupling portion 162*b*. In addition, at least a part of a blade assembly 170 to be described later may be disposed in the yaw slit 165. In other words, it can be said that at least a part of the guide tube 171 of the blade assembly 170 may be disposed between the first jaw pulley coupling portion 162*a* and the second jaw pulley coupling portion 162*b*. As such, by arranging the blade assembly 170 including the guide tube 171 between the pulley 111 which is the first jaw pulley and the pulley 121 which the second jaw pulley, not only the pitch motion and the yaw motion of the end tool 100 but also a cutting motion using the blade 175 may be performed. This will be described in more detail later.

Meanwhile, a through hole is formed in the first jaw pulley coupling portion 162*a* such that the first rotation shaft 141 passes through the first jaw pulley coupling portion 162*a* and the pulley 111 and axially couples the first jaw pulley coupling portion 162*a* with the pulley 111. In an embodiment, a through hole is formed in the second jaw pulley coupling portion 162*b* such that the first rotation shaft 141 passes through the second jaw pulley coupling portion 162*b* and the pulley 121 and axially couples the first rotation shaft 141 and the pulley 121.

In this regard, as described above, the first rotation shaft 141, which is a yaw rotation shaft, may be formed by being divided into two parts of the first sub-shaft 141*a* and the second sub-shaft 141*b*, and the guide tube 171 may pass between the first sub-shaft 141*a* and the second sub-shaft 141*b* of the first rotation shaft 141.

In addition, the yaw slit 165 may be formed between the first jaw pulley coupling portion 162*a* and the second jaw pulley coupling portion 162*b*. Since the yaw slit 165 is formed in the end tool hub 160 as described above, the guide tube 171 may pass through the inside of the end tool hub 160.

In other words, the first rotation shaft 141 is vertically separated from the end tool hub 160 without passing therethrough, and the yaw slit 165 may be formed on a plane perpendicular to the first rotation shaft 141 in the vicinity of the first rotation shaft 141. Accordingly, the guide tube 171 is movable (movable left and right) in the yaw slit 165 while passing through the vicinity of the first rotation shaft 141.

Meanwhile, the yaw round portion 167 may be further formed in the body portion 161. The yaw round portion 167 may be formed to be rounded so as to have a certain curvature. In detail, when viewed from a plane perpendicular to the first rotation shaft 141 that is a yaw rotation shaft, the yaw round portion 167 may be formed to be rounded so as to have a certain curvature. For example, the yaw round portion 167 may be formed in a fan shape, and formed along a path in which the guide tube 171 is curved on an XY plane. The yaw round portion 167 as described above may guide a path of the guide tube 171 when the end tool 100 yaw-rotates.

The first pitch pulley portion 163*a* and the second pitch pulley portion 163*b*, which serve as end tool pitch pulleys, may be formed at the proximal end of the end tool hub 160. In this regard, the first pitch pulley portion 163*a* and the second pitch pulley portion 163*b* may be formed to face each other. Here, the first pitch pulley portion 163*a* and the second pitch pulley portion 163*b* may be formed to be approximately parallel to a plane perpendicular to a third rotation shaft 143, which is a pitch rotation shaft.

In detail, one end portion of the end tool hub 160 is formed in a disk shape like a pulley, and a groove around which a wire may be wound may be formed on an outer circumferential surface of the end tool hub 160, thereby forming the first pitch pulley portion 163*a* and the second pitch pulley portion 163*b*. The wire 303 and the wire 304 described above are coupled to the first pitch pulley portion 163*a* and the second pitch pulley portion 163*b*, which serve as end tool pitch pulleys, and a pitch motion is performed while the end tool hub 160 rotates about the third rotation shaft 143.

Meanwhile, although not illustrated in the drawings, a pitch pulley may be formed as a separate member from the end tool hub 160 and coupled to the end tool hub 160.

The first pitch pulley portion 163*a* and to the second pitch pulley portion 163*b* may be connected by the body portion 161. That is, the first pitch pulley portion 163*a* and the second pitch pulley portion 163*b*, which are parallel to each other, are coupled by the body portion 161 formed in a direction approximately perpendicular to the first pitch pulley portion 163*a* and the second pitch pulley portion 163*b*, and thus the first pitch pulley portion 163*a*, the second pitch pulley portion 163*b*, and the body portion 161 may form an approximately C-shape.

In other words, it may be said that the first pitch pulley portion 163*a* and the second pitch pulley portion 163*b* are formed to extend from the body portion 161 in the −X-axis direction.

Meanwhile, a through hole may be formed in the first pitch pulley portion 163*a* so that the third rotation shaft 143 may pass through the first pitch pulley portion 163*a*. A through hole is also formed in the second pitch pulley portion 163*b* so that the third rotation shaft 143 may pass through the second pitch pulley portion 163*b*.

In this case, as described above, the third rotation shaft 143, which is a pitch rotation shaft, may be formed by being divided into two parts of the first sub-shaft 143*a* and the second sub-shaft 143*b*, and the guide tube 171 may pass between the first sub-shaft 143*a* and the second sub-shaft 143*b* of the third rotation shaft 143.

The pitch slit 164 may be formed between the first pitch pulley portion 163*a* and the second pitch pulley portion 163*b*. Since the pitch slit 164 is formed in the end tool hub 160 as described above, the guide tube 171 may pass through the inside of the end tool hub 160.

In other words, the third rotation shaft 143 is horizontally separated into two parts without passing through the end tool hub 160, and the pitch slit 164 may be formed on a plane perpendicular to the third rotation shaft 143 in the vicinity of the third rotation shaft 143. Accordingly, the guide tube 171 is movable (movable up and down) in the pitch slit 164 while passing through the vicinity of the third rotation shaft 143.

Meanwhile, the pitch round portion 166 may be further formed in the body portion 161. The pitch round portion 166 may be formed to be rounded to have a certain curvature. In detail, when viewed from a plane perpendicular to the third rotation shaft 143, which is a pitch rotation shaft, the pitch round portion 166 may be formed to be rounded to have a certain curvature. For example, the pitch round portion 166 may be formed in a fan shape, and formed along a path in which the guide tube 171 is curved on an XZ plane. The pitch round portion 166 as described above may serve to guide a path of the guide tube 171 when the end tool 100 pitch-rotates.

Here, the pitch slit 164 and the yaw slit 165 may be formed to be connected to each other. Accordingly, the guide tube 171 and the blade wire 307 therein may be disposed to completely pass through the inside of the end tool hub 160. In addition, the blade 175 coupled to one end portion of the blade wire 307 may linearly reciprocate inside the first jaw 101 and the second jaw 102.

In an embodiment, since the blade wire 307 and the guide tube 171 are connected to the blade 175 through the end tool hub 160 and a space is needed in which the blade wire 307 and the guide tube 171 are able to be curved within the end tool hub 160, 1) the pitch slit 164 and the yaw slit 165 are formed within the end tool hub 160, wherein the pitch slit 164 and the yaw slit 165 correspond to a space in which the blade wire 307/the guide tube 171 passes therethrough and, at the same time, are bendable, 2) each of the rotation shafts is divided into two parts, and 3) the pitch round part 166 and the yaw round portion 167 are additionally formed to guide the bending of the blade wire 307 and the guide tube 171.

Jaw-Link-Jaw Pulley Connection Structure

Referring to FIGS. 9 to 14, the end tool 100 of the present disclosure includes the first jaw 101, the second jaw 102, the first link 180, the second link 190, the pulley 111, which is a first jaw pulley, and the pulley 112, which is a second jaw pulley. Hereinafter, the pulley 111 is referred to as the first jaw pulley 111, and the pulley 121 is referred to as the second jaw pulley 121.

The first jaw pulley 111 and the first link 180 may be fixedly coupled to each other.

In detail, a protrusion 111a is formed on the first jaw pulley 111 and a through hole (not illustrated) is formed in the first link 180, so that the protrusion 111a of the first jaw pulley 111 may be inserted into the through hole (not illustrated) of the first link 180. In an embodiment, the first sub-shaft 141a of the first rotation shaft 141 may be sequentially inserted through the first jaw pulley 111 and the first link 180. As a result, the first jaw pulley 111 and the first link 180 are coupled to each other at two points, and thus the first jaw pulley 111 and the first link 180 are fixedly coupled to each other.

That is, since the first link 180 does not rotate with respect to the first jaw pulley 111, when the first jaw pulley 111 rotates about the first rotation shaft 141, the first link 180 also rotates about the first rotation shaft 141 together with the first jaw pulley 111.

Meanwhile, the first link 180 and the first jaw 101 are fixedly coupled by a fixing member (a pin or the like).

In other words, the first jaw 101 and the first jaw pulley 111 are connected by the first link 180 and are in a state of being fixed relative to each other, so that one member does not rotate/move with respect to another member.

As a result, when the first jaw pulley 111 rotates about the first sub-shaft 141a of the first rotation shaft 141, the first link 180 and the first jaw 101 coupled thereto also rotate about the first sub-shaft 141a of the first rotation shaft 141 together with the first jaw pulley 111.

The second jaw pulley 121 and the second link 190 are axially coupled to each other at one point, so that the second link 190 is rotatably coupled to the second jaw pulley 121.

In detail, a protrusion 121a is formed on the second jaw pulley 121, and a through hole 190a is formed in the second link 190, and the protrusion 121a of the second jaw pulley 121 may be inserted into the through hole 190a of the second link 190. Accordingly, when the second jaw pulley 121 rotates, the second link 190 moves while rotating about the protrusion 121a.

The second link 190 and the second jaw 102 are axially coupled to each other at one point, and the second link 190 is coupled so as to be rotatable with respect to the second jaw pulley 121.

In detail, a through hole 190b is formed in the second link 190, a through hole 102a is also formed in the second jaw 102, and a fixing member 146 having a pin-shape passes through the through hole 190b and the through hole 102a to allow the second link 190 and the second jaw 102 to be axially coupled to each other.

In addition, the actuation rotation shaft 145 may be sequentially inserted through the second jaw 102, the first link 180, and the first jaw 101. Here, the actuation rotation shaft 145 may also be formed by being divided into two parts, similar to the other rotation shafts.

As a result, when the second jaw pulley 121 rotates about the first rotation shaft 141 while the first jaw pulley 111 is fixed, the second link 190 axially coupled to the second jaw pulley 121 is moved. In addition, when the second link 190 moves, the second jaw 102 axially coupled to the second link 190 also performs a motion by the second link 190, and at this point, the second jaw 102 pivots about the actuation rotation shaft 145.

Hereinafter, a yaw motion and an actuation motion of the end tool 100 will be described.

First, when the first jaw pulley 111 and the second jaw pulley 121 rotate together, 1) the first link 180 and the first jaw 101 coupled to the first link 180 also rotate about the first rotation shaft 141 together with the first jaw pulley 111, and 2) the second link 190 and the second jaw 102 coupled to the second link 190 also rotate about the first rotation shaft 141 together with the second jaw pulley 121, thereby performing a yaw motion.

Figure 15:
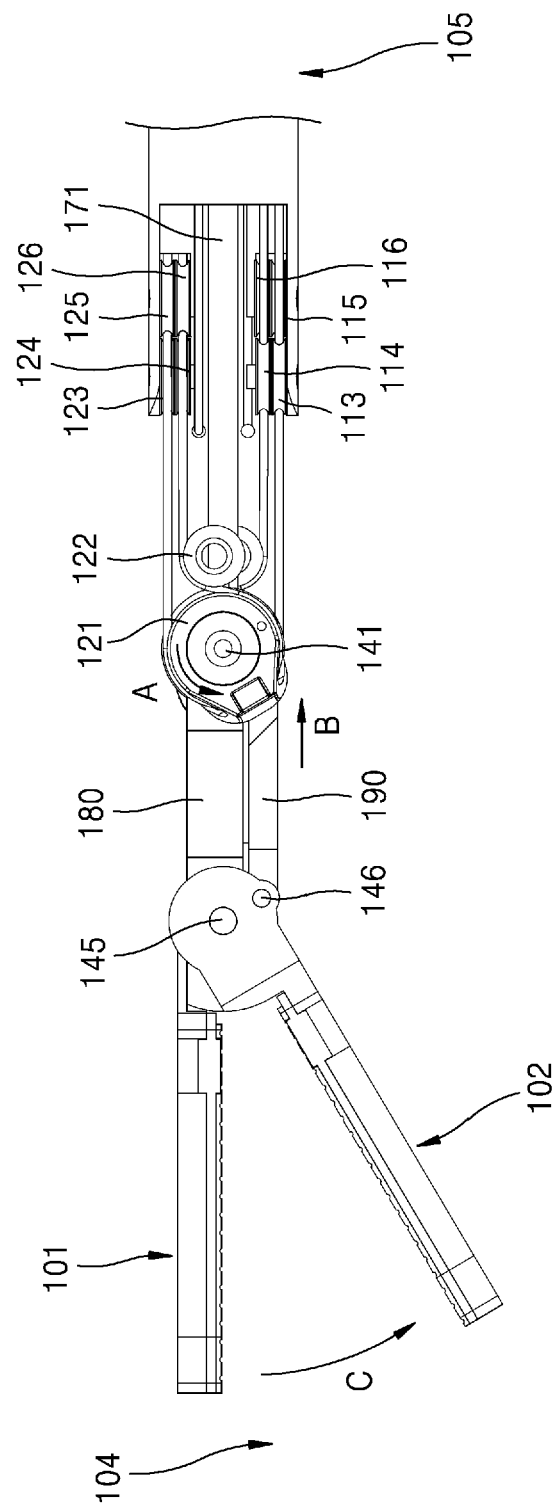
FIGS. 15 and 16 are perspective views illustrating an opening and closing motion of the end tool of the surgical instrument for electrocautery of FIG. 2.

Meanwhile, in a state in which the jaw 103 is closed as shown in FIG. 15, when only the second jaw pulley 121 rotates in a direction of an arrow A in FIG. 15, the second link 190 connected to the second jaw pulley 121 is moved in a direction of an arrow B in FIG. 15 by the second jaw pulley 121. In addition, as the second link 190 moves in the direction of the arrow B in FIG. 15, the second jaw 102 connected to the second link 190 is pulled in a direction of an arrow C in FIG. 15, and thus the second jaw 102 pivots about the actuation rotation shaft 145 in the direction of the arrow C in FIG. 15, thereby performing an actuation motion in which the jaw 103 is open.

In other words, when the manipulation portion 200 performs an actuation motion, only the second jaw pulley 121 rotates, and when the manipulation portion 200 performs a yaw motion, the first jaw pulley 111 and the second jaw pulley 121 rotate together in the same direction.

In other words, when the manipulation portion 200 performs a yaw motion, the first jaw wire and the second jaw wire are pulled together, and accordingly, the first jaw pulley 111 and the second jaw pulley 121 are rotated together, so that the rotation of the second jaw 102 with respect to the first jaw 101 does not occur.

Meanwhile, when the manipulation portion 200 performs an actuation motion, only the second jaw wire is pulled, and accordingly, only the second jaw pulley 121 is rotated while the first jaw pulley 111 is fixed, and thus the second link 190 is pulled while the actuation rotation shaft 145 is fixed, so that the second jaw 102 rotates about the actuation rotation shaft 145.

(Components Associated with Cautery and Cutting)

Referring to FIGS. 4 to 16, the end tool 100 of the first embodiment of the present disclosure may include the first jaw 101, the second jaw 102, a first electrode 151, a second electrode 152, the guide tube 171, and the blade 175 in order to perform cautery and cutting motion.

In this regard, components related to the driving of the blade, such as the guide tube 171 and the blade 175, may be collectively referred to as a blade assembly 170. In an embodiment of the present disclosure, by arranging the blade assembly 170 including the guide tube 171 and the blade 175 between the pulley 111 which is the first jaw pulley and the pulley 121 which the second jaw pulley, not only the pitch motion and the yaw motion of the end tool 100 but also the cutting motion using the blade 175 may be performed. This will be described in more detail.

As described above, the first jaw 101 is connected to the first link 180 and the first jaw pulley 111, and when the first jaw pulley 111 rotates around the first rotation shaft 141, the first jaw pulley 111 and the first link 180 rotate as one body around the first rotation shaft 141.

The first electrode 151 may be formed on a surface of the first jaw 101 facing the second jaw 102. The second electrode 152 may be formed on a surface of the second jaw 102 facing the first jaw 101.

In this regard, a slit 151a may be formed in the first electrode 151, and the blade 175 may move through the slit 151a. In an embodiment, a slit 152a may be formed in the second electrode 152, and the blade 175 may move through the slit 152a.

Meanwhile, a spacer 153 may be formed between the first jaw 101 and the first electrode 151, and a spacer 154 may be formed between the second jaw 102 and the second electrode 152. The spacer 153 and the spacer 154 may include an insulating material such as ceramic. In an embodiment, the first jaw 101 and the second jaw 102 each include a non-conductor, and thus, even without a separate insulator, the first jaw 101 and the second jaw 102 may remain insulated from each other until the first electrode 151 and the second electrode 152 come into contact with each other.

Although it is not illustrated in the drawings, one or more sensors (not illustrated) may be further formed at least one of the first jaw 101 and the second jaw 102. The sensor (not illustrated) may measure at least one of current, voltage, resistance, impedance, temperature, etc., when tissue is positioned between the first jaw 101 and the second jaw 102, a current flows into the first electrode 151 and the second electrode 152, and cautery is performed.

Alternatively, instead of providing a separate sensor, monitoring and controlling of at least one of current, voltage, resistance, impedance, and temperature may be directly performed by a generator (not illustrated) which supplies power to the electrodes.

The blade 175 may have, in one area thereof, an edge portion that is formed sharply and cuts a tissue. When at least a part of the blade 175 moves between the distal end 104 and the proximal end 105 of the end tool 100, a tissue placed between the first jaw 101 and the second jaw 102 may be cut.

In this regard, the end tool 100 of the electric cauterization surgical instrument 10 according to an embodiment of the present disclosure is characterized in that the guide tube 171 and the blade 175 are provided between the pulley 111 and the pulley 121. In addition, by providing the guide tube 171 and the blade 175, a multi-joint/multi-degree-of-freedom surgical instrument capable of pitch/yaw/actuation motions may also perform cautery and cutting. This will be described below in more detail.

So far, various types of surgical instruments for electrocautery have been developed. Among the various types of surgical instruments for electrocautery, a blood vessel resection device called 'Advanced Energy Device' or 'Vessel Sealer' has a sensing function added to the existing bipolar cautery method, so that power of different polarities may be supplied to two electrodes, and after denaturing a vessel with the heat generated therefrom for hemostasis, the stanched part may be cut with a blade. The completion of cautery may be measured by measuring the impedance of the tissue (or blood vessels) during the current flow, and after the cautery is completed, the current supply may be automatically terminated and the tissue may be cut with the blade.

In the case of such a bipolar blood vessel resection device, as a blade for cutting the tissue after cautery is essential, and an instrument for facilitating a linear motion of the blade needs to be provided additionally in the end tool, joint movements, such as a pitch/yaw movement may not be performed.

There have been attempts to implement joint movements using a curved joint constituted by several nodes connected to each other in the bipolar type blood vessel resection device; however, in such a case, the rotation angle may be limited, and the motions of the end tool may not be accurately controlled.

When the hemostasis and cutting are performed by using vibration of ultrasonic waves, due to the physical features of the ultrasonic waves, having a joint may not be an option.

In order to solve this problem, the end tool 100 of the electric cauterization surgical instrument 10 according to an embodiment of the present disclosure includes: the guide tube 171 disposed between the pulley 111 and the pulley 121; and the blade 175 that moves between a first position and a second position according to the movement of the blade wire 307 disposed inside the guide tube 171. By providing the guide tube 171 and the blade 175, in the case of a bipolar type surgical instrument for tissue cautery and cutting, the pitch/yaw/actuation motion may be performed using a pulley/wire method.

Figure 16:
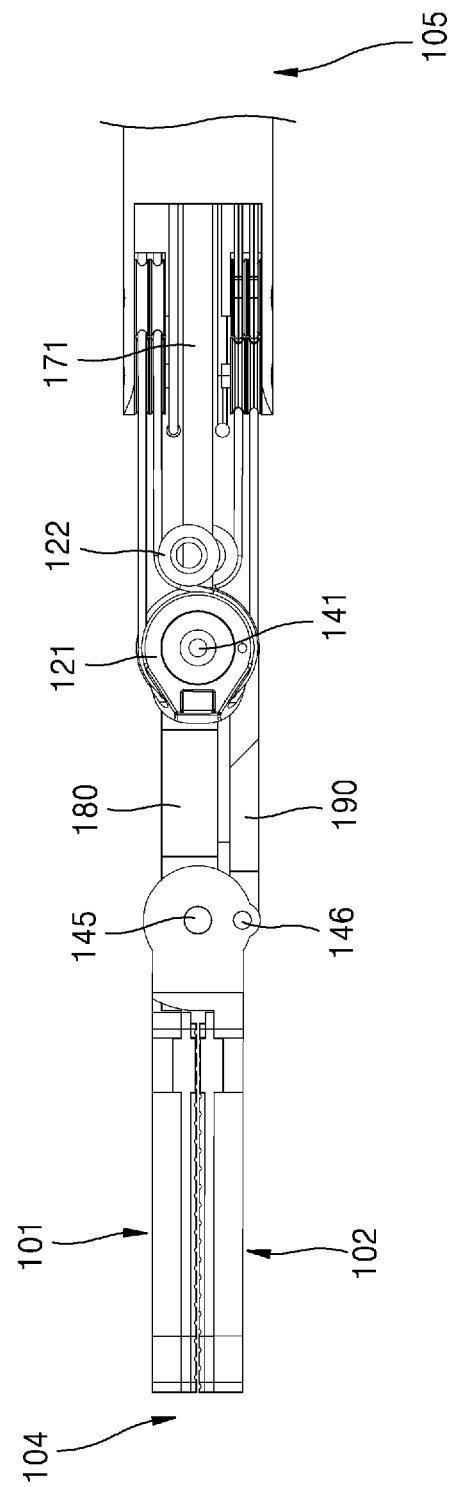

FIG. 15 is a view showing the end tool of the surgical instrument for electrocautery of FIG. 2, which is open, and FIG. 16 is a view showing the end tool of the surgical instrument for electrocautery of FIG. 2, which is closed. FIG. 17 is a view showing the blade wire 307 and the blade 175 which are located in a first position, FIG. 18 is a view showing the blade wire 307 and the blade 175 which are located in a second position, and FIG. 19 is a view showing the blade wire 307 and the blade 175 which are located in a third position.

In other words, referring to FIGS. 15 to 19, in the state where the first jaw 101 and the second jaw 102 are closed as shown in FIG. 16, when the cutting motion of FIGS. 17 to 19 is performed, the tissue between the first jaw 101 and the second jaw 102 may be cut.

In this regard, the first position illustrated in FIG. 17 may be defined as a state in which the blade 175 is maximally pulled in toward the proximal end 105 of the end tool 100. In an embodiment, it may be defined as a state in which the blade 175 is located adjacent to the pulley 111/the pulley 112.

Meanwhile, the third position illustrated in FIG. 19 may be defined as a state in which the blade 175 is drawn out as much as possible toward the distal end 104 of the end tool 100. In an embodiment, it may be defined as a state in which the blade 175 is located farthest from the pulley 111/the pulley 112.

First, as shown in FIG. 15, in the state where the first jaw 101 and the second jaw 102 are open, after arranging a tissue to be cut between the first jaw 101 and the second jaw 102, the actuation motion may be performed to make the first jaw 101 and the second jaw 102 to be close to each other as illustrated in FIG. 16.

Next, as shown in FIG. 17, in a state where the blade wire 307 and the blade 175 are positioned at the first position, currents of different polarities may flow into the first electrode 151 and the second electrode 152 to cauterize the tissue between the first jaw 101 and the second jaw 102. In this case, the generator (not illustrated) which supplies power to the electrodes may perform monitoring of at least one of current, voltage, resistance, impedance, and temperature, and discontinue the power supply when the cautery is completed.

As described above, when the cauterizing is completed and the blade wire 307 moves sequentially in the direction of arrow A1 in FIG. 18 and in the direction of arrow A2 in FIG. 19, the blade 175 coupled to the blade wire 307 moves from the first position of the proximal end 105 of the end tool 100 to the third position of the distal end 104 of the end tool 100, arriving the positions corresponding to FIGS. 18 an 19 sequentially.

As described above, the tissue between the first jaw 101 and the second jaw 102 may be cut by the blade 175 moving in the X-axis direction.

However, the linear motion of the blade 175 may refer to not only a motion in a strictly straight line, and but also the motion of cutting tissue in a straight-line in general even when the straight line is not completely straight, e.g., a line that is curved in the middle at a certain angle, or a line that includes a section with a gradual curvature, etc.

Meanwhile, when the blade wire 307 is pulled in the opposite direction in this state, the blade 175 coupled to the blade wire 307 returns to the first position.

According to the present disclosure, a multi-joint/multi-degree-of-freedom surgical instrument capable of pitch/yaw/actuation motions may also perform cautery and cutting.

(Manipulation Portion)

FIGS. 20 and 21 are perspective views illustrating the manipulation portion of the surgical instrument of FIG. 2. FIG. 22 is a view schematically illustrating only a configuration of pulleys and wires constituting joints of the surgical instrument for electrocautery of FIG. 2.

With reference to FIGS. 2 to 22, the manipulation portion 200 of the electric cauterization surgical instrument 10 according to the first embodiment of the present disclosure may include a first handle 204 which a user may hold, an actuation manipulation portion 203 configured to control the actuation motion of the end tool 100, a yaw manipulation portion 202 configured to control the yaw motion of the end tool 100, and a pitch manipulation portion 201 configured to control the pitch motion of the end tool 100. FIGS. 20 and 21 illustrate components only associated with the pitch/yaw/actuation motions of the electric cauterization surgical instrument 10.

In addition, the manipulation portion 200 of the electric cauterization surgical instrument 10 may further include a blade manipulation portion 260 performing cutting by controlling the movement of the blade 175 of the end tool 100, and a cauterizing manipulation portion 270 performing cauterizing by supplying electrical energy to the first electrode 151 and the second electrode 152 of the end tool 100.

The manipulation portion 200 may include a pulley 210, a pulley 211, a pulley 212, a pulley 213, a pulley 214, a pulley 215, a pulley 216, a pulley 217, and a pulley 218, which are associated with the rotational motion of the first jaw 101. In addition, the manipulation portion 200 may include a pulley 220, a pulley 221, a pulley 222, a pulley 223, a pulley 224, a pulley 225, a pulley 226, a pulley 227, and a pulley 228, which are associated with the rotational motion of the second jaw 102. In one embodiment, the manipulation portion 200 may include a pulley 231, a pulley 232, a pulley 233, and a pulley 234, which are associated with the pitch motion. The manipulation portion 200 may include a pulley 235 which is an intermediate pulley arranged in some positions of the curved portion 402 of the connection portion 400.

Here, the drawings illustrate that the pulleys facing each other are arranged in parallel with each other; however, the technical concepts of the present disclosure are not limited thereto, and each pulley may be formed in various positions and sizes suitable for the configuration of the manipulation portion 200.

In addition, the manipulation portion 200 of the first embodiment may include a rotation shaft 241, a rotation shaft 242, a rotation shaft 243, a rotation shaft 244, a rotation shaft 245, and a rotation shaft 246. Here, the rotation shaft 241 may function as a manipulation portion first jaw actuation rotation shaft, and the rotation shaft 242 may function as a manipulation portion second jaw actuation rotation shaft. In addition, the rotation shaft 243 may function as a manipulation portion yaw main rotation shaft, and the rotation shaft 244 may function as a manipulation portion yaw subsidiary rotation shaft. The rotation shaft 245 may function as a manipulation portion pitch subsidiary rotation shaft, and the rotation shaft 246 may function as a manipulation portion pitch main rotation shaft.

The rotation shaft 241, the rotation shaft 242, the rotation shaft 243, the rotation shaft 244, the rotation shaft 245, and the rotation shaft 246 may be sequentially arranged in a direction towards a proximal end 206 from a distal end 205.

One or more pulleys may be fit into each of the rotation shafts 241, 242, 243, 244, 245, and 246 which will be described in detail below.

The pulley 210 may function as a manipulation portion first jaw actuation pulley, the pulley 220 may function as a manipulation portion second jaw actuation pulley, and these components may be collectively referred to as a manipulation portion actuation pulley.

The pulley 211 and the pulley 212 may function as a manipulation portion first jaw yaw main pulley, the pulley 221 and the pulley 222 may function as a manipulation portion second jaw yaw main pulley, and these two components may collectively be referred to as a manipulation portion yaw main pulley.

The pulley 213 and the pulley 214 may function as a manipulation portion first jaw yaw subsidiary pulley, the pulley 223 and the pulley 224 may function as a manipulation portion second jaw yaw subsidiary pulley, and these two components may collectively be referred to as a manipulation portion yaw subsidiary pulley.

The pulley 215 and the pulley 216 may function as a manipulation portion first jaw pitch subsidiary pulley, the pulley 225 and the pulley 226 may function as a manipulation portion second jaw pitch subsidiary pulley, and these two components may collectively be referred to as a manipulation portion pitch subsidiary pulley.

The pulley 217 and the pulley 218 may function as a manipulation portion first jaw pitch main pulley, the pulley 227 and the pulley 228 may function as a manipulation portion second jaw pitch main pulley, and these two components may collectively be referred to as a manipulation portion pitch main pulley.

The pulley 231 and the pulley 232 may function as a manipulation portion pitch wire main pulley, and the pulley 233 and the pulley 234 may function as a manipulation portion pitch wire subsidiary pulley.

The components may be classified from the viewpoint of the manipulation portion in connection with each motion (i.e., pitch/yaw/actuation) as follows.

The pitch manipulation portion 201 controlling the pitch motion of the end tool 100 may include a pulley 215, a pulley 216, a pulley 217, a pulley 218, a pulley 225, a pulley 226, and a pulley 227, a pulley 228, a pulley 231, a pulley 232, a pulley 233, and a pulley 234. In addition, the pitch manipulation portion 201 may include the rotation shaft 245 and the rotation shaft 246. In one embodiment, the pitch manipulation portion 201 may further include a pitch frame 208.

The yaw manipulation portion 202 controlling the yaw motion of the end tool 100 may include a pulley 211, a pulley 212, a pulley 213, a pulley 214, a pulley 221, a pulley 222, a pulley 223, and a pulley 224. In addition, the yaw manipulation portion 202 may include the rotation shaft 243 and the rotation shaft 244. In one embodiment, the yaw manipulation portion 202 may further include a yaw frame 207.

The actuation manipulation portion 203 controlling the actuation motion of the end tool 100 may include the pulley 210, the pulley 220, the rotation shaft 241, and the rotation shaft 242. In one embodiment, the actuation manipulation portion 203 may further include a first actuation manipulation portion 251 and a second actuation manipulation portion 256.

Hereinafter, each component of the manipulation portion 200 will be described in more detail.

The first handle 204 may be held by a user, and more particularly, a user may hold the first handle 204 by wrapping it with his or her hand. The actuation manipulation portion 203 and the yaw manipulation portion 202 may be formed on the first handle 204, and the pitch manipulation portion 201 may be formed on one side of the yaw manipulation portion 202. In addition, another end of the pitch manipulation portion 201 may be connected to the curved portion 402 of the connection portion 400.

The actuation manipulation portion 203 may include the first actuation manipulation portion 251 and the second actuation manipulation portion 256. The first actuation manipulation portion 251 may include the rotation shaft 241, the pulley 210, a first actuation extension portion 252, and a first actuation gear 253. The second actuation manipulation portion 256 may include the rotation shaft 242, the pulley 220, a second actuation extension portion 257, and a second actuation gear 258. Here, ends of the first actuation extension portion 252 and the second actuation extension portion 257 may be formed in the shape of a ring, and may operate as a second handle.

The rotation shaft 241 and the rotation shaft 242, which are the actuation rotation shaft, may be formed to have a certain angle with the XY plane on which the connection portion 400 is formed. For example, the rotation shaft 241 and the rotation shaft 242 may be formed in a direction parallel with the Z-axis, and when the pitch manipulation portion 201 or the yaw manipulation portion 202 rotates, a coordinate system of the actuation manipulation portion 203 may be changed relatively. However, the technical ideas of the present disclosure are not limited thereto, and by an ergonomic design, the rotation shaft 241 and the rotation shaft 242 may be formed in various directions suitable for a hand shape of a user holding the actuation manipulation portion 203.

The pulley 210, the first actuation extension portion 252, and the first actuation gear 253 may be fixedly coupled to each other and rotatable together around the rotation shaft 241. Here, the pulley 210 may include one pulley or two pulleys fixedly coupled to each other.

Likewise, the pulley 220, the second actuation extension portion 257, and the second actuation gear 258 may be fixedly coupled to each other and rotatable together around the rotation shaft 242. Here, the pulley 220 may include one pulley or two pulleys fixedly coupled to each other.

The first actuation gear 253 and the second actuation gear 258 may be formed to engage with each other, and when either one of them rotates in one direction, the other one may rotate concurrently in the opposite direction.

In this regard, either of the first actuation manipulation portion 251 or the second actuation manipulation portion 256 may be a dummy manipulation portion to which no wire is connected. According to the present disclosure, the actuation motion may be a motion in which the second jaw 102 rotates around the actuation rotation shaft 145 while the first jaw 101 is stopped. Therefore, during the actuation motion, only the wire 302/the wire 306 connected to the second jaw 102 are moved, and the wire 301/the wire 305 connected to the first jaw 101 may not be moved. Therefore, the wire 302/the wire 306, which are a second jaw wire connected to the second jaw 102, may be coupled to either the first actuation manipulation portion 251 or the second actuation manipulation portion 256, and the wire 301/the wire 305, which is a first jaw wire connected to the first jaw 101, may not be coupled to the actuation manipulation portion 203. In this regard, the other actuation manipulation portion to which the second jaw wire is not coupled, may be a dummy manipulation portion.

In the related drawing, it is shown that the wire 302/the wire 306, which is the second jaw wire, are connected to the pulley 220 of the second actuation manipulation portion 256, and a wire is not connected to the pulley 210 of the first actuation manipulation portion 251. However, in other embodiment, opposite connection of wire and pulley compared to the aforementioned embodiment is possible.

As a result, only the wire 302/the wire 306, which are the second jaw wire, is coupled to the actuation manipulation portion 203, and therefore, when the actuation manipulation portion 203 is operated, the second jaw 102 alone rotates about the actuation rotation shaft 145 while the first jaw 101 is fixed.

Meanwhile, the related drawing illustrates an example of the actuation manipulation portion 203 in which the actuation manipulation portion 203 includes the first actuation manipulation portion 251 and the second actuation manipulation portion 256. In an embodiment, however, the actuation manipulation portion 203 of present disclosure may include one of the first actuation manipulation portion 251 and the second actuation manipulation portion 256. In this embodiment, the actuation manipulation portion 203 may be provided in the form of a ring rotating around a rotation shaft parallel to the Z axis. However, embodiments of the present disclosure are not limited thereto. In an embodiment, the actuation manipulation portion 203 may be formed to rotate around another axis (for example, the Y axis).

The yaw manipulation portion 202 may include the rotation shaft 243, the pulley 211 and the pulley 212, which are the manipulation portion first jaw yaw main pulleys, the pulley 221 and the pulley 222, which are the manipulation portion second jaw yaw main pulleys, and a yaw frame 207. In addition, the yaw manipulation portion 202 may further include the pulley 213 and the pulley 214, which are the manipulation portion first jaw yaw subsidiary pulley and arranged on one side of the pulley 211 and the pulley 212, and the pulley 223 and the pulley 224, which are the manipulation portion second jaw yaw subsidiary pulley and arranged on one side of the pulley 221 and the pulley 222. Here, the pulley 213, the pulley 214, the pulley 223, and the pulley 224 may be coupled to the pitch frame 208 to be described later.

The drawings illustrate that the yaw manipulation portion 202 includes the pulley 211, the pulley 212, the pulley 221, and the pulley 222, and as the pulley 211 faces the pulley 212 and the pulley 221 faces the pulley 222, two pulleys may be rotatable independently of each other; however the technical concepts of the present disclosure are not limited thereto. That is, one or more pulleys having the same diameter or different diameters may be provided according to the configuration of the yaw manipulation portion 202.

More specifically, on the first handle 204, the rotation shaft 243, which is the manipulation portion yaw main rotation shaft, may be formed on one side of the actuation manipulation portion 203. In this case, the first handle 204 may be formed to be rotatable around the rotation shaft 243.

Here, the rotation shaft 243 may be formed to have a certain angle with the XY plane on which the connection portion 400 is formed. For example, the rotation shaft 243 may be formed in a direction parallel with the Z-axis, and when the pitch manipulation portion 201 rotates, the coordinate system of the rotation shaft 243 may be changed relatively as described above. However, the technical ideas of the present disclosure are not limited thereto, and by an ergonomic design, the rotation shaft 243 may be formed in various directions suitable for a hand shape of a user holding the manipulation portion 200.

The pulley 211, the pulley 212, the pulley 221, and the pulley 222 may be coupled to the rotation shaft 243 to be rotatable around the rotation shaft 243. In addition, the wire 301 or the wire 305, which is the first jaw wire, may be wound around the pulley 211 and the pulley 212, and the wire 302 or the wire 306, which is the second jaw wire, may be wound around the pulley 221 and the pulley 222. In this case, the pulley 211 and the pulley 212 may be formed to face each other and the pulley 221 and the pulley 222 may be formed to face each other, respectively, thereby forming two independently rotatable pulleys. Accordingly, as the wire wound inward and the wire wound outward may be respectively wound around separate pulleys, the pulleys may operate without interfering with each other.

In this regard, the wire 301 and the wire 305, which are first jaw wires, may be fixedly coupled to the pulley 211/the pulley 212 by fastening member 324, respectively. In detail, the wire 305, which is the first jaw wire, may be fixedly coupled to the pulley 211 by the fastening member 324, and the wire 301, which is the first jaw wire, may be fixedly coupled to the pulley 212 by the fastening member 324.

Meanwhile, the wire 302 and the wire 306, which are second jaw wires, may be fixedly coupled to the pulley 220 of the actuation manipulation portion 203 via the pulley 221/the pulley 222.

The yaw frame 207 may rigidly connect the first handle 204, the rotation shaft 241, the rotation shaft 242, and the rotation shaft 243, and accordingly, the first handle 204, the yaw manipulation portion 202, and the actuation manipulation portion 203 may yaw-rotate around the rotation shaft 243 in an integrated manner.

In this regard, the pulley 211 or the pulley 212 may be fixedly coupled to the yaw frame 207, and when the yaw frame 207 rotates, may rotate together with the yaw frame 207.

The pitch manipulation portion 201 may include the rotation shaft 246, the pulley 217 and the pulley 218, which are the manipulation portion first jaw pitch main pulley, the pulley 227 and the pulley 228, which are the manipulation portion second jaw pitch main pulley, and the pitch frame 208. In addition, the pitch manipulation portion 201 may further include the rotation shaft 245, the pulley 215 and the pulley 216, which are the manipulation portion first jaw pitch subsidiary pulley and arranged on one side of the pulley 217 and the pulley 218, and the pulley 225 and the pulley 226, which are the manipulation portion second jaw pitch subsidiary pulley and arranged on one side of the pulley 227 and pulley 228. The pitch manipulation portion 201 may be connected to the curved portion 402 of the connection portion 400 through the rotation shaft 246.

More specifically, the pitch frame 208 may be a base frame of the pitch manipulation portion 201, and one end of the pitch frame 208 may be rotatably coupled to the rotation shaft 243. That is, the yaw frame 207 may be formed to be rotatable around the rotation shaft 243 with respect to the pitch frame 208.

As described above, the yaw frame 207 may connect the first handle 204, the rotation shaft 243, the rotation shaft 241, and the rotation shaft 242, and as the yaw frame 207 is axially coupled to the pitch frame 208, when the pitch frame 208 pitch-rotates around the rotation shaft 246, the yaw frame 207, the first handle 204, the rotation shaft 241, the rotation shaft 242, and the rotation shaft 243, which are connected to the pitch frame 208, may also pitch rotate. That is, when the pitch manipulation portion 201 rotates around the rotation shaft 246, the actuation manipulation portion 203 and the yaw manipulation portion 202 may be rotated together with the pitch manipulation portion 201. In other words, when the user pitch-rotates the first handle 204 around the rotation shaft 246, the actuation manipulation portion 203, the yaw manipulation portion 202, and the pitch manipulation portion 201 may also move together with the first handle 204.

The pulley 217, the pulley 218, the pulley 227, and the pulley 228 may be coupled to the rotation shaft 246 so that they are rotatable around the rotation shaft 246 of the pitch frame 208.

Here, the pulley 217 and the pulley 218 may face each other and rotate independently. Accordingly, as the wire wound inward and the wire wound outward may be respectively wound around separate pulleys, the pulleys may operate without interfering with each other. Likewise, the pulley 227 and the pulley 228 may face each other and rotate independently. Accordingly, as the wire wound inward and the wire wound outward may be respectively wound around separate pulleys, the pulleys may operate without interfering with each other.

Next, the motions of the wire 303 and the wire 304 which are the pitch wire are described below.

In the end tool 100, the first pitch pulley portion 163a and the second pitch pulley portion 163b, which may act as an end tool pitch pulley, may be formed on the end tool hub 160, and in the manipulation portion 200, the pulley 231 and the pulley 232, which are manipulation portion pitch pulleys, may be fixedly coupled to the pitch frame 208. These pulleys may be connected to each other by the wire 303 and the wire 304, which are the pitch wire, to facilitate the pitch motion of the end tool 100 according to the pitch manipulation of the manipulation portion 200. Here, the wire 303 may be fixedly coupled to the pitch frame 208 via the pulley 231 and the pulley 233, and the wire 304 may be fixedly coupled to the pitch frame 208 via the pulley 232 and the pulley 234. That is, the pitch frame 208, the pulley 231, and the pulley 232 may rotate together around the rotation shaft 246 by the pitch rotation of the manipulation portion 200. As a result, the wire 303 and the wire 304 may also move, and separately from the pitch motion of the end tool 100 by the wire 301, the wire 302, the wire 305, and the wire 306, which are the jaw wire, additional pitch rotation power may be transmitted.

The connection relation among the first handle 204, the pitch manipulation portion 201, the yaw manipulation portion 202, and the actuation manipulation portion 203 is described below. On the first handle 204, the rotation shaft 241, the rotation shaft 242, the rotation shaft 243, the rotation shaft 244, the rotation shaft 245, and the rotation shaft 246 may be formed. In this case, as the rotation shaft 241 and the rotation shaft 242 are directly formed on the first handle 204, the first handle 204 and the actuation manipulation portion 203 may be directly connected to each other. As the rotation shaft 243 is directly formed on the first handle 204, the first handle 204 and the yaw manipulation portion 202 may be directly connected to each other. As the pitch manipulation portion 201 is arranged on one side of the yaw manipulation portion 202 and connected to the yaw manipulation portion 202, the pitch manipulation portion 201 may not be directly connected to the first handle 204 and the pitch manipulation portion 201 and the first handle 204 may be indirectly connected to each other through the yaw manipulation portion 202.

With reference to the drawings, in the electric cauterization surgical instrument 10 according to the first embodiment, the pitch manipulation portion 201 and the end tool 100 may be formed on the same or parallel axis (i.e., the X-axis). That is, the rotation shaft 246 of the pitch manipulation portion 201 may be formed at one end of the curved portion 402 of the connection portion 400, and the end tool 100 may be formed at the other end of the connection portion 400.

In addition, one or more intermediate pulleys 235 changing or guiding a path of the wires may be arranged in some positions of the connection portion 400, in particular, in positions on the curved portion 402. At least a part of the wires may be wound around the intermediate pulleys 235 to guide the path of the wires so that the wires are arranged along the curved shape of the curved portion 402.

Here, the drawings illustrate that the connection portion 400 includes the curved portion 402 and thus is formed in a curved manner with a certain curvature; however, the technical concepts of the present disclosure are not limited thereto, and the connection portion 400 may be formed straightly, if necessary, or curved in one or more points. Even in such cases, the pitch manipulation portion 201 and the end tool 100 may be formed on the substantially same or parallel axis. In addition, although FIG. 2 illustrates that the pitch manipulation portion 201 and the end tool 100 are respectively formed on an axis parallel with the X-axis, the technical concepts of the present disclosure are not limited thereto, and the pitch manipulation portion 201 and the end tool 100 may be formed on different axes.

(Actuation Motion, Yaw Motion, Pitch Motion)

Actuation motion, yaw motion, and pitch motion in this embodiment will be described as follows.

First, the actuation motion is as follows.

When a user puts the index finger in a ring formed at the first actuation extension 252, puts the thumb in a ring formed at the second actuation extension 257, and rotates the first actuation extension 252 and the second actuation extension 257 using any one of or both the fingers, the pulley 210 and the first actuation gear 253 fixedly coupled to the first actuation extension 252 rotate around the rotation shaft 241, and the pulley 220 and the second actuation gear 258 fixedly coupled to the second actuation extension 257 rotate around the rotation shaft 242. In this regard, the pulley 210 and the pulley 220 rotate in opposite directions. When the pulley 220 rotates, the wire 302 and the wire 306 whose end portions are fixedly coupled to the pulley 220 by the fastening member 327, rotate together with the pulley 220 to move the wire 302 and the wire 306. This rotational force is transmitted to an end tool 100 through the power transmission portion 300, the second jaw 102 of the end tool 100 perform the actuation motion.

According to the present disclosure, the actuation motion may be a motion in which the second jaw 102 rotates around the actuation rotation shaft 145 while the first jaw 101 is stopped. In other words, when the actuation extensions 252 and 257 of the actuation manipulation portion 203 are rotated in such a direction that the actuation extensions 252 and 257 are closer to each other, while the first jaw 101 is fixed, the second jaw 102 rotates clockwise, and thus the end tool 100 is closed. In other words, when the actuation extensions 252 and 257 of the actuation manipulation portion 203 are rotated in such a direction that the actuation extensions 252 and 257 are farther away from each other, while the first jaw 101 is fixed, the second jaw 102 rotates counter-clockwise, and thus the end tool 100 is open.

In this embodiment, for the above-described actuation manipulation, the first actuation extension 252 and the second actuation extension 257 were provided to constitute a second handle, and two fingers were gripped to enable manipulation. However, unlike the above, the actuation manipulation portion 203 for actuation manipulation to open and close the two jaws of the end tool 100 with each other may be configured differently so that, for example, two actuation pulleys (the pulley 210 and the pulley 220) operate opposite to each other by one actuation rotating portion.

Next, the yaw motion is as follows.

When the user rotates a first handle 204 around a rotation shaft 243 while holding the first handle 204, the actuation manipulation portion 203 and the yaw manipulation portion 202 yaw-rotates around the rotation shaft 243. That is, when the pulley 211 and the pulley 212 of the yaw manipulation portion 202 to which wire 301 and wire 305 are fixedly coupled, rotate around the rotation shaft 243, the wire 301 and wire 305 wound on pulley 211 and pulley 212 are moved. Likewise, when the pulley 220 of the second actuation manipulation portion 256 to which the wire 302 and the wire 306 are fixedly coupled, rotates about the rotation shaft 243, the wire 302 and the wire 306 respectively wound around the pulley 221 and the pulley 222 move. In this case, to make the first jaw 101 and the second jaw 102 rotate in the same direction during a yaw rotation, the wire 301 and the wire 305, which are connected to the first jaw 101, are wound around the pulley 211 or the pulley 212, and the wire 302 and the wire 306, which are connected to the second jaw 102, are wound around the pulley 221, and the pulley 222. Moreover, this rotational force is transmitted to the end tool 100 through the power transmission portion 300, the two jaws 103 of the end tool 100 performs the yaw motion that rotates in the same direction.

In this case, since the yaw frame 207 connects the first handle 204, the rotation shaft 241, the rotation shaft 242, and the rotation shaft 243, the first handle 204, the yaw manipulation portion 202, and the actuation manipulation portion 203 rotate together around the rotation shaft 243.

Next, the pitch motion is as follows.

When the user rotates a first handle 204 around a rotation shaft 246 while holding the first handle 204, the actuation manipulation portion 203, the yaw manipulation portion 202, and the pitch manipulation portion 201 pitch rotates around the rotation shaft 243. That is, when the pulley 211 and the pulley 212 of the yaw manipulation portion 202 to which wire 301 and wire 305 are fixedly coupled, rotate around the rotation shaft 246, the wire 301 and the wire 305 wound around the pulley 217 and pulley 218 may be moved. Likewise, when the pulley 220 of the second actuation manipulation portion 256 to which the wire 302 and the wire 306 are fixedly coupled rotates about the rotation shaft 246, the wire 302 and the wire 306 respectively wound around the pulley 227 and the pulley 228 move. Here, as described above with reference to FIG. 5, the wire 301, the wire 305, the wire 302, and the wire 306, which are jaw wires, are wound around the pulley 217, the pulley 218, the pulley 227, and the pulley 228, which are manipulation portion pitch main pulleys, such that the wire 301 and wire 305, which are first jaw wires, move in the same direction and the wire 302 and the wire 306, which are second jaw wires, move in the same direction to enable pitch rotation of the first jaw 101 and the second jaw 102. Moreover, this rotational force is transmitted to an end tool 100 through a power transmission portion 300, two jaws 103 of the end tool 100 perform the pitch motion.

In this case, the pitch frame 208 is connected to the yaw frame 207 and the yaw frame 207 connects the first handle 204, the rotation shaft 241, the rotation shaft 242, and the rotation shaft 243. Therefore, when the pitch frame 208 rotates around the rotation shaft 246, the yaw frame 207, the first handle 204, the rotation shaft 241, the rotation shaft 242, and the rotation shaft 243 connected to the pitch frame 208, rotate together. That is, when the pitch manipulation portion 201 rotates around the rotation shaft 246, the actuation manipulation portion 203 and the yaw manipulation portion 202 may be rotated together with the pitch manipulation portion 201.

In summary, in an electric cauterization surgical instrument 10 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 100 is induced. Furthermore, auxiliary pulleys may be formed on one side of each pulley, and the wire may not be wound several times on one pulley by these auxiliary pulleys.

FIG. 22 is a schematic view of only the configuration of pulleys and wires constituting joints of the electric cauterization surgical instrument 10 according to an embodiment of the present disclosure shown in FIG. 2. In FIG. 22, intermediate pulleys that are for changing paths of wires and are not associated with joint motions are omitted.

Referring to FIG. 22, the manipulation portion 200 may include the pulley 210, the pulley 211, the pulley 212, the pulley 213, the pulley 214, the pulley 215, the pulley 216, the pulley 217, and the pulley 218, which are associated with the rotational motion of the first jaw 101.

Also, the manipulation portion 200 may include the pulley 220, the pulley 221, the pulley 222, the pulley 223, the pulley 224, the pulley 225, the pulley 226, the pulley 227, and the pulley 228 associated with the rotational motion of the second jaw 122. (The arrangement and the configuration of pulleys in the manipulation portion 200 are the same as the arrangement and the configuration of the pulleys in the end tool 100 in principle, and thus some of the reference numerals thereof will be omitted in the drawings.)

The pulley 211 and the pulley 212, and the pulley 221 and the pulley 222 may be formed to be rotatable independently of each other around the same axis, that is, the rotation shaft 243. In this case, the pulley 211 and the pulley 212 may be formed to face each other and the pulley 221 and the pulley 222 may be formed to face each other, respectively, thereby forming two independently rotatable pulleys.

The pulley 213 and the pulley 214, and the pulley 223 and the pulley 224 may be formed to be rotatable independently of each other around the same axis, that is, the rotation shaft 244. In this case, the pulley 213 and the pulley 214 may be formed to face each other as two independently rotatable pulleys, and, in this case, the two pulleys may be formed to have different diameters. Likewise, the pulley 223 and the pulley 224 may be formed to face each other as two independently rotatable pulleys, and, in this case, the two pulleys may be formed to have different diameters.

The pulley 215 and the pulley 216, and the pulley 225 and the pulley 226 may be formed to be rotatable independently of each other around the same axis, that is, the rotation shaft 245. In this case, the pulley 215 and the pulley 216 may be formed to have different diameters. Also, the pulley 225 and the pulley 226 may be formed to have different diameters.

The pulley 217 and the pulley 218, and the pulley 227 and the pulley 228 may be formed to be rotatable independently of each other around the same axis, that is, the rotation shaft 246.

The wire 301 sequentially passes through the pulley 217, the pulley 215, and the pulley 213 of the manipulation portion 200, is wound around the pulley 211, and then is coupled to the pulley 212 by the fastening member 324. Meanwhile, the wire 305 sequentially passes through the pulley 218, the pulley 216, and the pulley 214 of the manipulation portion 200 and is coupled to the pulley 211 by the fastening member 324. Therefore, when the pulley 211 rotates, the wire 301 and the wire 305 are wound around or unwound from the pulley 211, and thus the first jaw 101 rotates.

The wire 306 sequentially passes through the pulley 227, the pulley 225, the pulley 223, and the pulley 221 of the manipulation portion 200, is wound around the pulley 220, and then is coupled to the pulley 220 by a fastening member 327. Meanwhile, the wire 302 sequentially passes through the pulley 228, the pulley 226, the pulley 224, and the pulley 222 of the manipulation portion 200 and is coupled to the pulley 220 by the fastening member 327. Therefore, as the pulley 220 rotates, the wire 302 and the wire 306 are wound around or unwound from the pulley 220, and thus the second jaw 102 rotates.

(Pulley and Wire Conceptual Diagram)

FIGS. 24 and 25 are diagrams illustrating configurations of pulleys and wires associated with an actuation motion and a yaw motion of the electric cauterization surgical instrument 10 according to an embodiment of the present disclosure shown in FIG. 2 for a first jaw and a second jaw, respectively. FIG. 24 is a diagram showing only pulleys and wires associated with the second jaw, and FIG. 25 is a diagram showing only pulleys and wires associated with the first jaw. FIG. 23 is a perspective view showing the yaw motion of the surgical instrument of FIG. 2. Here, components associated with a cutting motion are omitted in FIG. 23.

First, the operation of wires in an actuation motion will be described.

Referring to FIG. 24, when the second actuation extension 257 rotates in the direction indicated by an arrow OPA2 around the rotation shaft 242, the pulley 220 connected to the second actuation extension 257 rotates, and the wire 302 and the wire 306 wound around the pulley 220 move in directions W2a and W2b, respectively. As a result, the second jaw 102 of the end tool 100 rotates in the direction indicated by an arrow EPA2. Therefore, when a user manipulates the first actuation extension 252 and the second actuation extension 257 in directions toward each other, a motion of moving the second jaw 102 of an end tool to be closer to the first jaw 101 is performed.

In this case, since the wire 301 and the wire 305, which are the first jaw wire, are not connected to the actuation manipulation portion 203, even when the actuation manipulation portion 203 operates, the wire 301 and the wire 305 do not move, and therefore the first jaw 101 does not rotate either.

Next, the operation of wires in a yaw motion will be described.

First, since the rotation shaft 243, the rotation shaft 241, and the rotation shaft 242 are connected to one another by a yaw frame (refer to 207 of FIG. 30), the rotation shaft 243, the rotation shaft 241, and the rotation shaft 242 rotate together.

Referring to FIG. 25, when the first handle 204 rotates in a direction indicated by an arrow OPY1 around the rotation shaft 243, the pulley 221, and the wire 301 and the wire 305 wound therearound rotate together around the rotation shaft 243. As a result, the wire 301 and the wire 305 wound around the pulley 221 move in a direction W1a and a direction W1b, respectively, and thus the first jaw 101 of the end tool 100 rotates in the direction indicated by an arrow EPY1.

Referring to FIG. 24, when the first handle 204 rotates in a direction indicated by an arrow OPY2 around the rotation shaft 243, the pulley 220, the pulley 221 and the pulley 222, and the wire 302 and the wire 306 wound therearound rotate together around the rotation shaft 243. As a result, the wire 302 and the wire 306 wound around the pulley 221 and the pulley 222 move in a direction opposite to the direction W1a and a direction opposite to the direction W1b, respectively, and thus the first jaw 101 of the end tool 100 rotates in the direction indicated by an arrow EPY2.

FIGS. 27 and 28 are diagrams illustrating configurations of pulleys and wires associated with a pitch motion of the electric cauterization surgical instrument 10 according to an embodiment of the present disclosure shown in FIG. 2, for a first jaw and a second jaw, respectively. FIG. 27 is a diagram showing only pulleys and wires associated with the first jaw, and FIG. 28 is a diagram showing only pulleys and wires associated with the second jaw. As shown in FIG. 9 and the like, there are two pulleys associated with the pitch motion, and wires are wound in the same path, which are indicated as single lines in FIGS. 27 and 28. FIG. 26 is a perspective view showing the pitch motion of the surgical instrument of FIG. 2. Here, components associated with a cutting motion are omitted in FIG. 26.

Referring to FIG. 27, when the first handle 204 is rotated in the direction indicated by an arrow OPP1 around the rotation shaft 246, pulleys including the pulley 211, the pulley 215, and the pulley 217, and wires including the wire 301 wound therearound, rotate around the rotation shaft 246 together. In this case, as shown in FIG. 22, the wire 301 and wire 305, which are first jaw wires, are wound on upper portions of the pulley 217 and the pulley 218, and thus the wire 301 and the wire 305 move in the direction indicated by an arrow W1. As a result, as described with reference to FIG. 5, the first jaw 101 of the end tool 100 rotates in the direction indicated by an arrow EPP1.

Referring to FIG. 28, when the first handle 204 is rotated in the direction indicated by an arrow OPP2 around the rotation shaft 246, pulleys including the pulley 220, the pulley 225, and the pulley 227, and wires including the wire 302 wound therearound rotate around the rotation shaft 246 together. In this case, as shown in FIG. 22, the wire 302 and wire 306, which are second jaw wires, are wound on lower portions the pulley 227 and the pulley 228, and thus the wire 302 and the wire 306 move in the direction indicated by an arrow W2. As a result, as described with reference to FIG. 5, the second jaw 102 of the end tool 100 rotates in the direction indicated by an arrow EPP2.

Therefore, an actuation motion, a yaw motion, and a pitch motion may be manipulated independently of one another.

As described through FIG. 1, the actuation manipulation portion 203, yaw manipulation portion 202, and pitch manipulation portion 201 have their own rotation shafts located at the back of each manipulation portion, so it is configured the same as the joint configuration of the end tool, allowing the user to perform intuitively matching operations.

Especially, in the electric cauterization surgical instrument 10 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 100 is induced. Furthermore, auxiliary pulleys may be formed on one side of each pulley, and the wire may not be wound several times on one pulley by these auxiliary pulleys, so that the wires wound on the pulley do not come into contact with each other, and the path of the wire that goes into the pulley and the wire that comes out is also formed safely, so the safety and efficiency of power transmission of the wire may be improved.

On the other hand, as described above, the yaw manipulation portion 202 and the actuation manipulation portion 203 are formed directly on the first handle 204. Therefore, when the first handle 204 rotates around the rotation shaft 246, the yaw manipulation portion 202 and the actuation manipulation portion 203 also rotate together with the first handle 204. Due to this, a coordinate system of the yaw manipulation portion 202 and the actuation manipulation portion 203 is not fixed, but continues to change relatively according to the rotation of the first handle 204. That is, in FIG. 2 and the like, the yaw manipulation portion 202 and the actuation manipulation portion 203 are illustrated as being parallel to a Z-axis. However, when the first handle 204 is rotated, the yaw manipulation portion 202 and the actuation manipulation portion 203 are not parallel to the Z-axis. That is, the coordinate system of the yaw manipulation portion 202 and the actuation manipulation portion 203 is changed according to the rotation of the first handle 204. However, in the present specification, for convenience of explanation, if there is no separate explanation, the coordinate system of the yaw manipulation portion 202 and the actuation manipulation portion 203 was described based on a state in which the first handle 204 is positioned vertically with respect to the connection portion 400 as illustrated in FIG. 2.

Pitch, Yaw, and Cutting Motions of End Tool

FIGS. 29 and 30 are views illustrating a process of performing an opening and closing motion while the end tool of the surgical instrument for electrocautery of FIG. 2 is yaw-rotated by −90°. In addition, FIGS. 31 and 32 are views illustrating a process of performing an opening and closing motion while the end tool of the surgical instrument for electrocautery of FIG. 2 is yaw-rotated by +90°.

As shown in FIGS. 29 and 32, the end tool of the surgical instrument for electrocautery according to the first embodiment of the present disclosure is formed to be capable of normally performing an opening and closing motion, that is, an actuation motion even in a state in which the jaws are yaw-rotated by −90° to +90°.

FIGS. 33 and 34 are views illustrating a process of performing a cutting motion while the end tool of the surgical instrument for electrocautery of FIG. 2 is yaw-rotated by +90°.

As shown in FIGS. 33 and 34, the end tool of the surgical instrument for electrocautery according to the first embodiment of the present disclosure is formed to be capable of normally performing a cutting motion even in a state in which the jaws are yaw-rotated by +90°.

FIG. 35 is a view illustrating a state in which the end tool of the surgical instrument for electrocautery of FIG. 2 is pitch-rotated by −90°, and FIG. 36 is a view illustrating a state in which the end tool of the surgical instrument for electrocautery of FIG. 2 is pitch-rotated by +90°. FIG. 37 is a cut-away perspective view of the end tool of the surgical instrument for electrocautery of FIG. 36. FIGS. 38 and 39 are views illustrating a process of performing a cutting motion while the end tool of the surgical instrument for electrocautery of FIG. 2 is pitch-rotated by −90°.

As shown in FIGS. 35 to 39, the end tool of the electric cauterization surgical instrument according to the first embodiment of the present disclosure is formed to be capable of normally performing a cutting motion even in a state in which the jaws are pitch-rotated by −90°.

On the other hand, FIG. 40 is a diagram showing a state in which jaws are pitch-rotated by −90° and yaw-rotated by +90° at the same time, and FIGS. 41, 42, and 43 are perspective views showing a cutting motion of the electric cauterization surgical instrument of FIG. 2 and show a process of performing a cutting motion in a state in which the jaws are pitch-rotated by −90° and yaw-rotated by +90° at the same time.

As shown in FIGS. 40 to 43, the end tool of the electric cauterization surgical instrument according to the first embodiment of the present disclosure is formed to be capable of normally performing a cutting motion even in a state in which the jaws are pitch-rotated by −90° and yaw-rotated by +90° at the same time.

First Modified Example of First Embodiment—Jaw Opening/Closing in Vertical Direction Hereinafter, an end tool 1100 of a surgical instrument according to a first modified example of the first embodiment of the present disclosure will be described. Here, the end tool 1100 of the surgical instrument according to the first modified example of the first embodiment of the present disclosure is different from the end tool (see 100 of FIG. 2 or the like) of the surgical instrument according to the first embodiment of the present disclosure described above in that an opening/closing direction of a jaw 103 is changed. The configuration changed from the first embodiment as described above will be described in detail later.

Figure 47:
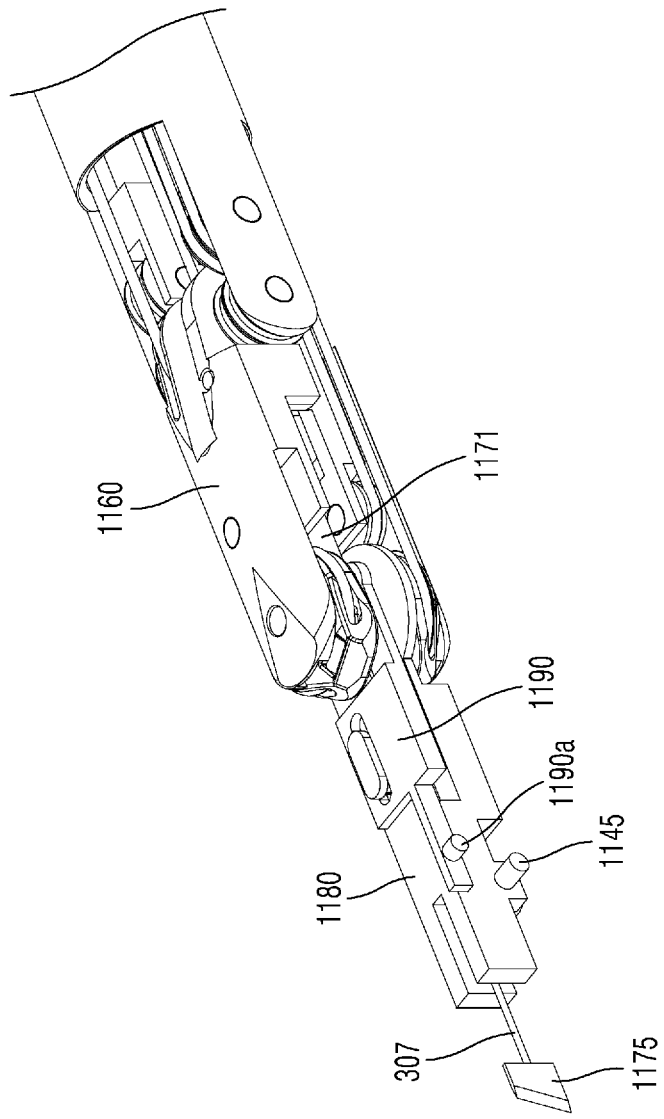

FIGS. 44, 45, 46, and 47 are views illustrating an end tool of a surgical instrument for electrocautery according to a first modified example of the first embodiment of the present disclosure, FIG. 48 is an exploded perspective view of the end tool of FIG. 44, and FIGS. 49 and 50 are views illustrating a process in which the end tool of the surgical instrument for electrocautery of FIG. 44 performs a cutting motion. Here, FIG. 47 illustrates a state in which a first jaw and a second jaw are removed.

Referring to FIGS. 44 to 50, the end tool 1100 of the first modified example of the first embodiment of the present disclosure includes a pair of jaws for performing a grip motion, that is, a first jaw 1101 and a second jaw 1102, and herein, each of the first jaw 1101 and the second jaw 1102 or a component encompassing the first jaw 1101 and the second jaw 1102 may be referred to as a jaw 1103.

Meanwhile, the end tool 1100 includes a plurality of pulleys including a pulley 1111 related to a rotational motion of the first jaw 1101. The pulleys related to the rotational motion of the first jaw 1101 described in the present embodiment are substantially the same as the pulley 111, the pulley 112, the pulley 113, the pulley 114, the pulley 115, and the pulley 116 described with reference to FIG. 8 or the like of the first embodiment, and thus, a detailed description thereof will be omitted herein.

Meanwhile, the end tool 1100 includes a plurality of pulleys including a pulley 1121 related to a rotational motion of the second jaw 1102. The pulleys related to the rotational motion of the second jaw 1102 described in the present embodiment are substantially the same as the pulley 121, the pulley 122, the pulley 123, the pulley 124, the pulley 125, and the pulley 126 described with reference to FIG. 8 or the like of the first embodiment, and thus, a detailed description thereof will be omitted herein.

Also, the end tool 1100 of the first modified example of the first embodiment of the present disclosure may include a rotation shaft 1141, a rotation shaft 1142, a rotation shaft 1143, and a rotation shaft 1144. Here, the rotation shaft 1141 and the rotation shaft 1142 may be inserted through an end tool hub 1160, and the rotation shaft 1143 and the rotation shaft 1144 may be inserted through a pitch hub 1150. The rotation shaft 1141, the rotation shaft 1142, the rotation shaft 1143, and the rotation shaft 1144 may be arranged sequentially from a distal end 1104 of the end tool 1100 toward a proximal end 1105.

Also, the end tool 1100 of the first modified example of the first embodiment of the present disclosure may include the end tool hub 1160 and the pitch hub 1150.

The rotation shaft 1141 and the rotation shaft 1142 may be inserted through the end tool hub 1160, and the pulley 1111 and the pulley 1121 axially coupled to the rotation shaft 1141 and at least a part of the first jaw 1101 and the second jaw 1102 coupled to the pulley 1111 and the pulley 1121 may be accommodated inside the end tool hub 1160.

Meanwhile, a first pitch pulley portion 1163a and a second pitch pulley portion 1163b, which serve as end tool pitch pulleys, may be formed at one end portion of the end tool hub 1160. The wire (see 303 of FIG. 6) and the wire (see 304 of FIG. 6) are coupled to the first pitch pulley portion 1163a and the second pitch pulley portion 1163b that serve as end tool pitch pulleys, and a pitch motion is performed while the end tool hub 1160 rotates about the rotation shaft 1143.

The rotation shaft 1143 and the rotation shaft 1144 may be inserted through the pitch hub 1150, and the pitch hub 1150 may be axially coupled to the end tool hub 1160 by the rotation shaft 1143. Accordingly, the end tool hub 1160 may be formed to be pitch-rotatable about the rotation shaft 1143 with respect to the pitch hub 1150.

Meanwhile, the end tool 1100 of the first modified example of the first embodiment of the present disclosure may further include components such as a first electrode 1151, a second electrode 1152, a guide tube 1171, and a blade 1175 in order to perform a cauterizing motion and a cutting motion. Here, components related to the driving of the blade, such as the guide tube 1171 and the blade 1175, may be collectively referred to as a blade assembly (see 170 of FIG. 6). In the first modified example of the present disclosure, by arranging the blade assembly (see 170 of FIG. 6) including the blade 1175 between the pulley 1111, which is a first jaw pulley, and the pulley 1121, which a second jaw pulley, the end tool 1100 may perform not only pitch and yaw motions but also a cutting motion using the blade. Components for performing a cauterizing motion and a cutting motion in the present embodiment are substantially the same as those described in the first embodiment, and thus a detailed description thereof will be omitted herein.

The surgical instrument for electrocautery according to the first modified example of the first embodiment of the present disclosure may include a wire 301, a wire 302, a wire 303, a wire 304, a wire 305, a wire 306, and a blade wire 307, as in the first embodiment of the present disclosure described with reference to FIG. 13 or the like.

Also, the surgical instrument for electrocautery according to the first modified example of the first embodiment of the present disclosure may include a fastening member 321, a fastening member 322, a fastening member 323, a fastening member 324, a fastening member 326, and a fastening member 327, which are coupled to respective end portions of the wires to couple the wires and the pulleys, as in the first embodiment of the present disclosure described with reference to FIG. 13 or the like.

Hereinafter, a first link 1180 and a second link 1190 of the first modified example of the first embodiment of the present disclosure will be described in more detail.

In the end tool 1100 of the first modified example of the first embodiment of the present disclosure, an actuation rotation shaft 1145 and a yaw rotation shaft 1141 are arranged perpendicular to each other. Accordingly, an opening/closing direction of the jaw 1103 is a vertical direction. Accordingly, an arrangement direction of the blade 1175 is also the vertical direction.

That is, in the case of the first embodiment of the present disclosure described with reference to FIG. 3 or the like, the actuation rotation shaft 145 and the yaw rotation shaft 141 are formed parallel to each other, and the two shafts may be formed parallel to the Z-axis. Accordingly, the opening/closing of the jaw 103 is performed on an XY plane perpendicular to the Z-axis.

On the other hand, in the end tool 1100 of the first modified example of the first embodiment of the present disclosure, the yaw rotation shaft 1141 is formed parallel to the Z-axis, whereas the actuation rotation shaft 1145 is formed parallel to the Y-axis. That is, the actuation rotation shaft 1145 and the yaw rotation shaft 1141 are arranged perpendicular to each other. In addition, the opening/closing of the jaw 1103 is performed on an XZ plane perpendicular to the Y-axis.

In detail, the end tool 1100 of the present disclosure includes the first jaw 1101, the second jaw 1102, the first link 1180, the second link 1190, the pulley 1111 that is a first jaw pulley, and the pulley 1121 that is a second jaw pulley. Hereinafter, the pulley 1111 is referred to as a first jaw pulley 1111, and the pulley 1121 is referred to as a second jaw pulley 1121.

The first jaw pulley 1111 and the first link 1180 are fixedly coupled to each other.

In detail, a protrusion 1111a is formed on the first jaw pulley 1111, a through hole (not shown) is formed in the first link 1180, and the protrusion 1111a of the first jaw pulley 1111 may be inserted into the through hole (not shown) of the first link 1180. In addition, the first rotation shaft 1141 may be sequentially inserted through the first jaw pulley 1111 and the first link 1180. As a result, the first jaw pulley 1111 and the first link 1180 are coupled to each other at two points, and thus the first jaw pulley 1111 and the first link 1180 are fixedly coupled to each other.

That is, since the first link 1180 does not rotate with respect to the first jaw pulley 1111, when the first jaw pulley 1111 rotates about the first rotation shaft 1141, the first link 1180 also rotates about the first rotation shaft 1141 together with the first jaw pulley 1111.

Meanwhile, the first link 1180 and the first jaw 1101 are fixedly coupled by a fixing member (a pin or the like).

In other words, the first jaw 1101 and the first jaw pulley 1111 are connected by the first link 1180 and are in a state of being fixed relative to each other, so that one member does not rotate/move with respect to the other member.

As a result, when the first jaw pulley 1111 rotates about the first rotation shaft 1141, the first link 1180 and the first jaw 1101 coupled to the first link 1180 rotate about the first rotation shaft 1141 together with the first jaw pulley 1111.

Meanwhile, the second jaw pulley 1121 and the second link 1190 are axially coupled to each other at one point, and the second link 1190 is coupled to the second jaw pulley 1121 so as to be rotatable or movable with respect to the second jaw pulley 1121.

In detail, a protrusion 1121a is formed on the second jaw pulley 1121, and a through hole 1190a is formed in the second link 1190, and the protrusion 1121a of the second jaw pulley 1121 may be inserted into the through hole 1190a of the second link 1190. Accordingly, when the second jaw pulley 1121 rotates, the second link 1190 moves while rotating about the protrusion 1121a.

The second link 1190 and the second jaw 1102 are axially coupled to each other at one point, and the second link 1190 is coupled so as to be rotatable or movable with respect to the second jaw pulley 1121.

In detail, a guide pin 1190b is formed on the second link 1190, a through hole 1102a is formed in the second jaw 1102, and the guide pin 1190b may be inserted through the through hole 1102a so that the second link 1190 and the second jaw 1102 may be axially coupled to each other.

In addition, the actuation rotation shaft 1145 may be sequentially inserted through the second jaw 1102, the first link 1180, and the first jaw 1101. Here, the actuation rotation shaft 1145 may also be formed by being divided into two parts, similar to the other rotation shafts.

Here, the yaw rotation shaft 1141 is formed parallel to the Z-axis, whereas the actuation rotation shaft 1145 may be formed parallel to the Y-axis. That is, the actuation rotation shaft 1145 and the yaw rotation shaft 1141 are arranged perpendicular to each other. Accordingly, the opening/closing of the jaw 1103 is performed on the XZ plane perpendicular to the Y-axis.

As a result, when the second jaw pulley 1121 rotates about the first rotation shaft 1141 while the first jaw pulley 1111 is fixed, the second link 1190 axially coupled to the second jaw pulley 1121 is moved. In addition, when the second link 1190 moves, the second jaw 1102 axially coupled to the second link 1190 also performs a motion by the second link 1190, and at this point, the second jaw 1102 rotates about the actuation rotation shaft 1145.

Hereinafter, a yaw motion and an actuation motion of the end tool 1100 will be described.

First, when the first jaw pulley 1111 and the second jaw pulley 1121 rotate together, 1) the first link 1180 and the first jaw 1101 coupled to the first link 1180 also rotate about the first rotation shaft 1141 together with the first jaw pulley 1111, and 2) the second link 1190 and the second jaw 1102 coupled to second link 1190 also rotate about the first rotation shaft 1141 together with the second jaw pulley 1121, thereby performing a yaw motion.

Figure 45:
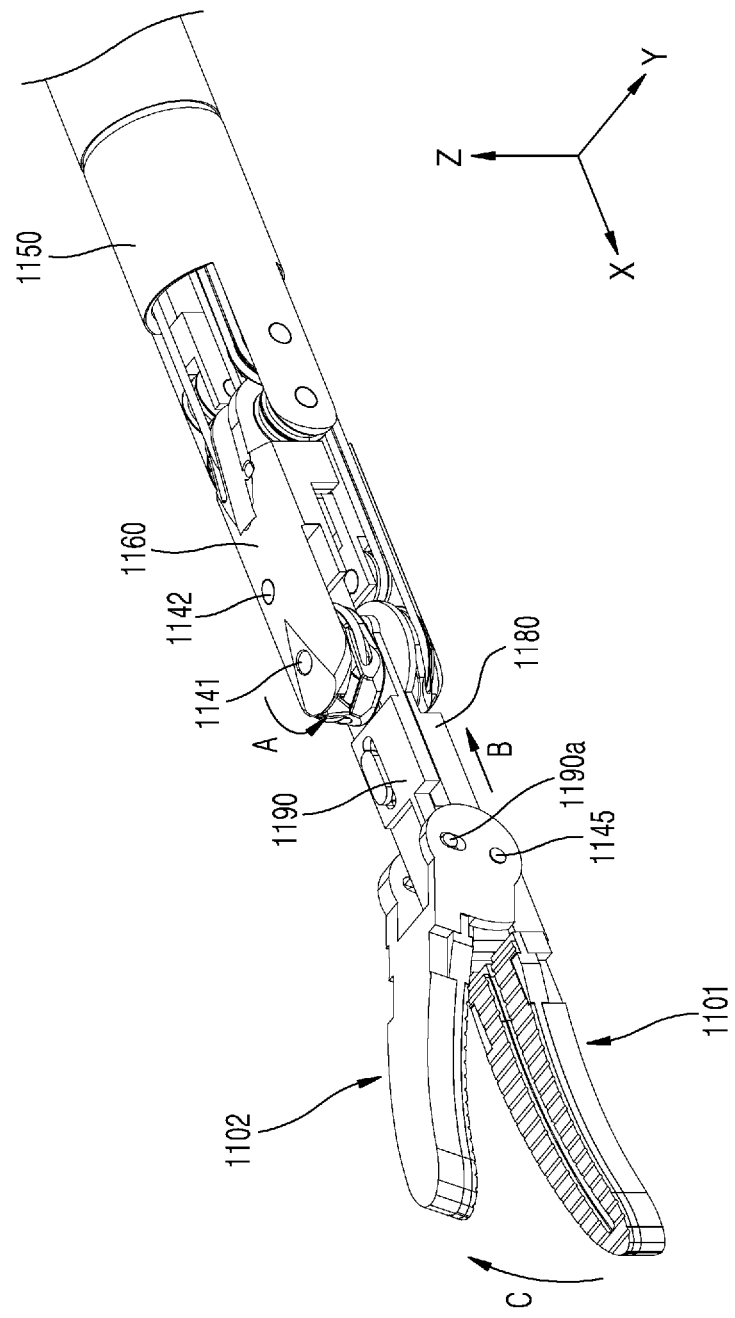
Figure 46:
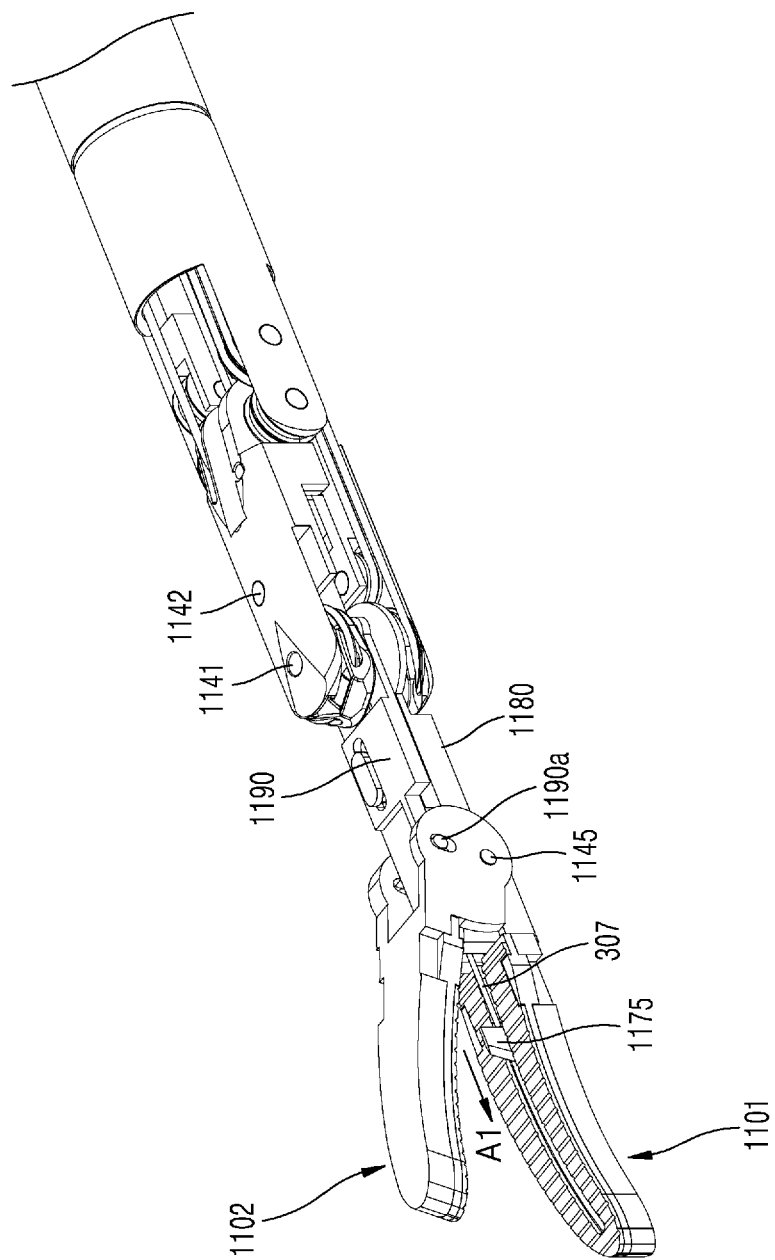

Meanwhile, in a state in which the jaw 1103 is closed as shown in FIG. 44, when only the second jaw pulley 1121 rotates in a direction of an arrow A in FIG. 45, the second link 1190 connected to the second jaw pulley 1121 is moved in a direction of an arrow B in FIG. 45 by the second jaw pulley 1121. In addition, as the second link 1190 moves in the direction of the arrow B in FIG. 45, the second jaw 1102 connected to the second link 1190 is pulled in a direction of an arrow C in FIG. 45, and thus the second jaw 1102 rotates about the actuation rotation shaft 1145 in the direction of the arrow C in FIG. 45, thereby performing an actuation motion in which the jaw 1103 is open.

In other words, when the manipulation portion 200 performs an actuation motion, only the second jaw pulley 1121 rotates, and when the manipulation portion 200 performs a yaw motion, the first jaw pulley 1111 and the second jaw pulley 1121 rotate together in the same direction.

In other words, when the manipulation portion 200 performs a yaw motion, the first jaw wire and the second jaw wire are pulled together, and accordingly, the first jaw pulley 1111 and the second jaw pulley 1121 are rotated together, so that the rotation of the second jaw 1102 with respect to the first jaw 1101 does not occur.

Meanwhile, when the manipulation portion 200 performs an actuation motion, only the second jaw wire is pulled, and accordingly, only the second jaw pulley 1121 is rotated while the first jaw pulley 1111 is fixed, and thus the second link 1190 is pulled while the actuation rotation shaft 1145 is fixed, so that the second jaw 1102 rotates about the actuation rotation shaft 1145.

As described above, in the end tool 1100 of the first modified example of the first embodiment of the present disclosure, the actuation rotation shaft 1145 and the yaw rotation shaft 1141 are arranged perpendicular to each other. Accordingly, each of the opening/closing direction of the jaw 1103 and the arrangement direction of the blade 1175 is also the vertical direction, so that a user may manipulate the end tool similarly to the existing surgical instrument.

Second Modified Example of First Embodiment-Engrave

Hereinafter, an end tool 1200 of a surgical instrument according to a second modified example of the first embodiment of the present disclosure will be described. Here, the end tool 1200 of the surgical instrument according to the second modified example of the first embodiment of the present disclosure is different from the end tool (see 100 of FIG. 2 or the like) of the surgical instrument according to the first embodiment of the present disclosure described above in that a configuration of an end tool hub 1260 serving as an auxiliary pulley is different. The configuration changed from the first embodiment as described above will be described in detail later.

FIGS. 51 and 52 are views illustrating the end tool of the surgical instrument for electrocautery according to the second modified example of the first embodiment of the present disclosure. FIG. 53 is a perspective view illustrating an end tool hub of the end tool of the surgical instrument for electrocautery of FIG. 51, FIGS. 54 and 55 are cut-away perspective views of the end tool hub of FIG. 53, and FIGS. 56 and 57 are perspective views of the end tool hub of FIG. 53. Here, FIG. 52 illustrates a state in which the end tool hub is removed.

Referring to FIGS. 51 to 57, the end tool 1200 of the second modified example of the first embodiment of the present disclosure includes a pair of jaws for performing a grip motion, that is, a first jaw 1201 and a second jaw 1202, and herein, each of the first jaw 1201 and the second jaw 1202 or a component encompassing the first jaw 1201 and the second jaw 1202 may be referred to as a jaw 1203.

Meanwhile, the end tool 1200 includes a plurality of pulleys including a pulley 1211 related to a rotational motion of the first jaw 1201. The pulleys related to the rotational motion of the first jaw 1201 described in the present embodiment are substantially the same as the pulley 113, the pulley 114, the pulley 115, and the pulley 116 described with reference to FIG. 8 or the like of the first embodiment, and thus, a detailed description thereof will be omitted herein.

Meanwhile, the end tool 1200 includes a plurality of pulleys including a pulley 1221 related to a rotational motion of the second jaw 1202. The pulleys related to the rotational motion of the second jaw 1202 described in the present embodiment are substantially the same as the pulley 123, the pulley 124, the pulley 125, and the pulley 126 described with reference to FIG. 8 or the like of the first embodiment, and thus, detailed descriptions thereof will be omitted herein.

Also, the end tool 1200 of the second modified example of the first embodiment of the present disclosure may include a rotation shaft 1241, a rotation shaft 1243, and a rotation shaft 1244. Here, the rotation shaft 1241 may be inserted through an end tool hub 1260, and the rotation shaft 1243 and the rotation shaft 1244 may be inserted through a pitch hub 1250. The rotation shaft 1241, the rotation shaft 1243, and the rotation shaft 1244 may be arranged sequentially from a distal end 1204 of the end tool 1200 toward a proximal end 1205.

Also, the end tool 1200 of the second modified example of the first embodiment of the present disclosure may further include a first link 1280 and a second link 1290.

Since the pulley 1211 is connected to the first jaw 1201 through the first link 1280, when the pulley 1211 rotates about the first rotation shaft 1241, the first jaw 1201 may also rotate about the first rotation shaft 1241 together with the pulley 1211.

Meanwhile, since the pulley 1221 is connected to the second jaw 1202 through the second link 1290, when the pulley 1221 rotates about the first rotation shaft 1241, the second jaw 1202 connected to the pulley 1221 may also rotate about the first rotation shaft 1241 or the actuation rotation shaft 1245.

Also, the end tool 1200 of the second modified example of the first embodiment of the present disclosure may include the end tool hub 1260 and the pitch hub 1250.

The rotation shaft 1241, which will be described later, is inserted through the end tool hub 1260, and the pulley 1211 and the pulley 1221, which are axially coupled to the rotation shaft 1241, and at least a part of the first jaw 1201 and the second jaw 1202 coupled the pulley 1211 and the pulley 1221 may be accommodated inside the end tool hub 1260. Here, in an embodiment of the present disclosure, a wire guide portion 1268 serving as an auxiliary pulley is formed in the end tool hub 1260. That is, a first wire guide portion 1268a and a second wire guide portion 1268b for guiding paths of the wire 305 and the wire 302 may be formed in the end tool hub 1260. The wire guide portions 1268 of the end tool hub 1260 may serve as the auxiliary pulleys (see 112 and 122 of FIG. 9) of the first embodiment and change the paths of the wires, and the first wire guide portion 1268a and the second wire guide portion 1268b of the end tool hub 1260 serving as the auxiliary pulleys will be described in more detail later.

Meanwhile, a first pitch pulley portion 1263a and a second pitch pulley portion 1263b, which serve as end tool pitch pulleys, may be formed at one end portion of the end tool hub 1260. The wire (see 303 of FIG. 6) and the wire (see 304 of FIG. 6) are coupled to the first pitch pulley portion 1263a and the second pitch pulley portion 1263b that serve as end tool pitch pulleys, and a pitch motion is performed while the end tool hub 1260 rotates about the rotation shaft 1243.

The rotation shaft 1243 and the rotation shaft 1244 are inserted through the pitch hub 1250, and the pitch hub 1250 may be axially coupled to the end tool hub 1260 and a pulley 1231 by the rotation shaft 1243. Accordingly, the end tool hub 1260 and the pulley 1231 may be formed to be pitch-rotatable about the rotation shaft 1243 with respect to the pitch hub 1250.

Meanwhile, the end tool 1200 of the second modified example of the first embodiment of the present disclosure may further include components such as a first electrode 1251, a second electrode 1252, a guide tube 1271, and a blade (see 175 of FIG. 6) in order to perform a cauterizing motion and a cutting motion. Here, components related to the driving of the blade, such as the guide tube 1271 and the blade (see 175 of FIG. 6), may be collectively referred to as a blade assembly (see 170 of FIG. 6). In one modified example of the present disclosure, by arranging the blade assembly (see 170 of FIG. 6) including the blade (see 175 of FIG. 6) between the pulley 1211, which is a first jaw pulley, and the pulley 1221, which a second jaw pulley, the end tool 1200 may perform not only pitch and yaw motions but also a cutting motion using the blade. Components for performing a cauterizing motion and a cutting motion in the present embodiment are substantially the same as those described in the first embodiment, and thus a detailed description thereof will be omitted herein.

The surgical instrument for electrocautery according to the second modified example of the first embodiment of the present disclosure may include a wire 301, a wire 302, a wire 303, a wire 304, a wire 305, a wire 306, and a blade wire 307, as in the first embodiment of the present disclosure described with reference to FIG. 13 or the like.

Also, the surgical instrument for electrocautery according to the second modified example of the first embodiment of the present disclosure may include a fastening member 321, a fastening member 322, a fastening member 323, a fastening member 324, a fastening member 326, and a fastening member 327, which are coupled to respective end portions of the wires to couple the wires and the pulleys, as in the first embodiment of the present disclosure described with reference to FIG. 13 or the like.

Hereinafter, the end tool hub 1260 of the second modified example of the first embodiment of the present disclosure will be described in more detail, and in particular, the wire guide portion 1268 of the end tool hub 1260 serving as an auxiliary pulley will be mainly described.

Referring to FIGS. 51 to 57, the end tool hub 1260 includes a body portion 1261, a first jaw pulley coupling portion 1262a, a second jaw pulley coupling portion 1262b, the first pitch pulley portion 1263a, the second pitch pulley portion 1263b, a pitch slit 1264, a yaw slit 1265, a pitch round portion 1266, a yaw round portion 1267, and the wire guide portion 1268. In addition, the wire guide portion 1268 may include the first wire guide portion 1268a and the second wire guide portion 1268b.

The first jaw pulley coupling portion 1262a and the second jaw pulley coupling portion 1262b may be formed at a distal end side of the end tool hub 1260. Here, the first jaw pulley coupling portion 1262a and the second jaw pulley coupling portion 1262b are formed to face each other, and the pulley 1211 and the pulley 1221 are accommodated therein. Here, the first jaw pulley coupling portion 1262a and the second jaw pulley coupling portion 1262b may be formed to be approximately parallel to a plane perpendicular to the first rotation shaft 1241 that is a yaw rotation shaft.

The first jaw pulley coupling portion 1262a and the second jaw pulley coupling portion 1262b are connected by the body portion 1261. That is, the first jaw pulley coupling portion 1262a and the second jaw pulley coupling portion 1262b, which are parallel to each other, are coupled by the body portion 1261 formed in a direction approximately perpendicular to the first jaw pulley coupling portion 1262a and the second jaw pulley coupling portion 1262b, so that the first jaw pulley coupling portion 1262a, the second jaw pulley coupling portion 1262b, and the body portion 1261 form an approximately C-shape, and the pulley 1211 and the pulley 1221 are accommodated therein.

In other words, it may be said that the first jaw pulley coupling portion 1262a and the second jaw pulley coupling portion 1262b are formed to extend in the X-axis direction from the body portion 1261.

Here, the pulley 1211, which is a first jaw pulley, is disposed close to the first jaw pulley coupling portion 1262a of the end tool hub 1260, and the pulley 1221, which is a second jaw pulley, is disposed close to the second jaw pulley coupling portion 1262b of the end tool hub 1260, and thus the yaw slit 1265 may be formed between the first jaw pulley coupling portion 1262a and the second jaw pulley coupling portion 1262b. In addition, at least a part of a blade assembly 1270 to be described later may be disposed in the yaw slit 1265. In other words, it may be said that at least a part of the guide tube 1271 of the blade assembly 1270 may be disposed between the first jaw pulley coupling portion 1262a and the second jaw pulley coupling portion 1262b. As described above, by arranging the blade assembly 1270 including the guide tube 1271 between the pulley 1211, which is a first jaw pulley, and the pulley 1221, which is a second jaw pulley, the end tool 1200 may perform not only pitch and yaw motions but also a cutting motion using the blade 1275.

Meanwhile, a through hole is formed in the first jaw pulley coupling portion 1262a such that the first rotation shaft 1241 passes through the first jaw pulley coupling portion 1262a and the pulley 1211 and axially couples the first jaw pulley coupling portion 1262a and the pulley 1211. Also, a through hole is formed in the second jaw pulley coupling portion 1262b such that the first rotation shaft 1241 passes through the second jaw pulley coupling portion 1262b and the pulley 1221 and axially couples the first rotation shaft 1241 and the pulley 1221.

Here, as described above, the first rotation shaft 1241, which is a yaw rotation shaft, may be formed by being divided into two parts of a first sub-shaft 1241a and a second sub-shaft 1241b, and the guide tube 1271 may pass between the first sub-shaft 1241a and the second sub-shaft 1241b of the first rotation shaft 1241.

In addition, the yaw slit 1265 may be formed between the first jaw pulley coupling portion 1262a and the second jaw pulley coupling portion 1262b. Since the yaw slit 1265 is formed in the end tool hub 1260 as described above, the guide tube 1271 may pass through the inside of the end tool hub 1260.

In other words, the first rotation shaft 1241 is vertically separated from the end tool hub 1260 without passing therethrough, and the yaw slit 1265 may be formed on a plane perpendicular to the first rotation shaft 1241 in the vicinity of the first rotation shaft 1241. Accordingly, the guide tube 1271 is movable (movable left and right) in the yaw slit 1265 while passing through the vicinity of the first rotation shaft 1241.

Meanwhile, the yaw round portion 1267 may be further formed in the body portion 1261. The yaw round portion 1267 may be formed to be rounded so as to have a predetermined curvature. In detail, when viewed from a plane perpendicular to the first rotation shaft 1241 that is a yaw rotation shaft, the yaw round portion 1267 may be formed to be rounded so as to have a predetermined curvature. The yaw round portion 1267 as described above may serve to guide a path of the guide tube 1271 when the end tool 1200 yaw-rotates.

The wire guide portion 1268, which guides a path of a wire passing through the inside of the end tool hub 1260, is formed at one side of the body portion 1261. Here, the wire guide portion 1268 includes the first wire guide portion 1268a and the second wire guide portion 1268b. Here, the first wire guide portion 1268a may be formed on an inner side surface of the first jaw pulley coupling portion 1262a. In addition, the second wire guide portion 1268b may be formed on an inner side surface of the second jaw pulley coupling portion 1262b.

Here, the wire guide portion 1268 may be formed in a semi-cylindrical shape with a cross section that is approximately semi-circular. In addition, the semi-circular portion may be disposed to protrude toward the pulley 1211 and the pulley 1221. In other words, it may be said that the wire guide portion 1268 is formed to protrude toward a space formed by the first jaw pulley coupling portion 1262a, the second jaw pulley coupling portion 1262b, and the body portion 1261. In other words, it may be said that, in the wire guide portion 1268, a region adjacent to the first jaw pulley coupling portion 1262a and the second jaw pulley coupling portion 1262b is formed to have a cross section that is curved with a predetermined curvature.

Alternatively, in other words, it may be also said that the wire guide portion 1268 serves as a kind of pulley member, which guides the paths of the wire 305 and the wire 302 by winding the wire 305 and the wire 302 around an outer circumferential surface thereof. However, here, the wire guide portion 1268 is not a member that rotates about a certain shaft like the original meaning pulley does, and it may be said that the wire guide portion 1268 is formed to be fixed as a part of the end tool hub 1260 and performs some similar functions of a pulley by winding a wire therearound.

Here, the wire guide portion 1268 is illustrated in the drawing as being formed in a semi-cylindrical shape with a cross section that is approximately semi-circular. That is, at least a part of the cross section of the wire guide portion 1268 on the XY plane is illustrated as having a certain arc shape. However, the concept of the present disclosure is not limited thereto, and the cross section may have a predetermined curvature like an oval or a parabola, or a corner of a polygonal column is rounded to a certain degree, so that the cross section may have various shapes and sizes suitable for guiding the paths of the wire 305 and the wire 302.

Here, a guide groove for guiding the paths of the wire 305 and the wire 302 well may be further formed in a part of the wire guide portion 1268, which is in contact with the wire 305 and the wire 302. The guide groove may be formed in a groove shape recessed to a certain degree from the protruding surface of the wire guide portion 1268.

Here, although the guide groove is illustrated in the drawing as being formed in the entire arc surface of the wire guide portion 1268, the concept of the present disclosure is not limited thereto, and the guide groove may be formed only in a part of the arc surface of the wire guide portion 1268 as necessary.

As described above, by further forming the guide groove in the wire guide portion 1268, unnecessary friction between the wires is reduced, so that durability of the wires may be improved.

The first pitch pulley portion 1263a and the second pitch pulley portion 1263b, which serve as end tool pitch pulleys, may be formed on a proximal end side of the end tool hub 1260. Here, the first pitch pulley portion 1263a and the second pitch pulley portion 1263b may be formed to face each other. Here, the first pitch pulley portion 1263a and the second pitch pulley portion 1263b may be formed to be approximately parallel to a plane perpendicular to a third rotation shaft 1243, which is a pitch rotation shaft.

In detail, one end portion of the end tool hub 1260 is formed in a disk shape to function as a pulley, and a groove may be formed to which a wire may be wound may be formed on an outer circumferential surface of the end tool hub 1260, thereby forming the first pitch pulley portion 1263a and the second pitch pulley portion 1263b. The wire 303 and the wire 304 described above are coupled to the first pitch pulley portion 1263a and the second pitch pulley portion 1263b, which serve as end tool pitch pulleys, and a pitch motion is performed while the end tool hub 1260 rotates about the third rotation shaft 1243.

Meanwhile, although not illustrated in the drawings, a pitch pulley may be formed as a separate member from the end tool hub 1260 and coupled to the end tool hub 1260.

The first pitch pulley portion 1263*a* and to the second pitch pulley portion 1263*b* are connected by the body portion 1261. That is, the first pitch pulley portion 1263*a* and the second pitch pulley portion 1263*b*, which are parallel to each other, are coupled by the body portion 1261 formed in a direction approximately perpendicular to the first pitch pulley portion 1263*a* and the second pitch pulley portion 1263*b*, and thus the first pitch pulley portion 1263*a*, the second pitch pulley portion 1263*b*, and the body portion 1261 form an approximately C-shape.

In other words, it may be said that the first pitch pulley portion 1263*a* and the second pitch pulley portion 1263*b* are formed to extend from the body portion 1261 in the X-axis direction.

Meanwhile, a through hole may be formed in the first pitch pulley portion 1263*a* so that the third rotation shaft 1243 may pass through the first pitch pulley portion 1263*a*. A through hole is also formed in the second pitch pulley portion 1263*b* so that the third rotation shaft 1243 may pass through the second pitch pulley portion 1263*b*.

In this case, as described above, the third rotation shaft 1243, which is a pitch rotation shaft, may be formed by being divided into two parts of a first sub-shaft 1243*a* and a second sub-shaft 1243*b*, and the guide tube 1271 may pass between the first sub-shaft 1243*a* and the second sub-shaft 1243*b* of the third rotation shaft 1243.

The pitch slit 1264 may be formed between the first pitch pulley portion 1263*a* and the second pitch pulley portion 1263*b*. Since the pitch slit 1264 is formed in the end tool hub 1260 as described above, the guide tube 1271 may pass through the inside of the end tool hub 1260.

In other words, the third rotation shaft 1243 is horizontally separated into two parts without passing through the end tool hub 1260, and the pitch slit 1264 may be formed on a plane perpendicular to the third rotation shaft 1243 in the vicinity of the third rotation shaft 1243. Accordingly, the guide tube 1271 is movable (movable up and down) in the pitch slit 1264 while passing through the vicinity of the third rotation shaft 1243.

Meanwhile, the pitch round portion 1266 may be further formed in the body portion 1261. The pitch round portion 1266 may be formed to be rounded to have a predetermined curvature. In detail, when viewed from a plane perpendicular to the third rotation shaft 1243, which is a pitch rotation shaft, the pitch round portion 1266 may be formed to be rounded to have a predetermined curvature. The pitch round portion 1266 as described above may serve to guide a path of the guide tube 1271 when the end tool 1200 pitch-rotates.

Here, the pitch slit 1264 and the yaw slit 1265 may be formed to be connected to each other. Accordingly, the guide tube 1271 and the blade wire 307 therein may be disposed to completely pass through the inside of the end tool hub 1260. In addition, the blade 1275 coupled to one end portion of the blade wire 307 may linearly reciprocate inside the first jaw 1201 and the second jaw 1202.

As described above, since the blade wire 307 and the guide tube 1271 need to be connected to the blade 1275 through the end tool hub 1260, and a space in which the blade wire 307 and the guide tube 1271 can be curved in the end tool hub 1260 is necessary, in the present disclosure, 1) spaces, through which the blade wire 307/the guide tube 1271 can pass and simultaneously can be bent, that is, the pitch slit 1264 and the yaw slit 1265 are formed in the end tool hub 1260, 2) the rotation shafts are formed by being divided into two parts, and 3) the pitch round portion 1266 and the yaw round portion 1267 are additionally formed to guide the bending of the blade wire 307/the guide tube 1271.

Hereinafter, the role and function of the wire guide portion 1268 will be described in more detail.

The wire guide portion 1268 may be in contact with the wire 305 and the wire 302 and may change the arrangement path of the wire 305 and the wire 302 to a certain degree to serve to increase a rotation radius of each of the first jaw 1201 and the second jaw 1202.

That is, when the auxiliary pulley is not disposed, each of the pulley 1211, which is a first jaw pulley, and the pulley 1221, which is a second jaw pulley, may rotate up to a right angle, but in the second modified example of the first embodiment of the present disclosure, by additionally providing the wire guide portion 1268 in the end tool hub 1260, the maximum rotation angle of each pulley may be increased.

This enables a motion that two jaws of the end tool 1200 to open for an actuation motion in a state in which the two jaws of the end tool 1200 are yaw-rotated by 90°. In other words, the range of yaw rotation in which an actuation motion is possible may be increased through the configuration of the wire guide portion 1268 of the end tool hub 1260.

Furthermore, by forming the wire guide portion 1268 in the end tool hub 1260 that already exists without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also the length of the end tool is shortened as much as the size of the auxiliary pulley, so that the length of the end tool is shortened during a pitch motion. Accordingly, a surgical motion may be more easily performed in a narrow space.

This will be described below in more detail.

In the end tool 1200 of the surgical instrument according to the second modified example of the first embodiment of the present disclosure, the arrangement path of a wire may be changed without a separate structure by forming the wire guide portion 1268 capable of changing the path of the wire on an inner side wall of the end tool hub 1260. As described above, as the arrangement path of the wire 305 and the wire 302 is changed to a certain degree by forming the wire guide portion 1268 in the end tool hub 1260, a tangential direction of the wire 305 and the wire 302 is changed, and accordingly, rotation angles of the fastening member 323 and the fastening member 326 that couple respective wires and pulleys may be increased.

That is, the fastening member 326 that couples the wire 302 and the pulley 1221 is rotatable until being located on a common internal tangent of the pulley 1221 and the wire guide portion 1268. Similarly, the fastening member (see 323 of FIG. 6) that couples the wire 305 and the pulley 1211 is rotatable until being located on a common internal tangent of the pulley 1211 and the wire guide portion 1268, so that a rotation angle of the fastening member (see 323 of FIG. 6) may be increased.

In other words, the wire 301 and the wire 305 wound on the pulley 1211 by the wire guide portion 1268 are arranged on one side with respect to a plane perpendicular to the Y-axis and passing through the X-axis. Simultaneously, the wire 302 and the wire 306 wound on the pulley 1221 by the wire guide portion 1268 are arranged on the other side with respect to the plane perpendicular to the Y-axis and passing through the X-axis.

In other words, a pulley 1213 and a pulley 1214 are arranged on one side with respect to the plane perpendicular to the Y-axis and passing through the X-axis, and a pulley 1223 and a pulley 1224 are arranged on the other side with respect to the plane perpendicular to the Y-axis and passing through the X-axis.

In other words, the wire 305 is located on the internal tangent of the pulley 1211 and the wire guide portion 1268, and a rotation angle of the pulley 1211 is increased by the wire guide portion 1268. Also, the wire 302 is located on the internal tangent of the pulley 1221 and the wire guide portion 1268, and the rotation angle of the pulley 1221 is increased by the wire guide portion 1268.

In the present modified example in which an auxiliary pulley is not formed and the wire guide portion 1268 capable of changing the path of a wire is formed on the inner side wall of the end tool hub 1260, the length of the end tool of the surgical instrument may be shortened as compared to the surgical instrument of the first embodiment in which a separate auxiliary pulley is formed. Since the length of the end tool is shortened as described above, a surgical operator may easily manipulate a surgical instrument, and a side effect of surgery may be reduced when the surgery is performed in a narrow surgical space in the human body.

According to the present disclosure as described above, as the rotation radius of the pulley 1211, which is a first jaw pulley, and the pulley 1221, which is a second jaw pulley, increase, a yaw motion range in which a normal opening/closing actuation motion and a normal cutting motion may be performed may be increased.

Third Modified Example of First Embodiment—Jaw Opening/Closing in Vertical Direction, Engrave Hereinafter, an end tool 1300 of a surgical instrument according to a third modified example of the first embodiment of the present disclosure will be described. Here, the end tool 1300 of the surgical instrument according to the third modified example of the first embodiment of the present disclosure is different from the end tool (see 100 of FIG. 2 or the like) of the surgical instrument according to the first embodiment of the present disclosure described above in that an opening/closing direction of a jaw 1303 is changed. Also, the end tool 1300 of the surgical instrument according to the third modified example of the first embodiment of the present disclosure is different from the end tool (see 100 of FIG. 2 or the like) of the surgical instrument according to the first embodiment of the present disclosure described above in that a configuration of an end tool hub 1360 serving as an auxiliary pulley is different.

In other words, the end tool 1300 of the surgical instrument according to the third modified example of the first embodiment of the present disclosure may be considered to combine the feature of the first modified example described with reference to FIG. 44 or the like and the feature of the second modified example described with reference to FIG. 51 or the like. The configuration changed from the first embodiment as described above will be described in detail later.

FIGS. 58 and 59 are views illustrating the end tool of the surgical instrument for electrocautery according to the third modified example of the first embodiment of the present disclosure, FIG. 60 is a perspective view illustrating an end tool hub of the end tool of the surgical instrument for electrocautery of FIG. 58, and FIG. 61 is a cut-away perspective view of the end tool hub of FIG. 60.

Hereinafter, a first link 1380 and a second link 1390 of the third modified example of the first embodiment of the present disclosure will be described in more detail.

In the end tool 1300 of the third modified example of the first embodiment of the present disclosure, an actuation rotation shaft 1345 and a yaw rotation shaft 1341 may be arranged perpendicular to each other. Accordingly, an opening/closing direction of the jaw 1303 is a vertical direction. Accordingly, an arrangement direction of a blade 1375 is also the vertical direction.

That is, in the case of the first embodiment of the present disclosure described with reference to FIG. 3 or the like, the actuation rotation shaft 145 and the yaw rotation shaft 141 are formed parallel to each other, and the two shafts may be formed parallel to the Z-axis. Accordingly, the opening/closing of the jaw 103 is performed on the XY plane perpendicular to the Z-axis.

On the other hand, in the end tool 1300 of the third modified example of the first embodiment of the present disclosure, the yaw rotation shaft 1341 is formed parallel to the Z-axis, whereas the actuation rotation shaft 1345 is formed parallel to the Y-axis. That is, the actuation rotation shaft 1345 and the yaw rotation shaft 1341 are arranged perpendicular to each other. In addition, the opening/closing of the jaw 1303 is performed on the XZ plane perpendicular to the Y-axis.

Here, the end tool 1300 of the present disclosure includes a first jaw 1301, a second jaw 1302, the first link 1380, the second link 1390, a pulley 1311, which is a first jaw pulley, and a pulley 1321, which is a second jaw pulley. A specific configuration of each component is the same as that in the first modified example described with reference to FIG. 44 or the like, and thus a detailed description thereof will be omitted.

Hereinafter, a yaw motion and an actuation motion of the end tool 1300 will be described. First, when the first jaw pulley 1311 and the second jaw pulley 1321 rotate together, 1) the first link 1380 and the first jaw 1301 coupled to the first link 1380 also rotate about a first rotation shaft 1341 together with the first jaw pulley 1311, and 2) the second link 1390 and the second jaw 1302 coupled to the second link 1390 also rotate about the first rotation shaft 1341 together with the second jaw pulley 1321, thereby performing a yaw motion.

Meanwhile, when only the second jaw pulley 1321 rotates, the second link 1390 connected to the second jaw pulley 1321 is moved by the second jaw pulley 1321. In addition, the second jaw 1302 connected to the second link 1390 is pulled while the second link 1390 is moving, and thus the second jaw 1302 performs an actuation motion by pivoting about the actuation rotation shaft 1345.

In other words, when the manipulation portion 200 performs an actuation motion, only the second jaw pulley 1321 rotates, and when the manipulation portion 200 performs a yaw motion, the first jaw pulley 1311 and the second jaw pulley 1321 rotate together in the same direction.

In other words, when the manipulation portion 200 performs a yaw motion, the first jaw wire and the second jaw wire are pulled together, and accordingly, the first jaw pulley 1311 and the second jaw pulley 1321 are rotated together, so that the rotation of the second jaw 1302 with respect to the first jaw 1301 does not occur.

Meanwhile, when the manipulation portion 200 performs an actuation motion, only the second jaw wire is pulled, and accordingly, only the second jaw pulley 1321 is rotated while the first jaw pulley 1311 is fixed, and thus the second link 1390 is pulled while the actuation rotation shaft 1345 is fixed, so that the second jaw 1302 rotates about the actuation rotation shaft 1345.

As described above, in the end tool 1300 of the third modified example of the first embodiment of the present disclosure, the actuation rotation shaft 1345 and the yaw rotation shaft 1341 may be arranged perpendicular to each other. Accordingly, each of the opening/closing direction of the jaw 1303 and the arrangement direction of the blade 1375 is also the vertical direction, so that a user may manipulate the end tool similarly to the existing surgical instrument.

Hereinafter, an end tool hub 1360 of the third modified example of the first embodiment of the present disclosure will be described in more detail, and in particular, a first wire guide portion 1368a and a second wire guide portion 1368b of the end tool hub 1360 serving as auxiliary pulleys will be mainly described.

Referring to FIGS. 58 to 61, the end tool hub 1360 includes a body portion 1361, a first jaw pulley coupling portion 1362a, a second jaw pulley coupling portion 1362b, a first pitch pulley portion 1363a, a second pitch pulley portion 1363b, a pitch slit 1364, a yaw slit 1365, a pitch round portion 1366, a yaw round portion 1367, and a wire guide portion 1368. Here, the wire guide portion 1368 includes the first wire guide portion 1368a and the second wire guide portion 1368b. A specific configuration of each component is the same as that in the second modified example described with reference to FIG. 51 or the like, and thus a detailed description thereof will be omitted.

Hereinafter, the role and function of the wire guide portion 1368 will be described in more detail.

The wire guide portion 1368 may be in contact with the wire 305 and the wire 302 and may change the arrangement path of the wire 305 and the wire 302 to a certain degree to serve to increase a rotation radius of each of the first jaw 1301 and the second jaw 1302.

That is, when the auxiliary pulley is not disposed, each of the pulley 1311, which is a first jaw pulley, and the pulley 1321, which is a second jaw pulley, may rotate up to a right angle, but in the third modified example of the first embodiment of the present disclosure, by additionally providing the wire guide portion 1368 in the end tool hub 1360, the maximum rotation angle of each pulley may be increased.

This enables a motion that two jaws of the end tool 1300 have to open for an actuation motion in a state in which the two jaws of the end tool 1300 are yaw-rotated by 90°. In other words, the range of yaw rotation in which an actuation motion is possible may be increased through the configuration of the wire guide portion 1368 of the end tool hub 1360.

Furthermore, by forming the wire guide portion 1368 in the end tool hub 1360 that already exists without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also the length of the end tool is shortened as much as the size of the auxiliary pulley, so that the length of the end tool is shortened during a pitch motion. Accordingly, a surgical motion may be more easily performed in a narrow space.

According to the present disclosure as described above, as the rotation radius of the pulley 1311, which is a first jaw pulley, and the pulley 1321, which is a second jaw pulley, increase, a yaw motion range in which a normal opening/closing actuation motion and a normal cutting motion may be performed may be increased.

Second Embodiment of Surgical Instrument for Electrocautery

Hereinafter, an end tool 500 of a surgical instrument according to a second embodiment of the present disclosure will be described. Here, the end tool 500 of the surgical instrument according to the second embodiment of the present disclosure is different from the end tool (see 100 of FIG. 2 or the like) of the surgical instrument according to the first embodiment of the present disclosure described above in that an opening/closing direction of a jaw 503 is changed. The configuration changed from the first embodiment as described above will be described in detail later.

FIG. 62 is a perspective view illustrating the surgical instrument for electrocautery according to the second embodiment of the present disclosure, FIGS. 63, 64, 65, 66, 67, and 68 are perspective views illustrating the end tool of the surgical instrument for electrocautery of FIG. 62, and FIGS. 69 and 70 are plan views illustrating the end tool of the surgical instrument for electrocautery of FIG. 62. FIGS. 71 and 72 are perspective views illustrating an end tool hub of the end tool of the surgical instrument for electrocautery of FIG. 62, and FIG. 73 is a cut-away perspective view of the end tool hub of FIG. 71. FIG. 74 is an exploded perspective view illustrating jaws-links-jaw pulleys of the end tool of the surgical instrument for electrocautery of FIG. 62, and FIGS. 75, 76, 77, and 78 are perspective views illustrating a second jaw pulley of the end tool of the surgical instrument for electrocautery of FIG. 62. FIGS. 79 and 80 are plan views illustrating an opening and closing motion of the end tool of the surgical instrument for electrocautery of FIG. 62, FIG. 81 is a view illustrating a jaw opening/closing process of the first embodiment of the present disclosure shown in FIG. 2 or the like, and FIG. 82 is a view illustrating a jaw opening/closing process of the second embodiment of the present disclosure. FIG. 83 is a view illustrating a case in which a pin/slot-type structure of the second embodiment of the present disclosure is configured in a normal pulley rather than a multi-layered pulley. FIGS. 84, 85, 86, and 87 are perspective views illustrating an opening and closing motion of the end tool of the surgical instrument for electrocautery of FIG. 62, and FIGS. 88, 89, and 90 are perspective views illustrating a cutting motion of the end tool of the surgical instrument for electrocautery of FIG. 62.

Referring to FIGS. 62 to 90, the end tool 500 of the second embodiment of the present disclosure includes a pair of jaws, that is, a first jaw 501 and a second jaw 502 for performing a grip motion, and here, each of the first jaw 501 and the second jaw 502 or a component encompassing the first jaw 501 and the second jaw 502 may be referred to as a jaw 503.

Meanwhile, the end tool 500 includes a plurality of pulleys including a pulley 511 related to a rotational motion of the first jaw 501. The pulleys related to the rotational motion of the first jaw 501 described in the present embodiment are substantially the same as the pulley 111, the pulley 112, the pulley 113, the pulley 114, the pulley 115, and the pulley 116 described with reference to FIG. 8 or the like of the first embodiment, and thus, a detailed description thereof will be omitted herein.

Meanwhile, the end tool 500 includes a plurality of pulleys including a pulley 521 related to a rotational motion of the second jaw 502. The pulleys related to the rotational motion of the second jaw 502 described in the present embodiment are substantially the same as the pulley 121, the pulley 122, the pulley 123, the pulley 124, the pulley 125, and the pulley 126 described with reference to FIG. 8 or the like of the first embodiment, and thus, detailed descriptions thereof will be omitted herein.

Also, the end tool 500 of the second embodiment of the present disclosure may include a rotation shaft 541, a rotation shaft 542, a rotation shaft 543, and a rotation shaft 544. Here, the rotation shaft 541 and the rotation shaft 542 may be inserted through an end tool hub 560, and the rotation shaft 543 and the rotation shaft 544 may be inserted through a pitch hub 550. The rotation shaft 541, the rotation shaft 542, the rotation shaft 543, and the rotation shaft 544 may be arranged sequentially from a distal end 504 towards a proximal end 505 of the end tool 500.

Meanwhile, the end tool 500 may further include an actuation rotation shaft 545. In detail, the actuation rotation shaft 545 may be provided in a coupling portion of the first jaw 501 and the second jaw 502, and the second jaw 502 rotates about the actuation rotation shaft 545 while the first jaw 501 is fixed, thereby performing an actuation motion. Here, the actuation rotation shaft 545 may be disposed closer to the distal end 504 than the first rotation shaft 541 is.

Here, each of the rotation shafts may include two shafts of a first sub-shaft and a second sub-shaft. Alternatively, it may be said that each of the rotation shafts is formed by being divided into two parts. The configuration of the rotation shafts in the present embodiment is substantially the same as that of the rotation shafts in the first embodiment, and thus a detailed description thereof will be omitted herein.

Also, the end tool 500 of the second embodiment of the present disclosure may include the end tool hub 560 and the pitch hub 550.

The rotation shaft 541 and the rotation shaft 542 are inserted through the end tool hub 560, and the pulley 511 and the pulley 521, which are axially coupled to the rotation shaft 541, and at least a part of the first jaw 501 and the second jaw 502 coupled to the pulley 511 and the pulley 521 may be accommodated inside the end tool hub 560.

Meanwhile, a first pitch pulley portion 563a and a second pitch pulley portion 563b, which serve as end tool pitch pulleys, may be formed at one end portion of the end tool hub 560. A wire 303 and a wire 304 are coupled to the first pitch pulley portion 563a and the second pitch pulley portion 563b, which serve as end tool pitch pulleys, and a pitch motion is performed while the end tool hub 560 rotates about the rotation shaft 543.

The rotation shaft 543 and the rotation shaft 544 are inserted through the pitch hub 550, and the pitch hub 550 may be axially coupled to the end tool hub 560 by the rotation shaft 543. Accordingly, the end tool hub 560 may be formed to be pitch-rotatable about the rotation shaft 543 with respect to the pitch hub 550.

The end tool hub 560 and the pitch hub 550 in the present embodiment are substantially the same as the components described in the first embodiment, and thus a detailed description thereof will be omitted herein.

Meanwhile, the end tool 500 of the second embodiment of the present disclosure may further include components such as a first electrode 551, a second electrode 552, a guide tube 571, and a blade 575 in order to perform a cauterizing motion and a cutting motion. Here, components related to the driving of the blade, such as the guide tube 571 and the blade 575, may be collectively referred to as a blade assembly 570. In one modified example of the present disclosure, by arranging the blade assembly 570 including the blade 575 between the pulley 511, which is a first jaw pulley, and the pulley 521, which a second jaw pulley, the end tool 500 may perform not only pitch and yaw motions but also a cutting motion using the blade. Components for performing a cauterizing motion and a cutting motion in the present embodiment are substantially the same as those described in the first embodiment, and thus a detailed description thereof will be omitted herein.

The surgical instrument for electrocautery according to the second embodiment of the present disclosure may include a wire 301, a wire 302, the wire 303, the wire 304, a wire 305, a wire 306, and a blade wire 307, as in the first embodiment of the present disclosure described with reference to FIG. 13 or the like.

Jaw-Link-Pulley Connection Structure

Hereinafter, a jaw-link-pulley connection structure according to the second embodiment of the present disclosure will be described in more detail.

Referring to FIGS. 64 to 70 and the like, the end tool 500 of the second embodiment of the present disclosure includes the first jaw 501, the second jaw 502, a first link 580, a second link 590, the pulley 511, which is a first jaw pulley, and the pulley 521, which is a second jaw pulley. Hereinafter, the pulley 511 is referred to as a first jaw pulley 511, and the pulley 521 is referred to as a second jaw pulley 521.

In detail, the second jaw pulley 521 may be formed of a kind of multi-layered pulley. In other words, the second jaw pulley 521 may be formed in a form in which two pulleys are combined, and two grooves may be formed on an outer circumferential surface of the second jaw pulley 521.

Here, a first coupling portion 521a may be formed on one surface of the second jaw pulley 521, and a second coupling portion 521b may be formed on the other surface of the second jaw pulley 521. Here, the positions of the first coupling portion 521a and the second coupling portion 521b are positions allowing the wire 302 and the wire 306 to overlap each other. In other words, the first coupling portion 521a and the second coupling portion 521b may be formed so that at least some of the wire 302 and the wire 306 wound on the second jaw pulley 521 overlap each other.

In other words, the first coupling portion 521a and the second coupling portion 521b are asymmetrically arranged when viewed on an XY plane, so that the first coupling portion 521a and the second coupling portion 521b are arranged to be biased in any one region of the second jaw pulley 521.

In other words, the first coupling portion 521a may be formed at a position at which the wire 302 may be wound on the outer circumferential surface of the second jaw pulley 521 by a central angle of between 90° to 360°. Likewise, the second coupling portion 521b may be formed at a position at which the wire 306 may be wound on the outer circumferential surface of the second jaw pulley 521 by a central angle of between 90° and 360°.

In addition, a fastening member 332 may be coupled to one end portion of the wire 302, and the fastening member 332 may be coupled to the first coupling portion 521a of the second jaw pulley 521. A fastening member 333 may be coupled to one end portion of the wire 306, and the fastening member 333 may be coupled to the second coupling portion 521b of the second jaw pulley 521.

This will be described from another perspective as follow.

When the wire 306 is referred to as a second jaw wire R and the wire 302 is referred to as a second jaw wire L, the first coupling portion 521a to which the second jaw wire R (306) is coupled is formed on a side opposite to one side to which the second jaw wire R (306) is input, so that a rotation angle of the second jaw pulley 521 is increased by extending the length of the second jaw wire R (306) wound on the second jaw pulley 521.

Also, the second coupling portion 521b to which the second jaw wire L 302 is coupled is formed on one side opposite to the other side to which the second jaw wire L 302 is input, so that the rotation angle of the second jaw pulley 521 may be increased by extending the length of the second jaw wire L 302 wound on the second jaw pulley 521.

A rotation radius of the second jaw pulley 521 may be increased by the first coupling portion 521a and the second coupling portion 521b. In addition, by increasing the length of the wire 302/wire 306 wound on the second jaw pulley 521 as described above, a long stroke of the second link 590 may be ensured. This will be described in more detail later.

The first jaw pulley 511 and the first link 580 may be integrally formed.

In detail, the first jaw pulley 511 is formed at one end portion of the first link 580. In addition, a slot 580a may be formed in the other end portion of the first link 580 along a lengthwise direction. In addition, a guide pin 590b of the second link 590 to be described later may be inserted into the slot 580a. In addition, a through hole 580b through which the actuation rotation shaft 545 is inserted and a coupling hole 580c to which the first jaw 501 is coupled may be formed at one side of the slot 580a.

Here, although not illustrated in the drawings, each of the first jaw pulley 511 and the first link 580 may be formed as a separate member, and the first jaw pulley 511 and the first link 580 may be fixedly coupled to each other.

In addition, a first sub-shaft 541a of the first rotation shaft 541 may be sequentially inserted through the first jaw pulley 511.

Since the first jaw pulley 511 and the first link 580 are integrally formed or fixedly coupled to each other as described above, the first link 580 does not rotate with respect to the first jaw pulley 511, and when the first jaw pulley 511 rotates about the first rotation shaft 541, the first link 580 also rotates about the first rotation shaft 541 together with the first jaw pulley 511.

Meanwhile, the first link 580 and the first jaw 501 are fixedly coupled by a fixing member (pin) or the like.

In other words, the first jaw 501 and the first jaw pulley 511 are connected by the first link 580 and are in a state of being fixed relative to each other, so that one member does not rotate/move with respect to the other member.

As a result, when the first jaw pulley 511 rotates about the first sub-shaft 541a of the first rotation shaft 541, the first link 580 and the first jaw 501 coupled thereto also rotate about the first sub-shaft 541a of the first rotation shaft 541 together with the first jaw pulley 511.

Meanwhile, a slot 502a may be formed in the second jaw 502 along a lengthwise direction. In addition, the guide pin 590b of the second link 590 to be described later may be inserted into the slot 502a.

Meanwhile, a through hole 590a may be formed at one end portion of the second link 590. In addition, the guide pin 590b may be formed to protrude from the other end portion of the second link 590.

The second jaw pulley 521 and the second link 590 are axially coupled to each other at one point, so that the second link 590 is rotatably coupled to the second jaw pulley 521. In detail, a protrusion 521c is formed on the second jaw pulley 521, and the protrusion 521c of the second jaw pulley 521 may be inserted into the through hole 590a of the second link 590. Accordingly, when the second jaw pulley 521 rotates, the second link 590 moves while rotating about the protrusion 521c.

Meanwhile, the guide pin 590b formed at the other end portion of the second link 590 may be inserted into the slot 580a of the first link 580 and the slot 502a of the second jaw 502.

Here, the second jaw 502 is axially coupled to the first link 580, and the second jaw 502 is pin-slot-coupled to the second link 590, and thus, when the second jaw pulley 521 rotates, the second jaw 502 is rotatable about the rotation shaft 545, which is an actuation rotation shaft, by to the second link 590 connected to the second jaw pulley 521.

In detail, the through hole 580b is formed in the first link 580, a through hole 502b is formed in the second jaw 502, and the actuation rotation shaft 545 is sequentially inserted through the second jaw 502 and the first link 580, so that the first link 580 may be axially coupled to the second jaw 502. Here, the actuation rotation shaft 545 may also be formed by being divided into two parts, similar to the other rotation shafts.

As a result, when the second jaw pulley 521 rotates about the first rotation shaft 541 while the first jaw pulley 511 is fixed, the second link 590 axially coupled to the second jaw pulley 521 is moved. Here, as the guide pin 590b of the second link 590 linearly moves along the slot 580a of the first link 580, the guide pin 590b of the second link 590 pushes the slot 502a of the second jaw 502, and accordingly, the second jaw 502 pivots about the actuation rotation shaft 545.

Hereinafter, a yaw motion and an actuation motion of the end tool 500 will be described.

First, when the first jaw pulley 511 and the second jaw pulley 521 rotate together, 1) the first link 580 and the first jaw 501 coupled to the first link 580 also rotate about the first rotation shaft 541 together with the first jaw pulley 511, and 2) the second link 590 and the second jaw 502 coupled to the second link 590 rotate about the first rotation shaft 541 together with the second jaw pulley 521, thereby performing a yaw motion.

Meanwhile, in a state in which the jaw 503 is closed as shown in FIG. 80, when only the second jaw pulley 521 rotates in a direction of an arrow A in FIG. 79, the second link 590 connected to the second jaw pulley 521 is moved in a direction of an arrow B in FIG. 79 by the second jaw pulley 521. In addition, as the second link 590 moves in the direction of the arrow B in FIG. 79, the second jaw 502 connected to the second link 590 is pulled in a direction of an arrow C in FIG. 79, and thus the second jaw 502 rotates about the actuation rotation shaft 545 in the direction of the arrow C in FIG. 79, thereby performing an actuation motion in which the jaw 503 is open.

In other words, when the manipulation portion 200 performs an actuation motion, only the second jaw pulley 521 rotates, and when the manipulation portion 200 performs a yaw motion, the first jaw pulley 511 and the second jaw pulley 521 rotate together in the same direction.

In other words, when the manipulation portion 200 performs a yaw motion, the first jaw wire and the second jaw wire are pulled together, and accordingly, the first jaw pulley 511 and the second jaw pulley 521 are rotated together, so that the rotation of the second jaw 502 with respect to the first jaw 501 does not occur.

Meanwhile, when the manipulation portion 200 performs an actuation motion, only the second jaw wire is pulled, and accordingly, only the second jaw pulley 521 is rotated while the first jaw pulley 511 is fixed, and thus the second link 590 is pulled while the actuation rotation shaft 545 is fixed, so that the second jaw 502 rotates about the actuation rotation shaft 545.

Here, in the end tool 500 of the second embodiment of the present disclosure, a pin/slot-type structure is employed to secure a grip force in the actuation motion.

In detail, in order to rotate the second jaw 502 by the same amount, in the pin/slot-type structure, the second link 590 must move a longer distance (that is, the second link 590 needs to have a long stroke). In addition, in order for the second link 590 to move a longer distance, the second jaw pulley 521 should rotate more. In other words, when the second jaw pulley 521 rotates further to rotate the second jaw 502 by the same amount, a greater force may be applied to the second jaw 502 by as much as the second jaw pulley 521 rotates further, so that a grip force in the actuation motion may be amplified.

In addition, in order to rotate the second jaw pulley 521 further as described above, the second jaw pulley 521 is formed in a multi-layered structure as described above to make the lengths of the wire 302 and the wire 306 wound on the second jaw pulley 521 to be longer, thereby securing a long stroke of the second link 590.

With such a structure, in the second embodiment of the present disclosure, the rotation angle of the second jaw pulley 521 during jaw opening/closing is increased as compared to that in the first embodiment of the present disclosure.

FIG. 81 is a view illustrating a jaw opening/closing process in the first embodiment of the present disclosure described with reference to FIG. 2 or the like, and FIG. 82 is a view illustrating a jaw opening/closing process according to the second embodiment of the present disclosure.

Referring to FIGS. 81 and 82, in order to rotate the second jaw 502 by the same angle, that is θ1, the second jaw pulley 121 of the first embodiment should rotate only by θ2, whereas the second jaw pulley 521 of the second embodiment should rotate only by θ3, and thus the second jaw pulley 521 of the second embodiment should rotate more than that of the first embodiment. In other words, it may be said that an operating angle of the second jaw pulley 521 in the second embodiment may be larger than that of the second jaw pulley 121 in the first embodiment.

Since the second jaw pulley 521 in the second embodiment rotates more than that in the first embodiment as described above, the moving distance of the second link 590 is increased. Accordingly, since the second jaw pulley 521 rotates further to rotate the second jaw 502 by the same angle, that is θ1, a greater force is applied to the second jaw 502.

Meanwhile, FIG. 83 is a view illustrating a case in which the pin/slot-type structure of the second embodiment of the present disclosure is configured in the normal pulley rather the multi-layered pulley.

When the pin/slot-type structure of the second embodiment of the present disclosure is configured in the normal pulley rather than the multi-layered pulley, the jaw 503 may be opened and closed in a neutral state (that is, a state in which the end tool is parallel to the connecting portion) as shown in FIGS. 83A and 83B. However, when a yaw motion is performed while the jaw 503 is open as shown in FIG. 83C, an operating range (angle) of the jaw 503 may be limited. In other words, when the jaw 503 is in the state of FIG. 83C, the jaw 503 may not rotate more as the jaw pulley comes into contact with the auxiliary pulley, and thus the rotation angle thereof is limited.

On the other hand, when the pin/slot-type structure is applied to the multi-layered pulley as in the second embodiment of the present disclosure, as shown in FIG. 91 or the like, the jaws may perform a normal opening and closing motion, that is, an actuation motion even in a state of jaws being yaw-rotated by +90° to −90°.

Pitch, Yaw, and Cutting Motions of End Tool

FIGS. 91 and 92 are views illustrating a process of performing an opening and closing motion while the end tool of the surgical instrument for electrocautery of FIG. 62 is yaw-rotated by −90°. In addition, FIGS. 93 and 94 are views illustrating a process of performing an opening and closing motion while the end tool of the surgical instrument for electrocautery of FIG. 62 is yaw-rotated by +90°.

As shown in FIGS. 91 to 94, the end tool of the surgical instrument for electrocautery according to the second embodiment of the present disclosure is formed to be capable of normally performing an opening and closing motion, that is, an actuation motion even in a state in which the jaws are yaw-rotated by +90° to −90°.

FIGS. 95 and 96 are views illustrating a process of performing a cutting motion while the end tool of the surgical instrument for electrocautery of FIG. 62 is yaw-rotated by +90°.

As shown in FIGS. 95 and 96, the end tool of the surgical instrument for electrocautery according to the second embodiment of the present disclosure is formed to be capable of normally performing a cutting motion even in a state in which the jaws are yaw-rotated by +90°.

FIG. 97 is a view illustrating a state in which the end tool of the surgical instrument for electrocautery of FIG. 62 is pitch-rotated by −90°, and FIG. 98 is a view illustrating a state in which the end tool of the surgical instrument for electrocautery of FIG. 62 is pitch-rotated by +90°. In addition, FIG. 99 is a cut-away perspective view of the end tool of the surgical instrument for electrocautery of FIG. 98. In addition, FIGS. 100, 101, and 102 are views illustrating a process of performing a cutting motion while the end tool of the surgical instrument for electrocautery of FIG. 62 is pitch-rotated by −90°.

As shown in FIGS. 97 to 102, the end tool of the surgical instrument for electrocautery according to the second embodiment of the present disclosure is formed to be capable of normally performing a cutting motion even in a state in which the jaws are pitch-rotated by −90°.

Meanwhile, FIG. 103 is a view illustrating a state in which the jaws are pitch-rotated by −90° and simultaneously yaw-rotated by +90°, and FIGS. 104, 105, and 106 are perspective views illustrating a cutting motion of the end tool of the surgical instrument for electrocautery of FIG. 62 and illustrate a state of performing a cutting motion while the jaws are pitch-rotated by −90° and simultaneously yaw-rotated by +90°.

As shown in FIGS. 103 to 106, the end tool of the surgical instrument for electrocautery according to the second embodiment of the present disclosure is formed to be capable of normally performing a cutting motion even in a state in which the jaws are pitch-rotated by −90° and simultaneously yaw-rotated by +90°.

First Modified Example of Second Embodiment—Jaw Opening/Closing in Vertical Direction Hereinafter, an end tool 2100 of a surgical instrument according to a first modified example of the second embodiment of the present disclosure will be described. Here, the end tool 2100 of the surgical instrument according to the first modified example of the second embodiment of the present disclosure is different from the end tool (see 500 of FIG. 62 or the like) of the surgical instrument according to the second embodiment of the present disclosure described above in that an opening/closing direction of a jaw 2103 is changed.

In other words, the end tool 2100 of the surgical instrument according to the first modified example of the second embodiment of the present disclosure may be considered to combine the feature of the first modified example of the first embodiment of the present disclosure described with reference to FIG. 44 or the like and the feature of the second embodiment of the present disclosure described with reference to FIG. 62 or the like.

FIGS. 107, 108, 109, and 110 are views illustrating the end tool of the surgical instrument for electrocautery according to the first modified example of the second embodiment of the present disclosure, FIGS. 111, 112, and 113 are views illustrating a process in which the end tool of the surgical instrument for electrocautery of FIG. 107 performs a cutting motion, and FIG. 114 is a view illustrating the end tool of the surgical instrument for electrocautery of FIG. 107.

Hereinafter, a first link 2180 and a second link 2190 of the first modified example of the second embodiment of the present disclosure will be described in more detail.

In the end tool 2100 of the first modified example of the second embodiment of the present disclosure, an actuation rotation shaft 2145 and a yaw rotation shaft 2141 are arranged perpendicular to each other. Accordingly, an opening/closing direction of the jaw 2103 is a vertical direction. Accordingly, an arrangement direction of a blade 2175 is also the vertical direction.

That is, in the case of the second embodiment of the present disclosure described with reference to FIG. 62 or the like, the actuation rotation shaft 545 and the yaw rotation shaft 541 are formed parallel to each other, and the two shafts may be formed parallel to a Z-axis. Accordingly, the opening/closing of the jaw 503 is performed on the XY plane perpendicular to the Z-axis.

On the other hand, in the end tool 2100 of the first modified example of the second embodiment of the present disclosure, the yaw rotation shaft 2141 is formed parallel to the Z-axis, whereas the actuation rotation shaft 2145 is formed parallel to a Y-axis. That is, the actuation rotation shaft 2145 and the yaw rotation shaft 2141 are arranged perpendicular to each other. In addition, the opening/closing of the jaw 2103 is performed on an XZ plane perpendicular to the Y-axis.

Here, the end tool 2100 of the present disclosure includes a first jaw 2101, a second jaw 2102, the first link 2180, the second link 2190, a pulley 2111, which is a first jaw pulley, and a pulley 2121 that is a second jaw pulley. A specific configuration of each component is the same as that in the first modified example of the first embodiment of the present disclosure described with reference to FIG. 44 or the like, and thus a detailed description thereof will be omitted.

Hereinafter, a yaw motion and an actuation motion of the end tool 2100 will be described.

First, when the first jaw pulley 2111 and the second jaw pulley 2121 rotate together, 1) the first link 2180 and the first jaw 2101 coupled to the first link 2180 also rotate about the first rotation shaft 2141 together with the first jaw pulley 2111, and 2) the second link 2190 and the second jaw 2102 coupled to the second link 2190 also rotate about the first rotation shaft 2141 together with the second jaw pulley 2121, thereby performing a yaw motion.

Meanwhile, when only the second jaw pulley 2121 rotates, the second link 2190 connected to the second jaw pulley 2121 is moved by the second jaw pulley 2121. In addition, the second jaw 2102 connected to the second link 2190 is pulled while the second link 2190 is moving, and thus the second jaw 2102 performs an actuation motion by rotating about the actuation rotation shaft 2145.

In other words, when the manipulation portion 200 performs an actuation motion, only the second jaw pulley 2121 rotates, and when the manipulation portion 200 performs a yaw motion, the first jaw pulley 2111 and the second jaw pulley 2121 rotate together in the same direction.

In other words, when the manipulation portion 200 performs a yaw motion, the first jaw wire and the second jaw wire are pulled together, and accordingly, the first jaw pulley 2111 and the second jaw pulley 2121 are rotated together, so that the rotation of the second jaw 2102 with respect to the first jaw 2101 does not occur.

Meanwhile, when the manipulation portion 200 performs an actuation motion, only the second jaw wire is pulled, and accordingly, only the second jaw pulley 2121 is rotated while the first jaw pulley 2111 is fixed, and thus the second link 2190 is pulled while the actuation rotation shaft 2145 is fixed, so that the second jaw 2102 rotates about the actuation rotation shaft 2145.

As described above, in the end tool 2100 of the first modified example of the second embodiment of the present disclosure, the actuation rotation shaft 2145 and the yaw rotation shaft 2141 are arranged perpendicular to each other. Accordingly, each of the opening/closing direction of the jaw 2103 and the arrangement direction of the blade 2175 is also the vertical direction, so that a user may manipulate the end tool similarly to the existing surgical instrument.

Second Modified Example of Second Embodiment-Engrave

Hereinafter, an end tool 2200 of a surgical instrument according to a second modified example of the second embodiment of the present disclosure will be described. Here, the end tool 2200 of the surgical instrument according to the second modified example of the second embodiment of the present disclosure is different from the end tool (see 500 of FIG. 62 or the like) of the surgical instrument according to the second embodiment of the present disclosure described above in that a configuration of an end tool hub 2260 serving as an auxiliary pulley is different.

In other words, the end tool 2200 of the surgical instrument according to the second modified example of the second embodiment of the present disclosure may be considered to combine the feature of the second modified example of the first embodiment of the present disclosure described with reference to FIG. 51 or the like and the feature of the second embodiment of the present disclosure described with reference to FIG. 62 or the like.

FIGS. 115 and 116 are views illustrating the end tool of the surgical instrument for electrocautery according to the second modified example of the second embodiment of the present disclosure, FIG. 117 is a perspective view illustrating the end tool hub of the end tool of the surgical instrument for electrocautery of FIG. 115, FIGS. 118 and 119 are cut-away perspective views of the end tool hub of FIG. 117, and FIGS. 120 and 121 are perspective views of the end tool hub of FIG. 117.

Hereinafter, the end tool hub 2260 of the second modified example of the second embodiment of the present disclosure will be described in more detail, and in particular, a first wire guide portion 2268a and a second wire guide portion 2268b of the end tool hub 2260 serving as auxiliary pulleys will be mainly described.

Referring to FIGS. 115 to 120, the end tool hub 2260 includes a body portion 2261, a first jaw pulley coupling portion 2262a, a second jaw pulley coupling portion 2262b, a first pitch pulley portion 2263a, a second pitch pulley portion 2263b, a pitch slit 2264, a yaw slit 2265, a pitch round portion 2266, a yaw round portion 2267, and a wire guide portion 2268. Here, the wire guide portion 2268 includes the first wire guide portion 2268a and the second wire guide portion 2268b. A specific configuration of each component is the same as that in the second modified example of the first embodiment of the present disclosure described with reference to FIG. 51 or the like, and thus a detailed description thereof will be omitted.

Hereinafter, the role and function of the wire guide portion 2268 will be described in more detail.

The wire guide portion 2268 may be in contact with the wire 305 and the wire 302 and may change the arrangement path of the wire 305 and the wire 302 to a certain degree to serve to increase a rotation radius of each of a first jaw 2201 and a second jaw 2202.

That is, when the auxiliary pulley is not disposed, each of a pulley 2211, which is a first jaw pulley, and a pulley 2221, which is a second jaw pulley, may rotate up to a right angle, but in the second modified example of the second embodiment of the present disclosure, by additionally providing the wire guide portion 2268 in the end tool hub 2260, the maximum rotation angle of each pulley may be increased.

This enables a motion that two jaws of the end tool 2200 have to open for an actuation motion in a state in which the two jaws of the end tool 2200 are yaw-rotated by 90°. In other words, the range of yaw rotation in which an actuation motion is possible may be increased through the configuration of the wire guide portion 2268 of the end tool hub 2260.

Furthermore, by forming the wire guide portion 2268 in the end tool hub 2260 that already exists without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also the length of the end tool is shortened as much as the size of the auxiliary pulley, so that the length of the end tool is shortened during a pitch motion. Accordingly, a surgical motion may be more easily performed in a narrow space.

According to the present disclosure as described above, as the rotation radius of the pulley 2211, which is a first jaw pulley, and the pulley 2221, which is a second jaw pulley, increase, a yaw motion range in which a normal opening/closing actuation motion and a normal cutting motion may be performed may be increased.

Third Modified Example of Second Embodiment—Jaw Opening/Closing in Vertical Direction-Engrave Hereinafter, an end tool 2300 of a surgical instrument according to a third modified example of the second embodiment of the present disclosure will be described. Here, the end tool 2300 of the surgical instrument according to the third modified example of the second embodiment of the present disclosure is different from the end tool (see 500 of FIG. 62 or the like) of the surgical instrument according to the second embodiment of the present disclosure described above in that an opening/closing direction of a jaw 2303 is changed. Also, the end tool 2300 of the surgical instrument according to the third modified example of the second embodiment of the present disclosure is different from the end tool (see 500 of FIG. 62 or the like) of the surgical instrument according to the second embodiment of the present disclosure described above in that a configuration of an end tool hub 2360 serving as an auxiliary pulley is different.

In other words, the end tool 2300 of the surgical instrument according to the third modified example of the second embodiment of the present disclosure may be considered to combine the feature of the first modified example of the second embodiment described with reference to FIG. 107 or the like and the feature of the second modified example of the second embodiment described with reference to FIG. 115 or the like. The configuration changed from the second embodiment as described above will be described in detail later.

FIGS. 122 and 123 are views illustrating the end tool of the surgical instrument for electrocautery according to the third modified example of the second embodiment of the present disclosure, and FIG. 124 is a perspective view illustrating an end tool hub of the end tool of the surgical instrument for electrocautery of FIG. 122.

Hereinafter, a first link 2380 and a second link 2390 of the third modified example of the second embodiment of the present disclosure will be described in more detail.

In the end tool 2300 of the third modified example of the second embodiment of the present disclosure, an actuation rotation shaft 2345 and a yaw rotation shaft 2341 are arranged perpendicular to each other. Accordingly, an opening/closing direction of the jaw 2303 is a vertical direction. Accordingly, an arrangement direction of a blade 2375 is also the vertical direction.

That is, in the case of the second embodiment of the present disclosure described with reference to FIG. 62 or the like, the actuation rotation shaft 545 and the yaw rotation shaft 541 are formed parallel to each other, and the two shafts may be formed parallel to the Z-axis. Accordingly, the opening/closing of the jaw 503 is performed on the XY plane perpendicular to the Z-axis.

On the other hand, in the end tool 2300 of the third modified example of the second embodiment of the present disclosure, the yaw rotation shaft 2341 is formed parallel to the Z-axis, whereas the actuation rotation shaft 2345 is formed parallel to the Y-axis. That is, the actuation rotation shaft 2345 and the yaw rotation shaft 2341 are arranged perpendicular to each other. In addition, the opening/closing of the jaw 2303 is performed on the XZ plane perpendicular to the Y-axis.

Here, the end tool 2300 of the present disclosure includes a first jaw 2301, a second jaw 2302, a first link 2380, a second link 2390, a pulley 2311, which is a first jaw pulley, and a pulley 2321 that is a second jaw pulley. A specific configuration of each component is the same as that in the first modified example of the second embodiment described with reference to FIG. 107 or the like, and thus a detailed description thereof will be omitted.

Hereinafter, a yaw motion and an actuation motion of the end tool 2300 will be described.

First, when the first jaw pulley 2311 and the second jaw pulley 2321 rotate together, 1) the first link 2380 and the first jaw 2301 coupled to the first link 2380 also rotate about a first rotation shaft 2341 together with the first jaw pulley 2311, and 2) the second link 2390 and the second jaw 2302 coupled to the second link 2390 also rotate about the first rotation shaft 2341 together with the second jaw pulley 2321, thereby performing a yaw motion.

Meanwhile, when only the second jaw pulley 2321 rotates, the second link 2390 connected to the second jaw pulley 2321 is moved by the second jaw pulley 2321. In addition, the second jaw 2302 connected to the second link 2390 is pulled while the second link 2390 is moving, and thus the second jaw 2302 performs an actuation motion by rotating about the actuation rotation shaft 2345.

In other words, when the manipulation portion 200 performs an actuation motion, only the second jaw pulley 2321 rotates, and when the manipulation portion 200 performs a yaw motion, the first jaw pulley 2311 and the second jaw pulley 2321 rotate together in the same direction.

In other words, when the manipulation portion 200 performs a yaw motion, the first jaw wire and the second jaw wire are pulled together, and accordingly, the first jaw pulley 2311 and the second jaw pulley 2321 are rotated together, so that the rotation of the second jaw 2302 with respect to the first jaw 2301 does not occur.

Meanwhile, when the manipulation portion 200 performs an actuation motion, only the second jaw wire is pulled, and accordingly, only the second jaw pulley 2321 is rotated while the first jaw pulley 2311 is fixed, and thus the second link 2390 is pulled while the actuation rotation shaft 2345 is fixed, so that the second jaw 2302 rotates about the actuation rotation shaft 2345.

As described above, in the end tool 2300 of the third modified example of the second embodiment of the present disclosure, the actuation rotation shaft 2345 and the yaw rotation shaft 2341 are arranged perpendicular to each other. Accordingly, each of the opening/closing direction of the jaw 2303 and the arrangement direction of the blade 2375 is also the vertical direction, so that a user may manipulate the end tool similarly to the existing surgical instrument.

Hereinafter, the end tool hub 2360 of the third modified example of the second embodiment of the present disclosure will be described in more detail, and in particular, a first wire guide portion 2368a and a second wire guide portion 2368b of the end tool hub 2360 serving as auxiliary pulleys will be mainly described.

Referring to FIGS. 122 to 124, the end tool hub 2360 includes a body portion 2361, a first jaw pulley coupling portion 2362a, a second jaw pulley coupling portion 2362b, a first pitch pulley portion 2363a, a second pitch pulley portion 2363b, a pitch slit 2364, a yaw slit 2365, a pitch round portion 2366, a yaw round portion 2367, and a wire guide portion 2368. Here, the wire guide portion 2368 includes the first wire guide portion 2368a and the second wire guide portion 2368b. A specific configuration of each component is the same as that in the second modified example of the second embodiment of the present disclosure described with reference to FIG. 115 or the like, and thus a detailed description thereof will be omitted.

Hereinafter, the role and function of the wire guide portion 2368 will be described in more detail.

The wire guide portion 2368 may be in contact with the wire 305 and the wire 302 and may change the arrangement path of the wire 305 and the wire 302 to a certain degree to serve to increase a rotation radius of each of the first jaw 2301 and the second jaw 2302.

That is, when the auxiliary pulley is not disposed, each of the pulley 2311, which is a first jaw pulley, and the pulley 2321, which is a second jaw pulley, may rotate up to a right angle, but in the third modified example of the second embodiment of the present disclosure, by additionally providing the wire guide portion 2368 in the end tool hub 2360, the maximum rotation angle of each pulley may be increased.

This enables a motion that two jaws of the end tool 2300 have to open for an actuation motion in a state in which the two jaws of the end tool 2300 are yaw-rotated by 90°. In other words, the range of yaw rotation in which an actuation motion is possible may be increased through the configuration of the wire guide portion 2368 of the end tool hub 2360.

Furthermore, by forming the wire guide portion 2368 in the end tool hub 2360 that already exists without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also the length of the end tool is shortened as much as the size of the auxiliary pulley, so that the length of the end tool is shortened during a pitch motion. Accordingly, a surgical motion may be more easily performed in a narrow space.

According to the present disclosure as described above, as the rotation radius of the pulley 2311, which is a first jaw pulley, and the pulley 2321, which is a second jaw pulley, increase, a yaw motion range in which a normal opening/closing actuation motion and a normal cutting motion may be performed may be increased.

As such, the present disclosure has been described with reference to one embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

The invention claimed is:
1. An end tool of a surgical instrument, the end tool comprising:
   a first jaw and a second jaw that are rotatable independently from each other;
   a first jaw pulley connected to the first jaw and formed to be rotatable about a first rotation shaft;
   a second jaw pulley connected to the second jaw, formed to be rotatable about the first rotation shaft, and formed to be spaced a predetermined distance from the first jaw pulley;
   a first link having one end coupled to the first jaw and the other end coupled to the first jaw pulley to connect the first jaw and the first jaw pulley;
   a second link having one end coupled to the second jaw and the other end coupled to the second jaw pulley to connect the second jaw and the second jaw pulley;

a blade assembly that includes a blade moving between a proximal end and a distal end of the first jaw, and of which at least a part is formed between the first jaw pulley and the second jaw pulley; and a blade wire of which at least a part is in contact with the blade assembly to transfer a driving force required to move the blade to the blade, wherein the blade assembly includes a guide tube that accommodates at least a part of the blade wire therein and is formed to be bendable to a certain degree, wherein the guide tube is formed to extend toward the blade through the first link.

2. The end tool of claim 1, wherein the blade wire passes through an inside of the guide tube and is connected to the blade.

3. The end tool of claim 1, wherein when the guide tube is curved to a certain degree, the blade wire inside the guide tube is also curved together with the guide tube.

4. The end tool of claim 1, wherein the blade wire is formed to be movable along the guide tube in the guide tube.

5. The end tool of claim 1, wherein the first link is fixedly coupled to each of the first jaw and the first jaw pulley, and when the first jaw pulley rotates about the first rotation shaft, the first link and the first jaw rotate about the first rotation shaft together with the first jaw pulley in an integrated manner.

6. The end tool of claim 1, wherein one end of the second link is connected to the second jaw pulley so that the second link is formed to be rotatable relative to the second jaw pulley, and the other end of the second link is connected to the second jaw so that the second jaw is formed to be movable relative to the second link.

7. The end tool of claim 6, wherein when the second jaw pulley rotates, the rotation of the second jaw pulley is transferred to the second jaw by the second link connected to the second jaw pulley.

8. The end tool of claim 6, further comprising an actuation rotation shaft inserted through the first link and the second jaw, wherein the second jaw is formed to be rotatable about the actuation rotation shaft with respect to the first link.

9. The end tool of claim 8, wherein a rotational motion of the second jaw pulley about the first rotation shaft is converted into a rotational motion of the second jaw about the actuation rotation shaft by the second link.

10. The end tool of claim 8, wherein when the second jaw pulley rotates, the second link connected to the second jaw pulley applies a force to the second jaw so that the second jaw rotates about the actuation rotation shaft.

11. The end tool of claim 8, wherein the first rotation shaft and the actuation rotation shaft are formed substantially parallel to each other.

12. The end tool of claim 8, wherein the first rotation shaft and the actuation rotation shaft are formed substantially perpendicular to each other.

13. The end tool of claim 1, further comprising:

an end tool hub including a first jaw pulley coupling portion, a second jaw pulley coupling portion, and a guide portion, wherein the first jaw pulley coupling portion and the second jaw pulley coupling portion are formed to face each other and the guide portion connects the first jaw pulley coupling portion and the second jaw pulley coupling portion, wherein the first jaw pulley is disposed adjacent to the first jaw pulley coupling portion of the end tool hub, the second jaw pulley is disposed adjacent to the second jaw pulley coupling portion of the end tool hub, and at least a part of the blade assembly is formed between the first jaw pulley and the second jaw pulley.

14. The end tool of claim 13, wherein the guide tube is formed to extend toward the first jaw or the second jaw through the end tool hub.

15. The end tool of claim 1, wherein when the second jaw pulley relatively rotates about the first rotation shaft with respect to the first jaw pulley, an actuation motion in which the second jaw relatively rotates with respect to the first jaw is performed.

16. The end tool of claim 1, wherein the blade moves between the proximal end and the distal end of the end tool by the blade wire.

17. An end tool of a surgical instrument, the end tool comprising:

a first jaw and a second jaw that are rotatable independently from each other;

a first jaw pulley connected to the first jaw and formed to be rotatable about a first rotation shaft;

a second jaw pulley connected to the second jaw, formed to be rotatable about the first rotation shaft, and formed to be spaced a predetermined distance from the first jaw pulley;

a blade assembly that includes a blade moving between a proximal end and a distal end of the first jaw, and of which at least a part is formed between the first jaw pulley and the second jaw pulley; and a blade wire of which at least a part is in contact with the blade assembly to transfer a driving force required to move the blade to the blade, wherein when the first jaw pulley and the second jaw pulley rotate in the same direction about the first rotation shaft, a yaw motion in which the first jaw and the second jaw rotate in the same direction is performed.

18. An end tool of a surgical instrument, the end tool comprising:

a first jaw and a second jaw that are rotatable independently from each other;

a first jaw pulley connected to the first jaw and formed to be rotatable about a first rotation shaft;

a second jaw pulley connected to the second jaw, formed to be rotatable about the first rotation shaft, and formed to be spaced a predetermined distance from the first jaw pulley;

a blade assembly that includes a blade moving between a proximal end and a distal end of the first jaw, and of which at least a part is formed between the first jaw pulley and the second jaw pulley;

a blade wire of which at least a part is in contact with the blade assembly to transfer a driving force required to move the blade to the blade;

a pair of end tool first jaw pitch main pulleys that are formed on one side of the first jaw pulley and formed to be rotatable about a third rotation shaft forming a certain angle with the first rotation shaft; and a pair of end tool second jaw pitch main pulleys formed on one side of the second jaw pulley and formed to be rotatable about the third rotation shaft.

19. The end tool of claim 18, wherein the end tool is formed to be yaw-rotatable about the first rotation shaft and simultaneously pitch-rotatable about the third rotation shaft.

20. The end tool of claim 18, further comprising:
- a first jaw wire of which at least a part is wound on the first jaw pulley and the pair of end tool first jaw pitch main pulleys; and
- a second jaw wire of which at least a part is wound on the second jaw pulley and the pair of end tool second jaw pitch main pulleys.

* * * * *